US009822374B2

(12) United States Patent
Katz et al.

(10) Patent No.: US 9,822,374 B2
(45) Date of Patent: Nov. 21, 2017

(54) PRODUCTION OF METABOLITES

(75) Inventors: Michael Patrik Katz, Malmo (SE); Thomas Durhuus, Copenhagen (DK); Hans Peter Smits, Holte (DK); Jochen Förster, Copenhagen V (DK)

(73) Assignee: EVOLVA SA, Reinach (CH)

( * ) Notice: Subject to any disclaimer, the term of this patent is extended or adjusted under 35 U.S.C. 154(b) by 0 days.

(21) Appl. No.: 13/700,011

(22) PCT Filed: May 24, 2011

(86) PCT No.: PCT/EP2011/058447
§ 371 (c)(1),
(2), (4) Date: Apr. 29, 2013

(87) PCT Pub. No.: WO2011/147818
PCT Pub. Date: Dec. 1, 2011

(65) Prior Publication Data

US 2013/0209613 A1 Aug. 15, 2013

(30) Foreign Application Priority Data

May 26, 2010 (GB) .................................. 1008826.8

(51) Int. Cl.

| | |
|---|---|
| ***C12N 15/81*** | (2006.01) |
| ***C12N 1/18*** | (2006.01) |
| ***C07K 14/37*** | (2006.01) |
| ***C07K 14/39*** | (2006.01) |
| ***C12N 9/10*** | (2006.01) |
| ***C12N 9/90*** | (2006.01) |
| ***C12P 7/22*** | (2006.01) |
| ***A23K 10/18*** | (2016.01) |
| ***C07K 14/395*** | (2006.01) |
| ***C12N 9/00*** | (2006.01) |

(52) U.S. Cl.
CPC .............. *C12N 15/81* (2013.01); *A23K 10/18* (2016.05); *C07K 14/37* (2013.01); *C07K 14/395* (2013.01); *C12N 1/18* (2013.01); *C12N 9/1029* (2013.01); *C12N 9/93* (2013.01); *C12P 7/22* (2013.01)

(58) Field of Classification Search
None
See application file for complete search history.

(56) References Cited

U.S. PATENT DOCUMENTS

| | | | |
|---|---|---|---|
| 4,865,973 | A | 9/1989 | Kollerup et al. |
| 5,391,724 | A | 2/1995 | Kindl et al. |
| 5,500,367 | A | 3/1996 | Hain et al. |
| 5,973,230 | A | 10/1999 | Kindl et al. |
| 6,020,129 | A | 2/2000 | Schroder et al. |
| 6,284,523 | B1 | 9/2001 | Daugulis et al. |
| 6,521,748 | B2 | 2/2003 | Tang |
| 7,604,968 | B2 | 10/2009 | Schmidt-Dannert et al. |
| 8,343,739 | B2 | 1/2013 | Katz et al. |
| 8,518,677 | B2 | 8/2013 | Schmidt et al. |
| 8,569,024 | B2 | 10/2013 | Stenhuus et al. |
| 8,895,287 | B2 | 11/2014 | Katz et al. |
| 2001/0053847 | A1 | 12/2001 | Tang |
| 2004/0023357 | A1 | 2/2004 | Breinig et al. |
| 2004/0059103 | A1 | 3/2004 | Huang |
| 2004/0078846 | A1 | 4/2004 | Desouza et al. |
| 2004/0229326 | A1 | 11/2004 | Ben-Bassat et al. |
| 2004/0234671 | A1 | 11/2004 | Ector et al. |
| 2005/0003474 | A1 | 1/2005 | Desouza et al. |
| 2005/0208643 | A1 | 9/2005 | Schmidt-Dannert et al. |
| 2006/0263864 | A1 * | 11/2006 | Busby .................... C12N 15/80 435/125 |
| 2008/0286844 | A1 | 11/2008 | Katz et al. |
| 2009/0035839 | A1 | 2/2009 | Katz et al. |
| 2009/0082286 | A1 | 3/2009 | Huang |
| 2011/0086399 | A1 | 4/2011 | Smits et al. |
| 2011/0124067 | A1 | 5/2011 | Stenhuus et al. |
| 2014/0024862 | A1 | 1/2014 | Katz et al. |

FOREIGN PATENT DOCUMENTS

| | | |
|---|---|---|
| CN | 1277954 | 12/2000 |
| EP | 0 309 862 | 4/1989 |
| EP | 0 464 461 | 1/1992 |

(Continued)

OTHER PUBLICATIONS

Beekwilder et al., Production of Resveratrol in Recombinant Microorganisms, Appl. Environ. Microbiol., 2006, 72, 5670-72.*
Schoonbeek et al., The ABC Transporter BcatrB Affects the Sensitivity of Botrytis cinerea to the Phytoalexin Resveratrol and the Fungicide Fenpiclonil, Molecular Plant-Microbe Interactions, 2001, 14, 562-71.*
Prestorious et al., Meeting the consumer challenge through genetically customized wine-yeast strains, Trends Biotech., 2002, 20, 426-32.*
Luttik et al., Alleviation of feedback inhibition in *Saccharomyces cerevisiae* aromatic amino acid biosynthesis: Quantification of metabolic impact, Metabolic Eng., 2008, 10, 141-53.*
Vuralhan et al., Physiological characterization of the ARO10-dependent, broad-substrate-specificity 2-oxo acid decarboxylase activity of *Saccharomyces cerevisiae*, App. Env. Microbiol., 2005, 71, 3276-84.*

(Continued)

*Primary Examiner* — Robert Mondesi
*Assistant Examiner* — Todd M Epstein
(74) *Attorney, Agent, or Firm* — McDonnell Boehnen Hulbert & Berghoff LLP

(57) ABSTRACT

A recombinant micro-organism such as *Saccharomyces cerevisiae* which produces and excretes into culture medium a stilbenoid metabolite product when grown under stilbenoid production conditions, which expresses in above native levels a ABC transporter which transports said stilbenoid out of said micro-organism cells to the culture medium. The genome of the *Saccharomyces cerevisiae* produces an auxotrophic phenotype which is compensated by a plasmid which also expresses one or more of said enzymes constituting said metabolic pathway producing said stilbenoid, an expression product of the plasmid is genetically modified to include a ubiquitination tag sequence. Expression of an enzyme participating in catabolism of phenylalanine by the Ehrlich pathway is optionally reduced compared to its native expression level.

15 Claims, 11 Drawing Sheets

(56) References Cited

FOREIGN PATENT DOCUMENTS

| | | |
|---|---|---|
| EP | 0 533 010 | 3/1993 |
| EP | 1 510 586 | 3/2005 |
| EP | 1 715 032 | 10/2006 |
| JP | 2005-53862 | 3/2005 |
| JP | 2001-008695 | 1/2011 |
| KR | 2004-0105110 | 12/2004 |
| WO | 00/73485 | 12/2000 |
| WO | WO 02/10407 | 2/2002 |
| WO | 2004/049832 | 6/2004 |
| WO | WO 2004/092344 | 10/2004 |
| WO | 2005/012507 | 2/2005 |
| WO | 2005/118814 | 12/2005 |
| WO | WO 2006/055322 | 5/2006 |
| WO | 2006/089898 | 8/2006 |
| WO | 2006/111163 | 10/2006 |
| WO | 2006/124999 | 11/2006 |
| WO | 2006/125000 | 11/2006 |
| WO | WO 2007/034190 | 3/2007 |
| WO | 2008/009728 | 1/2008 |
| WO | 2009/016108 | 2/2009 |
| WO | 2009/124879 | 10/2009 |
| WO | 2009/124966 | 10/2009 |
| WO | 2009/124967 | 10/2009 |
| WO | WO 2011/140344 | 11/2011 |
| WO | WO 2011/147818 | 12/2011 |
| ZA | 2004/008194 | 8/2005 |

OTHER PUBLICATIONS

Herrero et al., Engineering the *Saccharomyces cerevisiae* isoprenoid pathway for de novo production of aromatic monoterpenes in wine, Metabolic Eng., 2008, 10, 78-86.*

Uniprot, Accession No. P32449, 2010, www.uniprot.org.*

Uniprot, Accession No. P32178, 2010, www.uniprot.org.*

Servos et al., Gene SNQ2 of *Saccharomyces cerevisiae*, which confers resistance to 4-nitorquinoline-N-oxide and other chemicals, encodes a 169 kDa protein homologous to ATP-dependent permeases, Mol. Gen. Genet., 1993, 236, 214-18.*

Pan et al., Identification of molecular pathways affected by pterostilbene, a natural dimethylether analog of resveratrol, BMC Med. Gen., 2008, 1, 7.*

Gustafsson et al., Codon bias and heterologous protein expression, Trends Biotechnol., 2004, 22, 346-53.*

Zwiers et al., ABC transporters of the wheat pathogen Mycosphaerella graminicola function as protectants against biotic and xenobiotic toxic compounds, Mol. Gen. Genomics, 2003, 269, 499-507.*

Rodriguez et al., Establishment of a yeast platform strain for production of p-coumaric acid through metabolic engineering of aromatic amino acid biosynthesis, Metab. Eng., 2015, 31, 181-88.*

Appert et al., Structural and catalytic properties of the four phenylalanine ammonia-lyase isoenzymes from parsley (*Petroselinum crispum* Nym.) FEBS. 1994. 225, 491-499.

Becker et al., Metabolic engineering of *Saccharomyces cerevisiae* for the synthesis of the wine-related antioxidant resveratrol. FEMS Yeast Res. Oct. 2003;4(1):79-85.

Cochrane et al., The Arabidopsis phenylalanine ammonia lyase gene family: kinetic characterization of the four PAL isoforms. Phytochemistry. 2004. 65, 1557-1564.

Horinouchi. Combinatorial Biosynthesis of Non-bacterial and Unnatural Flavonoids, Stilbenoids and Curcuminoids by Microorganisms. J. Antibiot. 2008 61(12): 709-728.

Hwang et al., Production of Plant-Specific Flavanones by *Escherichia coli* containing an artificial gene cluster. Applied and Environmental Microbiology. 2003. vol. 69, No. 5, 2699-2706.

Jiang et al., Metabolic Engineering of the Phenylpropanoid Pathway in *Saccharomyces cerevisiae*. Applied and Environmental Microbiology. 2005. 71 (6):2962-2969.

Kaneko et al., Cinnamate: Coenzyme A Ligase from the Filamentous Bacterium Streptomyces coelicolor A3(2). Journal of Bacteriology. 2003. 185(1 ):20-27.

Kizer et al., Application of Functional Genomics to Pathway Optimization for Increased Isoprenoid Production. Applied and Environmental Microbiology. 2008. vol. 74, No. 10. 3229-3241.

Prather et al., De novo biosynthetic pathways: rational design of microbial chemical factories. Current Opinion in Biotechnology. 2008. 19:468-474.

Punt et al., Filamentous fungi as cell factories for heterologous protein production. Trends Biotechnol. May 2002;20(5):200-6.

Ro & Douglas. Reconstitution of the entry point of plant phenylpropanoid metabolism in yeast (*Saccharomyces cerevisiae*): implications for control of metabolic flux into the phenylpropanoid pathway. J Biol Chem. Jan. 23, 2004;279.(4):2600-7. Epub Nov. 7, 2003.

Roupe et al., Pharmacometrics of Stilbenes: Seguing Towards the Clinic. Current Clinical Pharmacology. 2006. 1, 81-101.

Schanz et al., Stilbene synthase from Scots pine (*Pinus sylvestris*). FEBS. 1992. 313, No. 1, 71-74.

Watts et al., Biosynthesis of plant-specific stilbene polyketides in metabolically engineered *Escherichia coli*. BMC Biotechnol. Mar. 21, 2006;6:22.

Wiebe Stable production of recombinant proteins in filamentous fungi-problems and improvements. Mycologist. 2003. 17.

Callemien et al., "Hop as an interesting source of resveratrol for brewers: Optimization of the extraction and quantitative study by liquid chromatography/atmospheric pressure chemical ionization tandem mass spectrometry" J Agric Food Chem. 53(2):424-29 (2005).

Gonzalez-Candelas et al. "The use of transgenic yeasts expressing a gene encoding a glycosyl-hydrolase as a tool to increase resveratol content in wine." Int J Food Microbiol. 59(3):179-83 (2000).

Lee et al. "Antibacterial and antifungal activity of pinosylvin, a constituent of pine" Fitoterapia, 76(2):258-60 (2005).

Samappito et al. "Aromatic and pyrone polyketides synthesized by a stilbene synthase from Rheum tataricum" Phytochemistry, 62(3):313-23 (2003).

Sengottuvelan & Nalini, "Dietary supplementation of resveratrol suppresses colonic tumour incidence in 1,2-dimethylhydrazine-treated rats by modulating biotransforming enzymes and aberrant crypt foci development." British Journal of Nutrition 96(1):145-53 (2006).

Serazetdinova et al., "Expression of transgenic stilbene synthases in wheat causes the accumulation of unknown stilbene derivatives with antifungal activity." Journal of Plant Physiology 162(9):985-1002 (2005).

Trantas et al. "Metabolic engineering of the complete pathway leading to heterologous biosynthesis of various flavonoids and stilbenoids in *Saccharomyces cerevisiae*", Metabolic Engineering, 11(6):355-66 (2009).

Watts et al. "Exploring recombinant flavonoid biosynthesis in metabolically engineered *Escherichia coli*" Chembiochem, 5(4):500-507 (2004).

The International Search Report for International Application No. PCT/EP2011/058447, dated Dec. 22, 2011, pp. 1-7.

The Written Opinion for International Application No. PCT/EP2011/058447, issued Nov. 27, 2012, pp. 1-11.

The International Preliminary Report on Patentability for International Application No. PCT/EP2011/058447, issued Nov. 27, 2012, pp. 1-12.

Andrade et al., The ABC transporter AtrB from Aspergillus nidulans mediates resistance to all major classes of fungicides and some natural toxic compounds. Microbiology. 2000:146:1987-97.

Aury et al., Global trends of whole-genome duplications revealed by the ciliate Paramecium tetraurelia. Nature. Nov. 9, 2006; 444(7116):171-8.

Banerjee et al., Responses of pathogenic and nonpathogenic yeast species to steroids reveal the functioning and evolution of multidrug resistance transcriptional networks. Eukaryot Cell. 2008:7:68-77.

Boer et al., The genome-wide transcriptional responses of *Saccharomyces cerevisiae* grown on glucose in aerobic chemostat cultures limited for carbon, nitrogen, phosphorus, or sulfur. J Biol. Chem. 2003:278:3265-74.

(56) References Cited

OTHER PUBLICATIONS

Chloupkova M, et al., Expression of 25 human ABC transporters in the yeast *Pichia pastoris* and characterization of the purified ABCC3 ATPase activity. Biochemistry. 2007:46:7992-8003.
Connolly et al., Heterologous expression of a pleiotropic drug resistance transporter from Phytophthora sojae in yeast transporter mutants. Curr Genet. 2005:48:356-65.
Del Sorbo et al., Multidrug resistance in Aspergillus nidulans involves novel ATP-binding cassette transporters. Mol Gen Genet. 1997:254:417-26.
Del Sorbo et al., Cloning and functional characterization of BcatrA, a gene encoding an ABC transporter of the plant pathogenic fungus Botryotinia fuckeliana (Botrytis cinerea). Mycol Res. 2008:112:737-46.
Domergue et al., In vivo characterization of the first acyl-CoA Delta6-desaturase from a member of the plant kingdom, the microalga Ostreococcus tauri. Biochem J. Jul. 15, 2005; 389 (Pt 2):483-90.
Ehlting et al., Three 4-coumarate:coenzyme A ligases in Arabidopsis thaliana represent two evolutionarily divergent classes in angiosperms. Plant J. 1999:19:9-20.
Erdeniz et al., Cloning-Free PCR-Based Allele Replacement Methods. Genome Res. 1997 7: 1174-1183.
Etschmann et al., Biotechnological production of 2-phenylethanol. Appl Microbiol Biotechnol 2002:59:1-8.
Giaever et al., Functional profiling of the *Saccharomyces cerevisiae* genome. Nature. 2002:418:387-91.
Gietz & Schiestl. Applications of high efficiency lithium acetate transformation of intact yeast cells using single-stranded nucleic acids as carrier. Yeast. 1991:7:253-63.
Gilon et al., Degradation signals for ubiquitin system proteolysis in *Saccharomyces cerevisiae*. The EMBO Journal. 1998:17:2759-2766.
Guengerich et al., Expression of human cytochrome P450 enzymes in yeast and bacteria and relevance to studies on catalytic specificity. Toxicology. 1993:82:21-37.
Hain et al., Disease resistance results from foreign phytoalexin expression in a novel plant. Nature. 1993:361:153-6.
Hamberger & Hahlbrock. The 4-coumarate:CoA ligase gene family in Arabidopsis thaliana comprises one rare, sinapate-activating and three commonly occurring isoenzymes. Proc Natl Acad Sci USA. 2004:101:2209-14.
Johansson & Hahn-Hagerdal. Overproduction of pentose phosphate pathway enzymes using a new CRE-loxP expression vector for repeated genomic integration in *Saccharomyces cerevisiae*. Yeast 2002:19:225-231.
Jungwirth & Kuchler. Yeast ABC transporters—a tale of sex, stress, drugs and aging. FEBS Lett. 2006:580:1131-8.
Kunji et al., Lactococcus lactis as host for overproduction of functional membrane proteins. Biochim Biophys Acta. 2003:1610:97-108.
Mizutani et al., Isolation of a cDNA and a genomic clone encoding cinnamate 4-hydroxylase from Arabidopsis and its expression manner in planta. Plant Physiol. 1997:113:755-63.
Mizutani & Ohta. Two isoforms of NADPD:cytochrome P450 reductase in Arabidopsis thaliana. Gene structure, heterologous expression in insect cells, and differential regulation. Plant Physiol. 1998:116:357-67.
Moriya et al., In vivo robustness analysis of cell division cycle genes in *Saccharomyces cerevisiae*. PLoS Genet. Jul. 2006; 2(7):e111. Epub Jun. 5, 2006. Erratum in: PLoS Genet. Dec. 2006; 2(12):e218.
Muhitch et al., Transgenic expression of the TRI101 or PDR5 gene increases resistance of tobacco to the phytotoxic effects of the trichothecene 4,15-diacetoxyscirpenol. Plant Sci. 2000:157:201-20T.
Mumberg et al., Yeast vectors for the controlled expression of heterologous proteins in different genetic backgrounds. Gene. 1995:156:119-22.
Niimi et al., Functional analysis of fungal drug efflux transporters by heterologous expression in *S. cerevisiae*. Jpn. J. Infect Disease 2005:58:1-7.
Pan et al., Identification of molecular pathways affected by pterostilbene, a natural dimethylether analog of resveratrol. BMC Med. Genomics. 2008:20:1-7.
Passorn et al., Heterologous expression of Mucor rouxii delta(12)-desaturase gene in *Saccharomyces cerevisiae*. Biochem. Biophys. Res. Commun. 263 (1):47-51 (1999).
Rogers et al., The pleitropic drug ABC transporters from *Saccharomyces cerevisiae*. J Mol Microbiol Biotechnol. 2001:3:207-14.
Servos et al., Gene SNQ2 of *Saccharomyces cerevisiae*, which confers resistance to 4-nitroquinoline-N-oxide and other chemicals, encodes a 169 kDa protein homologous to ATP-dependent permeases. Mol Gen Genet. Jan. 1993; 236(2-3):214-8.
Servos et al., A system of shuttle vectors and yeast host strains designed for efficient manipulation of DNA in *Saccharomyces cerevisiae*. Genetics. 1989:122:19-27.
Song et al., Engineering tolerance and accumulation of lead and cadmium in transgenic plants. Nat. Biotechnol. 2003:21:914-9.
Tavares & Gunnarsson. GenBank GU593327.1 Mortierella alpina strain CBS 608.70 delta-6 elongase mRNA, complete cds. Mar. 29, 2010, one page.
Trott et al., Activation of heat shock and antioxidant responses by the natural product celastrol: transcriptional signatures of a thiol-targeted molecule. Mol Biol Cell. 2008:19:1104-12.
Verduyn et al., Effect of benzoic acid on metabolic fluxes in yeasts: a continuous-culture study on the regulation of respiration and alcoholic fermentation. Yeast. 1992:8:501-17.
Werck-Reichhart & Feyereisen. Cytochromes P450: a success story. Genome Biology 2000:1:3003.1-3003.9.
Whisstock et al., "Prediction of protein function from protein sequence and structure", Quarterly Reviews of Biophysics 36(3): 307-340 (2003).
Yoon et al., Cre/loxP-mediated in vivo excision of large segments from yeast genome and their amplification based on the 2 mm plasmid-derived system. Gene 1998:223:67-76.
Zwiers et al., ABC transporters and azole susceptibility in laboratory strains of the wheat pathogen Mycosphaerella graminicola. Antimicrob Agents Chemother. Dec. 2002; 46(12):3900-6.
Yabusaki et al., "Primary Structure of *Saccharomyces cerevisiae* NADPH-Cytochrome P450 Reductase Deduced from Nucleotide Sequence of Its Cloned Gene", J. Biochem., 103(6):1004-10 (1988).
The International Search Report issued in International Application No. PCT/EP2006/060154 (published as WO 2006/089898); dated Jun. 20, 2006, pp. 1-4.
The International Search Report issued in International Application No. PCT/EP2007/057484 (published as WO 2008/009728); dated Oct. 17, 2007, pp. 1-5.
The International Search Report issued in International Application No. PCT/EP2008/059768 (published as WO 2009/016108); dated Apr. 9, 2009, pp. 1-6.
The International Search Report issued in International Application No. PCT/EP2009/053974 (published as WO 2009/124879); dated Oct. 5, 2009, pp. 1-6.
The International Search Report issued in International Application No. PCT/EP2009/054219 (published as WO 2009/124967); dated Oct. 2, 2009, pp. 1-5.
The International Search Report issued in International Application No. PCT/EP2011/058447 (published as WO 2011/147818); dated Aug. 22, 2011, pp. 1-7.
La Grange et al. "Cloning of the Bacillus pumilus beta-xylosidase gene (xynB) and its expression in *Saccharomyces cerevisiae*. Appl. Microbiol." Biotechnol. 47(3):262-266 (1997).
Le Dall et al., "Multiple-copy integration in the yeast Yarrowia lipolytica". Curr Genet. 26(1):38-44 (1994).
Lieutier et al., "Changes in phenolic metabolites of Scots pine phloem induced by Ophiostoma brunneo-ciliatum, a bark beetle-associated fungus". Eur. J.For Pathol. 26(3):145-158 (1996).
Lin et al. "Sequence and analysis of chromosome 2 of the plant Arabidopsis thaliana." Nature 402(6763):761-768 (1999).

(56) References Cited

OTHER PUBLICATIONS

Lindberg et al., "Antibacterial effects of knotwood extractives on paper mill bacteria". J Ind Microbiol Biotechnol. 31(3):137-147 (2004).
Lobo, "Benefits and risks of estrogen replacement therapy." Am. J. Obstet. Gynecol. 173(3 Pt 2):982-89 (1995).
Madzak et al., "Heterologous protein expression and secretion in the non-conventional yeast Yarrowia lipolytica: a review". J Biotechnol. 109(1-2):63-81 (2004).
Martin et al., "Engineering a mevalonate pathway in *Escherichia coli* for production of terpenoids". Nature biotechnology 21(7):796-802 (2003).
Melchior & Kindl, "Coordinate and elicitor dependent expression of stilbene synthase and phenylalanine ammonialyase genes in Vitis cv. Optima." Arch. Biochem. Biophys 288(2):552-57 (1991).
Melchior & Kindl, "Grapevine stilbene synthase cDNA only slightly differing from chalcone synthase cDNA is expressed in *Escherichia coli* into a catalytically active enzyme", FEBS Lett. 268(1):17-20 (Jul. 1990).
Mellanen et al., "Wood-derived estrogens: studies in vitro with breast cancer cell lines and in vivo in trout". Toxicol. App. Pharm. 136(2):381-88 (1996).
Merkulov et al., "Cloning and characterization of the Yarrowia lipolytica squalene synthase (SQSI) gene and functional complementation of the *Saccharomyces cerevisiae* erg9 mutation," Yeast 16(3):197-206 (2000).
Morita et al., "Novel polyketides synthesized with a higher plant stilbene synthase". Eur. J. Biochem. 268, 3759-3766 (2001).
Muller et al., "Comparison of expression systems in the yeasts *Saccharomyces cerevisiae, Hansenula polymorpha, Klyveromyces lactis, Schizosaccharomyces pombe* and *Yarrowia lipolytica.* Cloning of two novel promoters from Yarrowia lipolytica". Yeast 14(14):1267-83 (1998).
Nicaud et al., Protein expression and secretion in the yeast Yarrowia lipolytica. FEMS Yeast Res. 2(3):371-9 (2002).
Nisimoto, "Localization Cytochrome c-binding Domain on NADPH-Cytochrome P-450 Reductase", The Journal of Biological Chemistry, vol. 261, No. 30, pp. 14232-14239, 1986.
Pacher et al., "Antifungal stilbenoids from Stemona collinsae." J Nat Prod. 65 (6):820-827 (2002).
Pignede et al., "Autocloning and amplification of LIP2 in Yarrowia lipolytica." Appl. Environ Microbiol. 2000:66:3283-9.
Porter & Kasper, "NADPH-Cytochrome P-450 Oxidoreductase: Flavin Mononucleotide and Flavin Adenine Dinucleotide Domains Evolved from Different Flavoproteins", Biochemistry, 25:1682-1687 (1986).
Preisig-Muller et al., "Characterization of a pine multigene family containing elicitor-responsive stilbene synthase genes". Plant Molecular Biology. 39(2):221-229. (1999).
Raiber et al., "Molecular and enzymatic characterization of two stilbene synthases from Eastern white pine (Pinus strobus). A single Arg/His difference determines the activity and the pH dependence of the enzymes". FEBS Lett. 361 (2-3):299-302 (1995).
Richter & Wild, "Phenolic compounds in needles of Norway spruce trees in relation to novel forest decline: I. Studies on trees from site of the Northern Black Forest.", Biochem. Biophys. Pflanz 188, 305-320 (1992).
Ritter et al., "Structural Basis for the Entrance into the Phenylpropanoid Metabolism Catalyzed by Phenylalanine Ammonia-Lyase", The Plant Cell, 16(12):3426-3436 (Dec. 2004).
Ro et al. "Functional Characterization and Subcellular Localization of Poplar (Populus trichocarpa x Populus deltoides) . Cinnamate 4-Hydroxylase." Plant Physiol. 126, 2001. pp. 317-329 (2001).
Rosemann et al., "Biochemical Plant Responses to Ozone. II. Induction of Stilbene Biosynthesis in Scots Pine (*Pinus sylvestris* L.) Seedlings. Jr." Plant Physiol. 97, 1280-1286 (1991).
Rosler et al. "Maize phenylalanine ammonia-lyase has tyrosine ammonia-lyase activity." Plant Physiol. 113, 1997. pp. 175-179 (1997).
Rother et al ., "An active site homology model of phenylalanine ammonia-lyase from Petroselinum crispum," Eur. J. Biochem. 269(12):3065-75 (2002).
Rupasinghe et al., "Common active site architecture and binding strategy of four phenylpropanoid P450s from Arabidopsis thaliana as revealsed by molecular modeling", Protein Engineering, 16(10):721-31 (2003).
Schoppner & Kindl, "Purification and properties of a stilbene synthase from induced cell suspension cultures of peanut". J. Biol. Chem. 259, 6806-6811 (1984).
Schneider et al., "The substrate specificity-determining amino acid cod of 4-coumarate:CoA ligase", PNAS, vol. 100, No. 14, pp. 8601-8606, Jul. 2003.
Schroder et al., "Molecular analysis of resveratrol synthase. cDNA clones and relationship with chalcone synthase". Eur J Biochem 172(1): 161-69 (1988).
Schuster & Retey, "Serine-202 is the putative precursor of the active site dehydroalanine of phenylalanine ammonia lyase", FEBS Letters 349(2):252-54 (1994).
Schwede et al., "Crystal Structure of Histidine Ammonia-Lyase Revealing a Novel Polypeptide Modification as the Catalytic Electrophile", Biochemistry, 38(17):5355-61 (1999).
Seshime et al., "Genomic evidences for the existence of a phenylpropanoid metabolic pathway in Aspergillus oryzue." Biochem. Biophys. Res Commun. 337(3):747-51 (2005).
Sikorski & Hieter, "A system of shuttle vectors and yeast host strains designed for efficient manipulation of DNA in *Saccharomyces cerevisiae*", Genetics, vol. 122(1):19-27 (May 1989).
Skinnider & Stoessl, "The effect of the phytoalexins, lubimin, (−)-maackiain, pinosylvin, and the related compounds dehydroloroglossol and hordatine M on human lymphoblastoid cell lines". Experientia 42(5):568-570 (1986).
Stark et al., "Novel Type of In Situ Extraction: Use of Solvent Containing Microcapsules for the Bioconversion of 2-Phenylethanol From .sub.L-Phenylalanine by *Saccharomyces cerevisiae*", Biotechnology and Bioengineering, vol. 83 (4), pp. 376-385, 2003.
Stojanovic et al., "Efficiency and mechanism of the anti-oxidant action of trans-resveratrol and its analogues in the radical liposome oxidation". Arch. Biochem. Biophys. 391(1):79-89 (2001).
STN Search CAS directory pinosylvin chemical properties data, pp. 1-2, 2012.
Stuible et al., "Identification of the Substrate Specificity-conferring Amino Acid Residues of 4-Coumarate:Coenzyme A Ligase Allows the Rational Design of Mutant Enzymes with New Catalytic Properties", The Journal of Biological Chemistry, vol. 276, No. 29, pp. 26893-26897, 2001.
Suga et al., "Endogenous pine wood nematicidal substances in pines, *Pinus massoniana, P. strobus and P. palustris.*" Phytochemistry 33(6):1395-1401 (1993).
Suh et al., "Identification of amino acid residues important in the cyclization reactions of chalcone and stilbene synthases", Biochem. J. 350(Pt.1):229-35 (2000).
Tilburn et al., "Transformation by integration in Aspergillus nidulans", Gene, vol. 26, pp. 205-221, 1983.
Tropf et al., "Reaction mechanisms of homodimeric plant polyketide synthase (stilbenes and chalcone synthase). A single active site for the condensing reaction is sufficient for synthesis of stilbenes, chalcones, and 6'-deoxychalcones". J. Biol. Chem. 270, 7922-7928 (1995).
Uhlmann & Ebel, "Molecular Cloning and Expression of 4-Coumarate:Coenzyme A Ligase, an Enzyme Involved in the Resistance Response of Soybean (*Glycine max* L.) against Pathogen Attack", Plant Physiol. 102(4):1147-56 (1993).
Urban et al., "Characterization of recombinant plant cinnarnate 4-hydroxylase produced in yeast. Kinetic and spectral properties of the major plant P450 of the phenylpropanoid pathway". Eur J Biochem. 222(3):843-50 (1994).
Urban et al. "Cloning, Yeast Expression, and Characterization of the Coupling of Two Distantly Related Arabidopsis thaliana NADPH-Cytochrome 450 Reductases with P450 CYP73A5." J. Biol. Chem. 272: 19176-186 (1997).

(56) References Cited

OTHER PUBLICATIONS

Wang et al., "Three-dimensional structure of NADPH-cytochrome P450 reductase: Prototype for FMN- and FAD-containing enzymes", Proc. Natl. Acad. Sci. USA, vol. 94, pp. 8411-8416, Aug. 1997.
Watts et al., "Discovery of a substrate selectivity switch in tyrosine ammonia-lyase, a member of the aromatic amino acid lyase family". Chem Biol. 13:1317-26 (2006).
Wiese et al., "Structural organization and differential expression of three stilbene synthase genes located on a 13 kb grapevine DNA fragment." Plant Mol Biol 26(2):667-77 (1994).
Abe et al., "Enzymatic formation of long-chain polyketide pyrones by plant type III polyketide synthases", Phytochemistry, vol. 6, pp. 2447-2453 (2004).
Aggarwal et al., "Role of resveratrol in prevention and therapy of cancer: preclinical and clinical studies". Anticancer Res. 24(5A):2783-840 (2004).
Allina et al., "4-coumarate: Coenzyme A ligase in hybrid poplar. Properties of enzymes, cDNA cloning, and analysis of recombinant clones". Plant Physiol. 116, 743-754 (1998).
Aoyama et al. "NADPH-cytochrome P-450 reductase of yeast microsomes." Arch. Biochem. Biophys. 185, 1978. pp. 362-369 (1978).
Austin et al., "An Aldol Switch Discovered in Stilbene Synthases Mediated Cyclization Specificity of Type III Polyketide Synthases", Chemistry & Biology, vol. 11, pp. 1179-1194, Sep. 2004.
Baedeker et al., "Autocatalytic Peptide Cyclization during Chain Folding of Histidine Ammonia-Lyase", Structure, vol. 10, pp. 61-67, Jan. 2002.
Baedeker et al., "Structures of two histidine ammonia-lyase modifications and implications for the catalytic mechanism", Eur. J. Biochem., vol. 269, pp. 1790-1797, 2002.
Berner et al., "Genes and enzymes involved in caffeic acid biosynthesis in the actinomycete Saccharothrix espanaensis", J Bacteriol, 2006:188:2666-73.
Blanquet et al."Recombinant Saccharomyces cerevisiae Expressing P450 in Artificial Digestive Systems: a Model for Biodetoxication in the Human Digestive Environment." Applied and Environmental Microbiology, 69(5):2884-2892 (2003).
Caruso et al., "Structural basis for antioxidant activity of trans-resveratrol: ab initio calculations and crystal and molecular structure", J Agric Food Chem., vol. 52, pp. 7279-7285, 2004.
Celotti et al."Resveratrol content of some wines obtained from dried Valpolicella grapes: Recioto and Amarone." Journal of Chromatography A. 730(1-2):47-52 (1996).
Chen et al., "One-step transformation of the dimorphic yeast Yarrowia lipolytica." Appl Microbiol Biotechnol. 48(2):232-5 (1997).
Cordero-Otero et al., "Efficient selection of hygromycin-B-resistant Yarrowia lipolytica transformants". Appl Microbiol Biotechnol. 46(2):143-48 (1996).
Costa et al., "Characterization in vitro and in vivo of the putative multigene 4-coumarate:CoA ligase network in Arabidopsis: syringyl lignin and sinapate/sinapyl alcohol derivative formation", Phytochemistry, 66(17):2072-91 (2005).
Couzin, "Scientific community. Aging Research's Family Feud." Science 303(5662):1276-79 (2004).
Fickers et al., "New disruption cassettes for rapid gene disruption and marker rescue in the yeast Yarrowia lipolytica." J Microbiol Methods. 55(3):727-37 (2003).
Filpula et al. "Nucleotide sequence of gene for phenylalanine ammonia-lyase from Rhodotorula rubra." Nucleic Acids Res. 16(23):11381 (1988).
Gehlert et al., "Stilbene synthase from seedlings of Pinus sylvestris—purification and induction in response to fungal infection". Mol. Plant-Microbe Interaction 3(6):444-49 (1990).
Gehm et al. "Resveratrol, a polyphenolic compound found in grapes and wine, is an agonist for the estrogen receptor." Proc. Natl. Acad. Sci. USA 94, 1997. pp. 14138-14143 (1997).
Gems et al., "An autonomously replicating plasmid transforms Aspergillus nidulans at high frequency". Gene 98(1):61-67 (1991).
Gonzalez-Candelas et al. "The use of transgenic yeasts expressing a gene encoding a glycosyl-hydrolase as a tool to increase resveratrol content in wine." Int J Food Microbiol. 59(3):179-83 (2000).
Guerra et al., "A novel system of genetic transformation allows multiple integrations of a desired gene in *Saccharomyces cerevisiae* chromosomes", J Microbiol Methods, vol. 67, pp. 437-445, 2006.
Hall, "Longevity research. In Vino Vitalis? Compounds Activate Life-Extending Genes." Science 301(5637):1165 (2003).
Hart, "Role of phytostilbenes in decay and disease resistance". Annu. Rev. Phytopathology 19, 437-458 (1981).
Hart & Shrimpton, "Role of stilbenes in resistance of wood to decay". Phytopathology 69, 1138-1143 (1979).
Hasemann et al., "Structure and function of cytochromes P450:a comparative analysis of three crystal structures", Structure, 3(1):41-62 (Jan. 1995). PMID: 7743131.
Hemingway et al., "Polyphenols in Ceratocystis minor infected Pinus taeda: Fungal Metabolites, phloem and xylem phenols". J. Agric. Food Chem., 25, 717-722 (1977).
Huang, "Diet for cancer prevention." Food Sci.(Shipin Kexue; Taipei) 24(6):713-727 (1997).
Hubbard et al., "NADPH-Cytochrome P450 Oxidoreductase: Structural Basis for Hydride and Electron Transfer." J. Biol. Chem. 276:29163-70 (2001).
Jang et al. "Cancer Chemopreventive Activity of Resveratrol, a Natural Product Derived from Grapes." Science 275 (5297):218-20 (1997).
Jeandet et al. "Effect of Enological Practices on the Resveratrol Isomer Content of Wine." J. Agric. Food Chem. 43, 1995. pp. 316-319 (1995).
Jeandet et al. "Occurence of a resveratrol.cndot.—D-glucoside in wine: Preliminary studies." Vitis 33, pp. 183-184 (1994).
Jeandet et al., "Phytoalexins from the Vitaeae: Biosynthesis, Phytoalexin Gene Expression in Transgenic Plants, Antifungal Activity, and Metabolism", J. Agric. Food Chem., 50(10):2731-41 (2002).
Juretzek et al., "Vectors for gene expression and amplification in the yeast Yarrowia lipolytica", Yeast. 18(2):97-113 (2001).
Juvvadi et al., "Genomics reveals traces of fungal phenylpropanoid-flavonoid metabolic pathway in the filamentous fungus Aspergillus oryzae." J Microbiol. 43(6):475-486 (2005).
Kindl, Biosynthesis of stilbenes. In Higuchi T, ed, Biosynthesis and Biodegradation of Wood Components. Academic Press, London, pp. 349-377. (1985).
Koopmann et al. "Regulation and Functional Expression of Cinnamate 4-Hydroxylase from Parsley." Plant Physiol. 119(1):49-56 (1999).
Kopp, "Resveratrol, a phytooestrogen found in red wine. A possible explanation for the conundrum of the "French Paradox"?" Eur. J. Endocrinol. 138, 1998. pp. 619-620.
Kodan et al., "A stilbene synthase from Japanese red pine (*Pinus densiflora*): Implications for phytoalexin accumulationand down-regulation of flavonoid biosynthesis". Proc. Natl. Acad. Sci. 99, 3335-3339 (2002).
Kyndt et al. "Characterization of a bacterial tyrosine ammonia lyase, a biosynthetic enzyme for the photoactive yellow protein." FEBS Lett. 512(1-3):240-44 (2002).
Zahir et al., "Isolation and characterization of novel organic solvent-tolerant bacteria" Extremophiles 10(2):129-38 (2006; Epub Oct. 20, 2005).
Bateman et al., "Pfam 3.1: 1313 multiple alignments and profile HMMs match the majority of proteins." Nucl. Acids Res., 27(1):260-62 (Jan. 1999).
Bu et al., "High-throughput Caco-2 cell permeability screening by cassette dosing and sample pooling approaches using direct injection/on-line guard cartridge extraction/tandem mass spectrometry," Rapid Communications in Mass Spectrometry 14(6):523-28 (Mar. 2000).
Chenna et al., "Multiple sequence alignment with the Clustal series of programs." Nucl. Acids Res., 31(13):3497-500 (Jul. 2003).

(56) References Cited

OTHER PUBLICATIONS

Decendit et al., "Galloylated catechins and stilbene diglucosides in Vitis vinifera cell suspension cultures" Phytochemistry 60(8):795-98 (Aug. 2002).
Escribano-Bailon et al., "Coupling Reactions between Flavylium Ions and Catechin" Phytochemistry 41(6):1583-92 (1996).
Gao & Ming, "Bioavailability challenges associated with development of anti-cancer phenolics." Mini Rev Med Chem 10(6):550-67 (Jun. 2010).
The International Search Report issued in International Application No. PCT/EP2014/067520 (published as WO 2015/028324); dated Mar. 2, 2015, pp. 1-9.
Hano et al., "Sequential glucosylation determined by NMR in the biosynthesis of mulberroside D, a cis-oxyresveratrol diglucoside, in *Morus alba* L. cell cultures," Cell. Mol. Life Sci. 53(3):237-41 (Mar. 1997).
Hansen et al., "Substrate specificities of family 1 UGTs gained by domain swapping." Phytochemistry 70(4):473-82 (Mar. 2009; Epub Mar. 2, 2009).
Horinouchi et al., "Combinatorial biosynthesis of plant medicinal polyketides by microorganisms" Current Opinion in Chemical Biology 13(2):197-2014 (Apr. 2009).
Kapetanovic et al., "Pharmacokinetics, oral bioavailability, and metabolic profile of resveratrol and its dimethylether analog, pterostilbene, in rats." Cancer Chemother Pharmacol 68(3):593-601 (Sep. 2011; Epub Nov. 30, 2010).
Kirino et al., "Analysis and functionality of major polyphenolic components of Polygonum cuspidatum (itadori)." J Nutr Sci Vitaminol 58(4):278-86 (2012).
Koopman et al., "De novo production of the flavonoid naringenin in engineered *Saccharomyces cerevisiae*." Microb Cell Fact. 11:155 pp. 1-15 (Dec. 2012).
Larronde et al., "New stilbenoid glucosides isolated from Vitis vinifera cell suspension cultures (cv. Cabernet Sauvignon)." Planta Med. 71(9):888-90 (Sep. 2005).
Li et al., "De novo production of resveratrol from glucose or ethanol by engineered *Saccharomyces cerevisiae*." 32:1-11 (Nov. 2015; Epub Sep. 4, 2015).
Mora-Pale et al., "Metabolic engineering and in vitro biosynthesis of phytochemicals and non-natural analogues". Plant Science 210:10-24 (May 2013).
Orsini et al., "Isolation, synthesis, and antiplatelet aggregation activity of resveratrol 3-O-beta-D-glucopyranoside and related compounds." J. Nat. Prod. 60(11):1082-87 (Nov. 1997).
Osmani et al., "Catalytic key amino acids and UDO-sugar donor specificity of a plant glucuronosyltransferase, UGT94B1: molecular modeling substantiated by site-specific mutagenesis and biochemical analyses." Plant Physiol. 148(3):1295-1308 (Nov. 2008; Epub Oct. 1, 2008).
Ozaki et al., "Regioselective glucosidation of-resveratrol inexpressing glucosyltransferase from Phytolacca americana" Biotechnology Letters 34(3):475-81 (Nov. 2011).
Park et al., "Bioconversion of Piceid to Piceid Glucoside Using Amylosucrase from Alteromonas macleodii Deep Ecotype," J. Microbiol. Biotechnol. 22(12):1698-1704 (Dec. 2012).
Park et al., "Enzymatic synthesis of piceid glucosides using maltosyltransferase from Caldicellulosiruptor bescii DSM 5725" J. Agric. Food Chem. 60(33):8183-89 (Aug. 2012; Epub Aug. 8, 2012).
Regev-Shoshani et al., "Glycosylation of resveratrol protects it from enzymic oxidation." Biochem J. 374(Pt 1):157-63 (Aug. 2003).
Sawada et al., "UDP-glucuronic acid:anthocyanin glucuronosyltransferase from red daisy (Bellis perennis) flowers. Enzymology and phylogenetics of a novel glucuronosyltransferase involved in flower pigment biosynthesis." J Biol Chem. 280(2):899-906 (Jan. 2005; Epub Oct. 7, 2004).
Schmidheini et al., "A single point mutation results in a constitutively activated and feedback-resistant chorismate mutase of *Saccharomyces cerevisiae*." 171(3):1245-53 (Mar. 1989).
Schmidlin et al., "A stress-inducible resveratrol O-methyltransferase involved in the biosynthesis of pterostilbene in grapevine." Plant Physiol 148(3):1630-39 (Nov. 2008; Epub Sep. 17, 2008).
Shao et al., "Phenolic and Triterpenoid glycosides from Aster batangensis" Phytochemistry 41(6):1593-98 (1996).
Shi et al., "Improving production of malonyl coenzyme A-derived metabolites by abolishing Snf1-dependent regulation of Acc1." 6(3):e01130-14 (May 2014).
Sonnhammer et al., "Pfam: multiple sequence alignments and HMM-profiles of protein domains." Nucl. Acids Res. 26(1):320-22 (Jan. 1998).
Sonnhammer et al., "Pfam: a comprehensive database of protein domain families based on seed alignments" Proteins, 28(3):405-20 (Jul. 1997).
5UN et al., "In vitro testing of drug absorption for drug 'developability' assessment: forming an interface between in vitro preclinical data and clinical outcome." Curr. Opin. Drug Discov. Devel. 7(1):75-85 (Jan. 2004).
Waffo-Teguo et aL, "Isolation, identification, and antioxidant activity of three stilbene glucosides newly extracted from vitis vinifera cell cultures" J. Nat. Prod. 61(5):655-57 (May 1998).
Wang et al., "Pterostilbene production by microorganisms expressing resveratrol O-methyltransferase." Ann Microbiol. pp. 1-10 (published online: Jun. 26, 2014).
Wang et al., "Structure, mechanism and engineering of plant natural product glycosyltransferases" FEBS Letters 583(20):3303-09 (Oct. 2009).
Weis et al., "Regioselective glucosylation of aromatic compounds: screening of a recombinant glycosyltransferase library to identify biocatalysts." Angew. Chem. Int. Ed. 45(21): 3534-38 (May 2006).
Yeo et al., "Quantification of pinosylvin in rat plasma by liquid chromatography-tandem mass spectrometry: applicatio to a preclinical pharmacokinetic study" J Chromatogr B Analyt Technol Biomed Life Sci. 931:68-74 (Jul. 2013; Epub May 28, 2013).
Yeo et al., "Pharmacokinetics of pterostilbene in Sprague-Dawley rats: the impacts of aqueous solubility, fasting, dose escalation, and dosing route on bioavailability." Mol Nutr Food Res 57(6):1015-25 (Jun. 2013; Epub Feb. 13, 2013). PMID: 23417986.
Katsuyama et al., "Precursor-directed biosynthesis of stilbene methyl ethers in *Escherichia coli*" Biotechnology Journal 2(10):1286-93 (Oct. 2007).
Zhou et al., "Inhibition of xanthine and monoamine oxidases by stilbenoids from Veratrum taliense." Planta Med. 67(2):158-61 (Mar. 2001).
Zhou et al., "Assessing the regioselectivity of OleD-catalyzed glycosylation with a diverse set of acceptors." J. Nat. Prod. 76(2):279-86 (Feb. 2013; Epub Jan. 29, 2013).

* cited by examiner

TGTTGGAATAAAAATCAACTATCATCTATTAACTAGTATTTACATTACTAGTATAT

TATCATATACGGTGTTAGAAGATGACATAAATGATGAGAAACAGTCATCTAAATTA

GTGGAAGCTGAAATGCAAGGATTGATAATGTAATAaGATCtATGAATAACATATAA

AACGAAAAGAGGAATAATCATAATATTATATGTAGAAATATAGATTCCCTTTTGTG

GATTCCTATATCCTCGAGGAGAACTTCTAGTATATTCTGTATACCTAATATTATAG

CCTTTATCAACAATGGAATCCCAACAATTATCTCAAAATTCACCTATTTCTCA

Figure 14

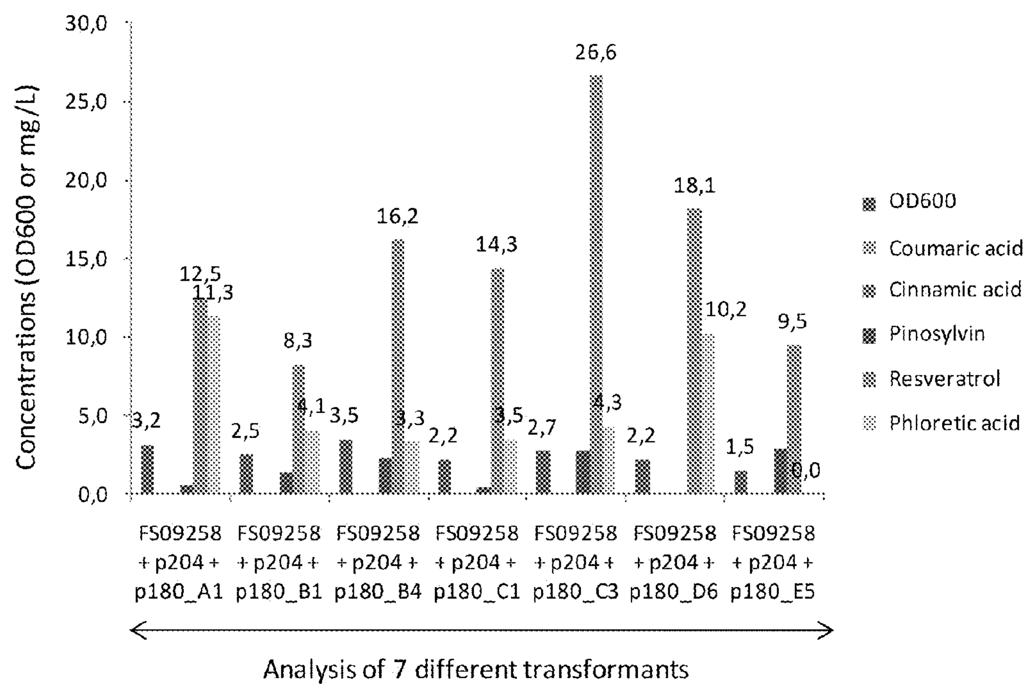

Figure 15

Resveratrol pathway titer (mg/l)
Biomass (g/l), DO (%)
Fermentation time (hrs.)
0.095
0.025
Resveratrol
Coumaric acid
Phloretic acid
Dihydroresveratrol
Biomass
DO
0
1000
2000
3000
4000
5000
6000
0
10
20
30
40
50
60
70
80
90
100
0
20
40
60
80
100
120
140

SEQUENCE LISTING

```
<160> NUMBER OF SEQ ID NOS: 192

<210> SEQ ID NO 1
<211> LENGTH: 16
<212> TYPE: PRT
<213> ORGANISM: Artificial Sequence
<220> FEATURE:
<223> OTHER INFORMATION: Ubiquitination tag

<400> SEQUENCE: 1

Ala Cys Lys Asn Trp Phe Ser Ser Leu Ser His Phe Val Ile His Leu
1               5                   10                  15


<210> SEQ ID NO 2
<211> LENGTH: 35
<212> TYPE: PRT
<213> ORGANISM: Artificial Sequence
<220> FEATURE:
<223> OTHER INFORMATION: Ubiquitination tag

<400> SEQUENCE: 2
```

```
Ser Leu Ile Ser Leu Pro Leu Pro Thr Arg Val Lys Phe Ser Ser Leu
1               5                   10                  15

Leu Leu Ile Arg Ile Met Lys Ile Ile Thr Met Thr Phe Pro Lys Lys
            20                  25                  30

Leu Arg Ser
        35


<210> SEQ ID NO 3
<211> LENGTH: 16
<212> TYPE: PRT
<213> ORGANISM: Artificial Sequence
<220> FEATURE:
<223> OTHER INFORMATION: Ubiquitination tag

<400> SEQUENCE: 3

Phe Tyr Tyr Pro Ile Trp Phe Ala Arg Val Leu Leu Val His Tyr Gln
1               5                   10                  15


<210> SEQ ID NO 4
<211> LENGTH: 46
<212> TYPE: PRT
<213> ORGANISM: Artificial Sequence
<220> FEATURE:
<223> OTHER INFORMATION: Ubiquitination tag

<400> SEQUENCE: 4

Ser Asn Pro Phe Ser Ser Leu Phe Gly Ala Ser Leu Leu Ile Asp Ser
1               5                   10                  15

Val Ser Leu Lys Ser Asn Trp Asp Thr Ser Ser Ser Ser Cys Leu Ile
            20                  25                  30

Ser Phe Phe Ser Ser Val Met Phe Ser Ser Thr Thr Arg Ser
        35                  40                  45


<210> SEQ ID NO 5
<211> LENGTH: 39
<212> TYPE: PRT
<213> ORGANISM: Artificial Sequence
<220> FEATURE:
<223> OTHER INFORMATION: Ubiquitination tag

<400> SEQUENCE: 5

Cys Arg Gln Arg Phe Ser Cys His Leu Thr Ala Ser Tyr Pro Gln Ser
1               5                   10                  15

Thr Val Thr Pro Phe Leu Ala Phe Leu Arg Arg Asp Phe Phe Phe Leu
            20                  25                  30

Arg His Asn Ser Ser Ala Asp
        35


<210> SEQ ID NO 6
<211> LENGTH: 46
<212> TYPE: PRT
<213> ORGANISM: Artificial Sequence
<220> FEATURE:
<223> OTHER INFORMATION: Ubiquitination tag

<400> SEQUENCE: 6

Gly Ala Pro His Val Val Leu Phe Asp Phe Glu Leu Arg Ile Thr Asn
1               5                   10                  15

Pro Leu Ser His Ile Gln Ser Val Ser Leu Gln Ile Thr Leu Ile Phe
            20                  25                  30

Cys Ser Leu Pro Ser Leu Ile Leu Ser Lys Phe Leu Gln Val
        35                  40                  45
```

<210> SEQ ID NO 7
<211> LENGTH: 39
<212> TYPE: PRT
<213> ORGANISM: Artificial Sequence
<220> FEATURE:
<223> OTHER INFORMATION: Ubiquitination tag

<400> SEQUENCE: 7

```
Asn Thr Pro Leu Phe Ser Lys Ser Phe Ser Thr Thr Cys Gly Val Ala
1               5                   10                  15

Lys Lys Thr Leu Leu Leu Ala Gln Ile Ser Ser Leu Phe Phe Leu Leu
            20                  25                  30

Leu Ser Ser Asn Ile Ala Val
        35
```

<210> SEQ ID NO 8
<211> LENGTH: 45
<212> TYPE: PRT
<213> ORGANISM: Artificial Sequence
<220> FEATURE:
<223> OTHER INFORMATION: Ubiquitination tag

<400> SEQUENCE: 8

```
Pro Thr Val Lys Asn Ser Pro Lys Ile Phe Cys Leu Ser Ser Ser Pro
1               5                   10                  15

Tyr Leu Ala Phe Asn Leu Glu Tyr Leu Ser Leu Arg Ile Phe Ser Thr
            20                  25                  30

Leu Ser Lys Cys Ser Asn Thr Leu Leu Thr Ser Leu Ser
        35                  40                  45
```

<210> SEQ ID NO 9
<211> LENGTH: 30
<212> TYPE: PRT
<213> ORGANISM: Artificial Sequence
<220> FEATURE:
<223> OTHER INFORMATION: Ubiquitination tag

<400> SEQUENCE: 9

```
Ser Asn Gln Leu Lys Arg Leu Trp Leu Trp Leu Leu Glu Val Arg Ser
1               5                   10                  15

Phe Asp Arg Thr Leu Arg Arg Pro Trp Ile His Leu Pro Ser
            20                  25                  30
```

<210> SEQ ID NO 10
<211> LENGTH: 50
<212> TYPE: PRT
<213> ORGANISM: artificial
<220> FEATURE:
<223> OTHER INFORMATION: Ubiquitination tag

<400> SEQUENCE: 10

```
Ser Ile Ser Phe Val Ile Arg Ser His Ala Ser Ile Arg Met Gly Ala
1               5                   10                  15

Ser Asn Asp Phe Phe His Lys Leu Tyr Phe Thr Lys Cys Leu Thr Ser
            20                  25                  30

Val Ile Leu Ser Lys Phe Leu Ile His Leu Leu Leu Arg Ser Thr Pro
        35                  40                  45

Arg Val
    50
```

<210> SEQ ID NO 11

<211> LENGTH: 48
<212> TYPE: DNA
<213> ORGANISM: Artificial Sequence
<220> FEATURE:
<223> OTHER INFORMATION: Ubiquitination tag

<400> SEQUENCE: 11
gcttgtaaaa attggtttc ttctttgtct cattttgtta ttcatttg 48

<210> SEQ ID NO 12
<211> LENGTH: 48
<212> TYPE: DNA
<213> ORGANISM: Artificial Sequence
<220> FEATURE:
<223> OTHER INFORMATION: Ubiquitination tag

<400> SEQUENCE: 12
ttttattatc caatttggtt tgctagagtt ttgttggttc attatcaa 48

<210> SEQ ID NO 13
<211> LENGTH: 5
<212> TYPE: PRT
<213> ORGANISM: Artificial Sequence
<220> FEATURE:
<223> OTHER INFORMATION: Ubiquitination tag

<400> SEQUENCE: 13

Phe Ser Ser Leu Ala
1 5

<210> SEQ ID NO 14
<211> LENGTH: 2154
<212> TYPE: DNA
<213> ORGANISM: Artificial Sequence
<220> FEATURE:
<223> OTHER INFORMATION: Arabidopsis thaliana codon optimised

<400> SEQUENCE: 14
atggaccaaa ttgaagcaat gctatgcggt ggtggtgaaa agaccaaggt ggccgtaacg 60
acaaaaactc ttgcagatcc tttgaattgg ggtctggcag ctgaccagat gaaaggtagc 120
catctggatg aagttaagaa gatggttgag gaatacagaa gaccagtcgt aaatctaggc 180
ggcgagacat tgacgatagg acaggtagct gctatttcga ccgttggcgg ttcagtgaag 240
gtagaacttg cagaaacaag tagagccgga gttaaggctt catcagattg ggtcatggaa 300
agtatgaaca agggcacaga ttcctatggc gttaccacag gctttggtgc tacctctcat 360
agaagaacta aaaatggcac tgctttgcaa acagaactga tcagattcct taacgccggt 420
attttcggta atacaaagga aacttgccat acattacccc aatcggcaac aagagctgct 480
atgcttgtta gggtgaacac tttgttgcaa ggttactctg gaataaggtt tgaaattctt 540
gaggccatca cttcactatt gaaccacaac atttctcctt cgttgccctt aagaggaaca 600
ataactgcca gcggtgattt ggttcccctt tcatatatcg caggcttatt aacgggaaga 660
cctaattcaa aggccactgg tccagacgga gaatccttaa ccgctaagga agcatttgag 720
aaagctggta tttcaactgg tttctttgat ttgcaaccca aggaaggttt agccctggtg 780
aatggcaccg ctgtcggcag cggtatggca tccatggtgt tgtttgaagc taacgtacaa 840
gcagttttgg ccgaagtttt gtccgcaatt tttgccgaag tcatgagtgg aaaacctgag 900
tttactgatc acttgaccca caggttaaaa catcacccag gacaaattga agcagcagct 960
atcatggagc acattttgga cggctctagc tacatgaagt tagcccagaa ggttcatgaa 1020

```
atggaccctt tgcaaaaacc caaacaagat agatatgctt taaggacatc cccacaatgg   1080

cttggccctc aaattgaagt aattagacaa gctacaaagt ctatagaaag agagatcaac   1140

tctgttaacg ataatccact tattgatgtg tcgaggaata aggcaataca tggaggcaat   1200

ttccagggta cacccatagg agtcagtatg gataatacca ggcttgccat agccgcaatt   1260

ggcaaattaa tgtttgccca attttctgaa ttggtcaatg acttctacaa taacggtttg   1320

ccttcgaatc tgaccgcatc ttctaaccct agtcttgatt atggtttcaa aggtgctgag   1380

atagcaatgg caagctattg ttcagagctg caatatctag ccaacccagt aacctctcat   1440

gtacaatcag ccgaacaaca caatcaggat gttaattctt tgggcctgat ttcatcaaga   1500

aaaacaagcg aggccgttga tatccttaaa ttaatgtcca caacattttt agtgggtata   1560

tgccaggccg tagatttgag acacttggaa gagaatttga gacagacagt gaaaaatacc   1620

gtatcacagg ttgcaaaaaa ggttctaact acaggtatca atggtgaatt gcacccatca   1680

agattctgtg aaaaagattt attaaaagtt gtagatagag aacaagtatt tacttacgtt   1740

gacgatccat gtagcgctac ttatccattg atgcagagat tgagacaagt tattgtagat   1800

cacgctttat ccaatggtga aactgagaaa aatgccgtta cttcaatatt ccaaaagata   1860

ggtgcctttg aagaagaact gaaggcagtt ttaccaaagg aagtcgaagc tgctagagcc   1920

gcatacggaa atggtactgc ccctatacca aatagaatca aagagtgtag gtcgtaccct   1980

ttgtacagat tcgttagaga agagttggga accaaattac taactggtga aaaagtcgtt   2040

agcccaggtg aagaatttga caaggtattc acagctatgt gcgagggaaa gttgatagat   2100

ccacttatgg attgcttgaa agagtggaat ggtgcaccta ttccaatctg ctaa         2154
```

```
<210> SEQ ID NO 15
<211> LENGTH: 1518
<212> TYPE: DNA
<213> ORGANISM: Artificial Sequence
<220> FEATURE:
<223> OTHER INFORMATION: Arabidopsis thaliana codon optimised

<400> SEQUENCE: 15

atggatttgt tattgctgga aaagtcactt attgctgtat ttgtggcagt tattctagcc     60

acggttattt ctaaattaag aggtaagaaa ctaaaactac ctcctggtcc catccccata    120

ccaatttttg gtaattggtt gcaagtgggc gatgatttga atcacagaaa tttggtagac    180

tatgctaaga agttcggtga ccttttcttg cttagaatgg gtcaaaggaa tttggtagtg    240

gttagctcac ctgatttgac taaggaggtc ttattaacgc aaggcgttga gtttggctcc    300

agaactagaa atgttgtgtt tgatattttc actggtaaag gtcaagatat ggtttttaca    360

gtttacggtg agcactggag aaaaatgaga agaatcatga ccgtaccatt ctttactaac    420

aaggttgttc aacaaaatag agaaggttgg gagtttgagg cagcttccgt agtggaagac    480

gtaaagaaaa atccagattc ggccacaaag ggtatagtac taagaaaaag actacaattg    540

atgatgtaca acaatatgtt cagaattatg tttgacagaa gatttgaaag tgaagatgac    600

cctttgttcc tgagacttaa ggctttgaat ggtgaaagat cgagattggc tcaaagtttc    660

gaatataatt acggtgactt tattccaatc ttaagaccat tttgagaggg ctatttgaaa    720

atttgccaag acgtcaagga taggaggatc gctcttttca agaagtactt tgtggacgag    780

agaaagcaaa tagcttcttc caagcccaca ggttcggaag gtttaaaatg tgcaattgat    840

catattttag aagctgaaca aaaaggtgaa attaacgaag ataatgtttt gtacattgta    900

gaaaatatca atgtggctgc aatagaaaca accttatggt caatagaatg ggtattgct     960
```

```
gaattggtga atcacccaga aatacaatct aaactgagaa acgagctaga taccgtttta   1020

ggtccaggtg tccaagttac agaacctgat ttgcataagt taccctactt gcaagctgtg   1080

gttaaagaaa ccttgagatt gagaatggct attcctcttc tagttcctca tatgaaccta   1140

catgatgcta aactggccgg ttatgatatt ccagcagaaa gtaagatttt agtaaatgca   1200

tggtggttgg ccaacaatcc aaacagttgg aaaaagcctg aagaattcag acctgaaaga   1260

ttcttcgaag aggaatctca tgttgaagcc aacggaaatg acttcagata tgtacctttt   1320

ggcgttggca gaagatcgtg tccaggaata atactagcct taccaatatt gggtatcaca   1380

attggtagga tggttcaaaa ttttgagttg ctaccaccac ccggacaatc gaaagtcgat   1440

acttcagaga aaggaggaca attctcattg catattttga atcattccat tatagtcatg   1500

aaacccagaa attgttaa                                                 1518
```

<210> SEQ ID NO 16
<211> LENGTH: 2136
<212> TYPE: DNA
<213> ORGANISM: Artificial Sequence
<220> FEATURE:
<223> OTHER INFORMATION: Arabidopsis thaliana codon optimised

<400> SEQUENCE: 16

```
atgtccagta gctcttcctc ctcaacctcg atgatcgact taatggctgc tattataaaa     60

ggagaaccag ttatagttag tgaccctgct aacgcaagcg cttacgaatc cgttgcagcc    120

gagttgtcaa gtatgcttat agaaaataga cagtttgcta tgattgtaac gaccagcatc    180

gccgttttaa ttggttgcat cgtgatgttg gtgtggagga ggagcggttc gggcaattca    240

aagagggttg aaccactaaa gccattagtt atcaaaccta gagaagagga aattgacgat    300

ggaaggaaga aagtcactat attcttcggc acccaaacag gtacagctga aggttttgct    360

aaggctctag gagaagaagc aaaagctaga tatgaaaaga cgagattcaa aattgtcgat    420

ctggatgact atgccgccga tgatgacgaa tacgaagaaa aattgaagaa agaagatgtc    480

gcatttttct tccttgccac ctacggcgac ggtgaaccaa cagataatgc cgcaaggttt    540

tacaagtggt ttactgaagg taatgacaga ggagaatggc tgaagaattt gaaatatggt    600

gtgttcggcc ttggtaacag acagtacgag cattttaata aggtcgctaa ggttgtagat    660

gatatacttg ttgaacaagg tgctcaaagg ttagtgcagg tgggcttggg tgacgatgat    720

caatgtattg aagatgactt tactgcttgg agagaagcct tgtggcctga attagatact    780

atccttagag aagaaggtga cactgctgtt gctacccccct acactgcagc agtcctagaa    840

tatagagtct caatccatga ttcagaagac gccaaattca atgatattaa catggccaac    900

ggtaacggtt acaccgtttt tgacgcacaa catccataca aagctaatgt tgctgttaaa    960

agggaacttc acaccccaga aagtgacagg tcatgtatac atttggaatt tgatatcgct   1020

ggtagtggtt tgacttacga aacaggtgac catgtcggag tactttgcga taatttgtca   1080

gaaactgttg atgaagcttt gaggttattg gatatgtcac cagatactta cttctcattg   1140

catgcagaaa aagaagacgg aactccaata tcaagctcgc ttccccctcc attccctccc   1200

tgtaacttaa gaacagccct aactagatat gcttgtttac tgtcttctcc aaagaaaagt   1260

gctttggttg cattggcagc ccacgcatcc gatcctaccg aagctgagag attaaagcat   1320

ttggcttcac cagccggtaa agatgaatac agtaagtggg tagtggagag ccaaagatcg   1380

cttttagaag tgatggctga gtttccaagt gctaaacctc ctctgggtgt atttttcgct   1440
```

```
ggtgtggccc caagattgca gcctagattt tattccatat cctcatctcc aaaaattgcc   1500

gaaaccagaa ttcacgtgac atgtgctctg gtctacgaaa agatgccaac aggtaggatt   1560

cacaagggtg tctgttctac ctggatgaaa aatgctgtac cctatgaaaa atccgaaaat   1620

tgttctagtg caccaatttt cgtaagacaa tctaatttca agttaccaag cgattctaaa   1680

gtacccatta ttatgatcgg tccaggtact ggtttggccc cattcagagg cttcttgcaa   1740

gaaagattgg ctttagtgga gagtggagtt gaattgggtc cttcagtttt attctttggt   1800

tgtagaaaca gaagaatgga ctttatctac gaagaagaat tgcagagatt tgttgaaagt   1860

ggtgcattgg ccgaattgag tgttgcattc agcagggaag gtccaaccaa agaatacgtt   1920

caacacaaga tgatggacaa ggcttctgat atctggaata tgatttccca aggtgcttat   1980

ttgtatgttt gtggtgacgc taaaggaatg gctagagatg ttcatagatc actgcataca   2040

atcgcacaag aacaaggtag catggattca acaaaagcag agggctttgt aaagaatctt   2100

cagacaagcg gtagatatct gagagatgta tggtaa                             2136
```

<210> SEQ ID NO 17
<211> LENGTH: 1686
<212> TYPE: DNA
<213> ORGANISM: Artificial Sequence
<220> FEATURE:
<223> OTHER INFORMATION: Arapidopsis thaliana codon optimised

<400> SEQUENCE: 17

```
atggcccccc aagaacaggc agttagccaa gtaatggaaa aacagtcaaa taataacaat     60

agtgatgtca tattcaggag taagttgcct gatatatata tccccaacca cttatctttg    120

catgattaca tatttcaaaa tatctctgag ttcgctacaa agccttgcct tatcaatggt    180

ccaactggac atgtctacac ttattcagat gttcatgtaa tatcaagaca aattgcagct    240

aattttcaca agttgggcgt gaatcagaac gacgtagtta tgttgctgtt acctaactgt    300

ccagagtttg ttctatcatt tcttgcagct tccttcaggg gtgcaaccgc cacagccgca    360

aatccctttt tcacccctgc tgaaatagct aagcaagcta aagctagtaa tacaaagttg    420

attattactg aagctaggta tgtggataaa attaagcctt tgcaaaacga tgatggtgtt    480

gtgatcgttt gcatagatga caacgagtcc gtaccaattc cagaaggctg tctgagattc    540

actgagttaa ctcaatcgac aaccgaggct agtgaagtca ttgattcagt agaaatttca    600

cccgatgatg tggtggctct tccatactca tcaggtacaa ccggtcttcc taagggtgtt    660

atgttgaccc ataaaggatt agttacttca gttgctcaac aagtggacgg tgaaaaccca    720

aacttatatt ttcactccga cgacgtaatt ctatgtgtcc ttccaatgtt ccacatatac    780

gccttaaatt ctattatgtt gtgtggttta agagtaggtg ccgcaatcct tatcatgccc    840

aaatttgaga ttaacctatt actagaattg atacagagat gtaaagttac cgtcgctcct    900

atggttccac caatagtgct ggctatcgct aaatcaagtg aaactgaaaa atatgatttg    960

tcatctataa gagtcgttaa gagcggagct gcacctttag gcaaggagct agaggatgct   1020

gtaaatgcca agttccccaa tgctaagttg ggtcaaggtt atggcatgac cgaagccgga   1080

ccagttctag caatgtcctt aggtttcgcc aaggaaccct ttccagtaaa aagtggagca   1140

tgtggtacag tagttaggaa cgcagagatg aaaatcgttg atcccgatac tggtgactca   1200

ctatctagaa atcaaccagg tgaaatttgt attaggggac atcaaatcat gaaaggctac   1260

ttaaataatc cagctgctac agccgaaacc attgataaag atggctggtt gcatactggt   1320

gacataggtt tgatagatga tgatgacgaa ttattcattg ttgatagatt gaaggaactt   1380
```

```
atcaaatata agggctttca agttgctcca gctgaactag aagcacttct tataggacat   1440

ccagatatta ctgatgtagc tgttgttgct atgaaagaag aagcagctgg tgaggtccca   1500

gtggcttttg tggtgaaatc gaaggactcc gaactgtctg aggatgatgt aaagcaattc   1560

gttagtaaac aagtggtttt ctataaaaga attaataagg ttttcttcac cgaatctatt   1620

cccaaagccc ccagcggcaa gattttaagg aaagacttga gagcaaaact agcaaacggt   1680

ctttaa                                                              1686
```

<210> SEQ ID NO 18
<211> LENGTH: 1179
<212> TYPE: DNA
<213> ORGANISM: Vitis vinifera

<400> SEQUENCE: 18

```
atggcatccg tagaggagtt cagaaatgca cagagggcaa aaggtccagc aaccatattg     60

gctattggaa cagccacccc tgatcactgt gtttatcaat ctgattacgc tgattactat    120

ttcagagtaa ctaaaagtga acatatgaca gaacttaaga aaaagtttaa tagaatttgt    180

gataaatcta tgataaagaa aagatacata catctaactg aagaaatgtt agaggaacat    240

ccaaatatag gtgcatatat ggcaccatct ttgaatatta gacaagaaat cataacagcc    300

gaggtaccta gactaggtag agacgcagcc ttgaaagctt taaaggaatg gggacaacca    360

aaatctaaga ttacacattt ggttttctgt acaacttccg gtgtcgaaat gccaggtgct    420

gattataaac tagcaaacct attgggatta gagacctctg ttagaagagt tatgttgtat    480

catcaaggtt gttacgccgg aggtacagtg cttagaactg ctaaggattt ggcagaaaat    540

aacgccggtg ctagggtttt agtcgtctgc agtgaaatca ctgtcgtaac tttcagaggt    600

ccatcagaag atgctctaga cagtttggtc ggacaagcat tgtttggcga tggatcttcc    660

gccgtaattg taggcagcga tcctgatgtg tccattgaaa gaccactatt tcaattagtt    720

tctgctgctc aaacttttat tccaaattcc gccggtgcca tagcaggaaa cttgagagaa    780

gttggtttga cttttcattt gtggcctaat gtcccaacct taatttcaga aaacatcgaa    840

aaatgcttaa ctcaagcctt tgacccattg ggcataagcg actggaactc attgttttgg    900

attgctcatc caggtggtcc agcaatttta gacgcagtgg aggcaaaact aaacttagag    960

aagaaaaagt tggaagctac aagacacgtt ctatcagagt atggcaacat gagctctgcc   1020

tgcgttttat tcattctaga tgagatgagg aagaagtctt taaagggtga aaaagccaca   1080

accggagaag gtttagattg ggtgttcta tttggtttcg gtcctggctt aacaattgag   1140

acagtggtgt tacactctgt tccaactgtc actaactaa                          1179
```

<210> SEQ ID NO 19
<211> LENGTH: 1671
<212> TYPE: DNA
<213> ORGANISM: Arabidopsis thaliana

<400> SEQUENCE: 19

```
atgacgacac aagatgtgat agtcaatgat cagaatgatc agaaacagtg tagtaatgac     60

gtcattttcc gatcgagatt gcctgatata tacatcccta accacctccc actccacgac    120

tacatcttcg aaaatatctc agagttcgcc gctaagccat gcttgatcaa cggtcccacc    180

ggcgaagtat acacctacgc cgatgtccac gtaacatctc ggaaactcgc cgccggtctt    240

cataacctcg gcgtgaagca acacgacgtt gtaatgatcc tcctcccgaa ctctcctgaa    300
```

```
gtagtcctca ctttccttgc cgcctccttc atcggcgcaa tcaccacctc cgcgaacccg    360

ttcttcactc cggcggagat ttctaaacaa gccaaagcct ccgcggcgaa actcatcgtc    420

actcaatccc gttacgtcga taaaatcaag aacctccaaa acgacggcgt tttgatcgtc    480

accaccgact ccgacgccat ccccgaaaac tgcctccgtt tctccgagtt aactcagtcc    540

gaagaaccac gagtggactc aataccggag aagatttcgc cagaagacgt cgtggcgctt    600

cctttctcat ccggcacgac gggtctcccc aaaggagtga tgctaacaca caaaggtcta    660

gtcacgagcg tggcgcagca agtcgacggc gagaatccga atctttactt caacagagac    720

gacgtgatcc tctgtgtctt gcctatgttc catatatacg ctctcaactc catcatgctc    780

tgtagtctca gagttggtgc cacgatcttg ataatgccta agttcgaaat cactctcttg    840

ttagagcaga tacaaaggtg taaagtcacg gtggctatgg tcgtgccacc gatcgtttta    900

gctatcgcga agtcgccgga gacggagaag tatgatctga gctcggttag gatggttaag    960

tctggagcag ctcctcttgg taaggagctt gaagatgcta ttagtgctaa gtttcctaac   1020

gccaagcttg gtcagggcta tgggatgaca gaagcaggtc cggtgctagc aatgtcgtta   1080

gggtttgcta aagagccgtt tccagtgaag tcaggagcat gtggtacggt ggtgaggaac   1140

gccgagatga agatacttga tccagacaca ggagattctt tgcctaggaa caaacccggc   1200

gaaatatgca tccgtggcaa ccaaatcatg aaaggctatc tcaatgaccc cttggccacg   1260

gcatcgacga tcgataaaga tggttggctt cacactggag acgtcggatt tatcgatgat   1320

gacgacgagc ttttcattgt ggatagattg aaagaactca tcaagtacaa aggatttcaa   1380

gtggctccag ctgagctaga gtctctcctc ataggtcatc cagaaatcaa tgatgttgct   1440

gtcgtcgcca tgaaggaaga agatgctggt gaggttcctg ttgcgtttgt ggtgagatcg   1500

aaagattcaa atatatccga agatgaaatc aagcaattcg tgtcaaaaca ggttgtgttt   1560

tataagagaa tcaacaaagt gttcttcact gactctattc ctaaagctcc atcagggaag   1620

atattgagga aggatctaag agcaagacta gcaaatggat taatgaacta g            1671
```

<210> SEQ ID NO 20
<211> LENGTH: 40
<212> TYPE: DNA
<213> ORGANISM: Arabidopsis thaliana

<400> SEQUENCE: 20

```
gcgaattctt atgacgacac aagatgtgat agtcaatgat                            40
```

<210> SEQ ID NO 21
<211> LENGTH: 42
<212> TYPE: DNA
<213> ORGANISM: Arabidopsis thaliana

<400> SEQUENCE: 21

```
gcactagtat cctagttcat taatccattt gctagtcttg ct                         42
```

<210> SEQ ID NO 22
<211> LENGTH: 39
<212> TYPE: DNA
<213> ORGANISM: Arabidopsis thaliana

<400> SEQUENCE: 22

```
ctcactaaag ggcggccgca tggaccaaat tgaagcaat                             39
```

<210> SEQ ID NO 23
<211> LENGTH: 35

<212> TYPE: DNA
<213> ORGANISM: Arabidopsis thaliana

<400> SEQUENCE: 23
taagagctca gatctttagc agattggaat aggtg 35

<210> SEQ ID NO 24
<211> LENGTH: 35
<212> TYPE: DNA
<213> ORGANISM: Arabidopsis thaliana

<400> SEQUENCE: 24
gaagaagacc tcgagatgga tttgttattg ctgga 35

<210> SEQ ID NO 25
<211> LENGTH: 56
<212> TYPE: DNA
<213> ORGANISM: Arabidopsis thaliana

<400> SEQUENCE: 25
agtagatgga gtagatggag tagatggagt agatggacaa tttctgggtt tcatga 56

<210> SEQ ID NO 26
<211> LENGTH: 54
<212> TYPE: DNA
<213> ORGANISM: Arabidopsis thaliana

<400> SEQUENCE: 26
ccatctactc catctactcc atctactcca tctactagga ggagcggttc gggc 54

<210> SEQ ID NO 27
<211> LENGTH: 37
<212> TYPE: DNA
<213> ORGANISM: Arabidopsis thaliana

<400> SEQUENCE: 27
gctagccgcg gtaccttacc atacatctct cagatat 37

<210> SEQ ID NO 28
<211> LENGTH: 35
<212> TYPE: DNA
<213> ORGANISM: Arabidopsis thaliana

<400> SEQUENCE: 28
gaagaagacc tcgagatgga tttgttattg ctgga 35

<210> SEQ ID NO 29
<211> LENGTH: 37
<212> TYPE: DNA
<213> ORGANISM: Arabidopsis thaliana

<400> SEQUENCE: 29
gctagccgcg gtaccttacc atacatctct cagatat 37

<210> SEQ ID NO 30
<211> LENGTH: 39
<212> TYPE: DNA
<213> ORGANISM: Arabidopsis thaliana

<400> SEQUENCE: 30
ctcactaaag ggcggccgca tggaccaaat tgaagcaat 39

<210> SEQ ID NO 31

```
<211> LENGTH: 35
<212> TYPE: DNA
<213> ORGANISM: Arabidopsis thaliana

<400> SEQUENCE: 31

taagagctca gatctttagc agattggaat aggtg                              35


<210> SEQ ID NO 32
<211> LENGTH: 35
<212> TYPE: DNA
<213> ORGANISM: Arabidopsis thaliana

<400> SEQUENCE: 32

gaagaagacc tcgagatgga tttgttattg ctgga                              35


<210> SEQ ID NO 33
<211> LENGTH: 37
<212> TYPE: DNA
<213> ORGANISM: Arabidopsis thaliana

<400> SEQUENCE: 33

acctagagca ccaccacaat ttctgggttt catgact                            37


<210> SEQ ID NO 34
<211> LENGTH: 36
<212> TYPE: DNA
<213> ORGANISM: Arabidopsis thaliana

<400> SEQUENCE: 34

ggtgctattc tagttggtag gaggagcggt tcgggc                             36


<210> SEQ ID NO 35
<211> LENGTH: 37
<212> TYPE: DNA
<213> ORGANISM: Arabidopsis thaliana

<400> SEQUENCE: 35

gctagccgcg gtaccttacc atacatctct cagatat                            37


<210> SEQ ID NO 36
<211> LENGTH: 49
<212> TYPE: DNA
<213> ORGANISM: Saccharomyces cerevisiae

<400> SEQUENCE: 36

ccagctcaat cagttccagc tctttcagtt cctaaagttt acagttacc               49


<210> SEQ ID NO 37
<211> LENGTH: 50
<212> TYPE: DNA
<213> ORGANISM: Saccharomyces cerevisiae

<400> SEQUENCE: 37

aactagaact gattgagcag ttggtgatgg tttactttgg ttttcagagg              50


<210> SEQ ID NO 38
<211> LENGTH: 35
<212> TYPE: DNA
<213> ORGANISM: Arabidopsis thaliana

<400> SEQUENCE: 38

gaagaagacc tcgagatgga tttgttattg ctgga                              35
```

<210> SEQ ID NO 39
<211> LENGTH: 37
<212> TYPE: DNA
<213> ORGANISM: Arabidopsis thaliana

<400> SEQUENCE: 39
gctagccgcg gtaccttacc atacatctct cagatat 37

<210> SEQ ID NO 40
<211> LENGTH: 33
<212> TYPE: DNA
<213> ORGANISM: Vitis vinifera

<400> SEQUENCE: 40
ccggatccat ggcatccgta gaggagttca gaa 33

<210> SEQ ID NO 41
<211> LENGTH: 37
<212> TYPE: DNA
<213> ORGANISM: Vitis vinifera

<400> SEQUENCE: 41
cgctcgagtc attagttagt gacagttgga acagagt 37

<210> SEQ ID NO 42
<211> LENGTH: 31
<212> TYPE: DNA
<213> ORGANISM: Arabidopsis thaliana

<400> SEQUENCE: 42
ttgaaaattc gaattcatgg ccccccaaga a 31

<210> SEQ ID NO 43
<211> LENGTH: 40
<212> TYPE: DNA
<213> ORGANISM: Arabidopsis thaliana

<400> SEQUENCE: 43
gcgaagaatt gttaattaat taaagaccgt ttgctagttt 40

<210> SEQ ID NO 44
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 44
atggcatccg tagaggagtt c 21

<210> SEQ ID NO 45
<211> LENGTH: 37
<212> TYPE: DNA
<213> ORGANISM: Vitis vinifera

<400> SEQUENCE: 45
cgctcgagtc attagttagt gacagttgga acagagt 37

<210> SEQ ID NO 46
<211> LENGTH: 41
<212> TYPE: DNA
<213> ORGANISM: Saccharomyces cerevisiae

<400> SEQUENCE: 46
gcgagctcag tttatcatta tcaatactcg ccatttcaaa g 41

<210> SEQ ID NO 47
<211> LENGTH: 46
<212> TYPE: DNA
<213> ORGANISM: Saccharomyces cerevisiae

<400> SEQUENCE: 47
cgtctagaat ccgtcgaaac taagttctgg tgttttaaaa ctaaaa 46

<210> SEQ ID NO 48
<211> LENGTH: 44
<212> TYPE: DNA
<213> ORGANISM: Saccharomyces cerevisiae

<400> SEQUENCE: 48
gcgagctcat agcttcaaaa tgtttctact cctttttac tctt 44

<210> SEQ ID NO 49
<211> LENGTH: 45
<212> TYPE: DNA
<213> ORGANISM: Saccharomyces cerevisiae

<400> SEQUENCE: 49
cgtctagaaa acttagatta gattgctatg ctttctttct aatga 45

<210> SEQ ID NO 50
<211> LENGTH: 50
<212> TYPE: DNA
<213> ORGANISM: Saccharomyces cerevisiae

<400> SEQUENCE: 50
ttgcgtattg ggcgctcttc cgagctcagt ttatcattat caatactcgc 50

<210> SEQ ID NO 51
<211> LENGTH: 35
<212> TYPE: DNA
<213> ORGANISM: Saccharomyces cerevisiae

<400> SEQUENCE: 51
atggatcctc tagaatccgt cgaaactaag ttctg 35

<210> SEQ ID NO 52
<211> LENGTH: 41
<212> TYPE: DNA
<213> ORGANISM: Saccharomyces cerevisiae

<400> SEQUENCE: 52
atgaattctc tagaaaactt agattagatt gctatgcttt c 41

<210> SEQ ID NO 53
<211> LENGTH: 44
<212> TYPE: DNA
<213> ORGANISM: Saccharomyces cerevisiae

<400> SEQUENCE: 53
tgataatgat aaactgagct cggaagagcg cccaatacgc aaac 44

<210> SEQ ID NO 54
<211> LENGTH: 41
<212> TYPE: DNA
<213> ORGANISM: Saccharomyces cerevisiae

<400> SEQUENCE: 54
atgaattctc tagaaaactt agattagatt gctatgcttt c 41

<210> SEQ ID NO 55
<211> LENGTH: 35
<212> TYPE: DNA
<213> ORGANISM: Saccharomyces cerevisiae

<400> SEQUENCE: 55
atggatcctc tagaatccgt cgaaactaag ttctg 35

<210> SEQ ID NO 56
<211> LENGTH: 1373
<212> TYPE: DNA
<213> ORGANISM: Artificial Sequence
<220> FEATURE:
<223> OTHER INFORMATION: Constructed TEF2/TDH3 fusion promoter

<400> SEQUENCE: 56
atgaattctc tagaaaactt agattagatt gctatgcttt ctttctaatg agcaagaagt 60
aaaaaaagtt gtaatagaac aagaaaaatg aaactgaaac ttgagaaatt gaagaccgtt 120
tattaactta aatatcaatg ggaggtcatc gaaagagaaa aaaatcaaaa aaaaaatttt 180
caagaaaaag aaacgtgata aaaattttta ttgccttttt cgacgaagaa aaagaaacga 240
ggcggtctct tttttctttt ccaaaccttt agtacgggta attaacgaca ccctagagga 300
agaaagaggg gaaatttagt atgctgtgct tgggtgtttt gaagtggtac ggcgatgcgc 360
ggagtccgag aaaatctgga agagtaaaaa aggagtagaa acattttgaa gctatgagct 420
ccagcttttg ttccctttag tgagggttaa ttgcgcgctt ggcgtaatca tggtcatagc 480
tgtttcctgt gtgaaattgt tatccgctca caattccaca caacatagga gccggaagca 540
taaagtgtaa agcctggggt gcctaatgag tgaggtaact cacattaatt gcgttgcgct 600
cactgcccgc tttccagtcg ggaaacctgt cgtgccagct gcattaatga atcggccaac 660
gcgcggggag aggcggtttg cgtattgggc gctcttccga gctcagttta tcattatcaa 720
tactcgccat ttcaaagaat acgtaaataa ttaatagtag tgattttcct aactttattt 780
agtcaaaaaa ttagcctttt aattctgctg taacccgtac atgcccaaaa tagggggcgg 840
gttacacaga atatataaca tcgtaggtgt ctgggtgaac agtttattcc tggcatccac 900
taaatataat ggagcccgct ttttaagctg gcatccagaa aaaaaaagaa tcccagcacc 960
aaaatattgt tttcttcacc aaccatcagt tcataggtcc attctcttag cgcaactaca 1020
gagaacaggg gcacaaacag gcaaaaaacg ggcacaacct caatggagtg atgcaacctg 1080
cctggagtaa atgatgacac aaggcaattg acccacgcat gtatctatct cattttctta 1140
caccttctat taccttctgc tctctctgat ttggaaaaag ctgaaaaaaa aggttgaaac 1200
cagttccctg aaattattcc cctacttgac taataagtat ataaagacgg taggtattga 1260
ttgtaattct gtaaatctat ttcttaaact tcttaaattc tacttttata gttagtcttt 1320
tttttagttt taaaacacca gaacttagtt tcgacggatt ctagaggatc cat 1373

<210> SEQ ID NO 57
<211> LENGTH: 43
<212> TYPE: DNA
<213> ORGANISM: Artificial Sequence
<220> FEATURE:
<223> OTHER INFORMATION: Synthetic oligonucleotide

<400> SEQUENCE: 57
gcgcggccgc tctagaaaac ttagattaga ttgctatgct ttc 43

<210> SEQ ID NO 58
<211> LENGTH: 36
<212> TYPE: DNA
<213> ORGANISM: Artificial Sequence
<220> FEATURE:
<223> OTHER INFORMATION: Synthetic oligonucleotide

<400> SEQUENCE: 58
attcgtacgt ctagaatccg tcgaaactaa gttctg 36

<210> SEQ ID NO 59
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 59
atgcgtaagg agaaaatacc gcatcagg 28

<210> SEQ ID NO 60
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 60
ctctcagtac aatctgctct gatgccg 27

<210> SEQ ID NO 61
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 61
ctctcagtac aatctgctct gatgccg 27

<210> SEQ ID NO 62
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 62
cggtattttc tccttacgca tggaaagcgc gcctcgttca gaatg 45

<210> SEQ ID NO 63
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 63
tcgacggatc tatgcggtgt gaaatacc 28

<210> SEQ ID NO 64
<211> LENGTH: 28
<212> TYPE: DNA
<213> ORGANISM: Artificial Sequence

```
<220> FEATURE:
<223> OTHER INFORMATION: Synthetic oligonucleotide

<400> SEQUENCE: 64

actctcagta caatctgctc tgatgccg                                          28


<210> SEQ ID NO 65
<211> LENGTH: 48
<212> TYPE: DNA
<213> ORGANISM: Artificial Sequence
<220> FEATURE:
<223> OTHER INFORMATION: Synthetic oligonucleotide

<400> SEQUENCE: 65

agagcagatt gtactgagag tcatcagagc agattgtact gagagtgc                    48


<210> SEQ ID NO 66
<211> LENGTH: 47
<212> TYPE: DNA
<213> ORGANISM: Artificial Sequence
<220> FEATURE:
<223> OTHER INFORMATION: Synthetic oligonucleotide

<400> SEQUENCE: 66

cacaccgcat agatccgtcg aggattttgc cgatttcggc ctattgg                     47


<210> SEQ ID NO 67
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 67

atgccgcata gttaagcca                                                    19


<210> SEQ ID NO 68
<211> LENGTH: 40
<212> TYPE: DNA
<213> ORGANISM: Artificial Sequence
<220> FEATURE:
<223> OTHER INFORMATION: Synthetic oligonucleotide

<400> SEQUENCE: 68

tggcttaact atgcggcatg agcgacctca tgctatacct                             40


<210> SEQ ID NO 69
<211> LENGTH: 41
<212> TYPE: DNA
<213> ORGANISM: Artificial Sequence
<220> FEATURE:
<223> OTHER INFORMATION: Synthetic oligonucleotide

<400> SEQUENCE: 69

tctcagtaca atctgctctg ctgtggataa ccgtattacc g                           41


<210> SEQ ID NO 70
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 70

cagagcagat tgtactgaga gtg                                               23
```

<210> SEQ ID NO 71
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 71
agagcagatt gtactgagag taagatgcaa gagttcgaat ctcttagcaa 50

<210> SEQ ID NO 72
<211> LENGTH: 46
<212> TYPE: DNA
<213> ORGANISM: Artificial Sequence
<220> FEATURE:
<223> OTHER INFORMATION: Synthetic oligonucleotide

<400> SEQUENCE: 72
cacaccgcat agatccgtcg atcgactacg tcgtaaggcc gtttct 46

<210> SEQ ID NO 73
<211> LENGTH: 31
<212> TYPE: DNA
<213> ORGANISM: Artificial Sequence
<220> FEATURE:
<223> OTHER INFORMATION: Synthetic oligonucleotide

<400> SEQUENCE: 73
aagatgcaag agttcgaatc tcttagcaac c 31

<210> SEQ ID NO 74
<211> LENGTH: 42
<212> TYPE: DNA
<213> ORGANISM: Artificial Sequence
<220> FEATURE:
<223> OTHER INFORMATION: Synthetic oligonucleotide

<400> SEQUENCE: 74
cagagcagat tgtactgaga ggagcgacct catgctatac ct 42

<210> SEQ ID NO 75
<211> LENGTH: 42
<212> TYPE: DNA
<213> ORGANISM: Artificial Sequence
<220> FEATURE:
<223> OTHER INFORMATION: Synthetic oligonucleotide

<400> SEQUENCE: 75
agattcgaac tcttgcatct tctgtggata accgtattac cg 42

<210> SEQ ID NO 76
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 76
ctcattttgt tattcatttg taaaaaactg tattataagt aaatgcatgt 50

<210> SEQ ID NO 77
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 77
tccttatatg tagctttcga cat 23

<210> SEQ ID NO 78
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 78
atgtcgaaag ctacatataa ggaacgtg 28

<210> SEQ ID NO 79
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 79
caaatgaata acaaaatgag acaaagaaga aaaccaattt ttacaagcgt tttgctggcc 60

<210> SEQ ID NO 80
<211> LENGTH: 4506
<212> TYPE: DNA
<213> ORGANISM: Saccharomyces cerevisiae

<400> SEQUENCE: 80
atgagcaata tcaaaagcac gcaagatagc tctcataatg ctgtcgctag aagctcaagc 60
gcttcttttg cagcttcaga agaatcattt acgggcataa cccatgacaa agatgagcag 120
agcgataccc cggcggataa actaacaaaa atgctgacag gacctgcaag agacactgcg 180
agccagatta gtgccactgt gtctgaaatg gcgccagatg tcgtatctaa agtggagtca 240
tttgcagatg cactatcccg tcatacaacg agaagcggtg cctttaatat ggattcagat 300
agtgacgatg ggttcgatgc ccatgccatc tttgaaagtt ttgtaagaga cgctgatgag 360
caaggcatcc atatccgcaa ggctggtgtt accatagagg acgtaagcgc taaaggtgtg 420
gatgcgagtg ccctagaagg tgctaccttt ggtaacattc tttgtttacc gttgaccatc 480
tttaaaggta ttaaggctaa gaggcatcaa aagatgagac agatcataag caatgtcaat 540
gccctggcag aagcgggtga aatgattttg gttcttggaa ggcctggtgc tggttgttcc 600
tcctttttaa aagtaacagc tggtgaaata gatcagtttg ccggtggtgt ttccggtgaa 660
gtagcatatg atggtattcc ccaagaagaa atgatgaaac gatataaagc agatgttatt 720
tacaatggtg agttggatgt tcatttccct tatttaacag ttaagcaaac tttggatttc 780
gctattgcct gcaaaacgcc tgctctcaga gtcaataacg tttccaaaaa ggaatacatt 840
gcatccagaa gagatttata tgcaaccatt ttcggtctaa ggcataccta taataccaaa 900
gttggtaacg atttcgttag aggtgtatct ggtggtgaac gtaagcgtgt ttccattgcc 960
gaggctttgg cagccaaagg ttccatttac tgttgggata atgccactag aggtttggat 1020
gcgtctacgg ccttagaata cgcaaaagcc atccgtatta tgacaaactt attgaaatca 1080
accgcttttg ttacaattta tcaggcaagt gaaaacattt acgaaacatt tgataaagtc 1140
actgtccttt attctggtaa gcaaatttat tttggtttga tccacgaggc aaaaccttat 1200
ttcgcaaaaa tgggttattt gtgtcctcca aggcaagcaa cagctgaatt tttaaccgcg 1260

-continued

```
ttgactgatc caaatggatt ccatctgatc aagccaggtt atgaaaataa agtaccaaga   1320
accgctgagg aattcgaaac atattggtta aattctccag agtttgctca aatgaaaaaa   1380
gatatcgctg cttataaaga gaaggtcaat accgaaaaga ctaaagaagt ttatgacgaa   1440
tcgatggctc aagagaaatc caaatatacg agaaagaagt cttattatac agtgtcatat   1500
tgggaacaag ttaaactgtg tacccaacgt gggttccaaa gaatttacgg taacaagagt   1560
tatacagtca tcaatgtctg ctctgcaata attcaatctt ttattactgg atcattattt   1620
tacaataccc cttcatccac ttccggtgct tttcaagag gtggtgtgtt gtattttgcg    1680
ctactatatt attctttgat gggactggcg aatatttctt ttgaacatag gccaatctta   1740
caaaagcaca agggctattc tttgtatcat ccttcagctg aggcaattgg ctccactctg   1800
gcatctttcc ccttcagaat gattggtttg acctgtttct ttatcatttt attcttccta   1860
tctgggttgc acagaacagc gggatcattt tttaccatct atttgttctt aaccatgtgt   1920
tcagaggcga tcaatggttt atttgagatg gtttcttcag tatgtgacac tctttctcaa   1980
gctaactcta tctcgggtat tctgatgatg tctatctcaa tgtactctac ctatatgatc   2040
caattgcctt cgatgcatcc atggtttaaa tggatatcgt acgtactacc tatcaggtac   2100
gccttcgagt cgatgttaaa tgccgaattt cacggtaggc atatggattg tgctaacact   2160
ctagtaccca gtggaggaga ctatgataat ttatccgatg actacaaagt atgtgctttt   2220
gttggttcga aaccaggtca gtcttatgtg cttggtgatg actaccttaa aaatcaattt   2280
cagtacgttt ataagcacac gtggagaaac tttggtatct tgtggtgctt ttttactggg   2340
tatgttgttt tgaaagtgat attcacagaa tataagaggc ctgtgaaagg tggtggtgat   2400
gctcttatct tcaagaaagg atcaaaaaga tttatcgcac atgcagatga agaatctcca   2460
gacaatgtca atgatataga tgccaaagag caattctcca gtgaaagtag cggcgcaaat   2520
gatgaagtat ttgatgattt agaagccaaa ggtgttttca tttggaagga cgtatgcttt   2580
actattccat atgaaggcgg taagagaatg cttttggata atgtttcagg ttattgtatt   2640
ccaggtacca tgacggcctt gatgggagag tcaggtgctg gtaaaacaac tttgttaaat   2700
actcttgctc aaagaaatgt cggtatcatt actggtgata tgcttgtcaa tggacgtccc   2760
attgatgcga gtttcgaaag gcgtacaggt tatgtacaac aacaggatat acatatcgca   2820
gagttaactg ttagggaatc gttgcagttt tctgctcgta tgcgtcgccc tcagcatttg   2880
cctgattctg aaaaaatgga ttatgtggaa aaaatcatca gagttttggg aatggaagag   2940
tatgcggaag cccttgttgg tgaggttggt tgtggtttaa acgttgaaca gagaaagaag   3000
ctgtctattg gtgttgaact agtcgccaaa ccagacttat tattattcct cgatgaacct   3060
acatcaggtt tggattctca atcttcatgg gccattattc aattattaag aaagttatca   3120
aaagctggcc aatccattct ttgtacgatc catcaacctt cagctactct gttcgaagag   3180
tttgatagat tactactttt gaggaagggt ggacaaactg tttatttcgg agatattggt   3240
aagaactctg ccaccatttt gaactacttt gaaaggaatg ggcaagaaa atgtgattct    3300
agtgaaaatc ctgctgaata tattttagag gctattggtg ccggtgccac agcatccgtc   3360
aaagaagact ggcacgaaaa atggttgaac tctgtcgagt ttgaacaaac aaaagaaaaa   3420
gtacaggatt taataaatga tttatcgaaa caagaaacta aatccgaagt tggagacaaa   3480
ccttccaaat atgctacttc ttatgcttac cagttcagat atgttttaat cagaacctct   3540
acttcatttt ggagaagtct gaattacatc atgtcaaaga tgatgctaat gctggttggt   3600
ggtctgtata ttggtttcac atttttcaat gttggtaaaa gttatgtcgg cttacaaaat   3660
```

```
gcgatgttcg cggcatttat ctctattatc ttgtctgctc ctgcaatgaa ccaaatccaa   3720

ggacgtgcta ttgcctccag agaacttttt gaagttaggg aatcccaatc taacatgttt   3780

cactggtcgc tggtgttgat cactcagtac ttgagcgaac ttccctatca tttatttttt   3840

tcgacaattt tctttgtctc atcgtatttt ccattaagaa tcttcttcga agcgtcaaga   3900

tctgcggtgt actttttgaa ttactgcatt atgttccagt tatactatgt tggtcttggc   3960

ttaatgatcc tatatatgtc accgaacctt ccatccgcta atgttatctt aggtttgtgt   4020

ctgtcattta tgctttcttt ctgtggtgtt acacaacctg tctcattgat gcctggcttc   4080

tggacattca tgtggaaggc ttccccatac acatatttgg ttcagaatct ggtcggaatt   4140

atgctgcaca aaaaaccagt cgtatgcaaa aagaaagaac taaactactt caacccacca   4200

aacggctcaa cgtgtggaga gtacatgaaa cccttttttgg aaaaagctac tggttacatc   4260

gaaaatcctg atgctacgtc agattgtgca tactgtattt acgaagttgg agataattat   4320

ttgacacata tcagctctaa gtatagctac ttgtggagaa attttggaat attttggatt   4380

tacattttct tcaatatcat tgctatggtt tgtgtgtatt acctcttcca tgtaagacaa   4440

tcttccttcc taagccccgt atctatactc aataaaatta aaaacataag gaaaaagaag   4500

cagtaa                                                              4506
```

<210> SEQ ID NO 81
<211> LENGTH: 49
<212> TYPE: DNA
<213> ORGANISM: Saccharomyces cerevisiae

<400> SEQUENCE: 81

```
tcgacggatt ctagaggatc catgagcaat atcaaaagca cgcaagata                49
```

<210> SEQ ID NO 82
<211> LENGTH: 59
<212> TYPE: DNA
<213> ORGANISM: Saccharomyces cerevisiae

<400> SEQUENCE: 82

```
atcttagcta gccgcggtac cttactgctt ctttttcctt atgtttttaa ttttattga      59
```

<210> SEQ ID NO 83
<211> LENGTH: 4320
<212> TYPE: DNA
<213> ORGANISM: Artificial Sequence
<220> FEATURE:
<223> OTHER INFORMATION: Botryis cinerea optimised for Saccharomyces cerevisiae expression

<400> SEQUENCE: 83

```
atggcagcaa tagagccaga aggtttttct agtatcgtta gaccacacga ggaacatggt     60

aatgcattaa caagagcttt gtcatcatct tctgcatttt ctgatagaaa aagacaaaga    120

gcttacgatt cttcagatga agataataaa aaagagaagt ctatggctgc tgattggtca    180

ttgatgccag aattacaggc tatgcaacaa caaagtgata aagaccaggc taaaagaaga    240

gatttaggtg taacttggaa aaacttgact gttaaaggta ttggtgctga tgctgctatt    300

aatgaaaacg ttggttctca gttcaatatt ccaaagttga ttaaagaagg tagaactaaa    360

ccaccattac gtacactagt tgataactca cacggttgtg ttaagccagg tgaaatgttg    420

ctagttttgg gtagaccagg tgcgggttgc acaactttac taaagatgtt ggctaacact    480

agaggtggtt acgctgaagt aacaggtgat gttcattttg gttctttaaa ccatactgaa    540
```

```
gctcatcaat acagaggtca aatcgtaatg aacactgaag aagaattatt ctttccaaca    600
ttaactgttg gtcaaacaat agactttgcc actaggatga aggttccatt ccatagacct    660
tcaaattctg gttctccaga agaatatcaa caggctaaca gagatttctt gttaaaatct    720
atgggtattt ctcatacaca tgaaacaaag gttggtaatg aatacgtaag aggtgtaagt    780
ggtggtgaaa gaaaaagagt ttcgattata gaaatgttag catctagagg ttctgttatg    840
tgttgggata atagtactag ggtctagat gcttcttcag ctcttgacta taccaaagct    900
attagagcta tgacagatat ttttggtatg gcatctattg tgacattata ccaagccggt    960
aatggtattt ataatttgtt tgataaggtt ctagtattgg atgaaggtaa acaaatttac   1020
tacggtccaa tgaagcaggc tagaccattt atggaggaac taggtttcat ttgtgacgat   1080
tctgctaatg ttgctgactt cttaacaggt gtaactgttc ctactgaaag aaaaattaga   1140
gatgaatttc agaatagatt ccctagaact gccggtgaaa ttttggctgc ttataataga   1200
cactcaatta agaatgagat ggaaaaagaa tatgattatc caactactgc tatcgcaaag   1260
gaaagaaccg aagatttcag aacctcagtt caacatgaga agaatcccaa gttgggtaag   1320
gattctccat taactacttc atttatgacc caagttaaag catgtgttat tagacaatat   1380
caaattattt ggggtgacaa agctactttc attattaaac agttgtcaac tttagcacaa   1440
gccttgattg ctggtagttt gttctataat gcaccagcta atgcttcagg tctatttgtt   1500
aaatctggtg cattattttt gtcattatta ttcaatgcat tgttggctat gtctgaagtt   1560
actgattctt tttctggtag accagtttta gctaagcaca aagcgtttgc attttatcac   1620
cctgctgctt tctgtattgc ccaaattgct gcggatatac ctgtattgtt ggttcaagta   1680
tctcattttt ctttggttat gtattttatg gttggtttaa gacaagacgc tggtgcattt   1740
ttcacttatt ggattttgat tttcgcagct acaatgtgca tgactgcttt gttcagagct   1800
gttggtgctg gtttttctac ttttgatgct gcatctaaag tttcaggttt cttagtttca   1860
gcattgatta tgtacacagg ttatatgatt caaaaacccg atatgcatcc ttggtttgta   1920
tggatttact ggattgatcc tctagcttac ggtttttctg ctattttggc taacgagttc   1980
aaaggtcaaa ttattccatg cgttgctaat aatctagttc caaatggtcc aggttatgct   2040
gatttggctt ttcaagcatg tgccggtgtt ggtggtgctt tacctggtgc tacatcagta   2100
actggtgaac agtatttaaa ttctttgtct tactcttctt caaacatttg gagaaacttt   2160
ggtattttgt gggctttttg ggtattattc gttgttttga cgatttatta cacctcaaac   2220
tggtctgcca atggtggaaa atctggcatt ctattaatac caagagaaaa agctaaaaag   2280
aataccgcta tcttgaaagc tgccaacgct ggagatgaag aatctcaagc tattgaagag   2340
aaaagacaag ttcaatcaag accagcttct caagacacca aagttgcaga agaatctgat   2400
gatcaactaa tgagaaatac ttcggttttc acctggaaga atttaacata cactgttaaa   2460
acaccatctg gtgatagagt gctcttagat aatgttcaag gttgggttaa gccaggtatg   2520
ttaggtgctt tgatgggttc aagtggtgct ggaaaaacca ctttactaga tgttttggct   2580
caaagaaaga ctgatggtac aattaaaggt tctattctag tagatggaag acctttaaat   2640
gtttcttttc aaagatctgc tggttattgc gaacaattag atgtgcacga accattggca   2700
acagtacgtg aagccttaga attttctgct ttattgagac aatctagaac tgttccagat   2760
gccgaaaaat tgagatacgt tgatactatc attgatttgc tagaaatgca tgatatggaa   2820
aatactttga ttggtaacac cggtgctggt ttatcagttg aacaaagaaa aagattgact   2880
```

```
attggtgtag agttagttag taagcctagc attttgatat ttttggatga acctacatct   2940

ggtttagacg gacaggctgc ttttaatact gttagatttt taagaaagtt agctgatgtt   3000

ggtcaagcca ttttagttac aatccatcaa ccttcagctc aactcttcgc tcaatttgat   3060

tctctgttat tgttggctaa aggtggaaaa actgtttatt tcggtgatat cggtgaagat   3120

tctaagacca ttaaagaata cttcgctagg tatgatgctc cctgccctga aagttctaac   3180

ccagcagaac atatgattga cgttgtttca ggtaccttat ctaaaggtaa ggattggaat   3240

caagtatggt taaattctcc agagtatgaa tataccgtta aagaactaga tagaataatt   3300

gaaactgccg cagctgctcc tccaggtact gtagatgacg gatttgaatt tgctactccc   3360

ttatggcaac aaattaagtt agttacaaac agaatgaacg ttgctattta cagaaatact   3420

gattatatta acaataaatt tgctctacac attggttctg cattatttaa cggtttttca   3480

ttctggatga taaagcatag cgttggtggt ctacaattaa ggttatttac agtatttaat   3540

tttattttcg ttgcaccagg tgttatggcc cagttgcaac cattgttcct agaaagaaga   3600

gatatttatg aaaccagaga gaaaaagagt aagatgtatt cttggtgggc ttttgctact   3660

ggtaatgttg tatctgaatt accatactta gttatctgtg ctgtattata ctttgtttgt   3720

tggtattata ccgttggttt cccatctgat tctagtaagg caggttctgt tttgttcgtt   3780

atgatttgtt atgagttcat ttatacagga atcggtcagt ttgttgctgc ctatgctcca   3840

aacgttgttt tcgcctcttt ggtaaaccca ttggttatag gtaccttggt ttcattctgc   3900

ggagttttag taccatacgc tcaaattaca gagttctgga gatattggat gtactattta   3960

aaccctttta attatttgat gggttctttg ttggttttta cttcatggga cactccagtt   4020

aattgtaggg aatcagagtt tgcaattttc aacccagcta atggtacctg tggtgaatat   4080

ttgtcttctt atttgcaggg tatgggtgct gctgctaatt taattaatcc agatgctact   4140

gaaggttgta gagtttgtga atatactgtt ggaaacgatt atttgaaagg tttgaatttg   4200

aaaacatatt cttatggttg gagggacgct ggtatttgcg ctttattcgt tttctctggt   4260

tacggtctag tttttctatt gatgaagttg agaacaaaga aaacaaaagg tgctgaatga   4320
```

```
<210> SEQ ID NO 84
<211> LENGTH: 24
<212> TYPE: PRT
<213> ORGANISM: Botrytis cinerea
<220> FEATURE:
<221> NAME/KEY: misc_feature
<222> LOCATION: (24)..(24)
<223> OTHER INFORMATION: Xaa can be any naturally occurring amino acid
<220> FEATURE:
<221> NAME/KEY: misc_feature
<222> LOCATION: (24)..(24)
<223> OTHER INFORMATION: Xaa is an unknown amino acid

<400> SEQUENCE: 84

Gln Ala Lys Arg Arg Asp Leu Gly Val Thr Trp Lys Asn Leu Thr Val
1               5                   10                  15

Lys Gly Ile Gly Ala Asp Ala Xaa
            20


<210> SEQ ID NO 85
<211> LENGTH: 24
<212> TYPE: PRT
<213> ORGANISM: Unknown
<220> FEATURE:
<223> OTHER INFORMATION: Identified in search of Uniprot database for
      sequences similar to codon optomized ABC-transporter BcatrB from
      Botrytis cinerea
```

<400> SEQUENCE: 85

Gln Ala Lys Arg Arg Asp Leu Gly Val Thr Trp Lys Asn Leu Thr Val
1               5                   10                  15

Lys Gly Ile Gly Ala Asp Ala Ala
            20

<210> SEQ ID NO 86
<211> LENGTH: 24
<212> TYPE: PRT
<213> ORGANISM: Unknown
<220> FEATURE:
<223> OTHER INFORMATION: Identified in search of Uniprot database for sequences similar to codon optomized ABC-transporter BcatrB from Botrytis cinerea

<400> SEQUENCE: 86

Gln Val Lys Arg Arg Asp Leu Gly Val Thr Trp Arg Asn Leu Thr Val
1               5                   10                  15

Lys Gly Ile Gly Ala Asp Ala Ala
            20

<210> SEQ ID NO 87
<211> LENGTH: 24
<212> TYPE: PRT
<213> ORGANISM: Unknown
<220> FEATURE:
<223> OTHER INFORMATION: Identified in search of Uniprot database for sequences similar to codon optomized ABC-transporter BcatrB from Botrytis cinerea

<400> SEQUENCE: 87

Gln Val Lys Arg Arg Asp Leu Gly Val Thr Trp Lys Asn Leu Thr Val
1               5                   10                  15

Lys Gly Ile Gly Ala Asp Ala Ala
            20

<210> SEQ ID NO 88
<211> LENGTH: 24
<212> TYPE: PRT
<213> ORGANISM: Unknown
<220> FEATURE:
<223> OTHER INFORMATION: Identified in search of Uniprot database for sequences similar to codon optomized ABC-transporter BcatrB from Botrytis cinerea

<400> SEQUENCE: 88

Gly Ala Lys Asp Lys Lys Leu Gly Ile Thr Trp Thr Asp Leu Asp Ile
1               5                   10                  15

Lys Gly Ile Gly Ala Asp Ala Ala
            20

<210> SEQ ID NO 89
<211> LENGTH: 47
<212> TYPE: DNA
<213> ORGANISM: Botrytis cinerea

<400> SEQUENCE: 89
tcgacggatt ctagaggatc catggcagca atagagccag aaggttt                   47

<210> SEQ ID NO 90
<211> LENGTH: 52
<212> TYPE: DNA
<213> ORGANISM: Botrytis cinerea

<400> SEQUENCE: 90
atcttagcta gccgcggtac ctcattcagc accttttgtt ttctttgttc tc 52

<210> SEQ ID NO 91
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 91
ggtaccgcgg ctagctaaga tccg 24

<210> SEQ ID NO 92
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 92
ggatcctcta gaatccgtcg aaactaagtt 30

<210> SEQ ID NO 93
<211> LENGTH: 25
<212> TYPE: DNA
<213> ORGANISM: Kluyveromyces lactis

<400> SEQUENCE: 93
cttgacgttc gttcgactga tgagc 25

<210> SEQ ID NO 94
<211> LENGTH: 26
<212> TYPE: DNA
<213> ORGANISM: Kluyveromyces lactis

<400> SEQUENCE: 94
ctggaattcg atgatgtagt ttctgg 26

<210> SEQ ID NO 95
<211> LENGTH: 42
<212> TYPE: DNA
<213> ORGANISM: Saccharomyces cerevisiae

<400> SEQUENCE: 95
ctacatcatc gaattccagc tacgtatggt catttcttct tc 42

<210> SEQ ID NO 96
<211> LENGTH: 49
<212> TYPE: DNA
<213> ORGANISM: Saccharomyces cerevisiae

<400> SEQUENCE: 96
tttttgatta aaattaaaaa aactttttag tttatgtatg tgttttttg 49

<210> SEQ ID NO 97
<211> LENGTH: 50
<212> TYPE: DNA
<213> ORGANISM: Saccharomyces cerevisiae

<400> SEQUENCE: 97
agttttttta attttaatca aaaaatgagc gaagaaagct tattcgagtc 50

<210> SEQ ID NO 98
<211> LENGTH: 25
<212> TYPE: DNA
<213> ORGANISM: Saccharomyces cerevisiae

<400> SEQUENCE: 98
cacctaaaga cctcatggcg ttacc 25

<210> SEQ ID NO 99
<211> LENGTH: 24
<212> TYPE: DNA
<213> ORGANISM: Kluyveromyces lactis

<400> SEQUENCE: 99
cggtctgcat tggatggtgg taac 24

<210> SEQ ID NO 100
<211> LENGTH: 25
<212> TYPE: DNA
<213> ORGANISM: Kluyveromyces lactis

<400> SEQUENCE: 100
gagcaatgaa cccaataacg aaatc 25

<210> SEQ ID NO 101
<211> LENGTH: 44
<212> TYPE: DNA
<213> ORGANISM: Saccharomyces cerevisiae

<400> SEQUENCE: 101
caccatccaa tgcagaccgt tttagtttat gtatgtgttt tttg 44

<210> SEQ ID NO 102
<211> LENGTH: 27
<212> TYPE: DNA
<213> ORGANISM: Saccharomyces cerevisiae

<400> SEQUENCE: 102
tgttctgctc tcttcaattt tcctttc 27

<210> SEQ ID NO 103
<211> LENGTH: 43
<212> TYPE: DNA
<213> ORGANISM: Saccharomyces cerevisiae

<400> SEQUENCE: 103
ctggaattcg atgatgtagt ttctaatttt ctgcgctgtt tcg 43

<210> SEQ ID NO 104
<211> LENGTH: 22
<212> TYPE: DNA
<213> ORGANISM: Kluyveromyces lactis

<400> SEQUENCE: 104
ccaacaatga tgatatctga tc 22

<210> SEQ ID NO 105
<211> LENGTH: 40
<212> TYPE: DNA
<213> ORGANISM: Kluyveromyces lactis

<400> SEQUENCE: 105
ccgctgctag gcgcgccgtg ggcgcaatta taaaacactg 40

<210> SEQ ID NO 106
<211> LENGTH: 40
<212> TYPE: DNA
<213> ORGANISM: Kluyveromyces lactis

<400> SEQUENCE: 106
ccgctgctag gcgcgccgtg ggcgcaatta taaaacactg 40

<210> SEQ ID NO 107
<211> LENGTH: 38
<212> TYPE: DNA
<213> ORGANISM: Kluyveromyces lactis

<400> SEQUENCE: 107
gtcagcggcc gcatccctgc tacgctgcag gtcgacaa 38

<210> SEQ ID NO 108
<211> LENGTH: 21
<212> TYPE: DNA
<213> ORGANISM: Kluyveromyces lactis

<400> SEQUENCE: 108
atacatttgc cttttgaaaa c 21

<210> SEQ ID NO 109
<211> LENGTH: 22
<212> TYPE: DNA
<213> ORGANISM: Saccharomyces cerevisiae

<400> SEQUENCE: 109
gccgtcatat attactttga gc 22

<210> SEQ ID NO 110
<211> LENGTH: 40
<212> TYPE: DNA
<213> ORGANISM: Saccharomyces cerevisiae

<400> SEQUENCE: 110
gcagggatgc ggccgctgac acagaagtcg cgtcaacttg 40

<210> SEQ ID NO 111
<211> LENGTH: 25
<212> TYPE: DNA
<213> ORGANISM: Saccharomyces cerevisiae

<400> SEQUENCE: 111
cagaggtcgc ctgacgcata tacct 25

<210> SEQ ID NO 112
<211> LENGTH: 49
<212> TYPE: DNA
<213> ORGANISM: Saccharomyces cerevisiae

<400> SEQUENCE: 112
ccgctgctag gcgcgccgtg ctccagattt gccaaagaat aaggtcaac 49

<210> SEQ ID NO 113
<211> LENGTH: 42
<212> TYPE: DNA
<213> ORGANISM: Kluyveromyces lactis

<400> SEQUENCE: 113
gtcagcggcc gcatccctgc ttcggcttca tggcaattcc cg 42

<210> SEQ ID NO 114
<211> LENGTH: 44
<212> TYPE: DNA
<213> ORGANISM: Kluyveromyces lactis

<400> SEQUENCE: 114
cacggcgcgc ctagcagcgg taacgccagg gttttcccag tcac 44

<210> SEQ ID NO 115
<211> LENGTH: 38
<212> TYPE: DNA
<213> ORGANISM: Kluyveromyces lactis

<400> SEQUENCE: 115
gtcagcggcc gcatccctgc tacgctgcag gtcgacaa 38

<210> SEQ ID NO 116
<211> LENGTH: 23
<212> TYPE: DNA
<213> ORGANISM: Kluyveromyces lactis

<400> SEQUENCE: 116
cacactacac agattatacc atg 23

<210> SEQ ID NO 117
<211> LENGTH: 22
<212> TYPE: DNA
<213> ORGANISM: Kluyveromyces lactis

<400> SEQUENCE: 117
ttctctaacg acgacgaaat cg 22

<210> SEQ ID NO 118
<211> LENGTH: 42
<212> TYPE: DNA
<213> ORGANISM: Kluyveromyces lactis

<400> SEQUENCE: 118
cacggcgcgc ctagcagcgg aggccactag tggatctgat at 42

<210> SEQ ID NO 119
<211> LENGTH: 27
<212> TYPE: DNA
<213> ORGANISM: Saccharomyces cerevisiae

<400> SEQUENCE: 119
gaagaggagt agggaatatt actggct 27

<210> SEQ ID NO 120
<211> LENGTH: 47
<212> TYPE: DNA
<213> ORGANISM: Saccharomyces cerevisiae

<400> SEQUENCE: 120
gcagggatgc ggccgctgac actccaagct gcctttgtgt gcttaat 47

<210> SEQ ID NO 121
<211> LENGTH: 48
<212> TYPE: DNA
<213> ORGANISM: Saccharomyces cerevisiae

<400> SEQUENCE: 121

```
ccgctgctag gcgcgccgtg caagagttcc tcggtttgcc agttatta              48


<210> SEQ ID NO 122
<211> LENGTH: 32
<212> TYPE: DNA
<213> ORGANISM: Saccharomyces cerevisiae

<400> SEQUENCE: 122

cctgcgatgt atattttcct gtacaatcaa tc                               32


<210> SEQ ID NO 123
<211> LENGTH: 23
<212> TYPE: DNA
<213> ORGANISM: Saccharomyces cerevisiae

<400> SEQUENCE: 123

ctgggagcag atgacgagtt ggt                                         23


<210> SEQ ID NO 124
<211> LENGTH: 1191
<212> TYPE: DNA
<213> ORGANISM: Mucor rouxii

<400> SEQUENCE: 124

atggcaacca agagaaacgt tacctccaat gctcctgctg cagaagacat cagcatcagc     60

aacaaggctg tgattgatga agccattgaa agaaactggg agatccccaa tttcaccatc    120

aaggagatcc gtgatgctat cccagctcac tgtttccgtc gtgatacctt tagatccttt    180

acacatgttc ttcatgatat tatcatcatg tccatcttgg ccattggtgc ttcttacatt    240

gattccatcc ctaataccta tgctcgcatt gctctctggc ccttgtactg gatcgctcaa    300

ggtattgttg gcactggtgt ctgggtcatt ggtcatgaat gtggccatca agcattcagc    360

ccttcaaaga ctatcaataa tagcgttggt tacgttctcc acactgcttt attagtacct    420

tatcactcat ggagattctc tcactctaag catcataaag ccactggaca catgtcaaaa    480

gatcaggtct ttgtcccctc tactcgtaag gaatacggtt tgcctcctcg tgagcaagat    540

cctgaagttg atggacctca tgatgctctt gatgaagctc ccattgttgt cttgtatcgc    600

atgttccttc aatttacctt tggctggcct ctttatctct tcaccaatgt ctcaggtcaa    660

gattaccccg gttgggcttc tcatttcaac cccaagtgtg ctatctacga tgaaaaccaa    720

ttctgggatg ttatgagctc cactgctggt gtccttggca tgattggttt cttggcttac    780

tgtggtcaag tctttggctc tcttgctgtc atcaagtact atgttattcc ctatttgaat    840

gttaactttt ggttggttct gatcacttac ttgcaacaca ctgatcccaa gttgcctcat    900

taccgtgaaa atgtttggaa cttccaacgc ggtgctgctt taactgttga tcgttcttat    960

ggcttcctcc tcgactactt ccatcatcac atttctgata ctcatgttgc tcaccatttc   1020

ttctccacca tgcctcacta ccacgctgaa gaagctactg ttcatatcaa gaaggctctt   1080

ggtaagcact accactgcga caacacacct gtccctatcg ccttgtggaa ggtctggaag   1140

agctgtcgtt ttgttgaaga tgagggcgat gttgtcttct ttaagaacta a            1191


<210> SEQ ID NO 125
<211> LENGTH: 1371
<212> TYPE: DNA
<213> ORGANISM: Ostreococcus tauri

<400> SEQUENCE: 125

atgtgtgttg aaacagaaaa taacgatggt attcctaccg ttgaaattgc tttcgatggt     60
```

```
gaaagagaaa gagctgaagc aaatgttaag ttgtcagcag aaaagatgga acctgcagct    120

ttggcaaaga cttttgctag aagatatgtt gttattgaag gtgttgaata tgatgttact    180

gatttcaaac atccaggtgg tactgttatt ttctacgctt tatccaatac tggtgcagat    240

gctaccgaag cattcaagga atttcatcat agatccagaa aagctagaaa ggctttggca    300

gctttaccat ccagaccagc aaagaccgct aaagttgatg atgctgaaat gttgcaagat    360

tttgctaaat ggagaaagga attagaaaga gatggtttct ttaagccatc acctgcacat    420

gttgcatata gatttgcaga attagctgca atgtacgctt tgggtactta cttaatgtat    480

gctagatacg ttgtttcatc tgttttagtt tacgcatgtt tctttggtgc aagatgtggt    540

tgggttcaac atgaaggtgg tcattcctcc ttaaccggta acatttggtg ggataagaga    600

atacaagcat tcactgcagg tttcggttta gctggttcag gtgacatgtg gaactccatg    660

cataacaaac atcatgcaac tcctcaaaaa gttagacatg atatggatct ggatacaact    720

ccagctgttg ctttcttcaa caccgctgtt gaagataata gaccaagagg tttctctaaa    780

tactggttaa gattgcaagc atggactttt attccagtta catccggttt ggttttattg    840

ttttggatgt ttttcttaca tccttccaag gcattaaagg gtggtaaata tgaagaatta    900

gtttggatgt tggcagctca tgttattaga acatggacca ttaaggctgt tacaggtttc    960

actgcaatgc aatcttacgg tttatttttg gctacttctt gggtttcagg ttgttacttg   1020

tttgctcatt tctccacttc tcatacacat ctggatgttg ttccagctga tgaacatttg   1080

tcttgggtta gatacgcagt tgatcatact attgatattg atccatctca aggttgggtt   1140

aattggttga tgggttattt gaattgtcaa gttattcatc atttgttccc atctatgcct   1200

caattcagac aaccagaagt ttccagaaga ttcgttgctt ttgctaagaa atggaatttg   1260

aactacaaag ttatgactta cgctggtgca tggaaagcaa ctttaggtaa cttagataac   1320

gttggtaaac attattacgt tcatggtcaa cattctggta aaacagcata a            1371
```

<210> SEQ ID NO 126
<211> LENGTH: 957
<212> TYPE: DNA
<213> ORGANISM: Mortiella alpine

<400> SEQUENCE: 126

```
atggaatcta ttgctcaatt cttgccatca aagatgcctc aagatttgtt tattgatttg     60

gctgcagcta ttggtgttag agcagctcca tatgttgatc ctttggaagc agctttagtt    120

gcacaagctg aaaagtacat cccaactatc gttcatcata ctagaggttt cttggttgca    180

gttgaatcac ctttagttag agaattgcca ttgatgaacc ctttccatgt tttgttgatc    240

gttttggctt atttggttac tgtttttgtt ggtatgcaaa tcatgaagaa cttcgataga    300

ttcgaagtta agacattttc tttgttccat aacttctgtt tagtttctat ttcagcttat    360

atgtgtggtg gtattttgta cgaagcatac caagctaact acggtttatt cgaaaacgca    420

gctgatcata ctgcaaaagg ttttccaatg gctaagatga tctggttgtt ttatttctcc    480

aagatcatgg aatttgttga tacaatgatt atggttttga aaaagaataa cagacaaatt    540

tcatttttgc atgtttacca tcattcttca attttcacaa tctggtggtt ggttactttt    600

gttgcaccta atggtgaagc atatttctcc gcagctttaa acagttttat tcatgttatc    660

atgtacggtt actacttctt gtccgcatta ggttttaaac aagttagttt cgttaagttc    720

tacatcacca gatcacaaat gactcaattc tgtatgatgt caatccaatc cagttgggat    780
```

```
atgtatgcaa tgaaagtttt aggtagacca ggttatccat ttttcatcac tgctttgttg    840

tggttctaca tgtggacaat gttgggttta ttctataact tctacagaaa gaatgcaaag    900

ttggctaaac aagcaaaggc tgatgcagct aaagaaaagg ctagaaagtt acaataa       957
```

<210> SEQ ID NO 127
<211> LENGTH: 1542
<212> TYPE: DNA
<213> ORGANISM: Artificial Sequence
<220> FEATURE:
<223> OTHER INFORMATION: Paramecium tetraurelia codon optimised for Saccharomyces cerevisiae

<400> SEQUENCE: 127

```
atggaaggta tcatcactca attcggtatt ttgtttttgt tggctgcttt gtttattttc     60

gatggtttgt ttaaattggt tccattgtac gctatcatcg ctgaagttta ctctttgtat    120

ttggattctc aaaagagaac tccacaacaa aaggaattgt tgaaaaatca aaagttgact    180

tggcaagaat tgaagaaaca tgataaccaa tcttctgctt acgttgctat taaaggtaaa    240

gtttacgatg ttacttcttt cttgaactca catccaggtg gtagagaatt tttgttgttg    300

aattgtggta gagatgctac tttggctttc caatcttacc atccattttc tgataagcca    360

gaaaagttgt tggaaaagta tttgatcggt gacttgttga ctactgaatg gccaactttt    420

aaaccagatt ctggtttcta caaggaatgt actgaaagag ttaagaaata cttccaatct    480

aagggtatta atccaaagac tccaactcca ggtttggtta gagctatccc attgtggact    540

tgtttctttt acactttcta tttgactttc gtttctgatt ctttgggttt gactaagaga    600

attttgatcg gtactatctt cggtattttg caagctttga acactttgca tttgatgcat    660

gatgcttctc atggtgctgc tggtaataat gaaaaatggt ggtggttttt cggtagattg    720

actttggatt atatttctgg ttcttctatg gttgcttggc aaaatcaaca tgttgttggt    780

catcatcaat atactaatat tatgggttct gatccagata ttccacaatt gaaagaaggt    840

gacgttagaa gattggttaa ggaacaaatt tggtctgcta tgtacaagta ccaacatttg    900

tacatgccat tttgtacggt tttgttgtct ttgagatcaa gatactacga tgttttcgaa    960

atcttcttga aggaaactga tggtccagtt aaggttaacc caatctcttt gcaggataag   1020

ttgagacaag cttcttctaa gttgttgtgg ttgttttgga gatactattt gccagttcaa   1080

gttttcggca tgtctcaatg tcaattctgg ttcttgttca tctacgttga gttcatcact   1140

ggttactggt tggctattaa tttccaagtt tctcatgttt ctgatgaagc tgaatttttc   1200

tacaacaaca tggataaggc tgttaaaaat ggtactaacg aacaatggcc aattgaatgg   1260

gctgttttgc aaattaaatc ttctgttgat tactctcatg gtaactggtt catgacttat   1320

ttgtgtggtg ctttgaacta ccaagttgtt catcatttgt acccaggtgt ttctcaatat   1380

ttgtacccag aaatcgctcc aatcatcttg gaagtttgta agaaatacaa tttgaagtac   1440

aatttgttgc caggttttaa agaagcttgg aacggtcatt tcaaccattt gaaaaatatg   1500

ggtaaacaaa acaagtttgt tggttttgct aaaatggaat aa                      1542
```

<210> SEQ ID NO 128
<211> LENGTH: 38
<212> TYPE: DNA
<213> ORGANISM: Mucor Rouxii

<400> SEQUENCE: 128

```
tagaactaaa gggcggccgc atggcaacca agagaaac                             38
```

<210> SEQ ID NO 129
<211> LENGTH: 42
<212> TYPE: DNA
<213> ORGANISM: Mucor rouxii

<400> SEQUENCE: 129
ttaattaaga gctcagatct ttagttctta aagaagacaa ca 42

<210> SEQ ID NO 130
<211> LENGTH: 41
<212> TYPE: DNA
<213> ORGANISM: Ostreococcus tauri

<400> SEQUENCE: 130
tatagggccc gggcgtcgac atgtgtgttg aaacagaaaa t 41

<210> SEQ ID NO 131
<211> LENGTH: 41
<212> TYPE: DNA
<213> ORGANISM: Ostreococcus tauri

<400> SEQUENCE: 131
cggtaccaag cttactcgag ttatgctgtt ttaccagaat g 41

<210> SEQ ID NO 132
<211> LENGTH: 41
<212> TYPE: DNA
<213> ORGANISM: Mortellia alpine

<400> SEQUENCE: 132
tagaactaaa gggcggccgc atggaatcta ttgctcaatt c 41

<210> SEQ ID NO 133
<211> LENGTH: 42
<212> TYPE: DNA
<213> ORGANISM: mortiella alpine

<400> SEQUENCE: 133
ttaattaaga gctcagatct ttattgtaac tttctagcct tt 42

<210> SEQ ID NO 134
<211> LENGTH: 40
<212> TYPE: DNA
<213> ORGANISM: Paramecium tetraurelia

<400> SEQUENCE: 134
tatagggccc gggcgtcgac atggaaggta tcatcactca 40

<210> SEQ ID NO 135
<211> LENGTH: 42
<212> TYPE: DNA
<213> ORGANISM: Paramecium tetraurelia

<400> SEQUENCE: 135
cggtaccaag cttactcgag ttattccatt ttagcaaaac ca 42

<210> SEQ ID NO 136
<211> LENGTH: 40
<212> TYPE: DNA
<213> ORGANISM: Artificial Sequence
<220> FEATURE:
<223> OTHER INFORMATION: Synthetic oligonucleotide

<400> SEQUENCE: 136
tggcttaact atgcggcatg agcgacctca tgctatacct 40

<210> SEQ ID NO 137
<211> LENGTH: 41
<212> TYPE: DNA
<213> ORGANISM: Artificial Sequence
<220> FEATURE:
<223> OTHER INFORMATION: Synthetic oligonucleotide

<400> SEQUENCE: 137
tctcagtaca atctgctctg ctgtggataa ccgtattacc g 41

<210> SEQ ID NO 138
<211> LENGTH: 1113
<212> TYPE: DNA
<213> ORGANISM: Saccharomyces cerevisiae

<400> SEQUENCE: 138
atgtcagagt ctccaatgtt tgccgccaat ggtatgccta aggttaatca aggtgctgaa 60
gaagacgtga gaatactagg ctatgatcca ttagcaagtc cagcattact acaagtgcaa 120
atccccgcca ctcctacttc cttagagact gccaaaagag gtaggagaga agctattgat 180
atcattactg gtaaagatga tagagtgcta gtgatagtag gaccatgttc aattcatgat 240
ttggaagccg cccaagaata tgctttgaga ttgaaaaagt tgagcgatga attgaaagga 300
gatctgtcga taataatgag agcttacctg gaaaaaccaa gaactactgt tggttggaaa 360
ggtttaatta acgatcctga tgttaataac accttcaata ttaacaaggg attgcaatcg 420
gctagacaac ttttcgtcaa tttgaccaac atcggtctac ctattggttc agaaatgtta 480
gataccatca gccctcaata cctagccgat cttgttagtt tcggcgcaat aggcgctaga 540
acaacggagt ctcaacttca tagagaattg gcctctggtt tgtctttccc tgttggcttc 600
aaaaatggta ccgacggtac tctaaatgtt gctgtggatg cctgtcaagc agctgcccat 660
tctcatcatt tcatgggtgt aactttacac ggtgttgcag caatcacaac tacaaaaggc 720
aacgaacatt gctttgttat attaagaggc ggaaagaaag gtaccaatta tgacgctaaa 780
tccgtcgctg aggctaaggc acaattacct gctggttcga atggtttaat gattgactac 840
tctcatggca atagtaataa ggatttcaga aatcagccta aagttaacga cgttgtttgt 900
gaacaaatcg caaacggtga aaacgcaata actggtgtca tgatcgaatc gaatatcaat 960
gaaggaaatc aaggtattcc tgctgagggc aaggcaggct tgaaatacgg tgtttccatt 1020
acagatgcct gtattggatg ggaaactact gaagatgttc ttagaaagtt ggctgctgca 1080
gtgagacaaa gaagagaggt aaataagaag tag 1113

<210> SEQ ID NO 139
<211> LENGTH: 771
<212> TYPE: DNA
<213> ORGANISM: Saccharomyces cerevisiae

<400> SEQUENCE: 139
atggatttta caaagccaga aacggtttta aacctacaaa atattagaga tgaattggtg 60
aggatggaag acagtattat ttttaaattc atagaaagaa gccattttgc cacatgccca 120
agtgtttacg aagctaatca ccctggatta gagattccaa attttaaagg ctcgtttttg 180
gactgggcat tgagtaatct tgagatagca cattctagga tcagaagatt tgaatcccca 240
gatgagaccc cattcttccc agacaagatt caaaaatcat ttcttccttc aattaattac 300

```
cctcaaatct tggcaccata tgctccagaa gtaaactaca atgataagat aaagaaggtt    360

tatattgaaa agataatacc cctgatatct aagagggatg gagatgacaa gaacaatttt    420

tcatccgttg caactagaga cattgagtgt ctacaatcgt tgtctagaag aatacatttt    480

ggtaaatttg ttgcagaggc taaatttcaa tctgatatac ctttgtacac taaattaatt    540

aaaagtaagg atgtagaagg aattatgaaa aatataacaa attctgctgt ggaagagaaa    600

atcttagaaa gattgactaa aaaggctgaa gtttacggtg ttgatccaac caacgaatct    660

ggtgaaagga ggattactcc cgaatatttg gttaaaatat ataaagaaat tgtaataccc    720

attacaaaag aagtagaggt tgaatatcta ttgagaagat tggaagaatg a             771
```

<210> SEQ ID NO 140
<211> LENGTH: 1179
<212> TYPE: DNA
<213> ORGANISM: Artificial Sequence
<220> FEATURE:
<223> OTHER INFORMATION: Vitis pseudoreticulata codon optimised for Saccharomyces cerevisiae

<400> SEQUENCE: 140

```
atggcttctg ttgaagaaat tagaaatgct caaagagcta aaggtccagc tactattttg     60

gctattggta ctgctactcc agatcattgt gtttaccaat ctgattacgc tgattactac    120

ttcagagtta ctaagtctga acatatgact gaattgaaga aaaagttcaa cagaatttgt    180

gataaatcta tgatcaagaa aagatacatc catttgactg aagaaatgtt ggaagaacat    240

ccaaacatcg gtgcttacat ggctccatct ttgaacatca gacaagaaat catcactgct    300

gaagttccaa agttgggtaa agaagctgct ttgaaagctt tgaaagaatg gggtcaacca    360

aaatctaaaa ttactcattt ggttttctgt actacttctg gtgttgaaat gccaggtgct    420

gattataaat tggctaattt gttgggtttg gaaacttctg ttagaagagt tatgttgtat    480

catcaaggtt gttatgctgg tggtactgtt ttgagaactg ctaaagattt ggctgaaaat    540

aatgctggtg ctagagtttt ggttgtttgt tctgaaatta ctgttgttac ttttagaggt    600

ccatctgaag atgctttgga ttctttggtt ggtcaagctt tgtttggtga cggttctgct    660

gctgttattg ttggttctga tccagatatt tctattgaaa gaccattgtt tcaattggtt    720

tctgctgctc aaacttttat tccaaattct gctggtgcta ttgctggtaa tttgagagaa    780

gttggtttga ctttccattt gtggccaaac gttccaactt tgatctctga aaacatcgaa    840

aactgtttga ctaaggcttt cgatccaatc ggtatctctg attggaactc tttgttttgg    900

attgctcatc caggtggtcc agctattttg gatgctgttg aagctaaagt tggtttggat    960

aagcaaaagt tgaaggctac tagacatatc ttgtctgaat acggtaacat gtcttctgct   1020

tgtgttttgt ttattttgga tgaaatgaga aagaaatctt tgaaggaagg taaaactact   1080

actggtgaag gtttggattg ggtgttttg tttggttttg gtccaggttt gactattgaa   1140

actgttgttt tgcattctgt tggtactgat tctaattaa                          1179
```

<210> SEQ ID NO 141
<211> LENGTH: 37
<212> TYPE: DNA
<213> ORGANISM: Artificial Sequence
<220> FEATURE:
<223> OTHER INFORMATION: Synthetic oligonucleotide

<400> SEQUENCE: 141

```
ggcccgggcg tcgacatggc ttctgttgaa gaaatta                              37
```

<210> SEQ ID NO 142
<211> LENGTH: 37
<212> TYPE: DNA
<213> ORGANISM: Artificial Sequence
<220> FEATURE:
<223> OTHER INFORMATION: Synthetic oligonucleotide

<400> SEQUENCE: 142
ccaagcttac tcgagtcatt aattagaatc agtacca 37

<210> SEQ ID NO 143
<211> LENGTH: 33
<212> TYPE: DNA
<213> ORGANISM: Artificial Sequence
<220> FEATURE:
<223> OTHER INFORMATION: Synthetic oligonucleotide

<400> SEQUENCE: 143
ctaaagggcg gccgcatggc atccgtagag gag 33

<210> SEQ ID NO 144
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 144
tccatcgata ctagttcatt agttagtgac agttg 35

<210> SEQ ID NO 145
<211> LENGTH: 48
<212> TYPE: DNA
<213> ORGANISM: Artificial Sequence
<220> FEATURE:
<223> OTHER INFORMATION: Synthetic oligonucleotide

<400> SEQUENCE: 145
ctctacggat gccatgaatt ctctagaatc cgtcgaaact aagttctg 48

<210> SEQ ID NO 146
<211> LENGTH: 49
<212> TYPE: DNA
<213> ORGANISM: Artificial Sequence
<220> FEATURE:
<223> OTHER INFORMATION: Synthetic oligonucleotide

<400> SEQUENCE: 146
ttcaacagaa gccatggatc ctctagaaaa cttagattag attgctatg 49

<210> SEQ ID NO 147
<211> LENGTH: 40
<212> TYPE: DNA
<213> ORGANISM: Artificial Sequence
<220> FEATURE:
<223> OTHER INFORMATION: Synthetic oligonucleotide

<400> SEQUENCE: 147
gcaatggatc agttacgtta tatcttcgag cgtcccaaaa 40

<210> SEQ ID NO 148
<211> LENGTH: 39
<212> TYPE: DNA
<213> ORGANISM: Artificial Sequence
<220> FEATURE:
<223> OTHER INFORMATION: Synthetic oligonucleotide

<400> SEQUENCE: 148
ataacgtaac tgatccattg cttcctcgct cactgactc 39

<210> SEQ ID NO 149
<211> LENGTH: 33
<212> TYPE: DNA
<213> ORGANISM: Saccharomyces cerevisiae

<400> SEQUENCE: 149
tttcaaagaa tacgtttacc gacatttggg cgc 33

<210> SEQ ID NO 150
<211> LENGTH: 37
<212> TYPE: DNA
<213> ORGANISM: Saccharomyces cerevisiae

<400> SEQUENCE: 150
ttcaatttgg tccatacagt ttgtttttct taatatc 37

<210> SEQ ID NO 151
<211> LENGTH: 34
<212> TYPE: DNA
<213> ORGANISM: Saccharomyces cerevisiae

<400> SEQUENCE: 151
actaaagggc ggccgatgtc agagtctcca atgt 34

<210> SEQ ID NO 152
<211> LENGTH: 37
<212> TYPE: DNA
<213> ORGANISM: Saccharomyces cerevisiae

<400> SEQUENCE: 152
taagagctca gatctctact tcttatttac ctctctt 37

<210> SEQ ID NO 153
<211> LENGTH: 36
<212> TYPE: DNA
<213> ORGANISM: Saccharomyces cerevisiae

<400> SEQUENCE: 153
ggcccgggcg tcgacatgga ttttacaaag ccagaa 36

<210> SEQ ID NO 154
<211> LENGTH: 36
<212> TYPE: DNA
<213> ORGANISM: Saccharomyces cerevisiae

<400> SEQUENCE: 154
ccaagcttac tcgagtcatt cttccaatct tctcaa 36

<210> SEQ ID NO 155
<211> LENGTH: 38
<212> TYPE: DNA
<213> ORGANISM: Schizosaccharomyces pombe

<400> SEQUENCE: 155
caagataaac gaaggcaaag atgggtagga gggctttt 38

<210> SEQ ID NO 156
<211> LENGTH: 52
<212> TYPE: DNA

```
<213> ORGANISM: Schizosaccharomyces pombe

<400> SEQUENCE: 156

atgagacaaa gaagaaaacc aatttttaca agccaacact cccttcgtgc tt              52


<210> SEQ ID NO 157
<211> LENGTH: 55
<212> TYPE: DNA
<213> ORGANISM: Artificial Sequence
<220> FEATURE:
<223> OTHER INFORMATION: Synthetic oligonucleotide

<400> SEQUENCE: 157

tcttctttgt ctcattttgt tattcatttg tagtgacacc gattatttaa agctg          55


<210> SEQ ID NO 158
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 158

ctttgccttc gtttatcttg                                                  20


<210> SEQ ID NO 159
<211> LENGTH: 41
<212> TYPE: DNA
<213> ORGANISM: Artificial Sequence
<220> FEATURE:
<223> OTHER INFORMATION: Synthetic oligonucleotide

<400> SEQUENCE: 159

gcaatggcgg ccgcttacgt tatcttcctc gctcactgac t                          41


<210> SEQ ID NO 160
<211> LENGTH: 44
<212> TYPE: DNA
<213> ORGANISM: Artificial Sequence
<220> FEATURE:
<223> OTHER INFORMATION: Synthetic oligonucleotide

<400> SEQUENCE: 160

ataacgtaag cggccgccat tgcattggag acttgaccaa acct                       44


<210> SEQ ID NO 161
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 161

tgacaccgat tatttaaagc tgc                                              23


<210> SEQ ID NO 162
<211> LENGTH: 36
<212> TYPE: DNA
<213> ORGANISM: Artificial Sequence
<220> FEATURE:
<223> OTHER INFORMATION: Synthetic oligonucleotide

<400> SEQUENCE: 162

caagataaac gaaggatggg taaggaaaag actcac                                36
```

<210> SEQ ID NO 163
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 163
gcagctttaa ataatcggtt agaaaaactc atcgagcatc aaatg 45

<210> SEQ ID NO 164
<211> LENGTH: 41
<212> TYPE: DNA
<213> ORGANISM: Artificial Sequence
<220> FEATURE:
<223> OTHER INFORMATION: Synthetic oligonucleotide

<400> SEQUENCE: 164
aattggagct ccaccgcggc ttcgagcgtc ccaaaacctt c 41

<210> SEQ ID NO 165
<211> LENGTH: 38
<212> TYPE: DNA
<213> ORGANISM: Artificial Sequence
<220> FEATURE:
<223> OTHER INFORMATION: Synthetic oligonucleotide

<400> SEQUENCE: 165
gcttgatatc gaattcgagc gacctcatgc tatacctg 38

<210> SEQ ID NO 166
<211> LENGTH: 40
<212> TYPE: DNA
<213> ORGANISM: Artificial Sequence
<220> FEATURE:
<223> OTHER INFORMATION: Synthetic oligonucleotide

<400> SEQUENCE: 166
ctagtggatc ccccgggttg gagcgacctc atgctatacc 40

<210> SEQ ID NO 167
<211> LENGTH: 42
<212> TYPE: DNA
<213> ORGANISM: Artificial Sequence
<220> FEATURE:
<223> OTHER INFORMATION: Synthetic oligonucleotide

<400> SEQUENCE: 167
gaattcctgc agcccgggcg agcgtcccaa aaccttctca ag 42

<210> SEQ ID NO 168
<211> LENGTH: 37
<212> TYPE: DNA
<213> ORGANISM: Artificial Sequence
<220> FEATURE:
<223> OTHER INFORMATION: Synthetic oligonucleotide

<400> SEQUENCE: 168
ggcgaagaat tgttaattaa gagctctgat cttatcg 37

<210> SEQ ID NO 169
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 169
ggcgcagcaa gtcgacggcg ag 22

<210> SEQ ID NO 170
<211> LENGTH: 40
<212> TYPE: DNA
<213> ORGANISM: Artificial Sequence
<220> FEATURE:
<223> OTHER INFORMATION: Synthetic oligonucleotide

<400> SEQUENCE: 170
gggaacaaaa gctgggtacc ctgtggataa ccgtattacc 40

<210> SEQ ID NO 171
<211> LENGTH: 39
<212> TYPE: DNA
<213> ORGANISM: Artificial Sequence
<220> FEATURE:
<223> OTHER INFORMATION: Synthetic oligonucleotide

<400> SEQUENCE: 171
aattggagct ccaccgcggg agcgacctca tgctatacc 39

<210> SEQ ID NO 172
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 172
gaggagaact tctagtatat tctgtatacc 30

<210> SEQ ID NO 173
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 173
gaggatatag gaatccacaa aaggg 25

<210> SEQ ID NO 174
<211> LENGTH: 38
<212> TYPE: DNA
<213> ORGANISM: Artificial Sequence
<220> FEATURE:
<223> OTHER INFORMATION: Synthetic oligonucleotide

<400> SEQUENCE: 174
atctatgaat aacatataaa acgaaaagag gaataatc 38

<210> SEQ ID NO 175
<211> LENGTH: 31
<212> TYPE: DNA
<213> ORGANISM: Artificial Sequence
<220> FEATURE:
<223> OTHER INFORMATION: Synthetic oligonucleotide

<400> SEQUENCE: 175
cttattacat tatcaatcct tgcatttcag c 31

<210> SEQ ID NO 176
<211> LENGTH: 8402

```
<212> TYPE: DNA
<213> ORGANISM: Artificial Sequence
<220> FEATURE:
<223> OTHER INFORMATION: Yeast vector Rho0021

<400> SEQUENCE: 176

tcgcgcgttt cggtgatgac ggtgaaaacc tctgacacat gcagctcccg gagacggtca     60

cagcttgtct gtaagcggat gccgggagca gacaagcccg tcagggcgcg tcagcgggtg    120

ttggcgggtg tcggggctgg cttaactatg cggcatcaga gcagattgta ctgagagtgc    180

accatatcga ctacgtcgta aggccgtttc tgacagagta aaattcttga gggaactttc    240

accattatgg gaaatgcttc aagaaggtat tgacttaaac tccatcaaat ggtcaggtca    300

ttgagtgttt tttatttgtt gtattttttt tttttagag aaaatcctcc aatatcaaat    360

taggaatcgt agtttcatga ttttctgtta cacctaactt tttgtgtggt gccctcctcc    420

ttgtcaatat taatgttaaa gtgcaattct ttttccttat cacgttgagc cattagtatc    480

aatttgctta cctgtattcc tttactatcc tcctttttct ccttcttgat aaatgtatgt    540

agattgcgta tatagtttcg tctaccctat gaacatattc cattttgtaa tttcgtgtcg    600

tttctattat gaatttcatt tataaagttt atgtacaaat atcataaaaa aagagaatct    660

ttttaagcaa ggattttctt aacttcttcg gcgacagcat caccgacttc ggtggtactg    720

ttggaaccac ctaaatcacc agttctgata cctgcatcca aaaccttttt aactgcatct    780

tcaatggcct taccttcttc aggcaagttc aatgacaatt tcaacatcat tgcagcagac    840

aagatagtgg cgatagggtc aaccttattc tttggcaaat ctggagcaga accgtggcat    900

ggttcgtaca aaccaaatgc ggtgttcttg tctggcaaag aggccaagga cgcagatggc    960

aacaaaccca aggaacctgg gataacggag gcttcatcgg agatgatatc accaaacatg   1020

ttgctggtga ttataatacc atttaggtgg gttgggttct taactaggat catggcggca   1080

gaatcaatca attgatgttg aaccttcaat gtagggaatt cgttcttgat ggtttcctcc   1140

acagtttttc tccataatct tgaagaggcc aaaagattag ctttatccaa ggaccaaata   1200

ggcaatggtg gctcatgttg tagggccatg aaagcggcca ttcttgtgat tctttgcact   1260

tctggaacgg tgtattgttc actatcccaa gcgacaccat caccatcgtc ttcctttctc   1320

ttaccaaagt aaatacctcc cactaattct ctgacaacaa cgaagtcagt acctttagca   1380

aattgtggct tgattggaga taagtctaaa agagagtcgg atgcaaagtt acatggtctt   1440

aagttggcgt acaattgaag ttctttacgg atttttagta aaccttgttc aggtctaaca   1500

ctaccggtac cccatttagg accacccaca gcacctaaca aaacggcatc agccttcttg   1560

gaggcttcca gcgcctcatc tggaagtgga acacctgtag catcgatagc agcaccacca   1620

attaaatgat tttcgaaatc gaacttgaca ttggaacgaa catcagaaat agctttaaga   1680

accttaatgg cttcggctgt gatttcttga ccaacgtggt cacctggcaa aacgacgatc   1740

ttcttagggg cagacattag aatggtatat ccttgaaata tatatatata tattgctgaa   1800

atgtaaaagg taagaaaagt tagaaagtaa gacgattgct aaccacctat tggaaaaaac   1860

aataggtcct taaataatat tgtcaacttc aagtattgtg atgcaagcat ttagtcatga   1920

acgcttctct attctatatg aaaagccggt tccggcgctc tcacctttcc tttttctccc   1980

aatttttcag ttgaaaaagg tatatgcgtc aggcgacctc tgaaattaac aaaaaatttc   2040

cagtcatcga atttgattct gtgcgatagc gcccctgtgt gttctcgtta tgttgaggaa   2100

aaaaataatg gttgctaaga gattcgaact cttgcatctt acgatacctg agtattccca   2160
```

```
cagttaactg cggtcaagat atttcttgaa tcaggcgcct tagaccgctc ggccaaacaa   2220
ccaattactt gttgagaaat agagtataat tatcctataa atataacgtt tttgaacaca   2280
catgaacaag gaagtacagg acaattgatt ttgaagagaa tgtggatttt gatgtaattg   2340
ttgggattcc atttttaata aggcaataat attaggtatg tagatatact agaagttctc   2400
ctcgaccgtc gatatgcggt gtgaaatacc gcacagatgc gtaaggagaa aataccgcat   2460
caggaaattg taaacgttaa tattttgtta aaattcgcgt taaatttttg ttaaatcagc   2520
tcatttttta accaataggc cgaaatcggc aaaatccctt ataaatcaaa agaatagacc   2580
gagatagggt tgagtgttgt tccagtttgg aacaagagtc cactattaaa gaacgtggac   2640
tccaacgtca aagggcgaaa aaccgtctat cagggcgatg gcccactacg tgaaccatca   2700
ccctaatcaa gttttttggg gtcgaggtgc cgtaaagcac taaatcggaa ccctaaaggg   2760
agcccccgat ttagagcttg acggggaaag ccggcgaacg tggcgagaaa ggaagggaag   2820
aaagcgaaag gagcgggcgc tagggcgctg gcaagtgtag cggtcacgct gcgcgtaacc   2880
accacacccg ccgcgcttaa tgcgccgcta cagggcgcgt ccattcgcca ttcaggctgc   2940
gcaactgttg ggaagggcga tcggtgcggg cctcttcgct attacgccag ctgaattgga   3000
gcgacctcat gctatacctg agaaagcaac ctgacctaca ggaaagagtt actcaagaat   3060
aagaattttc gttttaaaac ctaagagtca ctttaaaatt tgtatacact tatttttttt   3120
ataacttatt taataataaa aatcataaat cataagaaat tcgcttattt agaagtgtca   3180
acaacgtatc taccaacgat ttgacccttt tccatctttt cgtaaatttc tggcaaggta   3240
gacaagccga caaccttgat tggagacttg accaaacctc tggcgaagaa ttgttaatta   3300
agagctcaga tcttatcgtc gtcatccttg taatccatcg atactagtgc ggccgccctt   3360
tagttctaga aaacttagat tagattgcta tgctttcttt ctaatgagca agaagtaaaa   3420
aaagttgtaa tagaacaaga aaaatgaaac tgaaacttga gaaattgaag accgtttatt   3480
aacttaaata tcaatgggag gtcatcgaaa gagaaaaaaa tcaaaaaaaa aattttcaag   3540
aaaaagaaac gtgataaaaa tttttattgc ctttttcgac gaagaaaaag aaacgaggcg   3600
gtctcttttt tcttttccaa acctttagta cgggtaatta acgacaccct agaggaagaa   3660
agaggggaaa tttagtatgc tgtgcttggg tgttttgaag tggtacggcg atgcgcggag   3720
tccgagaaaa tctggaagag taaaaaagga gtagaaacat tttgaagcta tgagctccag   3780
cttttgttcc ctttagtgag ggttaattgc gcgcttggcg taatcatggt catagctgtt   3840
tcctgtgtga aattgttatc cgctcacaat tccacacaac ataggagccg gaagcataaa   3900
gtgtaaagcc tggggtgcct aatgagtgag gtaactcaca ttaattgcgt tgcgctcact   3960
gcccgctttc cagtcgggaa acctgtcgtg ccagctgcat taatgaatcg gccaacgcgc   4020
ggggagaggc ggtttgcgta ttgggcgctc ttccgagctc agtttatcat tatcaatact   4080
cgccatttca aagaatacgt aaataattaa tagtagtgat tttcctaact ttatttagtc   4140
aaaaaattag ccttttaatt ctgctgtaac ccgtacatgc ccaaaatagg gggcgggtta   4200
cacagaatat ataacatcgt aggtgtctgg gtgaacagtt tattcctggc atccactaaa   4260
tataatggag cccgcttttt aagctggcat ccagaaaaaa aaagaatccc agcaccaaaa   4320
tattgttttc ttcaccaacc atcagttcat aggtccattc tcttagcgca actacagaga   4380
acaggggcac aaacaggcaa aaaacgggca caacctcaat ggagtgatgc aacctgcctg   4440
gagtaaatga tgacacaagg caattgaccc acgcatgtat ctatctcatt ttcttacacc   4500
ttctattacc ttctgctctc tctgatttgg aaaaagctga aaaaaaaggt tgaaaccagt   4560
```

```
tccctgaaat tattccccta cttgactaat aagtatataa agacggtagg tattgattgt   4620
aattctgtaa atctatttct taaacttctt aaattctact tttatagtta gtcttttttt   4680
tagttttaaa acaccagaac ttagtttcga cggattctag actcactata gggcccgggc   4740
gtcgacatgg aacagaagtt gatttccgaa gaagacctcg agtaagcttg gtaccgcggc   4800
tagctaagat ccgctctaac cgaaaaggaa ggagttagac aacctgaagt ctaggtccct   4860
atttattttt ttatagttat gttagtatta agaacgttat ttatatttca aatttttctt   4920
tttttctgt acagacgcgt gtacgcatgt aacattatac tgaaaacctt gcttgagaag   4980
gttttgggac gctcgaagat ccagctgcat taatgaatcg gccaacgcgc ggggagaggc   5040
ggtttgcgta ttgggcgctc ttccgcttcc tcgctcactg actcgctgcg ctcggtcgtt   5100
cggctgcggc gagcggtatc agctcactca aaggcggtaa tacggttatc cacagaatca   5160
ggggataacg caggaaagaa catgtgagca aaaggccagc aaaaggccag gaaccgtaaa   5220
aaggccgcgt tgctggcgtt tttccatagg ctccgccccc ctgacgagca tcacaaaaat   5280
cgacgctcaa gtcagaggtg gcgaaacccg acaggactat aaagatacca ggcgtttccc   5340
cctggaagct ccctcgtgcg ctctcctgtt ccgaccctgc cgcttaccgg atacctgtcc   5400
gcctttctcc cttcgggaag cgtggcgctt tctcatagct cacgctgtag gtatctcagt   5460
tcggtgtagg tcgttcgctc caagctgggc tgtgtgcacg aaccccccgt tcagcccgac   5520
cgctgcgcct tatccggtaa ctatcgtctt gagtccaacc cggtaagaca cgacttatcg   5580
ccactggcag cagccactgg taacaggatt agcagagcga ggtatgtagg cggtgctaca   5640
gagttcttga agtggtggcc taactacggc tacactagaa ggacagtatt tggtatctgc   5700
gctctgctga agccagttac cttcggaaaa agagttggta gctcttgatc cggcaaacaa   5760
accaccgctg gtagcggtgg tttttttgtt tgcaagcagc agattacgcg cagaaaaaaa   5820
ggatctcaag aagatccttt gatcttttct acggggtctg acgctcagtg gaacgaaaac   5880
tcacgttaag ggattttggt catgagatta tcaaaaagga tcttcaccta gatcctttta   5940
aattaaaaat gaagttttaa atcaatctaa agtatatatg agtaaacttg gtctgacagt   6000
taccaatgct taatcagtga ggcacctatc tcagcgatct gtctatttcg ttcatccata   6060
gttgcctgac tccccgtcgt gtagataact acgatacggg agggcttacc atctggcccc   6120
agtgctgcaa tgataccgcg agacccacgc tcaccggctc cagatttatc agcaataaac   6180
cagccagccg gaagggccga gcgcagaagt ggtcctgcaa ctttatccgc ctccatccag   6240
tctattaatt gttgccggga agctagagta agtagttcgc cagttaatag tttgcgcaac   6300
gttgttgcca ttgctacagg catcgtggtg tcacgctcgt cgtttggtat ggcttcattc   6360
agctccggtt cccaacgatc aaggcgagtt acatgatccc ccatgttgtg caaaaaagcg   6420
gttagctcct tcggtcctcc gatcgttgtc agaagtaagt tggccgcagt gttatcactc   6480
atggttatgg cagcactgca taattctctt actgtcatgc catccgtaag atgcttttct   6540
gtgactggtg agtactcaac caagtcattc tgagaatagt gtatgcggcg accgagttgc   6600
tcttgcccgg cgtcaatacg ggataatacc gcgccacata gcagaacttt aaaagtgctc   6660
atcattggaa aacgttcttc ggggcgaaaa ctctcaagga tcttaccgct gttgagatcc   6720
agttcgatgt aacccactcg tgcacccaac tgatcttcag catcttttac tttcaccagc   6780
gtttctgggt gagcaaaaac aggaaggcaa aatgccgcaa aaaagggaat aagggcgaca   6840
cggaaatgtt gaatactcat actcttcctt tttcaatatt attgaagcat ttatcaggt   6900
```

```
tattgtctca tgagcggata catatttgaa tgtatttaga aaaataaaca aataggggtt   6960
ccgcgcacat ttccccgaaa agtgccacct gaacgaagca tctgtgcttc attttgtaga   7020
acaaaaatgc aacgcgagag cgctaatttt tcaaacaaag aatctgagct gcatttttac   7080
agaacagaaa tgcaacgcga aagcgctatt ttaccaacga agaatctgtg cttcattttt   7140
gtaaaacaaa aatgcaacgc gagagcgcta atttttcaaa caaagaatct gagctgcatt   7200
tttacagaac agaaatgcaa cgcgagagcg ctattttacc aacaaagaat ctatacttct   7260
tttttgttct acaaaaatgc atcccgagag cgctattttt ctaacaaagc atcttagatt   7320
actttttttc tcctttgtgc gctctataat gcagtctctt gataactttt tgcactgtag   7380
gtccgttaag gttagaagaa ggctactttg gtgtctattt tctcttccat aaaaaaagcc   7440
tgactccact tcccgcgttt actgattact agcgaagctg cgggtgcatt ttttcaagat   7500
aaaggcatcc ccgattatat tctataccga tgtggattgc gcatactttg tgaacagaaa   7560
gtgatagcgt tgatgattct tcattggtca gaaaattatg aacggtttct tctattttgt   7620
ctctatatac tacgtatagg aaatgtttac attttcgtat tgttttcgat tcactctatg   7680
aatagttctt actacaattt ttttgtctaa agagtaatac tagagataaa cataaaaaat   7740
gtagaggtcg agtttagatg caagttcaag gagcgaaagg tggatgggta ggttatatag   7800
ggatatagca cagagatata tagcaaagag atacttttga gcaatgtttg tggaagcggt   7860
attcgcaata ttttagtagc tcgttacagt ccggtgcgtt tttggttttt tgaaagtgcg   7920
tcttcagagc gcttttggtt ttcaaaagcg ctctgaagtt cctatacttt ctagagaata   7980
ggaacttcgg aataggaact tcaaagcgtt tccgaaaacg agcgcttccg aaaatgcaac   8040
gcgagctgcg cacatacagc tcactgttca cgtcgcacct atatctgcgt gttgcctgta   8100
tatatatata catgagaaga acggcatagt gcgtgtttat gcttaaatgc gtacttatat   8160
gcgtctattt atgtaggatg aaaggtagtc tagtacctcc tgtgatatta tcccattcca   8220
tgcggggtat cgtatgcttc cttcagcact accctttagc tgttctatat gctgccactc   8280
ctcaattgga ttagtctcat ccttcaatgc tatcatttcc tttgatattg gatcatacta   8340
agaaaccatt attatcatga cattaaccta taaaaatagg cgtatcacga ggccctttcg   8400
tc                                                                  8402
```

<210> SEQ ID NO 177
<211> LENGTH: 10220
<212> TYPE: DNA
<213> ORGANISM: Artificial Sequence
<220> FEATURE:
<223> OTHER INFORMATION: Yeast vector Rho0039

<400> SEQUENCE: 177

```
tcgcgcgttt cggtgatgac ggtgaaaacc tctgacacat gcagctcccg gagacggtca     60
cagcttgtct gtaagcggat gccgggagca gacaagcccg tcagggcgcg tcagcgggtg    120
ttggcgggtg tcggggctgg cttaactatg cggcatcaga gcagattgta ctgagagtgc    180
accatatcga ctacgtcgta aggccgtttc tgacagagta aaattcttga gggaactttc    240
accattatgg gaaatgcttc aagaaggtat tgacttaaac tccatcaaat ggtcaggtca    300
ttgagtgttt tttatttgtt gtattttttt ttttttagag aaaatcctcc aatatcaaat    360
taggaatcgt agtttcatga ttttctgtta cacctaactt tttgtgtggt gccctcctcc    420
ttgtcaatat taatgttaaa gtgcaattct ttttccttat cacgttgagc cattagtatc    480
aatttgctta cctgtattcc tttactatcc tcctttttct ccttcttgat aaatgtatgt    540
```

```
agattgcgta tatagtttcg tctaccctat gaacatattc cattttgtaa tttcgtgtcg    600
tttctattat gaatttcatt tataaagttt atgtacaaat atcataaaaa aagagaatct    660
ttttaagcaa ggattttctt aacttcttcg gcgacagcat caccgacttc ggtggtactg    720
ttggaaccac ctaaatcacc agttctgata cctgcatcca aaaccttttt aactgcatct    780
tcaatggcct taccttcttc aggcaagttc aatgacaatt tcaacatcat tgcagcagac    840
aagatagtgg cgatagggtc aaccttattc tttggcaaat ctggagcaga accgtggcat    900
ggttcgtaca aaccaaatgc ggtgttcttg tctggcaaag aggccaagga cgcagatggc    960
aacaaaccca aggaacctgg gataacggag gcttcatcgg agatgatatc accaaacatg   1020
ttgctggtga ttataatacc atttaggtgg gttgggttct taactaggat catggcggca   1080
gaatcaatca attgatgttg aaccttcaat gtagggaatt cgttcttgat ggtttcctcc   1140
acagtttttc tccataatct tgaagaggcc aaaagattag ctttatccaa ggaccaaata   1200
ggcaatggtg gctcatgttg tagggccatg aaagcggcca ttcttgtgat tctttgcact   1260
tctggaacgg tgtattgttc actatcccaa gcgacaccat caccatcgtc ttcctttctc   1320
ttaccaaagt aaatacctcc cactaattct ctgacaacaa cgaagtcagt acctttagca   1380
aattgtggct tgattggaga taagtctaaa agagagtcgg atgcaaagtt acatggtctt   1440
aagttggcgt acaattgaag ttctttacgg atttttagta aaccttgttc aggtctaaca   1500
ctaccggtac cccatttagg accacccaca gcacctaaca aaacggcatc agccttcttg   1560
gaggcttcca gcgcctcatc tggaagtgga acacctgtag catcgatagc agcaccacca   1620
attaaatgat tttcgaaatc gaacttgaca ttggaacgaa catcagaaat agctttaaga   1680
accttaatgg cttcggctgt gatttcttga ccaacgtggt cacctggcaa aacgacgatc   1740
ttcttagggg cagacattag aatggtatat ccttgaaata tatatatata tattgctgaa   1800
atgtaaaagg taagaaaagt tagaaagtaa gacgattgct aaccacctat tggaaaaaac   1860
aataggtcct taaataatat tgtcaacttc aagtattgtg atgcaagcat ttagtcatga   1920
acgcttctct attctatatg aaaagccggt tccggcgctc tcacctttcc tttttctccc   1980
aatttttcag ttgaaaaagg tatatgcgtc aggcgacctc tgaaattaac aaaaaatttc   2040
cagtcatcga atttgattct gtgcgatagc gcccctgtgt gttctcgtta tgttgaggaa   2100
aaaaataatg gttgctaaga gattcgaact cttgcatctt acgatacctg agtattccca   2160
cagttaactg cggtcaagat atttcttgaa tcaggcgcct tagaccgctc ggccaaacaa   2220
ccaattactt gttgagaaat agagtataat tatcctataa atataacgtt tttgaacaca   2280
catgaacaag gaagtacagg acaattgatt ttgaagagaa tgtggatttt gatgtaattg   2340
ttgggattcc atttttaata aggcaataat attaggtatg tagatatact agaagttctc   2400
ctcgaccgtc gatatgcggt gtgaaatacc gcacagatgc gtaaggagaa aataccgcat   2460
caggaaattg taaacgttaa tattttgtta aaattcgcgt taaatttttg ttaaatcagc   2520
tcatttttta accaataggc cgaaatcggc aaaatccctt ataaatcaaa agaatagacc   2580
gagatagggt tgagtgttgt tccagtttgg aacaagagtc cactattaaa gaacgtggac   2640
tccaacgtca aagggcgaaa aaccgtctat cagggcgatg gcccactacg tgaaccatca   2700
ccctaatcaa gttttttggg gtcgaggtgc cgtaaagcac taaatcggaa ccctaaaggg   2760
agcccccgat ttagagcttg acggggaaag ccggcgaacg tggcgagaaa ggaagggaag   2820
aaagcgaaag gagcgggcgc tagggcgctg gcaagtgtag cggtcacgct gcgcgtaacc   2880
```

```
accacacccg ccgcgcttaa tgcgccgcta cagggcgcgt ccattcgcca ttcaggctgc   2940
gcaactgttg ggaagggcga tcggtgcggg cctcttcgct attacgccag ctgaattgga   3000
gcgacctcat gctatacctg agaaagcaac ctgacctaca ggaaagagtt actcaagaat   3060
aagaattttc gttttaaaac ctaagagtca ctttaaaatt tgtatacact tattttttt    3120
ataacttatt taataataaa aatcataaat cataagaaat tcgcttattt agaagtgtca   3180
acaacgtatc taccaacgat ttgacccttt tccatctttt cgtaaatttc tggcaaggta   3240
gacaagccga caaccttgat tggagacttg accaaacctc tggcgaagaa ttgttaatta   3300
agagctcaga tctctacttc ttatttacct ctcttctttg tctcactgca gcagccaact   3360
ttctaagaac atcttcagta gtttcccatc caatacaggc atctgtaatg gaaacaccgt   3420
atttcaagcc tgccttgccc tcagcaggaa taccttgatt tccttcattg atattcgatt   3480
cgatcatgac accagttatt gcgttttcac cgtttgcgat ttgttcacaa acaacgtcgt   3540
taactttagg ctgatttctg aaatccttat tactattgcc atgagagtag tcaatcatta   3600
aaccattcga accagcaggt aattgtgcct tagcctcagc gacggattta gcgtcataat   3660
tggtaccttt ctttccgcct cttaatataa caaagcaatg ttcgttgcct tttgtagttg   3720
tgattgctgc aacaccgtgt aaagttacac ccatgaaatg atgagaatgg gcagctgctt   3780
gacaggcatc cacagcaaca tttagagtac cgtcggtacc atttttgaag ccaacaggga   3840
aagacaaacc agaggccaat tctctatgaa gttgagactc cgttgttcta gcgcctattg   3900
cgccgaaact aacaagatcg gctaggtatt gagggctgat ggtatctaac atttctgaac   3960
caataggtag accgatgttg gtcaaattga cgaaaagttg tctagccgat tgcaatccct   4020
tgttaatatt gaaggtgtta ttaacatcag gatcgttaat taaacctttc caaccaacag   4080
tagttcttgg tttttccagg taagctctca ttattatcga cagatctcct ttcaattcat   4140
cgctcaactt tttcaatctc aaagcatatt cttgggcggc ttccaaatca tgaattgaac   4200
atggtcctac tatcactagc actctatcat ctttaccagt aatgatatca atagcttctc   4260
tcctacctct tttggcagtc tctaaggaag taggagtggc ggggatttgc acttgtagta   4320
atgctggact tgctaatgga tcatagccta gtattctcac gtcttcttca gcaccttgat   4380
taaccttagg cataccattg gcggcaaaca ttggagactc tgacatcggc cgccctttag   4440
ttctagaaaa cttagattag attgctatgc tttctttcta atgagcaaga agtaaaaaaa   4500
gttgtaatag aacaagaaaa atgaaactga aacttgagaa attgaagacc gtttattaac   4560
ttaaatatca atgggaggtc atcgaaagag aaaaaaatca aaaaaaaaat tttcaagaaa   4620
aagaaacgtg ataaaaattt ttattgcctt tttcgacgaa gaaaaagaaa cgaggcggtc   4680
tctttttct tttccaaacc tttagtacgg gtaattaacg acaccctaga ggaagaaaga    4740
ggggaaattt agtatgctgt gcttgggtgt tttgaagtgg tacggcgatg cgcggagtcc   4800
gagaaaatct ggaagagtaa aaaaggagta gaaacatttt gaagctatga gctccagctt   4860
ttgttccctt tagtgagggt taattgcgcg cttggcgtaa tcatggtcat agctgtttcc   4920
tgtgtgaaat tgttatccgc tcacaattcc acacaacata ggagccggaa gcataaagtg   4980
taaagcctgg ggtgcctaat gagtgaggta actcacatta attgcgttgc gctcactgcc   5040
cgctttccag tcgggaaacc tgtcgtgcca gctgcattaa tgaatcggcc aacgcgcggg   5100
gagaggcggt ttgcgtattg ggcgctcttc cgagctcagt ttatcattat caatactcgc   5160
catttcaaag aatacgtaaa taattaatag tagtgatttt cctaacttta tttagtcaaa   5220
aaattagcct tttaattctg ctgtaacccg tacatgccca aaataggggg cgggttacac   5280
```

```
agaatatata acatcgtagg tgtctgggtg aacagtttat tcctggcatc cactaaatat   5340
aatggagccc gctttttaag ctggcatcca gaaaaaaaaa gaatcccagc accaaaatat   5400
tgttttcttc accaaccatc agttcatagg tccattctct tagcgcaact acagagaaca   5460
ggggcacaaa caggcaaaaa acgggcacaa cctcaatgga gtgatgcaac ctgcctggag   5520
taaatgatga cacaaggcaa ttgacccacg catgtatcta tctcattttc ttacaccttc   5580
tattaccttc tgctctctct gatttggaaa aagctgaaaa aaaaggttga aaccagttcc   5640
ctgaaattat tcccctactt gactaataag tatataaaga cggtaggtat tgattgtaat   5700
tctgtaaatc tatttcttaa acttcttaaa ttctactttt atagttagtc tttttttttag   5760
ttttaaaaca ccagaactta gtttcgacgg attctagact cactataggg cccgggcgtc   5820
gacatggatt ttacaaagcc agaaacggtt ttaaacctac aaaatattag agatgaattg   5880
gtgaggatgg aagacagtat tatttttaaa ttcatagaaa gaagccattt tgccacatgc   5940
ccaagtgttt acgaagctaa tcaccctgga ttagagattc caaattttaa aggctcgttt   6000
ttggactggg cattgagtaa tcttgagata gcacattcta ggatcagaag atttgaatcc   6060
ccagatgaga ccccattctt cccagacaag attcaaaaat catttcttcc ttcaattaat   6120
taccctcaaa tcttggcacc atatgctcca gaagtaaact acaatgataa gataaagaag   6180
gtttatattg aaaagataat accccctgata tctaagaggg atggagatga caagaacaat   6240
ttttcatccg ttgcaactag agacattgag tgtctacaat cgttgtctag aagaatacat   6300
tttggtaaat ttgttgcaga ggctaaattt caatctgata tacctttgta cactaaatta   6360
attaaaagta aggatgtaga aggaattatg aaaaatataa caaattctgc tgtggaagag   6420
aaaatcttag aaagattgac taaaaaggct gaagtttacg gtgttgatcc aaccaacgaa   6480
tctggtgaaa ggaggattac tcccgaatat ttggttaaaa tatataaaga aattgtaata   6540
cccattacaa aagaagtaga ggttgaatat ctattgagaa gattggaaga atgactcgag   6600
taagcttggt accgcggcta gctaagatcc gctctaaccg aaaaggaagg agttagacaa   6660
cctgaagtct aggtccctat ttattttttt atagttatgt tagtattaag aacgttattt   6720
atatttcaaa tttttctttt ttttctgtac agacgcgtgt acgcatgtaa cattatactg   6780
aaaaccttgc ttgagaaggt tttgggacgc tcgaagatcc agctgcatta atgaatcggc   6840
caacgcgcgg ggagaggcgg tttgcgtatt gggcgctctt ccgcttcctc gctcactgac   6900
tcgctgcgct cggtcgttcg gctgcggcga gcggtatcag ctcactcaaa ggcggtaata   6960
cggttatcca cagaatcagg ggataacgca ggaaagaaca tgtgagcaaa aggccagcaa   7020
aaggccagga accgtaaaaa ggccgcgttg ctggcgtttt tccataggct ccgcccccct   7080
gacgagcatc acaaaaatcg acgctcaagt cagaggtggc gaaacccgac aggactataa   7140
agataccagg cgtttccccc tggaagctcc ctcgtgcgct ctcctgttcc gaccctgccg   7200
cttaccggat acctgtccgc ctttctccct tcgggaagcg tggcgctttc tcatagctca   7260
cgctgtaggt atctcagttc ggtgtaggtc gttcgctcca agctgggctg tgtgcacgaa   7320
ccccccgttc agcccgaccg ctgcgcctta tccggtaact atcgtcttga gtccaacccg   7380
gtaagacacg acttatcgcc actggcagca gccactggta acaggattag cagagcgagg   7440
tatgtaggcg gtgctacaga gttcttgaag tggtggccta actacggcta cactagaagg   7500
acagtatttg gtatctgcgc tctgctgaag ccagttacct tcggaaaaag agttggtagc   7560
tcttgatccg gcaaacaaac caccgctggt agcggtggtt tttttgtttg caagcagcag   7620
```

```
attacgcgca gaaaaaaagg atctcaagaa gatcctttga tcttttctac ggggtctgac   7680
gctcagtgga acgaaaactc acgttaaggg attttggtca tgagattatc aaaaaggatc   7740
ttcacctaga tccttttaaa ttaaaaatga agttttaaat caatctaaag tatatatgag   7800
taaacttggt ctgacagtta ccaatgctta atcagtgagg cacctatctc agcgatctgt   7860
ctatttcgtt catccatagt tgcctgactc cccgtcgtgt agataactac gatacgggag   7920
ggcttaccat ctggccccag tgctgcaatg ataccgcgag acccacgctc accggctcca   7980
gatttatcag caataaacca gccagccgga agggccgagc gcagaagtgg tcctgcaact   8040
ttatccgcct ccatccagtc tattaattgt tgccgggaag ctagagtaag tagttcgcca   8100
gttaatagtt tgcgcaacgt tgttgccatt gctacaggca tcgtggtgtc acgctcgtcg   8160
tttggtatgg cttcattcag ctccggttcc caacgatcaa ggcgagttac atgatccccc   8220
atgttgtgca aaaaagcggt tagctccttc ggtcctccga tcgttgtcag aagtaagttg   8280
gccgcagtgt tatcactcat ggttatggca gcactgcata attctcttac tgtcatgcca   8340
tccgtaagat gcttttctgt gactggtgag tactcaacca agtcattctg agaatagtgt   8400
atgcggcgac cgagttgctc ttgcccggcg tcaatacggg ataataccgc gccacatagc   8460
agaactttaa aagtgctcat cattggaaaa cgttcttcgg ggcgaaaact ctcaaggatc   8520
ttaccgctgt tgagatccag ttcgatgtaa cccactcgtg cacccaactg atcttcagca   8580
tcttttactt tcaccagcgt ttctgggtga gcaaaaacag gaaggcaaaa tgccgcaaaa   8640
aagggaataa gggcgacacg gaaatgttga atactcatac tcttcctttt tcaatattat   8700
tgaagcattt atcagggtta ttgtctcatg agcggataca tatttgaatg tatttagaaa   8760
aataaacaaa taggggttcc gcgcacattt ccccgaaaag tgccacctga acgaagcatc   8820
tgtgcttcat tttgtagaac aaaaatgcaa cgcgagagcg ctaatttttc aaacaaagaa   8880
tctgagctgc atttttacag aacagaaatg caacgcgaaa gcgctatttt accaacgaag   8940
aatctgtgct tcatttttgt aaaacaaaaa tgcaacgcga gagcgctaat tttcaaaca    9000
aagaatctga gctgcatttt tacagaacag aaatgcaacg cgagagcgct attttaccaa   9060
caaagaatct atacttcttt tttgttctac aaaaatgcat cccgagagcg ctatttttct   9120
aacaaagcat cttagattac tttttttctc ctttgtgcgc tctataatgc agtctcttga   9180
taactttttg cactgtaggt ccgttaaggt tagaagaagg ctactttggt gtctattttc   9240
tcttccataa aaaaagcctg actccacttc ccgcgtttac tgattactag cgaagctgcg   9300
ggtgcatttt ttcaagataa aggcatcccc gattatattc tataccgatg tggattgcgc   9360
atactttgtg aacagaaagt gatagcgttg atgattcttc attggtcaga aaattatgaa   9420
cggtttcttc tattttgtct ctatatacta cgtataggaa atgtttacat tttcgtattg   9480
ttttcgattc actctatgaa tagttcttac tacaattttt ttgtctaaag agtaatacta   9540
gagataaaca taaaaaatgt agaggtcgag tttagatgca agttcaagga gcgaaaggtg   9600
gatgggtagg ttatataggg atatagcaca gagatatata gcaaagagat acttttgagc   9660
aatgtttgtg gaagcggtat tcgcaatatt ttagtagctc gttacagtcc ggtgcgtttt   9720
tggtttttg aaagtgcgtc ttcagagcgc ttttggtttt caaaagcgct ctgaagttcc    9780
tatactttct agagaatagg aacttcggaa taggaacttc aaagcgtttc cgaaaacgag   9840
cgcttccgaa aatgcaacgc gagctgcgca catacagctc actgttcacg tcgcacctat   9900
atctgcgtgt tgcctgtata tatatataca tgagaagaac ggcatagtgc gtgtttatgc   9960
ttaaatgcgt acttatatgc gtctatttat gtaggatgaa aggtagtcta gtacctcctg  10020
```

```
tgatattatc ccattccatg cggggtatcg tatgcttcct tcagcactac cctttagctg  10080
ttctatatgc tgccactcct caattggatt agtctcatcc ttcaatgcta tcatttcctt  10140
tgatattgga tcatactaag aaaccattat tatcatgaca ttaacctata aaaataggcg  10200
tatcacgagg ccctttcgtc                                              10220
```

<210> SEQ ID NO 178
<211> LENGTH: 9668
<212> TYPE: DNA
<213> ORGANISM: Artificial Sequence
<220> FEATURE:
<223> OTHER INFORMATION: Yeast vector Rho0098

<400> SEQUENCE: 178

```
tcgcgcgttt cggtgatgac ggtgaaaacc tctgacacat gcagctcccg gagacggtca     60
cagcttgtct gtaagcggat gccgggagca gacaagcccg tcagggcgcg tcagcgggtg    120
ttggcgggtg tcggggctgg cttaactatg cggcatcaga gcagattgta ctgagagtgc    180
accataaatt cccgttttaa gagcttggtg agcgctagga gtcactgcca ggtatcgttt    240
gaacacggca ttagtcaggg aagtcataac acagtccttt cccgcaattt tctttttcta    300
ttactcttgg cctcctctag tacactctat atttttttat gcctcggtaa tgattttcat    360
tttttttttt cccctagcgg atgactcttt ttttttctta gcgattggca ttatcacata    420
atgaattata cattatataa agtaatgtga tttcttcgaa gaatatacta aaaaatgagc    480
aggcaagata aacgaaggca aagatgacag agcagaaagc cctagtaaag cgtattacaa    540
atgaaaccaa gattcagatt gcgatctctt taaagggtgg tcccctagcg atagagcact    600
cgatcttccc agaaaaagag gcagaagcag tagcagaaca ggccacacaa tcgcaagtga    660
ttaacgtcca cacaggtata gggtttctgg accatatgat acatgctctg gccaagcatt    720
ccggctggtc gctaatcgtt gagtgcattg gtgacttaca catagacgac catcacacca    780
ctgaagactg cgggattgct ctcggtcaag cttttaaaga ggccctactg gcgcgtggag    840
taaaaaggtt tggatcagga tttgcgcctt tggatgaggc actttccaga gcggtggtag    900
atctttcgaa caggccgtac gcagttgtcg aacttggttt gcaaagggag aaagtaggag    960
atctctcttg cgagatgatc ccgcattttc ttgaaagctt tgcagaggct agcagaatta   1020
ccctccacgt tgattgtctg cgaggcaaga atgatcatca ccgtagtgag agtgcgttca   1080
aggctcttgc ggttgccata agagaagcca cctcgcccaa tggtaccaac gatgttccct   1140
ccaccaaagg tgttcttatg tagtgacacc gattatttaa agctgcagca tacgatatat   1200
atacatgtgt atatatgtat acctatgaat gtcagtaagt atgtatacga acagtatgat   1260
actgaagatg acaaggtaat gcatcattct atacgtgtca ttctgaacga ggcgcgcttt   1320
cctttttttct ttttgctttt tctttttttt tctcttgaac tcgacggatc tatgcggtgt   1380
gaaataccgc acagatgcgt aaggagaaaa taccgcatca ggaaattgta aacgttaata   1440
ttttgttaaa attcgcgtta aatttttgtt aaatcagctc attttttaac caataggccg   1500
aaatcggcaa aatcccttat aaatcaaaag aatagaccga gatagggttg agtgttgttc   1560
cagtttggaa caagagtcca ctattaaaga acgtggactc caacgtcaaa gggcgaaaaa   1620
ccgtctatca gggcgatggc ccactacgtg aaccatcacc ctaatcaagt tttttggggt   1680
cgaggtgccg taaagcacta aatcggaacc ctaaagggag cccccgattt agagcttgac   1740
ggggaaagcc ggcgaacgtg gcgagaaagg aagggaagaa agcgaaagga gcgggcgcta   1800
```

```
gggcgctggc aagtgtagcg gtcacgctgc gcgtaaccac cacacccgcc gcgcttaatg   1860
cgccgctaca gggcgcgtcg cgccattcgc cattcaggct gcgcaactgt tgggaagggc   1920
gatcggtgcg ggcctcttcg ctattacgcc agctgaattg gagcgacctc atgctatacc   1980
tgagaaagca acctgaccta caggaaagag ttactcaaga ataagaattt tcgttttaaa   2040
acctaagagt cactttaaaa tttgtataca cttatttttt ttataactta tttaataata   2100
aaaatcataa atcataagaa attcgcttat ttagaagtgt caacaacgta tctaccaacg   2160
atttgaccct tttccatctt ttcgtaaatt tctggcaagg tagacaagcc gacaaccttg   2220
attggagact tgaccaaacc tctggcgaag aattgttaat taagagctca gatcttatcg   2280
tcgtcatcct tgtaatccat cgatactagt tcattagtta gtgacagttg gaacagagtg   2340
taacaccact gtctcaattg ttaagccagg accgaaacca aatagaacac cccaatctaa   2400
accttctccg gttgtggctt tttcaccctt taaagacttc ttcctcatct catctagaat   2460
gaataaaacg caggcagagc tcatgttgcc atactctgat agaacgtgtc ttgtagcttc   2520
caactttttc ttctctaagt ttagttttgc ctccactgcg tctaaaattg ctggaccacc   2580
tggatgagca atccaaaaca atgagttcca gtcgcttatg cccaatgggt caaaggcttg   2640
agttaagcat ttttcgatgt tttctgaaat taaggttggg acattaggcc acaaatgaaa   2700
agtcaaacca acttctctca agtttcctgc tatggcaccg gcggaatttg gaataaaagt   2760
ttgagcagca gaaactaatt gaaatagtgg tctttcaatg gacacatcag gatcgctgcc   2820
tacaattacg gcggaagatc catcgccaaa caatgcttgt ccgaccaaac tgtctagagc   2880
atcttctgat ggacctctga aagttacgac agtgatttca ctgcagacga ctaaaaccct   2940
agcaccggcg ttattttctg ccaaatcctt agcagttcta agcactgtac ctccggcgta   3000
acaaccttga tgatacaaca taactcttct aacagaggtc tctaatccca ataggtttgc   3060
tagtttataa tcagcacctg gcatttcgac accggaagtt gtacagaaaa ccaaatgtgt   3120
aatcttagat tttggttgtc cccattcctt taaagctttc aaggctgcgt ctctacctag   3180
tctaggtacc tcggctgtta tgatttcttg tctaatattc aaagatggtg ccatatatgc   3240
acctatattt ggatgttcct ctaacatttc ttcagttaga tgtatgtatc ttttctttat   3300
catagattta tcacaaattc tattaaactt tttcttaagt tctgtcatat gttcactttt   3360
agttactctg aaatagtaat cagcgtaatc agattgataa acacagtgat caggggtggc   3420
tgttccaata gccaatatgg ttgctggacc ttttgccctc tgtgcatttc tgaactcctc   3480
tacggatgcc atgaattctc tagaatccgt cgaaactaag ttctggtgtt ttaaaactaa   3540
aaaaaagact aactataaaa gtagaattta agaagtttaa gaaatagatt tacagaatta   3600
caatcaatac ctaccgtctt tatatactta ttagtcaagt aggggaataa tttcagggaa   3660
ctggtttcaa cctttttttt cagctttttc caaatcagag agagcagaag gtaatagaag   3720
gtgtaagaaa atgagataga tacatgcgtg ggtcaattgc cttgtgtcat catttactcc   3780
aggcaggttg catcactcca ttgaggttgt gcccgttttt tgcctgtttg tgcccctgtt   3840
ctctgtagtt gcgctaagag aatggaccta tgaactgatg gttggtgaag aaaacaatat   3900
tttggtgctg ggattctttt tttttctgga tgccagctta aaaagcgggc tccattatat   3960
ttagtggatg ccaggaataa actgttcacc cagacaccta cgatgttata tattctgtgt   4020
aacccgcccc ctattttggg catgtacggg ttacagcaga attaaaaggc taattttttg   4080
actaaataaa gttaggaaaa tcactactat taattattta cgtattcttt gaaatggcga   4140
gtattgataa tgataaactg agctcggaag agcgcccaat acgcaaaccg cctctccccg   4200
```

```
cgcgttggcc gattcattaa tgcagctggc acgacaggtt tcccgactgg aaagcgggca   4260
gtgagcgcaa cgcaattaat gtgagttacc tcactcatta ggcaccccag gctttacact   4320
ttatgcttcc ggctcctatg ttgtgtggaa ttgtgagcgg ataacaattt cacacaggaa   4380
acagctatga ccatgattac gccaagcgcg caattaaccc tcactaaagg gaacaaaagc   4440
tggagctcat agcttcaaaa tgtttctact cctttttttac tcttccagat tttctcggac  4500
tccgcgcatc gccgtaccac ttcaaaacac ccaagcacag catactaaat ttcccctctt   4560
tcttcctcta gggtgtcgtt aattacccgt actaaaggtt tggaaaagaa aaaagagacc   4620
gcctcgtttc tttttcttcg tcgaaaaagg caataaaaat ttttatcacg tttctttttc   4680
ttgaaaattt ttttttgat tttttctct ttcgatgacc tcccattgat atttaagtta     4740
ataaacggtc ttcaatttct caagtttcag tttcattttt cttgttctat tacaactttt   4800
tttacttctt gctcattaga aagaaagcat agcaatctaa tctaagtttt ctagaggatc   4860
catggcttct gttgaagaaa ttagaaatgc tcaaagagct aaaggtccag ctactatttt   4920
ggctattggt actgctactc cagatcattg tgtttaccaa tctgattacg ctgattacta   4980
cttcagagtt actaagtctg aacatatgac tgaattgaag aaaaagttca acagaatttg   5040
tgataaatct atgatcaaga aaagatacat ccatttgact gaagaaatgt tggaagaaca   5100
tccaaacatc ggtgcttaca tggctccatc tttgaacatc agacaagaaa tcatcactgc   5160
tgaagttcca aagttgggta aagaagctgc tttgaaagct ttgaaagaat ggggtcaacc   5220
aaaatctaaa attactcatt tggttttctg tactacttct ggtgttgaaa tgccaggtgc   5280
tgattataaa ttggctaatt tgttgggttt ggaaacttct gttagaagag ttatgttgta   5340
tcatcaaggt tgttatgctg gtggtactgt tttgagaact gctaaagatt tggctgaaaa   5400
taatgctggt gctagagttt tggttgtttg ttctgaaatt actgttgtta cttttagagg   5460
tccatctgaa gatgctttgg attctttggt tggtcaagct ttgtttggtg acggttctgc   5520
tgctgttatt gttggttctg atccagatat ttctattgaa agaccattgt ttcaattggt   5580
ttctgctgct caaactttta ttccaaattc tgctggtgct attgctggta atttgagaga   5640
agttggtttg actttccatt tgtggccaaa cgttccaact ttgatctctg aaaacatcga   5700
aaactgtttg actaaggctt tcgatccaat cggtatctct gattggaact ctttgttttg   5760
gattgctcat ccaggtggtc cagctatttt ggatgctgtt gaagctaaag ttggtttgga   5820
taagcaaaag ttgaaggcta ctagacatat cttgtctgaa tacggtaaca tgtcttctgc   5880
ttgtgttttg tttatttgg atgaaatgag aaagaaatct ttgaaggaag gtaaaactac     5940
tactggtgaa ggtttggatt ggggtgtttt gtttggtttt ggtccaggtt tgactattga   6000
aactgttgtt ttgcattctg ttggtactga ttctaattaa tgactcgagt aagcttggta   6060
ccgcggctag ctaagatccg ctctaaccga aaaggaagga gttagacaac ctgaagtcta   6120
ggtccctatt tattttttta tagttatgtt agtattaaga acgttattta tatttcaaat   6180
ttttcttttt tttctgtaca gacgcgtgta cgcatgtaac attatactga aaaccttgct   6240
tgagaaggtt ttgggacgct cgaagatcca gctgcattaa tgaatcggcc aacgcgcggg   6300
gagaggcggt ttgcgtattg ggcgctcttc cgcttcctcg ctcactgact cgctgcgctc   6360
ggtcgttcgg ctgcggcgag cggtatcagc tcactcaaag gcggtaatac ggttatccac   6420
agaatcaggg gataacgcag gaaagaacat gtgagcaaaa ggccagcaaa aggccaggaa   6480
ccgtaaaaag gccgcgttgc tggcgttttt ccataggctc cgcccccctg acgagcatca   6540
```

```
caaaaatcga cgctcaagtc agaggtggcg aaacccgaca ggactataaa gataccaggc   6600
gtttcccct ggaagctccc tcgtgcgctc tcctgttccg accctgccgc ttaccggata   6660
cctgtccgcc tttctccctt cgggaagcgt ggcgctttct catagctcac gctgtaggta   6720
tctcagttcg gtgtaggtcg ttcgctccaa gctgggctgt gtgcacgaac cccccgttca   6780
gcccgaccgc tgcgccttat ccggtaacta tcgtcttgag tccaacccgg taagacacga   6840
cttatcgcca ctggcagcag ccactggtaa caggattagc agagcgaggt atgtaggcgg   6900
tgctacagag ttcttgaagt ggtggcctaa ctacggctac actagaagga cagtatttgg   6960
tatctgcgct ctgctgaagc cagttacctt cggaaaaaga gttggtagct cttgatccgg   7020
caaacaaacc accgctggta gcggtggttt ttttgtttgc aagcagcaga ttacgcgcag   7080
aaaaaaagga tctcaagaag atcctttgat cttttctacg gggtctgacg ctcagtggaa   7140
cgaaaactca cgttaaggga ttttggtcat gagattatca aaaaggatct tcacctagat   7200
ccttttaaat taaaaatgaa gttttaaatc aatctaaagt atatatgagt aaacttggtc   7260
tgacagttac caatgcttaa tcagtgaggc acctatctca gcgatctgtc tatttcgttc   7320
atccatagtt gcctgactcc ccgtcgtgta gataactacg atacgggagg gcttaccatc   7380
tggccccagt gctgcaatga taccgcgaga cccacgctca ccggctccag atttatcagc   7440
aataaaccag ccagccggaa gggccgagcg cagaagtggt cctgcaactt tatccgcctc   7500
catccagtct attaattgtt gccgggaagc tagagtaagt agttcgccag ttaatagttt   7560
gcgcaacgtt gttgccattg ctacaggcat cgtggtgtca cgctcgtcgt ttggtatggc   7620
ttcattcagc tccggttccc aacgatcaag gcgagttaca tgatccccca tgttgtgcaa   7680
aaaagcggtt agctccttcg gtcctccgat cgttgtcaga agtaagttgg ccgcagtgtt   7740
atcactcatg gttatggcag cactgcataa ttctcttact gtcatgccat ccgtaagatg   7800
cttttctgtg actggtgagt actcaaccaa gtcattctga gaatagtgta tgcggcgacc   7860
gagttgctct tgcccggcgt caatacggga taataccgcg ccacatagca gaactttaaa   7920
agtgctcatc attggaaaac gttcttcggg gcgaaaactc tcaaggatct taccgctgtt   7980
gagatccagt tcgatgtaac ccactcgtgc acccaactga tcttcagcat cttttacttt   8040
caccagcgtt tctgggtgag caaaaacagg aaggcaaaat gccgcaaaaa agggaataag   8100
ggcgacacgg aaatgttgaa tactcatact cttccttttt caatattatt gaagcattta   8160
tcagggttat tgtctcatga gcggatacat atttgaatgt atttagaaaa ataaacaaat   8220
aggggttccg cgcacatttc cccgaaaagt gccacctgaa cgaagcatct gtgcttcatt   8280
ttgtagaaca aaaatgcaac gcgagagcgc taatttttca aacaaagaat ctgagctgca   8340
tttttacaga acagaaatgc aacgcgaaag cgctatttta ccaacgaaga atctgtgctt   8400
catttttgta aaacaaaaat gcaacgcgag agcgctaatt tttcaaacaa agaatctgag   8460
ctgcattttt acagaacaga aatgcaacgc gagagcgcta ttttaccaac aaagaatcta   8520
tacttctttt ttgttctaca aaaatgcatc ccgagagcgc tatttttcta acaaagcatc   8580
ttagattact ttttttctcc tttgtgcgct ctataatgca gtctcttgat aactttttgc   8640
actgtaggtc cgttaaggtt agaagaaggc tactttggtg tctattttct cttccataaa   8700
aaaagcctga ctccacttcc cgcgtttact gattactagc gaagctgcgg gtgcattttt   8760
tcaagataaa ggcatccccg attatattct ataccgatgt ggattgcgca tactttgtga   8820
acagaaagtg atagcgttga tgattcttca ttggtcagaa aattatgaac ggtttcttct   8880
attttgtctc tatatactac gtataggaaa tgtttacatt ttcgtattgt tttcgattca   8940
```

```
ctctatgaat agttcttact acaatttttt tgtctaaaga gtaatactag agataaacat   9000
aaaaaatgta gaggtcgagt ttagatgcaa gttcaaggag cgaaaggtgg atgggtaggt   9060
tatataggga tatagcacag agatatatag caaagagata cttttgagca atgtttgtgg   9120
aagcggtatt cgcaatattt tagtagctcg ttacagtccg gtgcgttttt ggttttttga   9180
aagtgcgtct tcagagcgct tttggttttc aaaagcgctc tgaagttcct atactttcta   9240
gagaatagga acttcggaat aggaacttca aagcgtttcc gaaaacgagc gcttccgaaa   9300
atgcaacgcg agctgcgcac atacagctca ctgttcacgt cgcacctata tctgcgtgtt   9360
gcctgtatat atatatacat gagaagaacg gcatagtgcg tgtttatgct taaatgcgta   9420
cttatatgcg tctatttatg taggatgaaa ggtagtctag tacctcctgt gatattatcc   9480
cattccatgc ggggtatcgt atgcttcctt cagcactacc ctttagctgt tctatatgct   9540
gccactcctc aattggatta gtctcatcct tcaatgctat catttccttt gatattggat   9600
catctaagaa accattatta tcatgacatt aacctataaa aataggcgta tcacgaggcc   9660
ctttcgtc                                                            9668
```

<210> SEQ ID NO 179
<211> LENGTH: 13130
<212> TYPE: DNA
<213> ORGANISM: Artificial Sequence
<220> FEATURE:
<223> OTHER INFORMATION: Plasmid p0160

<400> SEQUENCE: 179

```
tcgcgcgttt cggtgatgac ggtgaaaacc tctgacacat gcagctcccg gagacggtca     60
cagcttgtct gtaagcggat gccgggagca gacaagcccg tcagggcgcg tcagcgggtg    120
ttggcgggtg tcggggctgg cttaactatg cggcatcaga gcagattgta ctgagagtgc    180
accataccac agcttttcaa ttcaattcat catttttttt ttattctttt ttttgatttc    240
ggtttctttg aaattttttt gattcggtaa tctccgaaca gaaggaagaa cgaaggaagg    300
agcacagact tagattggta tatatacgca tatgtagtgt tgaagaaaca tgaaattgcc    360
cagtattctt aacccaactg cacagaacaa aaacctgcag gaaacgaaga taaatcatgt    420
cgaaagctac atataaggaa cgtgctgcta ctcatcctag tcctgttgct gccaagctat    480
ttaatatcat gcacgaaaag caaacaaact tgtgtgcttc attggatgtt cgtaccacca    540
aggaattact ggagttagtt gaagcattag gtcccaaaat ttgtttacta aaaacacatg    600
tggatatctt gactgatttt tccatggagg gcacagttaa gccgctaaag gcattatccg    660
ccaagtacaa tttttttactc ttcgaagaca gaaaatttgc tgacattggt aatacagtca    720
aattgcagta ctctgcgggt gtatacagaa tagcagaatg ggcagacatt acgaatgcac    780
acggtgtggt gggcccaggt attgttagcg gtttgaagca ggcggcagaa gaagtaacaa    840
aggaacctag aggccttttg atgttagcag aattgtcatg caagggctcc ctatctactg    900
gagaatatac taagggtact gttgacattg cgaagagcga caaagatttt gttatcggct    960
ttattgctca aagagacatg ggtggaagag atgaaggtta cgattggttg attatgacac   1020
ccggtgtggg tttagatgac aagggagacg cattgggtca acagtataga accgtggatg   1080
atgtggtctc tacaggatct gacattatta ttgttggaag aggactattt gcaaagggaa   1140
gggatgctaa ggtagagggt gaacgttaca gaaaagcagg ctgggaagca tatttgagaa   1200
gatgcggcca gcaaaacgct tgtaaaaatt ggttttcttc tttgtctcat tttgttattc   1260
```

```
atttgtaaaa aactgtatta taagtaaatg catgtatact aaactcacaa attagagctt   1320
caatttaatt atatcagtta ttaccctatg cggtgtgaaa taccgcacag atgcgtaagg   1380
agaaaatacc gcatcaggaa attgtaaacg ttaatatttt gttaaaattc gcgttaaatt   1440
tttgttaaat cagctcattt tttaaccaat aggccgaaat cggcaaaatc ccttataaat   1500
caaaagaata gaccgagata gggttgagtg ttgttccagt ttggaacaag agtccactat   1560
taaagaacgt ggactccaac gtcaaagggc gaaaaaccgt ctatcagggc gatggcccac   1620
tacgtgaacc atcaccctaa tcaagttttt tggggtcgag gtgccgtaaa gcactaaatc   1680
ggaaccctaa agggagcccc cgatttagag cttgacgggg aaagccggcg aacgtggcga   1740
gaaaggaagg gaagaaagcg aaaggagcgg gcgctagggc gctggcaagt gtagcggtca   1800
cgctgcgcgt aaccaccaca cccgccgcgc ttaatgcgcc gctacagggc gcgtccattc   1860
gccattcagg ctgcgcaact gttgggaagg gcgatcggtg cgggcctctt cgctattacg   1920
ccagctgaat tggagcgacc tcatgctata cctgagaaag caacctgacc tacaggaaag   1980
agttactcaa gaataagaat ttcgttttta aaacctaaga gtcactttaa aatttgtata   2040
cacttatttt ttttataact tatttaataa taaaaatcat aaatcataag aaattcgctt   2100
atttagaagt gtcaacaacg tatctaccaa cgatttgacc cttttccatc ttttcgtaaa   2160
tttctggcaa ggtagacaag ccgacaacct tgattggaga cttgaccaaa cctctggcga   2220
agaattgtta attaagagct cagatcttag cagattggaa taggtgcacc attccactct   2280
ttcaagcaat ccataagtgg atctatcaac tttccctcgc acatagctgt gaataccttg   2340
tcaaattctt cacctgggct aacgactttt tcaccagtta gtaatttggt tcccaactct   2400
tctctaacga atctgtacaa agggtacgac ctacactctt tgattctatt tggtataggg   2460
gcagtaccat ttccgtatgc ggctctagca gcttcgactt cctttggtaa aactgccttc   2520
agttcttctt caaaggcacc tatcttttgg aatattgaag taacggcatt tttctcagtt   2580
tcaccattgg ataaagcgtg atctacaata acttgtctca atctctgcat caatggataa   2640
gtagcgctac atggatcgtc aacgtaagta aatacttgtt ctctatctac aacttttaat   2700
aaatcttttt cacagaatct tgatgggtgc aattcaccat tgatacctgt agttagaacc   2760
ttttttgcaa cctgtgatac ggtatttttc actgtctgtc tcaaattctc ttccaagtgt   2820
ctcaaatcta cggcctggca tatacccact aaaaatgttg tggacattaa tttaaggata   2880
tcaacggcct cgcttgtttt tcttgatgaa atcaggccca aagaattaac atcctgattg   2940
tgttgttcgg ctgattgtac atgagaggtt actgggttgg ctagatattg cagctctgaa   3000
caatagcttg ccattgctat ctcagcacct ttgaaaccat aatcaagact agggttagaa   3060
gatgcggtca gattcgaagg caaaccgtta ttgtagaagt cattgaccaa ttcagaaaat   3120
tgggcaaaca ttaatttgcc aattgcggct atggcaagcc tggtattatc catactgact   3180
cctatgggtg taccctggaa attgcctcca tgtattgcct tattcctcga cacatcaata   3240
agtggattat cgttaacaga gttgatctct ctttctatag actttgtagc ttgtctaatt   3300
acttcaattt gagggccaag ccattgtggg gatgtcctta aagcatatct atcttgtttg   3360
ggtttttgca aagggtccat ttcatgaacc ttctgggcta acttcatgta gctagagccg   3420
tccaaaatgt gctccatgat agctgctgct tcaatttgtc ctgggtgatg ttttaacctg   3480
tgggtcaagt gatcagtaaa ctcaggtttt ccactcatga cttcggcaaa aattgcggac   3540
aaaacttcgg ccaaaactgc ttgtacgtta gcttcaaaca acaccatgga tgccataccg   3600
ctgccgacag cggtgccatt caccagggct aaaccttcct tgggttgcaa atcaaagaaa   3660
```

```
ccagttgaaa taccagcttt ctcaaatgct tccttagcgg ttaaggattc tccgtctgga   3720
ccagtggcct ttgaattagg tcttcccgtt aataagcctg cgatatatga aaggggaacc   3780
aaatcaccgc tggcagttat tgttcctctt aagggcaacg aaggagaaat gttgtggttc   3840
aatagtgaag tgatggcctc aagaatttca aaccttattc cagagtaacc ttgcaacaaa   3900
gtgttcaccc taacaagcat agcagctctt gttgccgatt ggggtaatgt atggcaagtt   3960
tcctttgtat taccgaaaat accggcgtta aggaatctga tcagttctgt ttgcaaagca   4020
gtgccatttt tagttcttct atgagaggta gcaccaaagc ctgtggtaac gccataggaa   4080
tctgtgccct tgttcatact ttccatgacc caatctgatg aagccttaac tccggctcta   4140
cttgtttctg caagttctac cttcactgaa ccgccaacgg tcgaaatagc agctacctgt   4200
cctatcgtca atgtctcgcc gcctagattt acgactggtc ttctgtattc ctcaaccatc   4260
ttcttaactt catccagatg gctacctttc atctggtcag ctgccagacc ccaattcaaa   4320
ggatctgcaa gagtttttgt cgttacggcc accttggtct tttcaccacc accgcatagc   4380
attgcttcaa tttggtccat tttgtatcta gaatccgtcg aaactaagtt ctggtgtttt   4440
aaaactaaaa aaaagactaa ctataaaagt agaatttaag aagtttaaga aatagattta   4500
cagaattaca atcaatacct accgtcttta tatacttatt agtcaagtag gggaataatt   4560
tcagggaact ggtttcaacc tttttttca gctttttcca aatcagagag agcagaaggt   4620
aatagaaggt gtaagaaaat gagatagata catgcgtggg tcaattgcct tgtgtcatca   4680
tttactccag gcaggttgca tcactccatt gaggttgtgc ccgtttttg cctgtttgtg   4740
cccctgttct ctgtagttgc gctaagagaa tggacctatg aactgatggt tggtgaagaa   4800
aacaatattt tggtgctggg attcttttt tttctggatg ccagcttaaa aagcgggctc   4860
cattatattt agtggatgcc aggaataaac tgttcaccca gacacctacg atgttatata   4920
ttctgtgtaa cccgccccct attttgggca tgtacgggtt acagcagaat taaaaggcta   4980
attttttgac taaataaagt taggaaaatc actactatta attatttacg tattctttga   5040
aatggcgagt attgataatg ataaactgag ctcggaagag cgcccaatac gcaaaccgcc   5100
tctccccgcg cgttggccga ttcattaatg cagctggcac gacaggtttc ccgactggaa   5160
agcgggcagt gagcgcaacg caattaatgt gagttacctc actcattagg caccccaggc   5220
tttacacttt atgcttccgg ctcctatgtt gtgtggaatt gtgagcggat aacaatttca   5280
cacaggaaac agctatgacc atgattacgc caagcgcgca attaaccctc actaaaggga   5340
acaaaagctg gagctcatag cttcaaaatg tttctactcc tttttactc ttccagattt   5400
tctcggactc cgcgcatcgc cgtaccactt caaaacaccc aagcacagca tactaaattt   5460
cccctctttc ttcctctagg gtgtcgttaa ttacccgtac taaaggtttg gaaaagaaaa   5520
aagagaccgc ctcgtttctt tttcttcgtc gaaaaaggca ataaaaattt ttatcacgtt   5580
tctttttctt gaaaattttt ttttgattt ttttctcttt cgatgacctc ccattgatat   5640
ttaagttaat aaacggtctt caatttctca agtttcagtt tcattttct tgttctatta   5700
caactttttt tacttcttgc tcattagaaa gaaagcatag caatctaatc taagttttct   5760
agatacaaaa tggaacagaa gttgatttcc gaagaagacc tcgagatgga tttgttattg   5820
ctggaaaagt cacttattgc tgtatttgtg gcagttattc tagccacggt tatttctaaa   5880
ttaagaggta agaaactaaa actacctcct ggtcccatcc ccataccaat ttttggtaat   5940
tggttgcaag tgggcgatga tttgaatcac agaaatttgg tagactatgc taagaagttc   6000
```

```
ggtgaccttt tcttgcttag aatgggtcaa aggaatttgg tagtggttag ctcacctgat   6060
ttgactaagg aggtcttatt aacgcaaggc gttgagtttg gctccagaac tagaaatgtt   6120
gtgtttgata ttttcactgg taaaggtcaa gatatggttt ttacagttta cggtgagcac   6180
tggagaaaaa tgagaagaat catgaccgta ccattcttta ctaacaaggt tgttcaacaa   6240
aatagagaag gttgggagtt tgaggcagct tccgtagtgg aagacgtaaa gaaaaatcca   6300
gattcggcca caaagggtat agtactaaga aaaagactac aattgatgat gtacaacaat   6360
atgttcagaa ttatgtttga cagaagattt gaaagtgaag atgacccttt gttcctgaga   6420
cttaaggctt tgaatggtga aagatcgaga ttggctcaaa gtttcgaata taattacggt   6480
gactttattc caatcttaag accatttttg agaggctatt tgaaaatttg ccaagacgtc   6540
aaggatagga ggatcgctct tttcaagaag tactttgtgg acgagagaaa gcaaatagct   6600
tcttccaagc ccacaggttc ggaaggttta aaatgtgcaa ttgatcatat tttagaagct   6660
gaacaaaaag gtgaaattaa cgaagataat gttttgtaca ttgtagaaaa tatcaatgtg   6720
gctgcaatag aaacaacctt atggtcaata gaatggggta ttgctgaatt ggtgaatcac   6780
ccagaaatac aatctaaact gagaaacgag ctagataccg ttttaggtcc aggtgtccaa   6840
gttacagaac ctgatttgca taagttaccc tacttgcaag ctgtggttaa agaaaccttg   6900
agattgagaa tggctattcc tcttctagtt cctcatatga acctacatga tgctaaactg   6960
gccggttatg atattccagc agaaagtaag attttagtaa atgcatggtg gttggccaac   7020
aatccaaaca gttggaaaaa gcctgaagaa ttcagacctg aaagattctt cgaagaggaa   7080
tctcatgttg aagccaacgg aaatgacttc agatatgtac cttttggcgt tggcagaaga   7140
tcgtgtccag gaataatact agccttacca atattgggta tcacaattgg taggatggtt   7200
caaaattttg agttgctacc accacccgga caatcgaaag tcgatacttc agagaaagga   7260
ggacaattct cattgcatat tttgaatcat tccattatag tcatgaaacc cagaaattgt   7320
ggtggtgctc taggtcctaa agtttacagt taccaagaag ttgccgaaca caatggccca   7380
gaaaatttct ggattatcat cgatgacaaa gtttacgatg tttctcaatt caaagatgaa   7440
catccaggtg gtgatgaaat tataatggat ttgggtggtc aagatgctac agaaagcttt   7500
gtcgatatcg gtcattctga cgaagcattg agactactga aaggtttata cattggtgac   7560
gttgacaaga ccagtgagcg cgtttctgtg gaaaaggtat ctacctctga aaaccaaagt   7620
aaaggtgcta ttctagttgg taggaggagc ggttcgggca attcaaagag ggttgaacca   7680
ctaaagccat tagttatcaa acctagagaa gaggaaattg acgatggaag gaagaaagtc   7740
actatattct tcggcaccca aacaggtaca gctgaaggtt ttgctaaggc tctaggagaa   7800
gaagcaaaag ctagatatga aaagacgaga ttcaaaattg tcgatctgga tgactatgcc   7860
gccgatgatg acgaatacga agaaaaattg aagaaagaag atgtcgcatt tttcttcctt   7920
gccacctacg gcgacggtga accaacagat aatgccgcaa ggttttacaa gtggtttact   7980
gaaggtaatg acagaggaga atggctgaag aatttgaaat atggtgtgtt cggccttggt   8040
aacagacagt acgagcattt taataaggtc gctaaggttg tagatgatat acttgttgaa   8100
caaggtgctc aaaggttagt gcaggtgggc ttgggtgacg atgatcaatg tattgaagat   8160
gactttactg cttggagaga agccttgtgg cctgaattag atactatcct tagagaagaa   8220
ggtgacactg ctgttgctac cccctacact gcagcagtcc tagaatatag agtctcaatc   8280
catgattcag aagacgccaa attcaatgat attaacatgg ccaacggtaa cggttacacc   8340
gtttttgacg cacaacatcc atacaaagct aatgttgctg ttaaaaggga acttcacacc   8400
```

```
ccagaaagtg acaggtcatg tatacatttg gaatttgata tcgctggtag tggtttgact   8460
tacgaaacag gtgaccatgt cggagtactt tgcgataatt tgtcagaaac tgttgatgaa   8520
gctttgaggt tattggatat gtcaccagat acttacttct cattgcatgc agaaaaagaa   8580
gacggaactc caatatcaag ctcgcttccc cctccattcc ctccctgtaa cttaagaaca   8640
gccctaacta gatatgcttg tttactgtct tctccaaaga aaagtgcttt ggttgcattg   8700
gcagcccacg catccgatcc taccgaagct gagagattaa agcatttggc ttcaccagcc   8760
ggtaaagatg aatacagtaa gtgggtagtg gagagccaaa gatcgctttt agaagtgatg   8820
gctgagtttc caagtgctaa acctcctctg ggtgtatttt tcgctggtgt ggccccaaga   8880
ttgcagccta gattttattc catatcctca tctccaaaaa ttgccgaaac cagaattcac   8940
gtgacatgtg ctctggtcta cgaaaagatg ccaacaggta ggattcacaa gggtgtctgt   9000
tctacctgga tgaaaaatgc tgtaccctat gaaaaatccg aaaattgttc tagtgcacca   9060
attttcgtaa gacaatctaa tttcaagtta ccaagcgatt ctaaagtacc cattattatg   9120
atcggtccag gtactggttt ggccccattc agaggcttct tgcaagaaag attggcttta   9180
gtggagagtg gagttgaatt gggtccttca gttttattct ttggttgtag aaacagaaga   9240
atggacttta tctacgaaga agaattgcag agatttgttg aaagtggtgc attggccgaa   9300
ttgagtgttg cattcagcag ggaaggtcca accaaagaat acgttcaaca caagatgatg   9360
gacaaggctt ctgatatctg gaatatgatt tcccaaggtg cttatttgta tgtttgtggt   9420
gacgctaaag gaatggctag agatgttcat agatcactgc atacaatcgc acaagaacaa   9480
ggtagcatgg attcaacaaa agcagagggc tttgtaaaga atcttcagac aagcggtaga   9540
tatctgagag atgtatggta aggtaccgcg gctagctaag atccgctcta accgaaaagg   9600
aaggagttag acaacctgaa gtctaggtcc ctatttattt ttttatagtt atgttagtat   9660
taagaacgtt atttatattt caaatttttc tttttttttct gtacagacgc gtgtacgcat   9720
gtaacattat actgaaaacc ttgcttgaga aggttttggg acgctcgaag atgcaatgga   9780
tcagttacgt tatcttcctc gctcactgac tcgctgcgct cggtcgttcg gctgcggcga   9840
gcggtatcag ctcactcaaa ggcggtaata cggttatcca cagaatcagg ggataacgca   9900
ggaaagaaca tgtgagcaaa aggccagcaa aaggccagga accgtaaaaa ggccgcgttg   9960
ctggcgtttt tccataggct ccgcccccct gacgagcatc acaaaaatcg acgctcaagt  10020
cagaggtggc gaaacccgac aggactataa agataccagg cgtttccccc tggaagctcc  10080
ctcgtgcgct ctcctgttcc gaccctgccg cttaccggat acctgtccgc ctttctccct  10140
tcgggaagcg tggcgctttc tcatagctca cgctgtaggt atctcagttc ggtgtaggtc  10200
gttcgctcca agctgggctg tgtgcacgaa ccccccgttc agcccgaccg ctgcgcctta  10260
tccggtaact atcgtcttga gtccaacccg gtaagacacg acttatcgcc actggcagca  10320
gccactggta acaggattag cagagcgagg tatgtaggcg gtgctacaga gttcttgaag  10380
tggtggccta actacggcta cactagaagg acagtatttg gtatctgcgc tctgctgaag  10440
ccagttacct tcggaaaaag agttggtagc tcttgatccg gcaaacaaac caccgctggt  10500
agcggtggtt tttttgtttg caagcagcag attacgcgca gaaaaaaagg atctcaagaa  10560
gatcctttga tcttttctac ggggtctgac gctcagtgga acgaaaactc acgttaaggg  10620
attttggtca tgagattatc aaaaaggatc ttcacctaga tccttttaaa ttaaaaatga  10680
agttttaaat caatctaaag tatatatgag taaacttggt ctgacagtta ccaatgctta  10740
```

```
atcagtgagg cacctatctc agcgatctgt ctatttcgtt catccatagt tgcctgactc  10800
cccgtcgtgt agataactac gatacgggag ggcttaccat ctggccccag tgctgcaatg  10860
ataccgcgag acccacgctc accggctcca gatttatcag caataaacca gccagccgga  10920
agggccgagc gcagaagtgg tcctgcaact ttatccgcct ccatccagtc tattaattgt  10980
tgccgggaag ctagagtaag tagttcgcca gttaatagtt tgcgcaacgt tgttgccatt  11040
gctacaggca tcgtggtgtc acgctcgtcg tttggtatgg cttcattcag ctccggttcc  11100
caacgatcaa ggcgagttac atgatccccc atgttgtgca aaaaagcggt tagctccttc  11160
ggtcctccga tcgttgtcag aagtaagttg gccgcagtgt tatcactcat ggttatggca  11220
gcactgcata attctcttac tgtcatgcca tccgtaagat gcttttctgt gactggtgag  11280
tactcaacca agtcattctg agaatagtgt atgcggcgac cgagttgctc ttgcccggcg  11340
tcaatacggg ataataccgc gccacatagc agaactttaa aagtgctcat cattggaaaa  11400
cgttcttcgg ggcgaaaact ctcaaggatc ttaccgctgt tgagatccag ttcgatgtaa  11460
cccactcgtg cacccaactg atcttcagca tcttttactt tcaccagcgt ttctgggtga  11520
gcaaaaacag gaaggcaaaa tgccgcaaaa aagggaataa gggcgacacg gaaatgttga  11580
atactcatac tcttcctttt tcaatattat tgaagcattt atcagggtta ttgtctcatg  11640
agcggataca tatttgaatg tatttagaaa aataaacaaa taggggttcc gcgcacattt  11700
ccccgaaaag tgccacctga acgaagcatc tgtgcttcat tttgtagaac aaaaatgcaa  11760
cgcgagagcg ctaatttttc aaacaaagaa tctgagctgc atttttacag aacagaaatg  11820
caacgcgaaa gcgctatttt accaacgaag aatctgtgct tcatttttgt aaaacaaaaa  11880
tgcaacgcga gagcgctaat ttttcaaaca aagaatctga gctgcatttt tacagaacag  11940
aaatgcaacg cgagagcgct attttaccaa caaagaatct atacttcttt tttgttctac  12000
aaaaatgcat cccgagagcg ctatttttct aacaaagcat cttagattac tttttttctc  12060
ctttgtgcgc tctataatgc agtctcttga taactttttg cactgtaggt ccgttaaggt  12120
tagaagaagg ctactttggt gtctattttc tcttccataa aaaaagcctg actccacttc  12180
ccgcgtttac tgattactag cgaagctgcg ggtgcatttt ttcaagataa aggcatcccc  12240
gattatattc tataccgatg tggattgcgc atactttgtg aacagaaagt gatagcgttg  12300
atgattcttc attggtcaga aaattatgaa cggtttcttc tattttgtct ctatatacta  12360
cgtataggaa atgtttacat tttcgtattg ttttcgattc actctatgaa tagttcttac  12420
tacaattttt ttgtctaaag agtaatacta gagataaaca taaaaaatgt agaggtcgag  12480
tttagatgca agttcaagga gcgaaaggtg gatgggtagg ttatataggg atatagcaca  12540
gagatatata gcaaagagat acttttgagc aatgtttgtg gaagcggtat tcgcaatatt  12600
ttagtagctc gttacagtcc ggtgcgtttt tggttttttg aaagtgcgtc ttcagagcgc  12660
ttttggtttt caaaagcgct ctgaagttcc tatactttct agagaatagg aacttcggaa  12720
taggaacttc aaagcgtttc cgaaaacgag cgcttccgaa aatgcaacgc gagctgcgca  12780
catacagctc actgttcacg tcgcacctat atctgcgtgt tgcctgtata tatatataca  12840
tgagaagaac ggcatagtgc gtgtttatgc ttaaatgcgt acttatatgc gtctatttat  12900
gtaggatgaa aggtagtcta gtacctcctg tgatattatc ccattccatg cggggtatcg  12960
tatgcttcct tcagcactac cctttagctg ttctatatgc tgccactcct caattggatt  13020
agtctcatcc ttcaatgcta tcatttcctt tgatattgga tcatactaag aaaccattat  13080
tatcatgaca ttaacctata aaaataggcg tatcacgagg ccctttcgtc             13130
```

<210> SEQ ID NO 180
<211> LENGTH: 9308
<212> TYPE: DNA
<213> ORGANISM: Artificial Sequence
<220> FEATURE:
<223> OTHER INFORMATION: Yeast vector p0161

<400> SEQUENCE: 180

```
tcgcgcgttt cggtgatgac ggtgaaaacc tctgacacat gcagctcccg gagacggtca     60

cagcttgtct gtaagcggat gccgggagca gacaagcccg tcagggcgcg tcagcgggtg    120

ttggcgggtg tcggggctgg cttaactatg cggcatcaga gcagattgta ctgagagtgc    180

accataaatt cccgttttaa gagcttggtg agcgctagga gtcactgcca ggtatcgttt    240

gaacacggca ttagtcaggg aagtcataac acagtccttt cccgcaattt tctttttcta    300

ttactcttgg cctcctctag tacactctat atttttttat gcctcggtaa tgattttcat    360

tttttttttt ccccctagcgg atgactcttt ttttttctta gcgattggca ttatcacata    420

atgaattata cattatataa agtaatgtga tttcttcgaa gaatatacta aaaaatgagc    480

aggcaagata aacgaaggca aagatgacag agcagaaagc cctagtaaag cgtattacaa    540

atgaaaccaa gattcagatt gcgatctctt taaagggtgg tcccctagcg atagagcact    600

cgatcttccc agaaaaagag gcagaagcag tagcagaaca ggccacacaa tcgcaagtga    660

ttaacgtcca cacaggtata gggtttctgg accatatgat acatgctctg gccaagcatt    720

ccggctggtc gctaatcgtt gagtgcattg gtgacttaca catagacgac catcacacca    780

ctgaagactg cgggattgct ctcggtcaag cttttaaaga ggccctactg gcgcgtggag    840

taaaaaggtt tggatcagga tttgcgcctt tggatgaggc actttccaga gcggtggtag    900

atctttcgaa caggccgtac gcagttgtcg aacttggttt gcaaagggag aaagtaggag    960

atctctcttg cgagatgatc ccgcattttc ttgaaagctt tgcagaggct agcagaatta   1020

ccctccacgt tgattgtctg cgaggcaaga atgatcatca ccgtagtgag agtgcgttca   1080

aggctcttgc ggttgccata agagaagcca cctcgcccaa tggtaccaac gatgttccct   1140

ccaccaaagg tgttcttatg tagtgacacc gattatttaa agctgcagca tacgatatat   1200

atacatgtgt atatatgtat acctatgaat gtcagtaagt atgtatacga acagtatgat   1260

actgaagatg acaaggtaat gcatcattct atacgtgtca ttctgaacga ggcgcgcttt   1320

ccttttttct tttgctttt tcttttttttt tctcttgaac tcgacggatc tatgcggtgt   1380

gaaataccgc acagatgcgt aaggagaaaa taccgcatca ggaaattgta aacgttaata   1440

ttttgttaaa attcgcgtta aatttttgtt aaatcagctc attttttaac caataggccg   1500

aaatcggcaa aatcccttat aaatcaaaag aatagaccga gatagggttg agtgttgttc   1560

cagtttggaa caagagtcca ctattaaaga acgtggactc caacgtcaaa gggcgaaaaa   1620

ccgtctatca gggcgatggc ccactacgtg aaccatcacc gctatacctg agaaagcaac   1680

ctgacctaca ggaaagagtt actcaagaat aagaattttc gttttaaaac ctaagagtca   1740

ctttaaaatt tgtatacact tatttttttt ataacttatt taataataaa aatcataaat   1800

cataagaaat tcgcttattt agaagtgtca acaacgtatc taccaacgat ttgacccttt   1860

tccatctttt cgtaaatttc tggcaaggta gacaagccga caaccttgat tggagacttg   1920

accaaacctc tggcgaagaa ttgttaatta agagctcaga tcttatcgtc gtcatccttg   1980

taatccatcg atactagttc attagttagt gacagttgga acagagtgta acaccactgt   2040
```

```
ctcaattgtt aagccaggac cgaaaccaaa tagaacaccc caatctaaac cttctccggt   2100
tgtggctttt tcacccttta aagacttctt cctcatctca tctagaatga ataaaacgca   2160
ggcagagctc atgttgccat actctgatag aacgtgtctt gtagcttcca actttttctt   2220
ctctaagttt agttttgcct ccactgcgtc taaaattgct ggaccacctg gatgagcaat   2280
ccaaaacaat gagttccagt cgcttatgcc caatgggtca aaggcttgag ttaagcattt   2340
ttcgatgttt tctgaaatta aggttgggac attaggccac aaatgaaaag tcaaaccaac   2400
ttctctcaag tttcctgcta tggcaccggc ggaatttgga ataaaagttt gagcagcaga   2460
aactaattga aatagtggtc tttcaatgga cacatcagga tcgctgccta caattacggc   2520
ggaagatcca tcgccaaaca atgcttgtcc gaccaaactg tctagagcat cttctgatgg   2580
acctctgaaa gttacgacag tgatttcact gcagacgact aaaaccctag caccggcgtt   2640
attttctgcc aaatccttag cagttctaag cactgtacct ccggcgtaac aaccttgatg   2700
atacaacata actcttctaa cagaggtctc taatcccaat aggtttgcta gtttataatc   2760
agcacctggc atttcgacac cggaagttgt acagaaaacc aaatgtgtaa tcttagattt   2820
tggttgtccc cattccttta aagctttcaa ggctgcgtct ctacctagtc taggtacctc   2880
ggctgttatg atttcttgtc taatattcaa agatggtgcc atatatgcac ctatatttgg   2940
atgttcctct aacatttctt cagttagatg tatgtatctt ttctttatca tagatttatc   3000
acaaattcta ttaaactttt tcttaagttc tgtcatatgt tcacttttag ttactctgaa   3060
atagtaatca gcgtaatcag attgataaac acagtgatca ggggtggctg ttccaatagc   3120
caatatggtt gctggacctt ttgccctctg tgcatttctg aactcctcta cggatgccat   3180
gaattctcta gaatccgtcg aaactaagtt ctggtgtttt aaaactaaaa aaaagactaa   3240
ctataaaagt agaatttaag aagtttaaga aatagattta cagaattaca atcaatacct   3300
accgtcttta tatacttatt agtcaagtag gggaataatt tcagggaact ggtttcaacc   3360
tttttttca gctttttcca aatcagagag agcagaaggt aatagaaggt gtaagaaaat   3420
gagatagata catgcgtggg tcaattgcct tgtgtcatca tttactccag gcaggttgca   3480
tcactccatt gaggttgtgc ccgtttttg cctgtttgtg cccctgttct ctgtagttgc   3540
gctaagagaa tggacctatg aactgatggt tggtgaagaa aacaatattt tggtgctggg   3600
attctttttt tttctggatg ccagcttaaa aagcgggctc cattatattt agtggatgcc   3660
aggaataaac tgttcaccca gacacctacg atgttatata ttctgtgtaa cccgcccccct   3720
attttgggca tgtacgggtt acagcagaat taaaaggcta attttttgac taaataaagt   3780
taggaaaatc actactatta attatttacg tattctttga aatggcgagt attgataatg   3840
ataaactgag ctcggaagag cgcccaatac gcaaaccgcc tctccccgcg cgttggccga   3900
ttcattaatg cagctggcac gacaggtttc ccgactggaa agcgggcagt gagcgcaacg   3960
caattaatgt gagttacctc actcattagg caccccaggc tttacacttt atgcttccgg   4020
ctcctatgtt gtgtggaatt gtgagcggat aacaatttca cacaggaaac agctatgacc   4080
atgattacgc caagcgcgca attaaccctc actaaaggga acaaaagctg gagctcatag   4140
cttcaaaatg tttctactcc tttttactc ttccagattt tctcggactc cgcgcatcgc   4200
cgtaccactt caaaacaccc aagcacagca tactaaattt cccctctttc ttcctctagg   4260
gtgtcgttaa ttacccgtac taaaggtttg gaaaagaaaa aagagaccgc ctcgtttctt   4320
tttcttcgtc gaaaaaggca ataaaaattt ttatcacgtt tctttttctt gaaaattttt   4380
tttttgattt ttttctcttt cgatgacctc ccattgatat ttaagttaat aaacggtctt   4440
```

```
caatttctca agtttcagtt tcatttttct tgttctatta caactttttt tacttcttgc   4500
tcattagaaa gaaagcatag caatctaatc taagttttct agaggatcca tggcttctgt   4560
tgaagaaatt agaaatgctc aaagagctaa aggtccagct actattttgg ctattggtac   4620
tgctactcca gatcattgtg tttaccaatc tgattacgct gattactact tcagagttac   4680
taagtctgaa catatgactg aattgaagaa aaagttcaac agaatttgtg ataaatctat   4740
gatcaagaaa agatacatcc atttgactga agaaatgttg gaagaacatc caaacatcgg   4800
tgcttacatg gctccatctt tgaacatcag acaagaaatc atcactgctg aagttccaaa   4860
gttgggtaaa gaagctgctt tgaaagcttt gaaagaatgg ggtcaaccaa aatctaaaat   4920
tactcatttg gttttctgta ctacttctgg tgttgaaatg ccaggtgctg attataaatt   4980
ggctaatttg ttgggtttgg aaacttctgt tagaagagtt atgttgtatc atcaaggttg   5040
ttatgctggt ggtactgttt tgagaactgc taaagatttg gctgaaaata atgctggtgc   5100
tagagttttg gttgtttgtt ctgaaattac tgttgttact tttagaggtc catctgaaga   5160
tgctttggat tctttggttg gtcaagcttt gtttggtgac ggttctgctg ctgttattgt   5220
tggttctgat ccagatattt ctattgaaag accattgttt caattggttt ctgctgctca   5280
aacttttatt ccaaattctg ctggtgctat tgctggtaat ttgagagaag ttggtttgac   5340
tttccatttg tggccaaacg ttccaacttt gatctctgaa aacatcgaaa actgtttgac   5400
taaggctttc gatccaatcg gtatctctga ttggaactct ttgttttgga ttgctcatcc   5460
aggtggtcca gctattttgg atgctgttga agctaaagtt ggtttggata agcaaaagtt   5520
gaaggctact agacatatct tgtctgaata cggtaacatg tcttctgctt gtgttttgtt   5580
tattttggat gaaatgagaa agaaatcttt gaaggaaggt aaaactacta ctggtgaagg   5640
tttggattgg ggtgttttgt ttggttttgg tccaggtttg actattgaaa ctgttgtttt   5700
gcattctgtt ggtactgatt ctaattaact cgagtaagct tggtaccgcg gctagctaag   5760
atccgctcta accgaaaagg aaggagttag acaacctgaa gtctaggtcc ctatttattt   5820
ttttatagtt atgttagtat taagaacgtt atttatattt caaatttttc ttttttttct   5880
gtacagacgc gtgtacgcat gtaacattat actgaaaacc ttgcttgaga aggttttggg   5940
acgctcgaag atataacgta actgatccat tgcttcctcg ctcactgact cgctgcgctc   6000
ggtcgttcgg ctgcggcgag cggtatcagc tcactcaaag gcggtaatac ggttatccac   6060
agaatcaggg gataacgcag gaaagaacat gtgagcaaaa ggccagcaaa aggccaggaa   6120
ccgtaaaaag gccgcgttgc tggcgttttt ccataggctc cgcccccctg acgagcatca   6180
caaaaatcga cgctcaagtc agaggtggcg aaacccgaca ggactataaa gataccaggc   6240
gtttccccct ggaagctccc tcgtgcgctc tcctgttccg accctgccgc ttaccggata   6300
cctgtccgcc tttctccctt cgggaagcgt ggcgctttct catagctcac gctgtaggta   6360
tctcagttcg gtgtaggtcg ttcgctccaa gctgggctgt gtgcacgaac cccccgttca   6420
gcccgaccgc tgcgccttat ccggtaacta tcgtcttgag tccaacccgg taagacacga   6480
cttatcgcca ctggcagcag ccactggtaa caggattagc agagcgaggt atgtaggcgg   6540
tgctacagag ttcttgaagt ggtggcctaa ctacggctac actagaagga cagtatttgg   6600
tatctgcgct ctgctgaagc cagttacctt cggaaaaaga gttggtagct cttgatccgg   6660
caaacaaacc accgctggta gcggtggttt ttttgtttgc aagcagcaga ttacgcgcag   6720
aaaaaaagga tctcaagaag atcctttgat cttttctacg gggtctgacg ctcagtggaa   6780
```

```
cgaaaactca cgttaaggga ttttggtcat gagattatca aaaaggatct tcacctagat   6840
ccttttaaat taaaaatgaa gttttaaatc aatctaaagt atatatgagt aaacttggtc   6900
tgacagttac caatgcttaa tcagtgaggc acctatctca gcgatctgtc tatttcgttc   6960
atccatagtt gcctgactcc ccgtcgtgta gataactacg atacgggagg gcttaccatc   7020
tggccccagt gctgcaatga taccgcgaga cccacgctca ccggctccag atttatcagc   7080
aataaaccag ccagccggaa gggccgagcg cagaagtggt cctgcaactt tatccgcctc   7140
catccagtct attaattgtt gccgggaagc tagagtaagt agttcgccag ttaatagttt   7200
gcgcaacgtt gttgccattg ctacaggcat cgtggtgtca cgctcgtcgt ttggtatggc   7260
ttcattcagc tccggttccc aacgatcaag gcgagttaca tgatccccca tgttgtgcaa   7320
aaaagcggtt agctccttcg gtcctccgat cgttgtcaga agtaagttgg ccgcagtgtt   7380
atcactcatg gttatggcag cactgcataa ttctcttact gtcatgccat ccgtaagatg   7440
cttttctgtg actggtgagt actcaaccaa gtcattctga gaatagtgta tgcggcgacc   7500
gagttgctct tgcccggcgt caatacggga taataccgcg ccacatagca gaactttaaa   7560
agtgctcatc attggaaaac gttcttcggg gcgaaaactc tcaaggatct taccgctgtt   7620
gagatccagt tcgatgtaac ccactcgtgc acccaactga tcttcagcat cttttacttt   7680
caccagcgtt tctgggtgag caaaaacagg aaggcaaaat gccgcaaaaa agggaataag   7740
ggcgacacgg aaatgttgaa tactcatact cttccttttt caatattatt gaagcattta   7800
tcagggttat tgtctcatga gcggatacat atttgaatgt atttagaaaa ataaacaaat   7860
aggggttccg cgcacatttc cccgaaaagt gccacctgaa cgaagcatct gtgcttcatt   7920
ttgtagaaca aaaatgcaac gcgagagcgc taatttttca aacaaagaat ctgagctgca   7980
tttttacaga acagaaatgc aacgcgaaag cgctatttta ccaacgaaga atctgtgctt   8040
catttttgta aaacaaaaat gcaacgcgag agcgctaatt tttcaaacaa agaatctgag   8100
ctgcattttt acagaacaga aatgcaacgc gagagcgcta ttttaccaac aaagaatcta   8160
tacttctttt ttgttctaca aaaatgcatc ccgagagcgc tatttttcta acaaagcatc   8220
ttagattact ttttttctcc tttgtgcgct ctataatgca gtctcttgat aactttttgc   8280
actgtaggtc cgttaaggtt agaagaaggc tactttggtg tctattttct cttccataaa   8340
aaaagcctga ctccacttcc cgcgtttact gattactagc gaagctgcgg gtgcattttt   8400
tcaagataaa ggcatccccg attatattct ataccgatgt ggattgcgca tactttgtga   8460
acagaaagtg atagcgttga tgattcttca ttggtcagaa aattatgaac ggtttcttct   8520
attttgtctc tatatactac gtataggaaa tgtttacatt ttcgtattgt tttcgattca   8580
ctctatgaat agttcttact acaatttttt tgtctaaaga gtaatactag agataaacat   8640
aaaaaatgta gaggtcgagt ttagatgcaa gttcaaggag cgaaaggtgg atgggtaggt   8700
tatataggga tatagcacag agatatatag caaagagata cttttgagca atgtttgtgg   8760
aagcggtatt cgcaatattt tagtagctcg ttacagtccg gtgcgttttt ggttttttga   8820
aagtgcgtct tcagagcgct tttggttttc aaaagcgctc tgaagttcct atactttcta   8880
gagaatagga acttcggaat aggaacttca aagcgtttcc gaaaacgagc gcttccgaaa   8940
atgcaacgcg agctgcgcac atacagctca ctgttcacgt cgcacctata tctgcgtgtt   9000
gcctgtatat atatatacat gagaagaacg gcatagtgcg tgtttatgct taaatgcgta   9060
cttatatgcg tctatttatg taggatgaaa ggtagtctag tacctcctgt gatattatcc   9120
cattccatgc ggggtatcgt atgcttcctt cagcactacc ctttagctgt tctatatgct   9180
```

gccactcctc aattggatta gtctcatcct tcaatgctat catttccttt gatattggat 9240
catctaagaa accattatta tcatgacatt aacctataaa aataggcgta tcacgaggcc 9300
ctttcgtc 9308

<210> SEQ ID NO 181
<211> LENGTH: 4677
<212> TYPE: DNA
<213> ORGANISM: Artificial Sequence
<220> FEATURE:
<223> OTHER INFORMATION: Plasmid p0246

<400> SEQUENCE: 181
tttgttattc atttgtagtg acaccgatta tttaaagctg cagcatacga tatatataca 60
tgtgtatata tgtataccta tgaatgtcag taagtatgta tacgaacagt atgatactga 120
agatgacaag gtaatgcatc attctatacg tgtcattctg aacgaggcgc gctttccttt 180
tttctttttg ctttttcttt ttttttctct tgaactcgac ggatcaaccc ttaatataac 240
ttcgtataat gtatgctata cgaagttatt aggttgcggt gtgaaatacc gcacagatgc 300
gtaaggagaa aataccgcat caggaaattg taagcgttaa tattttgtta aaattcgcgt 360
taaatttttg ttaaatcagc tcatttttta accaataggc cgaaatcggc aaaatccctt 420
ataaatcaaa agaatagacc gagatagggt tgagtgttgt tccagtttgg aacaagagtc 480
cactattaaa gaacgtggac tccaacgtca aagggcgaaa aaccgtctat cagggcgatg 540
gcccactacg tgaaccatca ccctaatcaa gtttttttggg gtcgaggtgc cgtaaagcac 600
taaatcggaa ccctaaaggg agcccccgat ttagagcttg acggggaaag ccggcgaacg 660
tggcgagaaa ggaagggaag aaagcgaaag gagcgggcgc tagggcgctg gcaagtgtag 720
cggtcacgct gcgcgtaacc accacacccg ccgcgcttaa tgcgccgcta cagggcgcgt 780
ccattcgcca ttcaggctgc gcaactgttg ggaagggcga tcggtgcggg cctcttcgct 840
attacgccag ctggcgaaag ggggatgtgc tgcaaggcga ttaagttggg taacgccagg 900
gttttcccag tcacgacgtt gtaaaacgac ggccagtgaa ttgtaatacg actcactata 960
gggcgaattg gagctccacc gcggtggcgg ccgctctaga actagtggat cccccgggct 1020
gcaggaattc gatatcaagc ttatcgatac cgtcgagcaa ttcttcgcca gaggtttggt 1080
caagtctcca atgcaatggc ggccgcttac gttatcttcc tcgctcactg actcgctgcg 1140
ctcggtcgtt cggctgcggc gagcggtatc agctcactca aaggcggtaa tacggttatc 1200
cacagaatca ggggataacg caggaaagaa catgtgagca aaaggccagc aaaaggccag 1260
gaaccgtaaa aaggccgcgt tgctggcgtt tttccatagg ctcggccccc ctgacgagca 1320
tcacaaaaat cgacgctcaa gtcagaggtg gcgaaacccg acaggactat aaagatacca 1380
ggcgtttccc cctggaagct ccctcgtgcg ctctcctgtt ccgaccctgc cgcttaccgg 1440
atacctgtcc gcctttctcc cttcgggaag cgtggcgctt tctcaatgct cacgctgtag 1500
gtatctcagt tcggtgtagg tcgttcgctc caagctgggc tgtgtgcacg aaccccccgt 1560
tcagcccgac cgctgcgcct tatccggtaa ctatcgtctt gagtccaacc cggtaagaca 1620
cgacttatcg ccactggcag cagccactgg taacaggatt agcagagcga ggtatgtagg 1680
cggtgctaca gagttcttga agtggtggcc taactacggc tacactagaa ggacagtatt 1740
tggtatctgc gctctgctga agccagttac cttcggaaaa agagttggta gctcttgatc 1800
cggcaaacaa accaccgctg gtagcggtgg tttttttgtt tgcaagcagc agattacgcg 1860

```
cagaaaaaaa ggatctcaag aagatccttt gatcttttct acggggtctg acgctcagtg   1920

gaacgaaaac tcacgttaag ggattttggt catgagatta tcaaaaagga tcttcaccta   1980

gatcctttta aattaaaaat gaagttttaa atcaatctaa agtatatatg agtaaacttg   2040

gtctgacagt taccaatgct taatcagtga ggcacctatc tcagcgatct gtctatttcg   2100

ttcatccata gttgcctgac tgcccgtcgt gtagataact acgatacggg agggcttacc   2160

atctggcccc agtgctgcaa tgataccgcg agacccacgc tcaccggctc cagatttatc   2220

agcaataaac cagccagccg gaagggccga gcgcagaagt ggtcctgcaa ctttatccgc   2280

ctccatccag tctattaatt gttgccggga agctagagta agtagttcgc cagttaatag   2340

tttgcgcaac gttgttgcca ttgctacagg catcgtggtg tcacgctcgt cgtttggtat   2400

ggcttcattc agctccggtt cccaacgatc aaggcgagtt acatgatccc ccatgttgtg   2460

aaaaaaagcg gttagctcct tcggtcctcc gatcgttgtc agaagtaagt tggccgcagt   2520

gttatcactc atggttatgg cagcactgca taattctctt actgtcatgc catccgtaag   2580

atgcttttct gtgactggtg agtactcaac caagtcattc tgagaatagt gtatgcggcg   2640

accgagttgc tcttgcccgg cgtcaatacg ggataatacc gcgccacata gcagaacttt   2700

aaaagtgctc atcattggaa aacgttcttc ggggcgaaaa ctctcaagga tcttaccgct   2760

gttgagatcc agttcgatgt aacccactcg tgcacccaac tgatcttcag catcttttac   2820

tttcaccagc gtttctgggt gagcaaaaac aggaaggcaa aatgccgcaa aaaagggaat   2880

aagggcgaca cggaaatgtt gaatactcat actcttcctt tttcaatatt attgaagcat   2940

ttatcagggt tattgtctca tgagcggata catatttgaa tgtatttaga aaaataaaca   3000

aataggggtt ccgcgcacat ttccccgaaa agtgccacct gacgtctaag aaaccattat   3060

tatcatgaca ttaacctata aaaataggcg tatcacgagg ccctttcgtc tcgcgcgttt   3120

cggtgatgac ggtgaaaacc tctgacacat gcagctcccg gagacggtca cagcttgtct   3180

gtaagcggat gccgggagca gacaagcccg tcagggcgcg tcagcgggtg ttggcgggtg   3240

tcggggctgg cttaactatg cggcatcaga gcagattgta ctgagagtgc accatgttgg   3300

aataaaaatc aactatcatc tattaactag tatttacatt actagtatat tatcatatac   3360

ggtgttagaa gatgacataa atgatgagaa acagtcatct aaattagtgg aagctgaaat   3420

gcaaggattg ataatgtaat aagatctatg aataacatat aaaacgaaaa gaggaataat   3480

cataatatta tatgtagaaa tatagattcc cttttgtgga ttcctatatc ctcgaggaga   3540

acttctagta tattctgtat acctaatatt atagccttta tcaacaatgg aatcccaaca   3600

attatctcaa aattcaccta tttctcaaac ccttaatata acttcgtata atgtatgcta   3660

tacgaagtta ttaggtaatt cccgttttaa gagcttggtg agcgctagga gtcactgcca   3720

ggtatcgttt gaacacggca ttagtcaggg aagtcataac acagtccttt cccgcaattt   3780

tctttttcta ttactcttgg cctcctctag tacactctat attttttat gcctcggtaa   3840

tgattttcat ttttttttt cccctagcgg atgactcttt ttttttctta gcgattggca   3900

ttatcacata atgaattata cattatataa agtaatgtga tttcttcgaa gaatatacta   3960

aaaaatgagc aggcaagata aacgaaggca aagatgggta ggagggcttt tgtagaaaga   4020

aatacgaacg aaacgaaaat cagcgttgcc atcgctttgg acaaagctcc cttacctgaa   4080

gagtcgaatt ttattgatga acttataact tccaagcatg caaaccaaaa gggagaacaa   4140

gtaatccaag tagacacggg aattggattc ctggatcaca tgtatcatgc actggctaaa   4200

catgcaggct ggagcttacg actttactca agaggtgatt taatcatcga tgatcatcac   4260
```

```
actgcagaag atactgctat tgcacttggt attgcattca agcaggctat gggtaacttt   4320
gccggcgtta aaagatttgg acatgcttat tgtccacttg acgaagccct ttctagaagc   4380
gtagttgact tgtcgggacg gccctatgct gttatcgatt tgggattaaa gcgtgaaaag   4440
gttggggaat tgtcctgtga aatgatccct cacttactat attccttttc ggtagcagct   4500
ggaattactt tgcatgttac ctgcttatat ggtagtaatg accatcatcg tgctgaaagc   4560
gcttttaaat ctctggctgt tgccatgcgc gcggctacta gtcttactgg aagttctgaa   4620
gtcccaagca cgaagggagt gttggcttgt aaaaattggt tttcttcttt gtctcat      4677
```

<210> SEQ ID NO 182
<211> LENGTH: 4775
<212> TYPE: DNA
<213> ORGANISM: Artificial Sequence
<220> FEATURE:
<223> OTHER INFORMATION: Plasmid p0249

<400> SEQUENCE: 182

```
ccgattattt aaagctgcag catacgatat atatacatgt gtatatatgt atacctatga     60
atgtcagtaa gtatgtatac gaacagtatg atactgaaga tgacaaggta atgcatcatt    120
ctatacgtgt cattctgaac gaggcgcgct ttcctttttt ctttttgctt tttctttttt    180
tttctcttga actcgacgga tcaaccctta atataacttc gtataatgta tgctatacga    240
agttattagg ttgcggtgtg aaataccgca cagatgcgta aggagaaaat accgcatcag    300
gaaattgtaa gcgttaatat tttgttaaaa ttcgcgttaa atttttgtta aatcagctca    360
ttttttaacc aataggccga aatcggcaaa atcccttata aatcaaaaga atagaccgag    420
atagggttga gtgttgttcc agtttggaac aagagtccac tattaaagaa cgtggactcc    480
aacgtcaaag ggcgaaaaac cgtctatcag ggcgatggcc cactacgtga accatcaccc    540
taatcaagtt ttttggggtc gaggtgccgt aaagcactaa atcggaaccc taaagggagc    600
ccccgattta gagcttgacg gggaaagccg gcgaacgtgg cgagaaagga agggaagaaa    660
gcgaaaggag cgggcgctag ggcgctggca agtgtagcgg tcacgctgcg cgtaaccacc    720
acacccgccg cgcttaatgc gccgctacag ggcgcgtcca ttcgccattc aggctgcgca    780
actgttggga agggcgatcg gtgcgggcct cttcgctatt acgccagctg gcgaaagggg    840
gatgtgctgc aaggcgatta agttgggtaa cgccagggtt ttcccagtca cgacgttgta    900
aaacgacggc cagtgaattg taatacgact cactataggg cgaattggag ctccaccgcg    960
gtggcggccg ctctagaact agtggatccc ccgggctgca ggaattcgat atcaagctta   1020
tcgataccgt cgagcaattc ttcgccagag gtttggtcaa gtctccaatg caatggcggc   1080
cgcttacgtt atcttcctcg ctcactgact cgctgcgctc ggtcgttcgg ctgcggcgag   1140
cggtatcagc tcactcaaag gcggtaatac ggttatccac agaatcaggg gataacgcag   1200
gaaagaacat gtgagcaaaa ggccagcaaa aggccaggaa ccgtaaaaag gccgcgttgc   1260
tggcgttttt ccataggctc ggcccccctg acgagcatca caaaaatcga cgctcaagtc   1320
agaggtggcg aaacccgaca ggactataaa gataccaggc gttccccccct ggaagctccc  1380
tcgtgcgctc tcctgttccg accctgccgc ttaccggata cctgtccgcc tttctccctt   1440
cgggaagcgt ggcgctttct caatgctcac gctgtaggta tctcagttcg gtgtaggtcg   1500
ttcgctccaa gctgggctgt gtgcacgaac cccccgttca gcccgaccgc tgcgccttat   1560
ccggtaacta tcgtcttgag tccaacccgg taagacacga cttatcgcca ctggcagcag   1620
```

```
ccactggtaa caggattagc agagcgaggt atgtaggcgg tgctacagag ttcttgaagt   1680
ggtggcctaa ctacggctac actagaagga cagtatttgg tatctgcgct ctgctgaagc   1740
cagttacctt cggaaaaaga gttggtagct cttgatccgg caaacaaacc accgctggta   1800
gcggtggttt ttttgtttgc aagcagcaga ttacgcgcag aaaaaaagga tctcaagaag   1860
atcctttgat cttttctacg gggtctgacg ctcagtggaa cgaaaactca cgttaaggga   1920
ttttggtcat gagattatca aaaaggatct tcacctagat ccttttaaat taaaaatgaa   1980
gttttaaatc aatctaaagt atatatgagt aaacttggtc tgacagttac caatgcttaa   2040
tcagtgaggc acctatctca gcgatctgtc tatttcgttc atccatagtt gcctgactgc   2100
ccgtcgtgta gataactacg atacgggagg gcttaccatc tggccccagt gctgcaatga   2160
taccgcgaga cccacgctca ccggctccag atttatcagc aataaaccag ccagccggaa   2220
gggccgagcg cagaagtggt cctgcaactt tatccgcctc catccagtct attaattgtt   2280
gccgggaagc tagagtaagt agttcgccag ttaatagttt gcgcaacgtt gttgccattg   2340
ctacaggcat cgtggtgtca cgctcgtcgt ttggtatggc ttcattcagc tccggttccc   2400
aacgatcaag gcgagttaca tgatccccca tgttgtgaaa aaagcggtt agctccttcg   2460
gtcctccgat cgttgtcaga agtaagttgg ccgcagtgtt atcactcatg gttatggcag   2520
cactgcataa ttctcttact gtcatgccat ccgtaagatg cttttctgtg actggtgagt   2580
actcaaccaa gtcattctga gaatagtgta tgcggcgacc gagttgctct tgcccggcgt   2640
caatacggga taataccgcg ccacatagca gaactttaaa agtgctcatc attggaaaac   2700
gttcttcggg gcgaaaactc tcaaggatct taccgctgtt gagatccagt tcgatgtaac   2760
ccactcgtgc acccaactga tcttcagcat cttttacttt caccagcgtt tctgggtgag   2820
caaaaacagg aaggcaaaat gccgcaaaaa agggaataag ggcgacacgg aaatgttgaa   2880
tactcatact cttccttttt caatattatt gaagcattta tcagggttat tgtctcatga   2940
gcggatacat atttgaatgt atttagaaaa ataaacaaat aggggttccg cgcacatttc   3000
cccgaaaagt gccacctgac gtctaagaaa ccattattat catgacatta acctataaaa   3060
ataggcgtat cacgaggccc tttcgtctcg cgcgtttcgg tgatgacggt gaaaacctct   3120
gacacatgca gctcccggag acggtcacag cttgtctgta agcggatgcc gggagcagac   3180
aagcccgtca gggcgcgtca gcgggtgttg gcgggtgtcg gggctggctt aactatgcgg   3240
catcagagca gattgtactg agagtgcacc atgttggaat aaaaatcaac tatcatctat   3300
taactagtat ttacattact agtatattat catatacggt gttagaagat gacataaatg   3360
atgagaaaca gtcatctaaa ttagtggaag ctgaaatgca aggattgata atgtaataag   3420
atctatgaat aacatataaa acgaaaagag gaataatcat aatattatat gtagaaatat   3480
agattccctt ttgtggattc ctatatcctc gaggagaact tctagtatat tctgtatacc   3540
taatattata gcctttatca acaatggaat cccaacaatt atctcaaaat tcacctattt   3600
ctcaaaccct taatataact tcgtataatg tatgctatac gaagttatta ggtaattccc   3660
gttttaagag cttggtgagc gctaggagtc actgccaggt atcgtttgaa cacggcatta   3720
gtcagggaag tcataacaca gtcctttccc gcaattttct tttctatta ctcttggcct   3780
cctctagtac actctatatt tttttatgcc tcggtaatga ttttcatttt tttttttccc   3840
ctagcggatg actctttttt tttcttagcg attggcatta tcacataatg aattatacat   3900
tatataaagt aatgtgattt cttcgaagaa tatactaaaa aatgagcagg caagataaac   3960
gaaggatggg taaggaaaag actcacgttt cgaggccgcg attaaattcc aacatggatg   4020
```

```
ctgatttata tgggtataaa tgggctcgcg ataatgtcgg gcaatcaggt gcgacaatct   4080

atcgattgta tgggaagccc gatgcgccag agttgtttct gaaacatggc aaaggtagcg   4140

ttgccaatga tgttacagat gagatggtca gactaaactg gctgacggaa tttatgcctc   4200

ttccgaccat caagcatttt atccgtactc ctgatgatgc atggttactc accactgcga   4260

tccccggcaa aacagcattc caggtattag aagaatatcc tgattcaggt gaaaatattg   4320

ttgatgcgct ggcagtgttc ctgcgccggt tgcattcgat tcctgtttgt aattgtcctt   4380

ttaacagcga tcgcgtattt cgtctcgctc aggcgcaatc acgaatgaat aacggtttgg   4440

ttgatgcgag tgattttgat gacgagcgta atggctggcc tgttgaacaa gtctggaaag   4500

aaatgcataa gcttttgcca ttctcaccgg attcagtcgt cactcatggt gatttctcac   4560

ttgataacct tatttttgac gaggggaaat taataggttg tattgatgtt ggacgagtcg   4620

gaatcgcaga ccgataccag gatcttgcca tcctatggaa ctgcctcggt gagttttctc   4680

cttcattaca gaaacggctt tttcaaaaat atggtattga taatcctgat atgaataaat   4740

tgcagtttca tttgatgctc gatgagtttt tctaa                              4775
```

<210> SEQ ID NO 183
<211> LENGTH: 9931
<212> TYPE: DNA
<213> ORGANISM: Artificial Sequence
<220> FEATURE:
<223> OTHER INFORMATION: Plasmid p0262

<400> SEQUENCE: 183

```
tcgcgcgttt cggtgatgac ggtgaaaacc tctgacacat gcagctcccg gagacggtca     60

cagcttgtct gtaagcggat gccgggagca gacaagcccg tcagggcgcg tcagcgggtg    120

ttggcgggtg tcggggctgg cttaactatg cggcatcaga gcagattgta ctgagagtgc    180

accatgttgg aataaaaatc aactatcatc tattaactag tatttacatt actagtatat    240

tatcatatac ggtgttagaa gatgacataa atgatgagaa acagtcatct aaattagtgg    300

aagctgaaat gcaaggattg ataatgtaat aagatctatg aataacatat aaaacgaaaa    360

gaggaataat cataatatta tatgtagaaa tatagattcc cttttgtgga ttcctatatc    420

ctcgaggaga acttctagta tattctgtat acctaatatt atagccttta tcaacaatgg    480

aatcccaaca attatctcaa aattcaccta tttctcaaac ccttaatata acttcgtata    540

atgtatgcta tacgaagtta ttaggtcgag gagaacttct agtatatcta catacctaat    600

attattgcct tattaaaaat ggaatcccaa caattacatc aaaatccaca ttctcttcaa    660

aatcaattgt cctgtacttc cttgttcatg tgtgttcaaa aacgttatat ttataggata    720

attatactct atttctcaac aagtaattgg ttgtttggcc gagcggtcta aggcgcctga    780

ttcaagaaat atcttgaccg cagttaactg tgggaatact caggtatcgt aagatgcaag    840

agttcgaatc tcttagcaac cattattttt ttcctcaaca taacgagaac acacaggggc    900

gctatcgcac agaatcaaat tcgatgactg gaaatttttt gttaatttca gaggtcgcct    960

gacgcatata cctttttcaa ctgaaaaatt gggagaaaaa ggaaaggtga gagcgccgga   1020

accggctttt catatagaat agagaagcgt tcacgactaa atgcttgcat cacaatactt   1080

gaagttgaca atattattta aggacctatt gttttttcca ataggtggtt agcaatcgtc   1140

ttactttcta acttttctta ccttttacat ttcagcaata tatatatata tatttcaagg   1200

atataccatt ctaatgtctg cccctaagaa gatcgtcgtt ttgccaggtg accacgttgg   1260
```

```
tcaagaaatc acagccgaag ccattaaggt tcttaaagct atttctgatg ttcgttccaa   1320
tgtcaagttc gatttcgaaa atcatttaat tggtggtgct gctatcgatg ctacaggtgt   1380
tccacttcca gatgaggcgc tggaagcctc caagaaggct gatgccgttt tgttaggtgc   1440
tgtgggtggt cctaaatggg gtactggtag tgttagacct gaacaaggtt tactaaaaat   1500
ccgtaaagaa cttcaattgt acgccaactt aagaccatgt aactttgcat ccgactctct   1560
tttagactta tctccaatca agccacaatt tgctaaaggt actgacttcg ttgttgtcag   1620
agaattagtg ggaggtattt actttggtaa gagaaaggaa gacgatggtg atggtgtcgc   1680
ttgggatagt gaacaataca ccgttccaga agtgcaaaga atcacaagaa tggccgcttt   1740
catggcccta caacatgagc caccattgcc tatttggtcc ttggataaag ctaatctttt   1800
ggcctcttca agattatgga gaaaaactgt ggaggaaacc atcaagaacg aatttcctac   1860
attgaaggtt caacatcaat tgattgattc tgccgccatg atcctagtta agaacccaac   1920
ccacctaaat ggtattataa tcaccagcaa catgtttggt gatatcatct ccgatgaagc   1980
ctccgttatc ccaggttcct tgggtttgtt gccatctgcg tccttggcct ctttgccaga   2040
caagaacacc gcatttggtt tgtacgaacc atgccacggt tctgctccag atttgccaaa   2100
gaataaggtt gaccctatcg ccactatctt gtctgctgca atgatgttga aattgtcatt   2160
gaacttgcct gaagaaggta aggccattga agatgcagtt aaaaaggttt tggatgcagg   2220
tatcagaact ggtgatttag gtggttccaa cagtaccacc gaagtcggtg atgctgtcgc   2280
cgaagaagtt aagaaaatcc ttgcttaaaa agattctctt tttttatgat atttgtacat   2340
aaactttata aatgaaattc ataatagaaa cgacacgaaa ttacaaaatg gaatatgttc   2400
atagggtaga cgaaactata tacgcaatct acatacattt atcaagaagg agaaaaagga   2460
ggatagtaaa ggaatacagg taagcaaatt gatactaatg gctcaacgtg ataaggaaaa   2520
agaattgcac tttaacatta atattgacaa ggaggagggc accacacaaa aagttaggtg   2580
taacagaaaa tcttgaaact acgattccta atttgatatt ggaggatttt ctctaaaaaa   2640
aaaaaaatac aacaaataaa aaacactcaa tgacctgacc atttgatgga gtttaagtca   2700
ataccttctt gaagcatttc ccataatggt gaaagttccc tcaagaattt tactctgtca   2760
gaaacggcct tacgacgtag tcgaaaccct taatataact tcgtataatg tatgctatac   2820
gaagttatta ggttgcggtg tgaaataccg cacagatgcg taaggagaaa ataccgcatc   2880
aggaaattgt aagcgttaat attttgttaa aattcgcgtt aaatttttgt taaatcagct   2940
cattttttaa ccaataggcc gaaatcggca aaatccctta taaatcaaaa gaatagaccg   3000
agatagggtt gagtgttgtt ccagtttgga acaagagtcc actattaaag aacgtggact   3060
ccaacgtcaa agggcgaaaa accgtctatc agggcgatgg cccactacgt gaaccatcac   3120
cctaatcaag ttttttgggg tcgaggtgcc gtaaagcact aaatcggaac cctaaaggga   3180
gcccccgatt tagagcttga cggggaaagc cggcgaacgt ggcgagaaag gaagggaaga   3240
aagcgaaagg agcgggcgct agggcgctgg caagtgtagc ggtcacgctg cgcgtaacca   3300
ccacacccgc cgcgcttaat gcgccgctac agggcgcgtc cattcgccat tcaggctgcg   3360
caactgttgg gaagggcgat cggtgcgggc ctcttcgcta ttacgccagc tggcgaaagg   3420
gggatgtgct gcaaggcgat taagttgggt aacgccaggg ttttcccagt cacgacgttg   3480
taaaacgacg gccagtgaat tgtaatacga ctcactatag ggcgaattgg agctccaccg   3540
cggcttcgag cgtcccaaaa ccttctcaag caaggttttc agtataatgt tacatgcgta   3600
cacgcgtctg tacagaaaaa aaagaaaaat ttgaaatata aataacgttc ttaatactaa   3660
```

```
cataactata aaaaaataaa tagggaccta gacttcaggt tgtctaactc cttccttttc   3720
ggttagagcg gatcttagct agccgcggta ccaagcttac tcgagttaat tagaatcagt   3780
accaacagaa tgcaaaacaa cagtttcaat agtcaaacct ggaccaaaac caaacaaaac   3840
accccaatcc aaaccttcac cagtagtagt tttaccttcc ttcaaagatt tctttctcat   3900
ttcatccaaa ataaacaaaa cacaagcaga agacatgtta ccgtattcag acaagatatg   3960
tctagtagcc ttcaactttt gcttatccaa accaacttta gcttcaacag catccaaaat   4020
agctggacca cctggatgag caatccaaaa caaagagttc caatcagaga taccgattgg   4080
atcgaaagcc ttagtcaaac agttttcgat gttttcagag atcaaagttg gaacgtttgg   4140
ccacaaatgg aaagtcaaac caacttctct caaattacca gcaatagcac cagcagaatt   4200
tggaataaaa gtttgagcag cagaaaccaa ttgaaacaat ggtctttcaa tagaaatatc   4260
tggatcagaa ccaacaataa cagcagcaga accgtcacca aacaaagctt gaccaaccaa   4320
agaatccaaa gcatcttcag atggacctct aaaagtaaca acagtaattt cagaacaaac   4380
aaccaaaact ctagcaccag cattattttc agccaaatct ttagcagttc tcaaaacagt   4440
accaccagca taacaacctt gatgatacaa cataactctt ctaacagaag tttccaaacc   4500
caacaaatta gccaatttat aatcagcacc tggcatttca acaccagaag tagtacagaa   4560
aaccaaatga gtaattttag attttggttg accccattct ttcaaagctt tcaaagcagc   4620
ttctttaccc aactttggaa cttcagcagt gatgatttct tgtctgatgt tcaaagatgg   4680
agccatgtaa gcaccgatgt ttggatgttc ttccaacatt tcttcagtca aatggatgta   4740
tcttttcttg atcatagatt tatcacaaat tctgttgaac tttttcttca attcagtcat   4800
atgttcagac ttagtaactc tgaagtagta atcagcgtaa tcagattggt aaacacaatg   4860
atctggagta gcagtaccaa tagccaaaat agtagctgga cctttagctc tttgagcatt   4920
tctaatttct tcaacagaag ccatggatcc tctagaaaac ttagattaga ttgctatgct   4980
ttctttctaa tgagcaagaa gtaaaaaaag ttgtaataga acaagaaaaa tgaaactgaa   5040
acttgagaaa ttgaagaccg tttattaact taaatatcaa tgggaggtca tcgaaagaga   5100
aaaaaatcaa aaaaaaaatt ttcaagaaaa agaaacgtga taaaaatttt tattgccttt   5160
ttcgacgaag aaaaagaaac gaggcggtct ctttttttctt ttccaaacct ttagtacggg   5220
taattaacga caccctagag gaagaaagag gggaaattta gtatgctgtg cttgggtgtt   5280
ttgaagtggt acggcgatgc gcggagtccg agaaaatctg gaagagtaaa aaaggagtag   5340
aaacattttg aagctatgag ctccagcttt tgttcccttt agtgagggtt aattgcgcgc   5400
ttggcgtaat catggtcata gctgtttcct gtgtgaaatt gttatccgct cacaattcca   5460
cacaacatag gagccggaag cataaagtgt aaagcctggg gtgcctaatg agtgaggtaa   5520
ctcacattaa ttgcgttgcg ctcactgccc gctttccagt cgggaaacct gtcgtgccag   5580
ctgcattaat gaatcggcca acgcgcgggg agaggcggtt tgcgtattgg gcgctcttcc   5640
gagctcagtt tatcattatc aatactcgcc atttcaaaga atacgtaaat aattaatagt   5700
agtgattttc ctaactttat ttagtcaaaa aattagcctt ttaattctgc tgtaacccgt   5760
acatgcccaa aatagggggc gggttacaca gaatatataa catcgtaggt gtctgggtga   5820
acagtttatt cctggcatcc actaaatata atggagcccg ctttttaagc tggcatccag   5880
aaaaaaaaag aatcccagca ccaaaatatt gttttcttca ccaaccatca gttcataggt   5940
ccattctctt agcgcaacta cagagaacag gggcacaaac aggcaaaaaa cgggcacaac   6000
```

-continued

```
ctcaatggag tgatgcaacc tgcctggagt aaatgatgac acaaggcaat tgacccacgc   6060
atgtatctat ctcattttct tacaccttct attaccttct gctctctctg atttggaaaa   6120
agctgaaaaa aaaggttgaa accagttccc tgaaattatt cccctacttg actaataagt   6180
atataaagac ggtaggtatt gattgtaatt ctgtaaatct atttcttaaa cttcttaaat   6240
tctactttta tagttagtct ttttttagt tttaaaacac cagaacttag tttcgacgga   6300
ttctagagaa ttcatggcat ccgtagagga gttcagaaat gcacagaggg caaaaggtcc   6360
agcaaccata ttggctattg gaacagccac ccctgatcac tgtgtttatc aatctgatta   6420
cgctgattac tatttcagag taactaaaag tgaacatatg acagaactta agaaaaagtt   6480
taatagaatt tgtgataaat ctatgataaa gaaaagatac atacatctaa ctgaagaaat   6540
gttagaggaa catccaaata taggtgcata tatggcacca tctttgaata ttagacaaga   6600
aatcataaca gccgaggtac ctagactagg tagagacgca gccttgaaag ctttaaagga   6660
atggggacaa ccaaaatcta agattacaca tttggttttc tgtacaactt ccggtgtcga   6720
aatgccaggt gctgattata aactagcaaa cctattggga ttagagacct ctgttagaag   6780
agttatgttg tatcatcaag gttgttacgc cggaggtaca gtgcttagaa ctgctaagga   6840
tttggcagaa aataacgccg gtgctagggt tttagtcgtc tgcagtgaaa tcactgtcgt   6900
aactttcaga ggtccatcag aagatgctct agacagtttg gtcggacaag cattgtttgg   6960
cgatggatct tccgccgtaa ttgtaggcag cgatcctgat gtgtccattg aaagaccact   7020
atttcaatta gtttctgctg ctcaaacttt tattccaaat tccgccggtg ccatagcagg   7080
aaacttgaga gaagttggtt tgacttttca tttgtggcct aatgtcccaa ccttaatttc   7140
agaaaacatc gaaaaatgct taactcaagc ctttgaccca ttgggcataa gcgactggaa   7200
ctcattgttt tggattgctc atccaggtgg tccagcaatt ttagacgcag tggaggcaaa   7260
actaaactta gagaagaaaa agttggaagc tacaagacac gttctatcag agtatggcaa   7320
catgagctct gcctgcgttt tattcattct agatgagatg aggaagaagt ctttaaaggg   7380
tgaaaaagcc acaaccggag aaggtttaga ttggggtgtt ctatttggtt tcggtcctgg   7440
cttaacaatt gagacagtgg tgttacactc tgttccaact gtcactaact aatgaactag   7500
tatcgatgga ttacaaggat gacgacgata agatctgagc tcttaattaa caattcttcg   7560
ccagaggttt ggtcaagtct ccaatcaagg ttgtcggctt gtctaccttg ccagaaattt   7620
acgaaaagat ggaaaagggt caaatcgttg gtagatacgt tgttgacact tctaaataag   7680
cgaatttctt atgatttatg atttttatta ttaaataagt tataaaaaaa ataagtgtat   7740
acaaatttta aagtgactct taggttttaa aacgaaaatt cttattcttg agtaactctt   7800
tcctgtaggt caggttgctt tctcaggtat agcatgaggt cgctcgaatt cgatatcaag   7860
cttatcgata ccgtcgagca attcttcgcc agaggtttgg tcaagtctcc aatgcaatgg   7920
cggccgctta cgttatcttc ctcgctcact gactcgctgc gctcggtcgt tcggctgcgg   7980
cgagcggtat cagctcactc aaaggcggta atacggttat ccacagaatc aggggataac   8040
gcaggaaaga acatgtgagc aaaaggccag caaaaggcca ggaaccgtaa aaaggccgcg   8100
ttgctggcgt ttttccatag gctcggcccc cctgacgagc atcacaaaaa tcgacgctca   8160
agtcagaggt ggcgaaaccc gacaggacta taaagatacc aggcgttccc cctggaagc   8220
tccctcgtgc gctctcctgt tccgaccctg ccgcttaccg gatacctgtc cgcctttctc   8280
ccttcgggaa gcgtggcgct ttctcaatgc tcacgctgta ggtatctcag ttcggtgtag   8340
gtcgttcgct ccaagctggg ctgtgtgcac gaacccccg ttcagcccga ccgctgcgcc   8400
```

```
ttatccggta actatcgtct tgagtccaac ccggtaagac acgacttatc gccactggca   8460
gcagccactg gtaacaggat tagcagagcg aggtatgtag gcggtgctac agagttcttg   8520
aagtggtggc ctaactacgg ctacactaga aggacagtat ttggtatctg cgctctgctg   8580
aagccagtta ccttcggaaa aagagttggt agctcttgat ccggcaaaca aaccaccgct   8640
ggtagcggtg gtttttttgt ttgcaagcag cagattacgc gcagaaaaaa aggatctcaa   8700
gaagatcctt tgatcttttc tacggggtct gacgctcagt ggaacgaaaa ctcacgttaa   8760
gggattttgg tcatgagatt atcaaaaagg atcttcacct agatcctttt aaattaaaaa   8820
tgaagtttta aatcaatcta aagtatatat gagtaaactt ggtctgacag ttaccaatgc   8880
ttaatcagtg aggcacctat ctcagcgatc tgtctatttc gttcatccat agttgcctga   8940
ctgcccgtcg tgtagataac tacgatacgg gagggcttac catctggccc cagtgctgca   9000
atgataccgc gagacccacg ctcaccggct ccagatttat cagcaataaa ccagccagcc   9060
ggaagggccg agcgcagaag tggtcctgca actttatccg cctccatcca gtctattaat   9120
tgttgccggg aagctagagt aagtagttcg ccagttaata gtttgcgcaa cgttgttgcc   9180
attgctacag gcatcgtggt gtcacgctcg tcgtttggta tggcttcatt cagctccggt   9240
tcccaacgat caaggcgagt tacatgatcc cccatgttgt gaaaaaaagc ggttagctcc   9300
ttcggtcctc cgatcgttgt cagaagtaag ttggccgcag tgttatcact catggttatg   9360
gcagcactgc ataattctct tactgtcatg ccatccgtaa gatgcttttc tgtgactggt   9420
gagtactcaa ccaagtcatt ctgagaatag tgtatgcggc gaccgagttg ctcttgcccg   9480
gcgtcaatac gggataatac cgcgccacat agcagaactt taaaagtgct catcattgga   9540
aaacgttctt cggggcgaaa actctcaagg atcttaccgc tgttgagatc cagttcgatg   9600
taacccactc gtgcacccaa ctgatcttca gcatctttta ctttcaccag cgtttctggg   9660
tgagcaaaaa caggaaggca aaatgccgca aaaaagggaa taagggcgac acggaaatgt   9720
tgaatactca tactcttcct ttttcaatat tattgaagca tttatcaggg ttattgtctc   9780
atgagcggat acatatttga atgtatttag aaaaataaac aaataggggt tccgcgcaca   9840
tttccccgaa aagtgccacc tgacgtctaa gaaaccatta ttatcatgac attaacctat   9900
aaaaataggc gtatcacgag gccctttcgt c                                 9931
```

<210> SEQ ID NO 184
<211> LENGTH: 8553
<212> TYPE: DNA
<213> ORGANISM: Artificial Sequence
<220> FEATURE:
<223> OTHER INFORMATION: Plasmid p0280

<400> SEQUENCE: 184

```
ccgattattt aaagctgcag catacgatat atatacatgt gtatatatgt atacctatga     60
atgtcagtaa gtatgtatac gaacagtatg atactgaaga tgacaaggta atgcatcatt    120
ctatacgtgt cattctgaac gaggcgcgct ttcctttttt ctttttgctt tttctttttt    180
tttctcttga actcgacgga tcaaccctta atataacttc gtataatgta tgctatacga    240
agttattagg ttgcggtgtg aaataccgca cagatgcgta aggagaaaat accgcatcag    300
gaaattgtaa gcgttaatat tttgttaaaa ttcgcgttaa atttttgtta aatcagctca    360
tttttaaccc aataggccga aatcggcaaa atcccttata aatcaaaaga atagaccgag    420
atagggttga gtgttgttcc agtttggaac aagagtccac tattaaagaa cgtggactcc    480
```

```
aacgtcaaag ggcgaaaaac cgtctatcag ggcgatggcc cactacgtga accatcaccc    540
taatcaagtt ttttggggtc gaggtgccgt aaagcactaa atcggaaccc taaagggagc    600
ccccgattta gagcttgacg gggaaagccg gcgaacgtgg cgagaaagga agggaagaaa    660
gcgaaaggag cgggcgctag ggcgctggca agtgtagcgg tcacgctgcg cgtaaccacc    720
acacccgccg cgcttaatgc gccgctacag ggcgcgtcca ttcgccattc aggctgcgca    780
actgttggga agggcgatcg gtgcgggcct cttcgctatt acgccagctg gcgaaagggg    840
gatgtgctgc aaggcgatta agttgggtaa cgccagggtt ttcccagtca cgacgttgta    900
aaacgacggc cagtgaattg taatacgact cactataggg cgaattggag ctccaccgcg    960
gcttcgagcg tcccaaaacc ttctcaagca aggttttcag tataatgtta catgcgtaca   1020
cgcgtctgta cagaaaaaaa agaaaaattt gaaatataaa taacgttctt aatactaaca   1080
taactataaa aaaataaata gggacctaga cttcaggttg tctaactcct tccttttcgg   1140
ttagagcgga tcttagctag ccgcggtacc aagcttactc gagtcattct tccaatcttc   1200
tcaatagata ttcaacctct acttcttttg taatgggtat tacaatttct ttatatattt   1260
taaccaaata ttcgggagta atcctccttt caccagattc gttggttgga tcaacaccgt   1320
aaacttcagc ctttttagtc aatctttcta agattttctc ttccacagca gaatttgtta   1380
tatttttcat aattccttct acatccttac ttttaattaa tttagtgtac aaaggtatat   1440
cagattgaaa tttagcctct gcaacaaatt taccaaaatg tattcttcta gacaacgatt   1500
gtagacactc aatgtctcta gttgcaacgg atgaaaaatt gttcttgtca tctccatccc   1560
tcttagatat caggggtatt atcttttcaa tataaacctt ctttatctta tcattgtagt   1620
ttacttctgg agcatatggt gccaagattt gagggtaatt aattgaagga agaaatgatt   1680
tttgaatctt gtctgggaag aatggggtct catctgggga ttcaaatctt ctgatcctag   1740
aatgtgctat ctcaagatta ctcaatgccc agtccaaaaa cgagccttta aaatttggaa   1800
tctctaatcc agggtgatta gcttcgtaaa cacttgggca tgtggcaaaa tggcttcttt   1860
ctatgaattt aaaaataata ctgtcttcca tcctcaccaa ttcatctcta atattttgta   1920
ggtttaaaac cgtttctggc tttgtaaaat ccatgtcgac gcccgggccc tatagtgagt   1980
ctagaatccg tcgaaactaa gttctggtgt tttaaaacta aaaaaaagac taactataaa   2040
agtagaattt aagaagttta agaaatagat ttacagaatt acaatcaata cctaccgtct   2100
ttatatactt attagtcaag taggggaata atttcaggga actggtttca accttttttt   2160
tcagcttttt ccaaatcaga gagagcagaa ggtaatagaa ggtgtaagaa aatgagatag   2220
atacatgcgt gggtcaattg ccttgtgtca tcatttactc caggcaggtt gcatcactcc   2280
attgaggttg tgcccgtttt ttgcctgttt gtgcccctgt tctctgtagt tgcgctaaga   2340
gaatggacct atgaactgat ggttggtgaa gaaaacaata ttttggtgct gggattcttt   2400
tttttctgg atgccagctt aaaaagcggg ctccattata tttagtggat gccaggaata   2460
aactgttcac ccagacacct acgatgttat atattctgtg taacccgccc cctattttgg   2520
gcatgtacgg gttacagcag aattaaaagg ctaatttttt gactaaataa agttaggaaa   2580
atcactacta ttaattattt acgtattctt tgaaatggcg agtattgata atgataaact   2640
gagctcggaa gagcgcccaa tacgcaaacc gcctctcccc gcgcgttggc cgattcatta   2700
atgcagctgg cacgacaggt ttcccgactg gaaagcgggc agtgagcgca acgcaattaa   2760
tgtgagttac ctcactcatt aggcacccca ggctttacac tttatgcttc cggctcctat   2820
gttgtgtgga attgtgagcg gataacaatt tcacacagga aacagctatg accatgatta   2880
```

```
cgccaagcgc gcaattaacc ctcactaaag ggaacaaaag ctggagctca tagcttcaaa   2940
atgtttctac tcctttttta ctcttccaga ttttctcgga ctccgcgcat cgccgtacca   3000
cttcaaaaca cccaagcaca gcatactaaa tttcccctct ttcttcctct agggtgtcgt   3060
taattacccg tactaaaggt ttggaaaaga aaaaagagac cgcctcgttt ctttttcttc   3120
gtcgaaaaag gcaataaaaa tttttatcac gtttcttttt cttgaaaatt ttttttttga   3180
tttttttctc tttcgatgac ctcccattga tatttaagtt aataaacggt cttcaatttc   3240
tcaagtttca gtttcatttt tcttgttcta ttacaacttt ttttacttct tgctcattag   3300
aaagaaagca tagcaatcta atctaagttt tctagaacta aagggcggcc gatgtcagag   3360
tctccaatgt ttgccgccaa tggtatgcct aaggttaatc aaggtgctga agaagacgtg   3420
agaatactag gctatgatcc attagcaagt ccagcattac tacaagtgca aatccccgcc   3480
actcctactt ccttagagac tgccaaaaga ggtaggagag aagctattga tatcattact   3540
ggtaaagatg atagagtgct agtgatagta ggaccatgtt caattcatga tttggaagcc   3600
gcccaagaat atgctttgag attgaaaaag ttgagcgatg aattgaaagg agatctgtcg   3660
ataataatga gagcttacct ggaaaaacca agaactactg ttggttggaa aggtttaatt   3720
aacgatcctg atgttaataa caccttcaat attaacaagg gattgcaatc ggctagacaa   3780
cttttcgtca atttgaccaa catcggtcta cctattggtt cagaaatgtt agataccatc   3840
agccctcaat acctagccga tcttgttagt ttcggcgcaa taggcgctag aacaacggag   3900
tctcaacttc atagagaatt ggcctctggt ttgtctttcc ctgttggctt caaaaatggt   3960
accgacggta ctctaaatgt tgctgtggat gcctgtcaag cagctgccca ttctcatcat   4020
ttcatgggtg taactttaca cggtgttgca gcaatcacaa ctacaaaagg caacgaacat   4080
tgctttgtta tattaagagg cggaaagaaa ggtaccaatt atgacgctaa atccgtcgct   4140
gaggctaagg cacaattacc tgctggttcg aatggtttaa tgattgacta ctctcatggc   4200
aatagtaata aggatttcag aaatcagcct aaagttaacg acgttgtttg tgaacaaatc   4260
gcaaacggtg aaaacgcaat aactggtgtc atgatcgaat cgaatatcaa tgaaggaaat   4320
caaggtattc ctgctgaggg caaggcaggc ttgaaatacg gtgtttccat tacagatgcc   4380
tgtattggat gggaaactac tgaagatgtt cttagaaagt tggctgctgc agtgagacaa   4440
agaagagagg taaataagaa gtagagatct gagctcttaa ttaacaattc ttcgccagag   4500
gtttggtcaa gtctccaatc aaggttgtcg gcttgtctac cttgccagaa atttacgaaa   4560
agatggaaaa gggtcaaatc gttggtagat acgttgttga cacttctaaa taagcgaatt   4620
tcttatgatt tatgattttt attattaaat aagttataaa aaaaataagt gtatacaaat   4680
tttaaagtga ctcttaggtt ttaaaacgaa aattcttatt cttgagtaac tctttcctgt   4740
aggtcaggtt gctttctcag gtatagcatg aggtcgctcg aattcgatat caagcttatc   4800
gataccgtcg agcaattctt cgccagaggt ttggtcaagt ctccaatgca atggcggccg   4860
cttacgttat cttcctcgct cactgactcg ctgcgctcgg tcgttcggct gcggcgagcg   4920
gtatcagctc actcaaaggc ggtaatacgg ttatccacag aatcagggga taacgcagga   4980
aagaacatgt gagcaaaagg ccagcaaaag gccaggaacc gtaaaaaggc cgcgttgctg   5040
gcgtttttcc ataggctcgg ccccccctgac gagcatcaca aaaatcgacg ctcaagtcag   5100
aggtggcgaa acccgacagg actataaaga taccaggcgt ttccccctgg aagctccctc   5160
gtgcgctctc ctgttccgac cctgccgctt accggatacc tgtccgcctt tctcccttcg   5220
```

-continued

```
ggaagcgtgg cgctttctca atgctcacgc tgtaggtatc tcagttcggt gtaggtcgtt   5280
cgctccaagc tgggctgtgt gcacgaaccc cccgttcagc ccgaccgctg cgccttatcc   5340
ggtaactatc gtcttgagtc caacccggta agacacgact tatcgccact ggcagcagcc   5400
actggtaaca ggattagcag agcgaggtat gtaggcggtg ctacagagtt cttgaagtgg   5460
tggcctaact acggctacac tagaaggaca gtatttggta tctgcgctct gctgaagcca   5520
gttaccttcg gaaaaagagt tggtagctct tgatccggca aacaaaccac cgctggtagc   5580
ggtggttttt ttgtttgcaa gcagcagatt acgcgcagaa aaaaaggatc tcaagaagat   5640
cctttgatct tttctacggg gtctgacgct cagtggaacg aaaactcacg ttaagggatt   5700
ttggtcatga gattatcaaa aaggatcttc acctagatcc ttttaaatta aaaatgaagt   5760
tttaaatcaa tctaaagtat atatgagtaa acttggtctg acagttacca atgcttaatc   5820
agtgaggcac ctatctcagc gatctgtcta tttcgttcat ccatagttgc ctgactgccc   5880
gtcgtgtaga taactacgat acgggagggc ttaccatctg gccccagtgc tgcaatgata   5940
ccgcgagacc cacgctcacc ggctccagat ttatcagcaa taaaccagcc agccggaagg   6000
gccgagcgca gaagtggtcc tgcaacttta tccgcctcca tccagtctat taattgttgc   6060
cgggaagcta gagtaagtag ttcgccagtt aatagtttgc gcaacgttgt tgccattgct   6120
acaggcatcg tggtgtcacg ctcgtcgttt ggtatggctt cattcagctc cggttcccaa   6180
cgatcaaggc gagttacatg atcccccatg ttgtgaaaaa aagcggttag ctccttcggt   6240
cctccgatcg ttgtcagaag taagttggcc gcagtgttat cactcatggt tatggcagca   6300
ctgcataatt ctcttactgt catgccatcc gtaagatgct tttctgtgac tggtgagtac   6360
tcaaccaagt cattctgaga atagtgtatg cggcgaccga gttgctcttg cccggcgtca   6420
atacgggata ataccgcgcc acatagcaga actttaaaag tgctcatcat tggaaaacgt   6480
tcttcggggc gaaaactctc aaggatctta ccgctgttga gatccagttc gatgtaaccc   6540
actcgtgcac ccaactgatc ttcagcatct tttactttca ccagcgtttc tgggtgagca   6600
aaaacaggaa ggcaaaatgc cgcaaaaaag ggaataaggg cgacacggaa atgttgaata   6660
ctcatactct tcctttttca atattattga agcatttatc agggttattg tctcatgagc   6720
ggatacatat ttgaatgtat ttagaaaaat aaacaaatag gggttccgcg cacatttccc   6780
cgaaaagtgc cacctgacgt ctaagaaacc attattatca tgacattaac ctataaaaat   6840
aggcgtatca cgaggccctt tcgtctcgcg cgtttcggtg atgacggtga aaacctctga   6900
cacatgcagc tcccggagac ggtcacagct tgtctgtaag cggatgccgg gagcagacaa   6960
gcccgtcagg gcgcgtcagc gggtgttggc gggtgtcggg gctggcttaa ctatgcggca   7020
tcagagcaga ttgtactgag agtgcaccat gttggaataa aaatcaacta tcatctatta   7080
actagtattt acattactag tatattatca tatacggtgt tagaagatga cataaatgat   7140
gagaaacagt catctaaatt agtggaagct gaaatgcaag gattgataat gtaataagat   7200
ctatgaataa catataaaac gaaaagagga ataatcataa tattatatgt agaaatatag   7260
attccctttt gtggattcct atatcctcga ggagaacttc tagtatattc tgtataccta   7320
atattatagc ctttatcaac aatggaatcc caacaattat ctcaaaattc acctatttct   7380
caaaccctta atataacttc gtataatgta tgctatacga agttattagg taattcccgt   7440
tttaagagct tggtgagcgc taggagtcac tgccaggtat cgtttgaaca cggcattagt   7500
cagggaagtc ataacacagt cctttcccgc aattttcttt ttctattact cttggcctcc   7560
tctagtacac tctatatttt tttatgcctc ggtaatgatt ttcatttttt tttttcccct   7620
```

```
agcggatgac tcttttttt tcttagcgat tggcattatc acataatgaa ttatacatta   7680

tataaagtaa tgtgatttct tcgaagaata tactaaaaaa tgagcaggca agataaacga   7740

aggatgggta aggaaaagac tcacgtttcg aggccgcgat taaattccaa catggatgct   7800

gatttatatg ggtataaatg ggctcgcgat aatgtcgggc aatcaggtgc gacaatctat   7860

cgattgtatg ggaagcccga tgcgccagag ttgtttctga aacatggcaa aggtagcgtt   7920

gccaatgatg ttacagatga gatggtcaga ctaaactggc tgacggaatt tatgcctctt   7980

ccgaccatca agcattttat ccgtactcct gatgatgcat ggttactcac cactgcgatc   8040

cccggcaaaa cagcattcca ggtattagaa gaatatcctg attcaggtga aaatattgtt   8100

gatgcgctgg cagtgttcct gcgccggttg cattcgattc ctgtttgtaa ttgtcctttt   8160

aacagcgatc gcgtatttcg tctcgctcag gcgcaatcac gaatgaataa cggtttggtt   8220

gatgcgagtg attttgatga cgagcgtaat ggctggcctg ttgaacaagt ctggaaagaa   8280

atgcataagc ttttgccatt ctcaccggat tcagtcgtca ctcatggtga tttctcactt   8340

gataacctta tttttgacga ggggaaatta ataggttgta ttgatgttgg acgagtcgga   8400

atcgcagacc gataccagga tcttgccatc ctatggaact gcctcggtga gttttctcct   8460

tcattacaga aacggctttt tcaaaaatat ggtattgata atcctgatat gaataaattg   8520

cagtttcatt tgatgctcga tgagtttttc taa                                8553
```

<210> SEQ ID NO 185
<211> LENGTH: 333
<212> TYPE: DNA
<213> ORGANISM: Artificial Sequence
<220> FEATURE:
<223> OTHER INFORMATION: TY delta sequence

<400> SEQUENCE: 185

```
tgttggaata aaaatcaact atcatctatt aactagtatt tacattacta gtatattatc     60

atatacggtg ttagaagatg acataaatga tgagaaacag tcatctaaat tagtggaagc    120

tgaaatgcaa ggattgataa tgtaataaga tctatgaata acatataaaa cgaaaagagg    180

aataatcata atattatatg tagaaatata gattcccttt tgtggattcc tatatcctcg    240

aggagaactt ctagtatatt ctgtatacct aatattatag cctttatcaa caatggaatc    300

ccaacaatta tctcaaaatt cacctatttc tca                                 333
```

<210> SEQ ID NO 186
<211> LENGTH: 4
<212> TYPE: PRT
<213> ORGANISM: Botrytis cinerea

<400> SEQUENCE: 186

Met Pro Glu Leu
1

<210> SEQ ID NO 187
<211> LENGTH: 4
<212> TYPE: PRT
<213> ORGANISM: Unknown
<220> FEATURE:
<223> OTHER INFORMATION: Identified in search of Uniprot database for sequences similar to codon optomized ABC-transporter BcatrB from Botrytis cinerea

<400> SEQUENCE: 187

Met Pro Glu Ile

1

<210> SEQ ID NO 188
<211> LENGTH: 4
<212> TYPE: PRT
<213> ORGANISM: Unknown
<220> FEATURE:
<223> OTHER INFORMATION: Identified in search of Uniprot database for sequences similar to codon optomized ABC-transporter BcatrB from Botrytis cinerea

<400> SEQUENCE: 188

Thr Glu Glu Leu
1

<210> SEQ ID NO 189
<211> LENGTH: 10
<212> TYPE: PRT
<213> ORGANISM: Botrytis cinerea

<400> SEQUENCE: 189

Gln Ala Met Gln Gln Gln Ser Asp Lys Asp
1 5 10

<210> SEQ ID NO 190
<211> LENGTH: 10
<212> TYPE: PRT
<213> ORGANISM: Unknown
<220> FEATURE:
<223> OTHER INFORMATION: Identified in search of Uniprot database for sequences similar to codon optomized ABC-transporter BcatrB from Botrytis cinerea

<400> SEQUENCE: 190

Gln Ala Met Arg Glu Gln Gly Glu Lys Asp
1 5 10

<210> SEQ ID NO 191
<211> LENGTH: 10
<212> TYPE: PRT
<213> ORGANISM: Unknown
<220> FEATURE:
<223> OTHER INFORMATION: Identified in search of Uniprot database for sequences similar to codon optomized ABC-transporter BcatrB from Botrytis cinerea

<400> SEQUENCE: 191

Gln Ala Ile Arg Asn Gln Glu Glu Lys Asp
1 5 10

<210> SEQ ID NO 192
<211> LENGTH: 10
<212> TYPE: PRT
<213> ORGANISM: Unknown
<220> FEATURE:
<223> OTHER INFORMATION: Identified in search of Uniprot database for sequences similar to codon optomized ABC-transporter BcatrB from Botrytis cinerea

<400> SEQUENCE: 192

Lys Gln Thr Gln Gln Gln Asn Glu Asn Asp
1 5 10

PRODUCTION OF METABOLITES

The present invention relates to the production of stilbenoids such as resveratrol or pinosylvin and other metabolites by genetically engineered micro-organisms.

Micro-organisms engineered to be able to produce resveratrol are disclosed in WO06/089898, WO2009/016108, WO2009/124879, and WO2009/124967. Pinosylvin producing micro-organisms are described in WO2008/009728. South African Patent 2004/8194 (University of Stellenbosch) and Becker et al disclosed a *Saccharomyces cerevisiae* for fermenting wine must having introduced therein a grapevine resveratrol synthase gene (vstl). WO2006/125000 discloses oleaginous cells having resveratrol production capacity. WO2006/124999 discloses bacteria producing resveratrol. PUFA producing yeasts are disclosed in WO2005/118814.

It is desirable to improve the quantity of stilbenoid or other metabolite such as PUFA produced by micro-organism cells and further to improve transport of metabolites out of the producing cells and into the medium in which they are growing.

One mechanism possessed by cells for transporting substances across their cell membranes is provided by ABC transporters (ATP Binding Cassette transporters). These are plasma membrane associated proteins which transport substances in a process driven by ATP. ABC-transporters are transmembrane spanning proteins that utilize ATP to transport various substrates across membranes, such as metabolic products, lipids, sterols and drugs. ABC-transporters can be found in all organisms, both eukaryotes and prokaryotes. In yeast and fungi they are also involved in drug resistance and responsible for the excretion of several xenobiotic compounds. *S. cerevisiae* has approximately 16 ABC related transporters (Rogers et al, 2001; Jungwirth and Kuchler 2006), and many of these ATP-dependent transporters are involved in the pleiotropic drug response (Jungwirth and Kuchler 2006).

Microarray studies have been performed in yeast fed with various substrates; a methylated resveratrol analogue called pterostilbene (Pan et al, 2008), and two steroids i) celastrol (Trott et al, 2008) and ii) progesterone (Banerjee et al, 2008). The steroids are similar to resveratrol in size and the overall flat structure.

When pterostilbene was fed to yeast the ABC transporters PDR5, PDR10, YOR1 and SNQ2 were induced (Pan et al, 2008), and progesterone and celastrol gave an induction of PDR5, PDR15, PDR10, SNQ2 (Benerjee et al, 2008) and PDR5, PDR10, PDR15, PDR16, SNQ2, YCF1, YOR1 (Trott et al, 2008), respectively.

Whilst these studies are concerned with the response of the micro-organism to exposure to the tested compounds and are not concerned with the transport from the micro-organisms of compounds produced by the micro-organism itself, we conjectured that up regulation of a relevant ABC transporter might improve resveratrol transport out of a resveratrol producing cell, with beneficial effect. We have now established that SNQ2 is an ABC transporter which is effective to transport resveratrol according to the reaction:

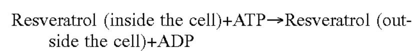

We have further established that this is effective to increase resveratrol production by cells.

Accordingly, in a first aspect, the present invention provides a recombinant micro-organism which produces and excretes into culture medium a stilbenoid metabolite product when grown under stilbenoid production conditions, which micro-organism expresses a transporter which transports said stilbenoid out of said micro-organism to said culture medium, wherein said transporter is exogenous to said micro-organism or is endogenous and is expressed at a level higher than the native expression level. The transporter is preferably an ABC transporter as described further below.

Strains of micro-organisms producing stilbenoids as described in our earlier teachings discussed above are effective to produce the stilbenoids but such strains generally evolve to decrease stilbenoid production over time. The heterologous genes needed for stilbenoid, e.g. resveratrol, production or the production of other metabolites may be included in multi-copy plasmids or integrative plasmids which also contain genes for expressing deficiency marker products necessary to complement an auxotrophic character in the host strain. This serves to maintain the plasmids, since their complete loss would render the host cell non-viable by virtue of its auxotrophic character and reduction of the copy number of the multi-copy plasmids would tend towards a similar result and be disadvantageous to survival and replication. Thus, any progeny cells that lack the required plasmid, or sufficient copies of it, will die off. This however gives rise to a 'tug of war' between the opposing forces of the requirement to maintain a sufficient copy number of the plasmids for producing the marker products on the one hand and the metabolic load imposed on the host cell by the presence of the plasmids and the resulting stilbenoid production. The metabolic load includes the energy consumption in DNA synthesis needed to replicate the expression system, expression of homologous and heterologous proteins located on the expression system, or products generated from the expressed proteins. Thus, we have found that an initially high copy number may decrease over generations of the cells.

The effectiveness of the compensation of micro-organisms from auxotrophy provided by the deficiency marker gene depends on the maintenance of a sufficient concentration of protein expressed by the gene within the cell. This in part depends on the lifetime of the protein in question. As discussed in Gilon et al: 1998, proteins to be degraded in eukaryotic cells are commonly marked for destruction by being tagged with ubiquitin. Ubiquitin tagged molecules are degraded by various mechanisms, but mainly by the 26S proteosome. Gilon reported that certain C-terminal sequences added to the end of a protein could increase the rate of ubiquitin tagging, leading to faster degradation of the protein.

We have now appreciated that providing C-terminal extensions of protein expression products of deficiency marker genes leading to the faster ubiquitination and degradation of those products would change the balance in the 'tug of war' referred to above. The cells would have a need for a greater copy number of the plasmids concerned in order to provide an increased supply of the expression products of the deficiency marker genes incorporated into the plasmids to compensate auxotrophy, and this would in turn lead to an increased copy number of the resveratrol pathway genes and higher resveratrol production. Moreover, this principle can be applied generally to metabolites produced by a metabolic pathway dependent on enzymes coded for by genes of a multicopy plasmid.

Accordingly, the present invention provides in a second aspect a recombinant micro-organism which produces and preferably excretes into culture medium a desired metabolite product when grown under desired metabolite production conditions, wherein the genome of the micro-organism produces a auxotrophic phenotype which auxotrophic phenotype is compensated by at least one expression product of a self-replicating multi-copy or integrative plasmid present in said micro-organism, which plasmid also expresses one or more enzymes participating in a metabolic pathway producing said desired metabolite, and wherein at least one said expression product of the self-replicating or integrative plasmid is genetically modified to include a ubiquitination tag sequence.

Resveratrol production in recombinant *S. cerevisiae* normally requires four heterologous genes, phenylalanine ammonia lyase, cinnamate-4-hydroxylase, 4-coumarate-CoA ligase and resveratrol synthase. The pathway is expressed as soluble cytosolic proteins with the exception of cinnamate-4-hydroxylase which is anchored in the ER membranes facing the cytosol. The resveratrol pathway prefers phenylalanine and malonyl-CoA as main precursors for the production.

In *S. cerevisiae* excess phenylalanine is degraded to phenylethanol or phenylacetate via the Erhlich pathway (Etschmann et al., 2002). One of the key enzymes for degradation of phenylalanine is phenylpyruvate decarboxylase (ARO10) (Vuralhan et al., 2005). ARO10 (YDR380w) encodes an enzyme, phenylpyruvate decarboxylase, that catalyses the decarboxylation of phenylpyruvate to phenylacetaldehyde, in the Ehrlich pathway (also called fusel alcohol pathway), which means the generation of alcohols from amino acids by transamination, followed by a decarboxylation and a final reduction step (transaminase=>decarboxylase=>reductase/dehydrogenase). To increase accessibility of phenylalanine, we have deleted ARO10 thereby removing a competing pathway consuming phenylalanine. We have found that deletion of the native yeast ARO10 gene function increases the yield of resveratrol and of coumaric acid in a resveratrol producing yeast. Similar principles may be applied to the production of other stilbenoid metabolites.

Accordingly, in a third aspect, the present invention provides a recombinant micro-organism which produces and excretes into culture medium a stilbenoid metabolite product when grown under stilbenoid production conditions, in which micro-organism expression of an enzyme participating in catabolism of phenylalanine by the Ehrlich pathway is reduced compared to its native expression level.

In accordance with the first aspect of the invention, the stilbenoid produced may be any of various stilbenoids but is preferably resveratrol.

Said ABC transporter may be the expression product of the gene SNQ2 of *Saccharomyces cerevisiae*. It may be the expression product of the gene BcatrB of *Botrytis cinerea.*

In the present context the term "micro-organism" relates to microscopic organisms, including bacteria, microscopic fungi, including yeast.

Preferably, the micro-organism is a recombinant *Saccharomyces cerevisiae*. However, numerous other micro-organisms which can be engineered to produce resveratrol or other stilbenoids are described in WO06/089898, WO2009/016108, WO2009/124879, WO2009/124967 and WO2008/009728. The first aspect of the invention may be applied to any of those micro-organisms. Thus, the micro-organism may be a fungus, and more specifically a filamentous fungus belonging to the genus of *Aspergillus*, e.g. *A. niger, A. awamori, A. oryzae, A. nidulans*, a yeast belonging to the genus of *Saccharomyces*, e.g. *S. cerevisiae, S. kluyveri, S. bayanus, S. exiguus, S. sevazzi, S. uvarum*, a yeast belonging to the genus *Kluyveromyces*, e.g. *K. lactis K. marxianus* var. *marxianus, K. thermotolerans*, a yeast belonging to the genus *Candida*, e.g. *C. utilis C. tropicalis, C. albicans, C. lipolytica, C. versatilis*, a yeast belonging to the genus *Pichia*, e.g. *P. stipidis, P. pastoris, P. sorbitophila*, or other yeast genera, e.g. *Cryptococcus, Debaromyces, Hansenula, Pichia, Yarrowia, Zygosaccharomyces* or *Schizosaccharomyces*. Concerning other micro-organisms a non-exhaustive list of suitable filamentous fungi is supplied: a species belonging to the genus *Penicillium, Rhizopus, Fusarium, Fusidium, Gibberella, Mucor, Mortierella, Trichoderma.*

Concerning bacteria a non-exhaustive list of suitable bacteria is given as follows: a species belonging to the genus *Bacillus*, a species belonging to the genus *Escherichia*, a species belonging to the genus *Lactobacillus*, a species belonging to the genus *Lactococcus*, a species belonging to the genus *Corynebacterium*, a species belonging to the genus *Acetobacter*, a species belonging to the genus *Acinetobacter*, a species belonging to the genus *Pseudomonas*, etc.

The preferred micro-organisms of the invention may be *S. cerevisiae, A. niger, A. oryzae, E. coli, L. lactis* or *B. subtilis.*

The constructed and engineered micro-organism can be cultivated using commonly known processes, including chemostat, batch, fed-batch cultivations, etc.

The following microorganism are preferred bacteria *Escherichia coli* and *Lactococcus* lactis, and fungi, *Aspergillus oryzae, Aspergillus niger* and ails yeast belonging to the genus of *Saccharomyces*

Preferably, a gene expressing said ABC Transporter is under the control of a promoter providing constitutive expression. The gene expressing said ABC Transporter may be endogenous or exogenous. If it is endogenous, it may optionally be present in a higher copy number than in the native micro-organism. However, a higher level of expression may be obtained by virtue of placing the relevant gene under the control of a stronger promoter, whether constitutive or inducible.

A preferred micro-organism may have genes expressing enzymes providing a stilbenoid producing metabolic pathway including at least phenylalanine ammonia lyase (PAL), 4-coumarate-CoA ligase (4CL1) and stilbene synthase or may have genes expressing enzymes providing a stilbenoid producing metabolic pathway including at least phenylalanine ammonia lyase (PAL), cinnamate 4-hydroxylase (4CH), 4-coumarate-CoA ligase (4CL1) and stilbene synthase. As an alternative to PAL, a TAL may be provided and the TAL pathway (for example, TAL, 4CL1, stilbene synthase) may be used. The stilbene synthase may be a resveratrol synthase or a pinosylvin synthase, but is preferably a resveratrol synthase (VST). Both a VST and an STS may be simultaneously present.

This first aspect of the invention relates to the use of ABC transporters to increase export of stilbenoids such as resveratrol or pinosylvin from cells of micro-organisms. We judged that identifying and over expressing a resveratrol transporter in micro-organisms, including in *S. cerevisiae*, would enable higher production of resveratrol since the accumulation of a high intracellular concentration of resveratrol could inhibit yeast growth and metabolism. Similar principles would apply to other stilbenoids. In silico searches were made using the BLAST tool at an *S. cerevisiae* genome database and blasting ABC transporters from other yeasts and fungi and from *S. cerevisiae* itself. The resulting candidates are shown in Table 1. Some more candidates than the previously described 16 ABC transporters (Rogers et al, 2001; Jungwirth and Kuchler 2006) were found in these homology searches.

TABLE 1

| ABC transporters in *S. cerevisiae* (Nomenclature according to *Saccharomyces* genome database). | |
|---|---|
| YOR153W-PDR5 | YCR011C-ADP1 |
| YDR406W-PDR15 | YPL270W-MDL2 |
| YOR328W-PDR10 | YLR188W-MDL1 |
| YNR070W-PDR18 | YDR135C-YCF1 |
| YPL058C-PDR12 | YLL048C-YBT1 |
| YDR011W-SNQ2 | YHL035C-VMR1 |
| YOR011W-AUS1 | YKL209C-STE6 |
| YIL013C-PDR11 | YMR301C-ATM1 |
| YOL075C | YLL015W-BPT1 |
| | YGR281W-YOR1 |

Putative resveratrol synthase genes have been described in the white root fungus *Botrytis Cinerea* (BcatrB gene accession number: AJ006217) (Schoonbeek et al, 2001) and the fungus *Aspergillus nidulans* (ATRB gene accession number: Z68905) (del Sorbo et al, 1997; Andrade et al, 2000). Deletion mutants of *Botrytis cinerea* (delta-BcatrB) and *Aspergillus Nidulans* (delta-ATRB) showed increased sensitivity towards resveratrol (Schoonbeek et al 2001, Andrade et al, 2000). These two proteins, ATRBp and BcatrBp, have highest homology (30-39%) to *S. cerevisiae* transporter genes encoded by genes PDR18, SNQ2, PDR10, PDR12, PDR5 and PDR15. We judged that at least one of the homologous genes in *S. cerevisiae* must be a resveratrol transporter. As shown in the examples below, both SNQ2 and BcatrBp are effective to increase resveratrol production in *S. cerevisiae.*

Many ABC-transporters from other organisms have been expressed in *S. cerevisiae* (Connolly et al, 2005; Del Sorbo et al, 2008; Nimii et al, 2005; Zwiers et al, 2002). However, ABC-transporters from *S. cerevisiae* have also been expressed in other organisms. This has been exemplified by the functional expression of YCF1 transporter in the plant *Arabidopsis thaliana* (Song et al, 2003) and PDR5, a close relative to SNQ2, in the tobacco plant (Muhitch et al, 2000). In general it seems that the functional expression of any ABC-transporter is possible across species barriers as has been exemplified by the expression of 25 human ABC-transporters in *Pichia pastoris* (Chloupkova et al, 2007). Even eukaryotic membrane bound transporters have been expressed in a prokaryotic organisms such as *Lactococcus lactis* (Kunji et al, 2003). Therefore it is likely that other organisms can be rendered tolerant to high levels of resveratrol by the heterologous expression of the SNQ2 or BcatrB from *S. cerevisiae* or *Botrytis cinerea.*

The second aspect of the invention relates to the use of ubiquitination tags and is useful either in isolation or in combination with the first aspect.

Said ubiquitination tag sequence is preferably a C-terminal extension of the said expression product.

Preferably, a said C-terminal extension of the said expression product satisfies the following criteria:

1. It is a nucleotide sequence coding for a peptide connected in frame to the N or C terminal end of an open reading frame of a gene.
2. The protein sequence consists of at least 10 amino acids and includes a hydrophobic region of at least five amino acids.
3. At least 40% of the amino acids in the hydrophobic should be amino acids with hydrophobic side chains.

Preferably the tag sequence has one of the following sequences:

```
                                            (SEQ ID NO 1)
ACKNWFSSLSHFVIHL

                                            (SEQ ID NO 2)
SLISLPLPTRVKFSSLLLIRIMKIITMTFPKKLRS

                                            (SEQ ID NO 3)
FYYPIWFARVLLVHYQ

                                            (SEQ ID NO 4)
SNPFSSLFGASLLIDSVSLKSNWDTSSSSCLISFFSSVMFSSTTRS

                                            (SEQ ID NO 5)
CRQRFSCHLTASYPQSTVTPFLAFLRRDFFFLRHNSSAD

                                            (SEQ ID NO 6)
GAPHVVLFDFELRITNPLSHIQSVSLQITLIFCSLPSLILSKFLQV

                                            (SEQ ID NO 7)
NTPLFSKSFSTTCGVAKKTLLLAQISSLFFLLLSSNIAV

                                            (SEQ ID NO 8)
PTVKNSPKIFCLSSSPYLAFNLEYLSLRIFSTLSKCSNTLLTSLS

                                            (SEQ ID NO 9)
SNQLKRLWLWLLEVRSFDRTLRRPWIHLPS

                                           (SEQ ID NO 10)
SISFVIRSHASIRMGASNDFFHKLYFTKCLTSVILSKFLIHLLLRSTPRV
```

examples of which can be encoded as follows:

```
                                            (SEQ ID NO 1)
1. ACKNWFSSLSHFVIHL

                                           (SEQ ID NO 11)
GCT TGT AAA AAT TGG TTT TCT TCT TTG TCT CAT TTT

GTT ATT CAT TTG

                                            (SEQ ID NO 3)
2. FYYPIWFARVLLVHYQ

                                           (SEQ ID NO 12)
TTT TAT TAT CCA ATT TGG TTT GCT AGA GTT TTG TTG

GTT CAT TAT CAA
```

The ubiquitination tag may also be FSSLA (SEQ ID NO 13).

Said expression product bearing the ubiquitination tag sequence is preferably the expression product of a marker including ura3 or his3 or trp1, leu2, lys2, or met15.

As in accordance with the first aspect of the invention, the desired metabolite product is preferably a stilbenoid but it may also be polyunsaturated fatty acid and either may be produced in an appropriate recombinant *Saccharomyces cerevisiae.*

Generally, all the preferred features of the first aspect of the invention may be employed in combination with the preferred features of the second aspect.

The 2 micron (2 μm) autonomously replicating system is used as a high copy number expression system with a high stability. A host cell containing an expression system with the 2 μm replication origin usually contains approximately 30-40 expression vector copies depending on the marker usage and metabolic load, also called tug of war (Moriya et al., 2006). Incorporation of a deficient marker like the leu2 deficiency marker (Moriya et al., 2006) can increase the copy number in the 2 μm expression system from 30-40 to 150-160 copies.

Production of resveratrol in *S. cerevisiae* usually is enabled by expression of four heterologous genes, and the precursor's phenylalanine and malonyl-CoA (WO06/

089898). The four heterologous proteins may be located on either two plasmids containing two heterologous genes each or one plasmid containing the all four genes, constituting the resveratrol pathway. The expression system used contains a 2 μm as replication origin and a marker such as ura3 and/or his3 or one of the other markers mentioned above to complement the auxotrophic host strain. Expression of the resveratrol producing pathway on one plasmid results in an initial copy number determined by the tug of war (Moriya et al., 2006) resulting in a given titre of resveratrol. Using two plasmids elevates the final concentration showing that an increase in plasmid copy number affects resveratrol yield as shown in Example 35.

To increase the copy number equilibrium one needs to either engineer the host to better cope with the pressure conferred by the expression/production system or increase the need for the marker gene. The latter solution is used in examples according to this aspect of the invention, targeting the protein half-life of the marker gene product by fusing the coding sequence of the ura3 marker to a C-terminal tag that contains targeting sequences for the *S. cerevisiae* genes Ubc6 and Ubc7 (Gilon et al., 1998). This should decrease protein half-life and thereby increase the demand for marker gene copy number.

The third aspect of the invention is concerned with deletion or other negation of the function of the Erhlich pathway as it affects the precursors of the desired metabolite.

Said enzyme of which the activity is abolished or reduced may preferably be a phenylpyruvate decarboxylase. A gene expressing said enzyme may be deleted or functionally disabled, for instance by partial deletion or insertion of a nonsense sequence. Preferably, the micro-organism is a recombinant *Saccharomyces cerevisiae* and the said enzyme is encoded by Aro10.

The third aspect of the invention, including all its preferred features may be used in combination with either or both of the first and second aspects, including all or any of their preferred features.

Stilbenoid production may be still further increased by increasing expression of the gene ACC1 to increase the pool of malonyl-CoA available in the metabolic pathway, as described in WO2009/124879 and WO2009/124966.

Particularly preferred micro-organisms, especially *S. cerevisiae*, according to the invention contain four integrative plasmids that contain the plant heterologous resveratrol pathway genes and resveratrol transporter genes and carry a deletion in the genes Aro10, Ura3, His3, Leu2, Trp1 and an overexpression of the genes ACC1 and SNQ2.

In accordance with each aspect of the invention, it may be preferred to change and modify expression of the gene Aro4 and/or Aro7 at levels in excess of those produced in the wild type of the micro-organism. These genes are involved in the synthesis of aromatic amino acids and the improvement of stilbenoid production we have observed using them may be due to provision of higher levels of amino acid precursors.

In one preferred aspect, the invention provides a recombinant *Saccharomyces cerevisiae* having genes encoding enzymes constituting a metabolic pathway for the production of a stilbenoid and expressing a Transporter (preferably an ABC transporter) having exporting activity for the stilbenoid, wherein the genome of the *Saccharomyces cerevisiae* produces a auxotrophic phenotype which auxotrophic phenotype is compensated by at least one expression product of a self-replicating or integrative multi-copy plasmid present in said *Saccharomyces cerevisiae*, which plasmid also expresses one or more of said enzymes constituting said metabolic pathway producing said stilbenoid, and wherein at least one said expression product of the self-replicating or integrative plasmid is genetically modified to include a ubiquitination tag sequence.

Preferably, in such a recombinant organism, expression of an enzyme participating in catabolism of phenylalanine by the Ehrlich pathway is reduced compared to its native expression level as described above and preferably expression of the gene ACC1 is elevated above its native expression level.

In a particularly preferred embodiment, there is provided a recombinant *Saccharomyces cerevisiae* having a TRP auxotrophic, URA auxotrophic, LEU auxotrophic and HIS auxotrophic chromosomal phenotype and having incorporated therein an integrating plasmid containing the gene SNQ2 of *Saccharomyces cerevisiae* under the control of a TDH3 constitutive promoter, which plasmid restores TRP prototrophy, and further containing a first self-replicating multi-copy plasmid containing the genes 4CL2, VST1 and URA3 C-terminally extended by the ubiquitination tag sequence GCT TGT AAA AAT TGG TTT TCT TCT TTG TCT CAT TTT GTT ATT CAT TTG, a second self-replicating, multi-copy plasmid containing the genes PAL2, C4H:CYB5:ATR2, HIS3, 4CL2, and VST1, and a third self-replicating multi-copy plasmid containing the genes VST1, 4CL2, LEU2, C4H:CYB5:ATR2, and PAL2.

In another particularly preferred embodiment there is provided a recombinant *Saccharomyces cerevisiae* having a TRP auxotrophic, URA auxotrophic, LEU auxotrophic and HIS auxotrophic chromosomal phenotype and having incorporated therein an integrating plasmid containing the gene SNQ2 of *Saccharomyces cerevisiae* under the control of a TDH3 constitutive promoter, which plasmid restores TRP prototrophy, and further containing a first integrative plasmid containing the genes PAL2, C4H and C4H:CYB5:ATR2, a second integrative plasmid containing the genes VST, 4CL2 and HIS5 C-terminally extended by the ubiquitination tag sequence GCT TGT AAA AAT TGG TTT TCT TCT TTG TCT CAT TTT GTT ATT CAT TTG, and a third integrative plasmid containing the genes VST and STS.

The invention will be further described with reference to the accompanying drawings in which:

FIG. 14 shows a sequence referred to in Example 55 (SEQ ID NO 185);

FIG. 15 shows an analysis of a number of transformants FS09258+p0204+p0180 produced in Example 65.

Figure 1:
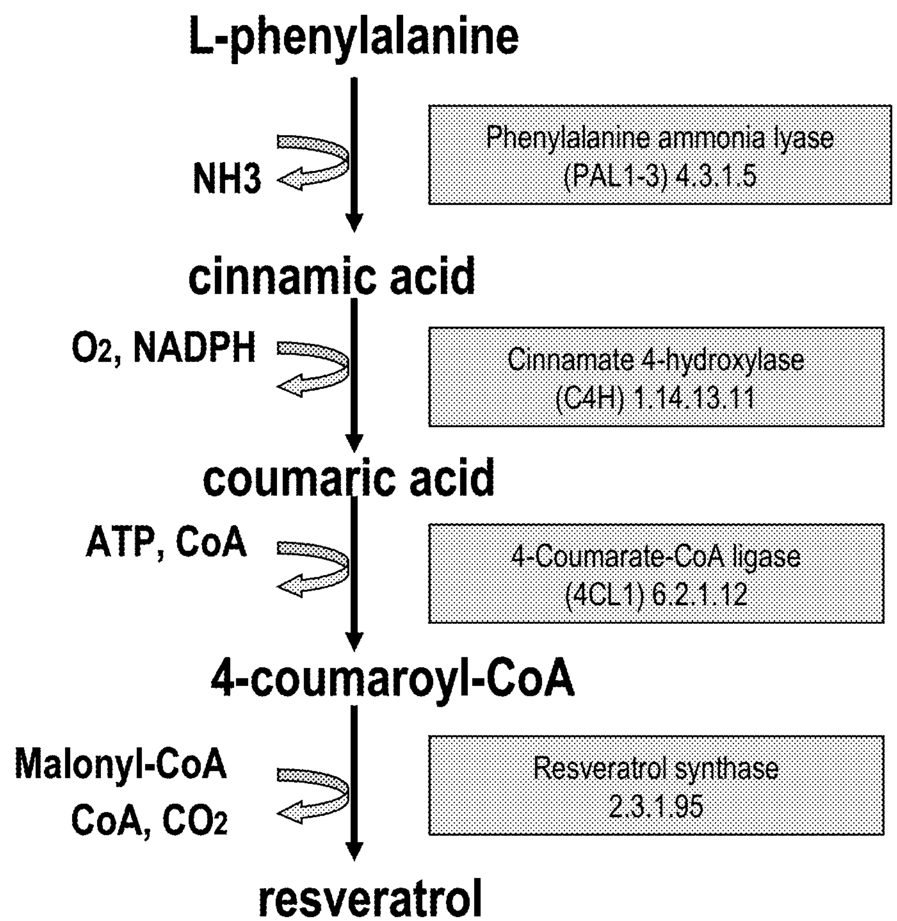
FIG. 1 shows a metabolic pathway producing resveratrol.
Figure 2:
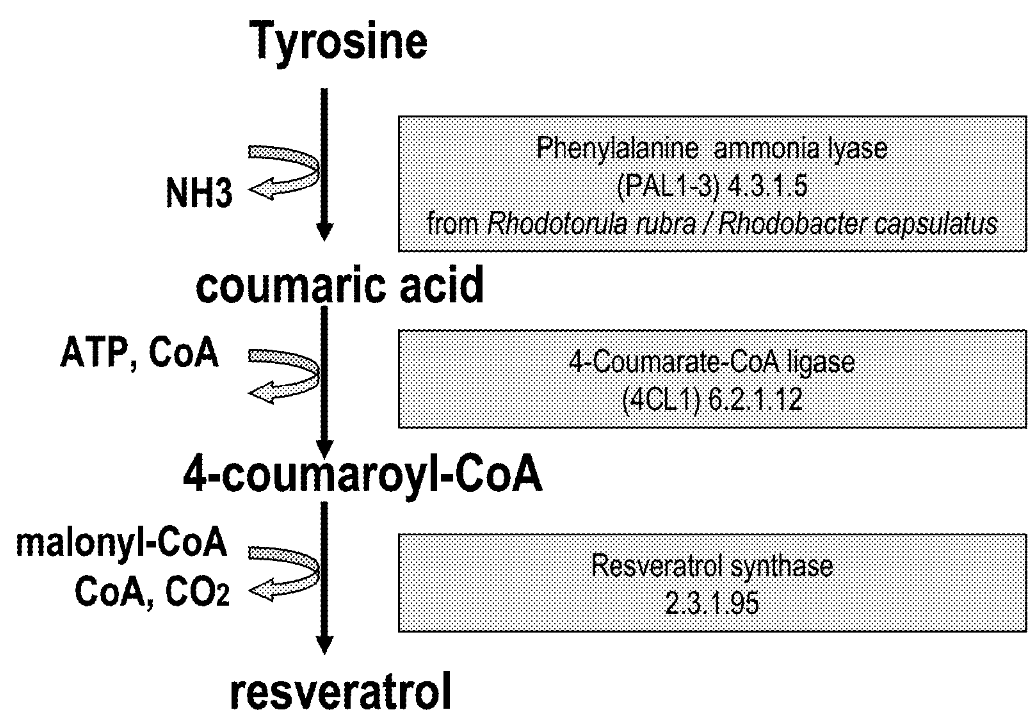
FIG. 2 shows an alternative metabolic pathway producing resveratrol.
Figure 3:
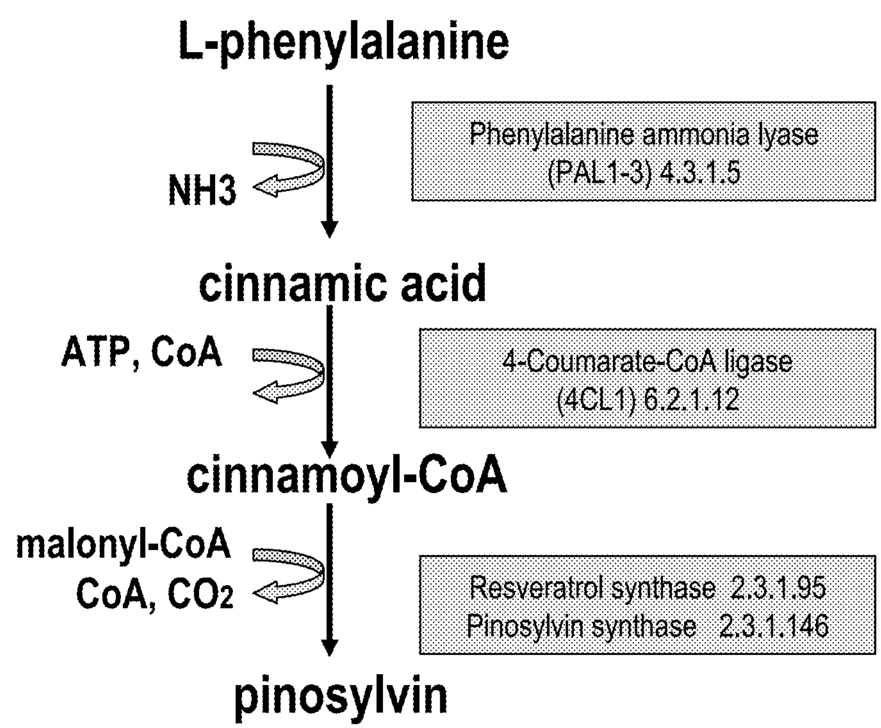
FIG. 3 shows a metabolic pathway producing pinosylvin.

As shown in FIG. 1, resveratrol can be formed from phenylalanine via a pathway in which it phenylalanine is transformed into cinnamic acid by a phenylalanine ammonia lyase (PAL1, PAL2, or PAL3), which is transformed into coumaric acid by the action of a cinnamate 4-hydroxylase (C4H). From coumaric acid is formed 4-coumaroyl-CoA by the action of a 4-coumarate-CoA ligase (4CL1). 4-coumaroyl-CoA is reacted with malonyl-CoA by a resveratrol synthase to produce resveratrol. An alternative pathway shown in FIG. 2 starts from tyrosine instead of phenylalanine and forms coumaric acid more directly. A pathway for producing pinosylvin shown in FIG. 3 resembles that of FIG. 1, but forms the stilbenoid from a reaction between malonyl-CoA and cinnamoyl-CoA catalysed either by a resveratrol synthase or more preferably by a pinosylvin synthase (i.e. a stilbene synthase having a preference for cinnamoyl-CoA as substrate).

A stilbenoid pathway may be provided in a micro-organism such as *Saccharomyces cerevisiae* by providing the genes needed to express the enzymes shown in the pathways of these figures.

A preferred recombinant *Saccharomyces cerevisiae* *FS*09258-51-53-32B-44 combining the various aspects of the invention will now be described in detail.

The recipient microorganism is a *Saccharomyces cerevisiae* with genotype MATalpha ura3-52 his3 MAL2-8c SUC2]. The following plasmids are introduced.

| Introduced genetic material<br>Introduced Vectors/Plasmids | |
|---|---|
| Plasmids/Strains | FS09258-51-53-32B-44 |
| RHO 0051 | + |
| RHO0053 | + |
| RHO0032B | + |
| RHO0044 | + |

+ Plasmid expressed in strain;
FS09258-51-53-32B-44 contains three multicopy plasmids that contain the plant heterologous resveratrol pathway genes.

The three plasmids vectors, RHO0053, RHO0032B and RHO0044, are based on Stratagene PESC-vectors, PESC-URA, PESC-HIS and PESC-LEU (www.stratagene.com) and have been modified by replacing the original inducible galactose promoters with yeast constitutive promoters. The three plasmids vectors, RHO0053, RHO0032B and RHO0044 further contain the plant resveratrol pathway genes, with the full set of resveratrol pathway genes included in each plasmid (see plasmids maps further below). The heterologous plant genes come from the non-pathogenic *Arabidopsis thaliana* and *Vitis vinifera* (grape) (resveratrol, synthase).

The plasmid Rho51 is also based on the Stratagene vector (pesc-trp) and also has strong constitutive promoters. In addition the 2-micron region, which signals self-replication and multi copy, has been removed, and thus this plasmid can only replicate as a single copy integrated in the yeast genome.

The plasmid RHO51 contains an over expression of a resveratrol transporter SNQ2. SNQ2 is as a plasma membrane ATP-binding cassette (ABC) transporter, multidrug transporter involved in multidrug resistance and has resistance to singlet oxygen species. SNQ2 was cloned between the BamHI and KpnI restriction sites of vector PSF57-TRP1 to generate vector RHO0051 (see plasmid features and map) under the control of TDH3 promoter. By cutting this vector with Hind III (which cuts in the end of TRP1 marker) and transforming a TRP-auxotrophic yeast the integrative vector integrates into chromosome of the deleted TRP1 promoter and restores the non-functional TRP1.

Figure 4:
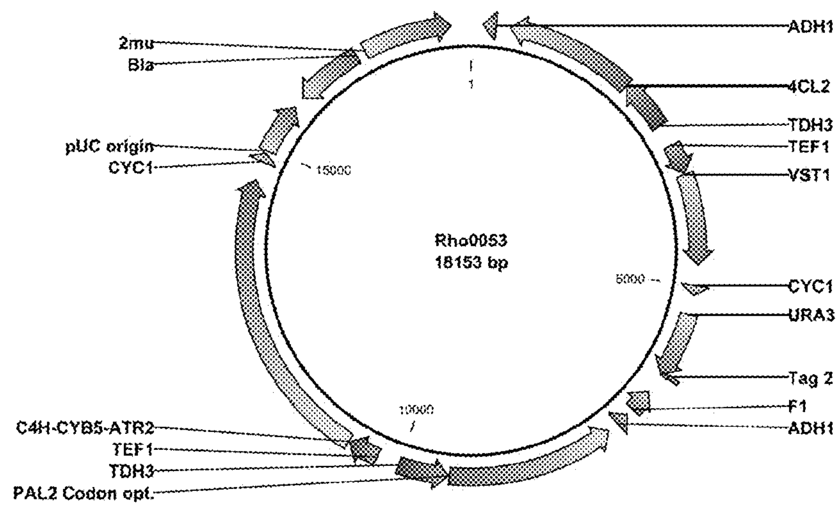
FIG. 4 shows the structure of a plasmid Rho0053 produced in Example 19.

Further detail of the plasmids appears below:

| Plasmid RHO0053 - see also FIG. 4<br>Features Rho0053 | | |
|---|---|---|
| Name | Type | Region |
| CYC1 | Terminator | 4987 . . . 5107 |
| ADH1 | Terminator | complement(157 . . . 321) |
| ADH1 | Terminator | complement(6884 . . . 7048) |
| CYC1 | Terminator | 14786 . . . 14906 |
| F1 | Replication origin | complement(6482 . . . 6788) |
| pUC origin | Replication origin | 14936 . . . 15603 |
| 2mu | Replication origin | 16745 . . . 17900 |
| TDH3 | Promoter | complement(2190 . . . 2844) |
| TEF1 | Promoter | 3134 . . . 3534 |
| TDH3 | Promoter | complement(9365 . . . 10019) |
| TEF1 | Promoter | 10309 . . . 10709 |
| Tag 2 | Promoter | 6169 . . . 6216 |
| 4CL2 | ORF | complement(507 . . . 2177) |
| VST1 | ORF | 3547 . . . 4725 |
| URA3 with TAG2 | ORF | 5365 . . . 6219/note = Length: 807 |
| PAL2 Codon opt. | ORF | complement(7199 . . . 9352) |
| Bla | ORF | complement(15751 . . . 16623) |
| C4H-CYB5-ATR2 | ORF | 10722 . . . 14540 |

Figure 5:
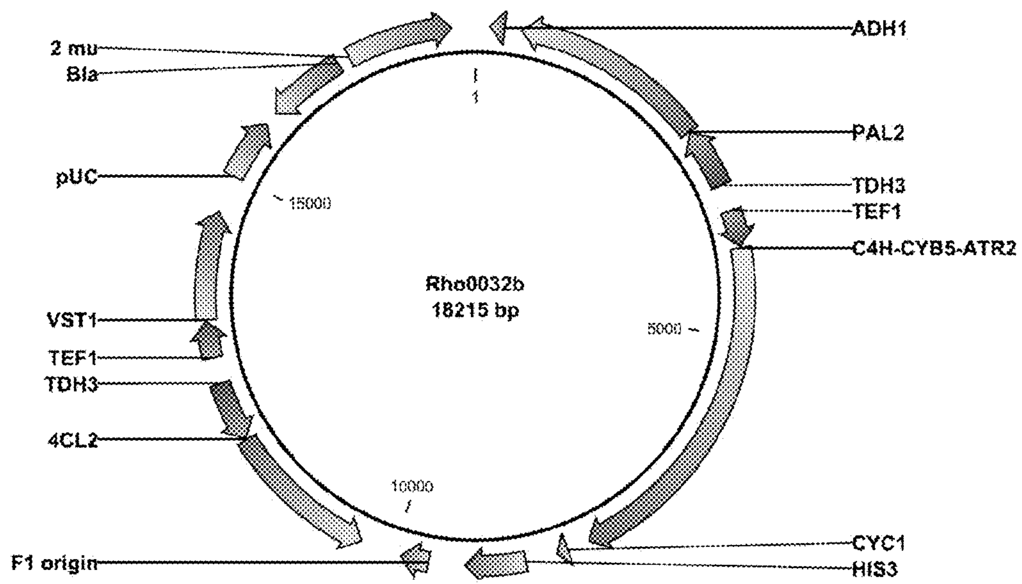
FIG. 5 shows the structure of a plasmid Rho0032B produced in Example 17.

| Plasmid RHO0032b see also FIG. 5<br>Features Rho0032b | | |
|---|---|---|
| Name | Type | Region |
| CYC1 | Terminator | 8094 . . . 8214 |
| ADH1 | Terminator | complement(157 . . . 321) |
| pUC | Replication origin | 14999 . . . 15666 |
| 2 mu | Replication origin | 16808 . . . 17963 |
| F1 origin | Replication origin | 9613 . . . 9919 |
| TEF1 | Promoter | 12996 . . . 13396 |
| TDH3 | Promoter | complement(12052 . . . 12706) |
| TDH3 | Promoter | complement(2673 . . . 3327) |
| TEF1 | Promoter | 3617 . . . 4017 |
| VST1 | ORF | 13409 . . . 14587 |
| 4CL2 | ORF | complement(10369 . . . 12039) |
| HIS3 | ORF | 8562 . . . 9221 |
| Bla | ORF | complement(15814 . . . 16674) |
| PAL2 | ORF | complement(507 . . . 2660) |
| C4H-CYB5-ATR2 | ORF | 4030 . . . 7848 |

Figure 6:
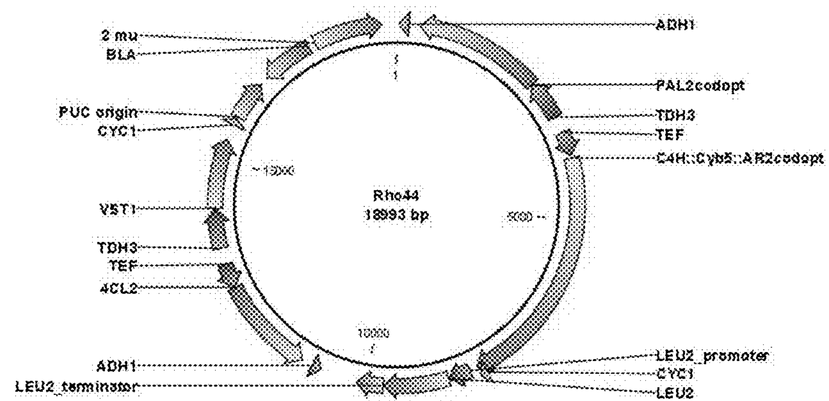
FIG. 6 shows the structure of a plasmid Rho0044 produced in Example 18.

| Plasmid RHO0044 - see also FIG. 6<br>Features Rho0044 | | |
|---|---|---|
| Name | Type | Region |
| LEU2_terminator | Terminator | 9721 . . . 10171 |
| CYC1 | Terminator | 7985 . . . 8105 |
| CYC1 | Terminator | 15627 . . . 15747 |

-continued

| Plasmid RHO0044 - see also FIG. 6 Features Rho0044 | | |
|---|---|---|
| Name | Type | Region |
| ADH1 | Terminator | complement(48 . . . 212) |
| ADH1 | Terminator | complement(10797 . . . 10961) |
| 2 mu | Replication origin | 17586 . . . 18741 |
| PUC origin | Replication origin | 15777 . . . 16444 |
| TDH3 | Promoter | 13514 . . . 14180 |
| TEF | Promoter | complement(12824 . . . 13236) |
| LEU2_promoter | Promoter | 8234 . . . 8613 |
| TEF | Promoter | 3502 . . . 3914 |
| TDH3 | Promoter | complement(2558 . . . 3223) |
| VST1 | ORF | 14187 . . . 15368 |
| 4CL2 | ORF | complement(11147 . . . 12817) |
| LEU2 | ORF | 8614 . . . 9720 |
| C4H::Cyb5::AR2codopt | ORF | 3957 . . . 8105 |
| PAL2codopt | ORF | complement(398 . . . 2551) |
| BLA | ORF | complement(16592 . . . 17464) |

Figure 7:
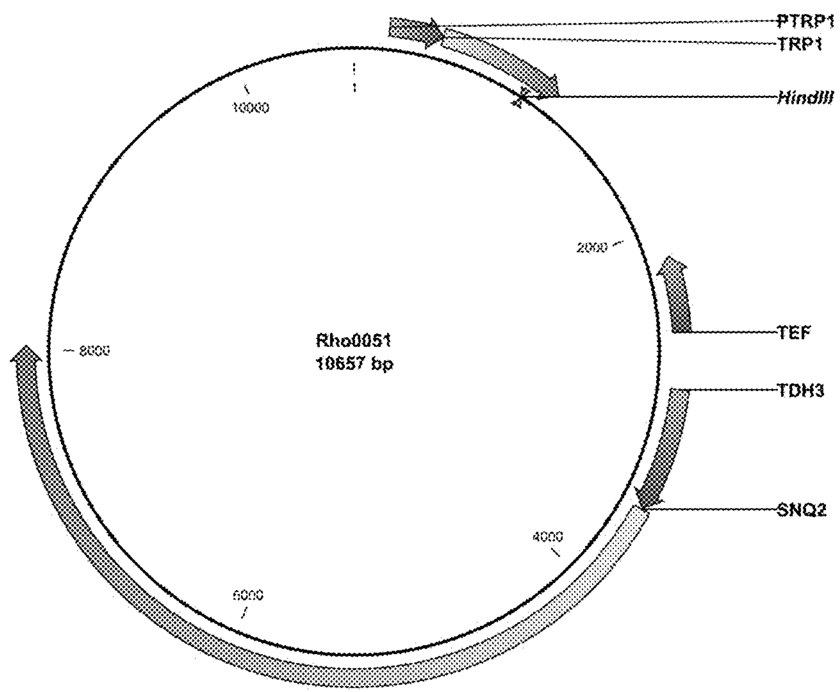
FIG. 7 shows the structure of a plasmid Rho0051 produced in Example 24.

| Plasmid RHO0051 - see also FIG. 7 Features Rho0051 | | |
|---|---|---|
| Name | Type | Region |
| PTRP1 | Promoter | 187 . . . 468 |
| TDH3 | Promoter | 2865 . . . 3514 |
| TEF | Promoter | complement(2164 . . . 2564) |
| SNQ2 | ORF | 3521 . . . 8026 |
| TRP1 | ORF | 469 . . . 1140 |

FS09258-51-53-32B-44 carries a deletion in the gene ARO10, Ura3, His3, Leu2, Trp1 and an over expression of the gene ACC1:

Over Expression of ACC1 by Promoter Exchange

ACC1 was over expressed using the native constitutive *S. cerevisiae* promoter TPI1 (Triose-phosphate isomerase). The TPI-ACC1 is a chromosomal up-regulation of the ACC1 gene by replacing the natural weak promoter of ACC1 with the constitutive native *S. cerevisiae* TPI promoter from the TPI gene (YDR050c) which encodes an abundant glycolytic enzyme, triose phosphate isomerase. The method used for promoter switch is described in (Erdeniz et al, 1997). ACC1 (YNR016c) encodes an enzyme, acetyl-CoA carboxylase, that catalyzes the carboxylation of acetyl-CoA to form malonyl-CoA. Malonyl-CoA is normally required for de novo biosynthesis of long-chain fatty acids in yeast and is also needed in for resveratrol synthesis (Resveratrol synthase reaction: 3 malonyl-CoA+4-coumaroyl-CoA=4 CoA+3,4',5-trihydroxy-stilbene+4 CO2).

Gene Deletion

Deletion of genes was performed using a cre-lox system (Gueldener et al, 2002) that leaves a short loxP-sequence in the shortened DNA.

In the following the deletions are further described: Ura3-52 is a common and well characterized auxotrophic marker and means that the natural Ura3 gene (or systematic gene name YEL021w) has been mutated by an insertion of a TY1 (transposable) element. The Ura3 gene encodes an enzyme, orotidine-5'-phosphate (OMP) decarboxylase, that catalyzes the sixth enzymatic step in the de novo biosynthesis of pyrimidines. This mutation is a non-reverting mutation (Rose and Winston, 1984).

His3 is also a common and well characterized marker and means that the His3 gene (YOR202w) is a non-reverting mutated form to render it auxotrophic. His3 encodes an enzyme, Imidazoleglycerol-phosphate dehydratase, that catalyzes the sixth step in histidine biosynthesis.

The leu2 is a common auxotrophic marker. Usually this auxotrophic markers consists of mutations and frame shift mutations in position leu2-3,112 (Meira et al, 1995). However, in this strain we have ourselves deleted major parts of the LEU2 gene using the method described previously (Erdeniz et al, 1997) to render the strain auxotrophic for Leu2 to avoid mutation strategies in our strains.

The Trp1 is a common auxotrophic marker in laboratory *S. cerevisiae* strains. We deleted major parts of the TRP1 gene using the method described, previously (Erdeniz et al, 1997) to render the strain auxotrophic for TRP1 to avoid mutation strategies in our strains.

ARO10 (YDR380w) encodes an enzyme, phenylpyruvate decarboxylase, that catalyzes the decarboxylation of phenylpyruvate to phenylacetaldehyde, in the Ehrlich pathway (also called fusel alcohol pathway), which means the generation of alcohols from amino acids by transamination, followed by a decarboxylation and a final reduction step. (transaminase=>decarboxylase=>reductase/dehydrogenase).

Resveratrol Pathway

The inserted heterologous genes encode enzymes involved in the phenylpropanoid pathway. This pathway involves the consumption of L-phenylalanine via cinnamic acid to coumaric acid to coumaryl-CoA. Finally the formation of resveratrol is made possible via resveratrol synthase from grape. The formed product resveratrol is a nutraceutical with anticarcinogenic and antioxidant properties. The genes are as follows:

a) Codon optimized phenylalanine ammonia lyase (PAL2) from *Arabidopsis thaliana* for expression in *S. cerevisiae* catalysing the deamination of phenylalanine into cinnamic acid.

b) A fused DNA fragment consisting of three genes (parts): Part i) a cinnamate 4-hydroxylase gene (C4H) from *Arabidopsis thaliana* codon optimized for expression in *S. cerevisiae;*

Part ii) Electron carrier Cytochrome b5 CYB5 encoded by *S. cerevisiae* native ORF YNL111c;

Part iii) a cytochrome p450 reductase gene (AR2) from *Arabidopsis thaliana*, codon optimized for expression in *S. cerevisiae.*

The three parts have been fused in such a way that they are expressed as one single enzyme and the orientation of the fused DNA fragment is >Start codon C4H::CYB5::AR2 stop codon<(where :: means fused genes in frame). This fusion constructs enables higher catalytic activities of the hydroxylation step (conversion of cinnamic acid into coumaric acid), than when C4H is expressed alone.

c) A non-codon-optimized 4-coumaroyl CoA-ligase (4CL2) from *Arabidopsis thaliana* catalyzing the activation of coumaric acid into coumaroyl-CoA while consuming ATP and acetyl-CoA.

d) Codon optimized resveratrol synthase from grape (*Vitis vinifera*) catalyzing the ring-folding reaction of one coumaroyl-CoA and 3 malonyl-CoA into resveratrol.

The Regulatory Sequences Permitting the Expression of Solely the Gene(s) of Interest.

TEF1 promoter from *S. cerevisiae* (Mumberg et al, 1995), which is the promoter of the gene YBR118w. This gene encodes a Translational elongation factor EF-1 alpha TDH3 promoter from *S. cerevisiae* (Mumberg et al, 1995), which is the promoter of the gene YGR192c. This gene encodes a glyceraldehydes 3-phosphate dehydrogenase.

CYC1 terminator from the *S. cerevisiae* gene YJR048w which encodes cytochrome C isoform 1

ADH1 terminator from the *S. cerevisiae* gene YOL086c which encodes alcohol dehydrogenase 1

LEU2 terminator from the *S. cerevisiae* gene YCL018W which encodes beta-isopropylmalate dehydrogenase The Nucleotide Sequences Needed for Vector Maintenance.

Ori F for replication and subcloning in *E. coli* (however has no function in *S. cerevisiae*)

2 micron on for replication in *S. cerevisiae*

Ampicillin resistance gene for selection in *E. coli* (however has no function and is not expressed in *S. cerevisiae*)

Amino acid auxotrophic markers URA3 and HIS3 and LEU2 and TRP1 for selection and maintenance in *S. cerevisiae.*

The invention will be further described and illustrated by the following examples.

In this work certain methods have been used which will be briefly described here.

Infusion Technology

Vector constructs were generated either using i) the standard restriction enzyme based cloning in combination with ligation using T4 DNA ligase or ii) the Infusion Technology (In-Fusion™ Dry-Down PCR Cloning Kit) from Clontech (Clontech, Mountain View, Calif.). This In-Fusion technology allows homologous recombination between a linearized plasmid and an insert generated by PCR containing homologous overhangs to the linearized vector. The linearized vector was either generated by restriction digest or by PCR using the Herculase® II Fusion DNA Polymerase (Agilent Technologies—Stratagene, La Jolla, Calif.) and primers with a melting temperature of 60 degree Celsius.

Bipartite Method of Over-Expression of Native Yeast Genes by Gene Targeting Method Based on *Kluyveromyces lactis* URA-Marker.

Over-expression of native yeasts genes with constitutive yeast promoters is carried out by means of a promoter-replacement method based on a linear, PCR-generated gene-targeting substrate and using *K. lactis* URA3 as a recyclable marker described previously (Erdeniz et al, 1997). This method includes the generation of an intermediate yeast strain, where the *Kluyveromyces lactis* URA3 marker gene is integrated in combination with two copies of the strong constitutive promoter sequence as a direct repeat on each side of the marker gene. The marker gene is then looped out through recombination mediated by the direct repeat, an event which is selected for by plating the intermediate strain on medium containing 5-fluoroorotic acid (5-FOA), which is toxic to cells expressing the URA3 gene. The result is a yeast strain, in which the native promoter has been replaced with the strong constitutive promoter. Integration of the above described promoter sequence and marker gene is directed to the correct location in the genome by means of PCR-generated target sequences.

The above described gene-targeting substrate can be constructed by means of multiple rounds of fusion-PCR. However, to avoid introduction of PCR-generated mutations, it is beneficial to use a bi-partite or even a quadruple gene-targeting substrate (Erdeniz et al, 1997).

For example, to over express a gene with the strong ADH1 promoter, this promoter has been introduced into intermediate working vectors on either side of *K. lactis* URA3, resulting in the vectors pWAD1, pWAD2, (WO2005/118814). With these vectors as templates, fragments can be amplified that contain (in the 5' to 3' direction) 1) the ADH1 coupled to two thirds of *K. lactis* URA3 towards the 5' end, using the primers AD-fw and Int3', and 2) two thirds of *K. lactis* URA3 towards the 3' end coupled to the ADH1, using the primers Int5' and AD-rv. Target sequences corresponding to a 300-500 bp sequence upstream of the gene to be overexpressed and a 300-500 bp starting with ATG of the gene to be over expressed, are amplified from genomic yeast DNA using suitable primers. The reverse primer used for amplification of the upstream target sequence contains a 5' overhang that allows fusion to fragment 1 described above. The forward primer used for amplification of the target sequence starting with ATG contains a 5' overhang that allows fusion with fragment 2 described above. Following fusion by PCR of the upstream target sequence with fragment 1, and fusion by PCR of fragment 2 with the target sequence starting with ATG, the two linear substrates that are ready for transformation.

Cre/Lox Method for Gene Deletion

Deletion of target genes was carried out by means of a method based on a linear, PCR-generated gene-targeting substrate using auxotrophic or antibiotic resistance marker flanked by a 34 bp sequences called loxP sites, together with a recombinase containing plasmid (Johansson and Hahn-Hägerdal, 2002, Yoon et al., 1998).

The method utilizes a cre-recombinase originating from the Bacteriophage P1 which recognizes and facilitates a recombination event between loxP sequences causing loss of the marker sequence between these sites. This method includes the generation of an intermediate yeast strain, where the chosen marker gene is integrated in combination with two copies of the loxP targeting sequences as a direct repeat on each side of the marker gene. The intermediate strain also contains an autonomously replicating plasmid bearing an auxotrophic or antibiotic resistance marker and a Cre-recombinase gene controlled by the galactose inducible promoter GAL1. The marker gene is then looped out through recombination mediated by the Cre-recombinase targeting the loxP sites, an event activated by galactose metabolism. The result is a yeast strain, in which the coding sequence of the target gene has been replaced by one loxP site.

The above described gene-targeting substrate can be constructed by means of fusion-PCR. However, to avoid introduction of PCR-generated mutations, it is beneficial to use a bi-partite or even a quadruple gene-targeting substrate (Erdeniz et al, 1997).

For example, to delete a target gene using a chosen marker, say *K. lactis* URA3 flanked by loxP sites, two 34 bp sites have been introduced into a working vector on either side, resulting in the vector pUG72 (Johansson and Hahn-Hägerdal, 2002). With this vector as template, fragments can be amplified that contain (in the 5' to 3' direction) i) the loxP sequence coupled to two thirds of *K. lactis* URA3 towards the 5' end, using the primers URA3_R 5'-ATACATTTGCCTTTTGAAAAC and X1_F 5'-GTCAGCGGCCGCATCCCTGCTACGCTGCAGGTCGACAA, and ii) two thirds of *K. lactis* URA3 towards the 3' end coupled to a loxP sequence, using the primers X2_R 5'-CACGGCGCGCCTAGCAGCGGAGGCCACTAGTGGATCTGATAT and URA3_F 5'-CCAACAATGATGATATCTGATC.

Target sequences corresponding to a 300-500 bp sequence upstream of the gene to be deleted and a 300-500 bp from the stop codon of the gene to be deleted, are amplified from genomic yeast DNA using suitable primers. The reverse primer used for amplification of the upstream target sequence contains a 5' overhang that allows fusion to fragment 1 described above. The forward primer used for amplification of the target sequence starting with the stop codon contains a 5' overhang that allows fusion with fragment 2 described above. Following fusion by PCR of the upstream target sequence with fragment 1, and fusion by PCR of fragment 2 with the target sequence starting with the stop codon, the two linear substrates are ready for transformation.

Yeast Transformations and Nomenclature

The transformation of yeast cells is conducted in accordance with methods known in the art, for instance by using lithium acetate transformation method (Gietz and Schiestl, 1991) followed by plating on selective medium, synthetic complete agar plates lacking amino acids corresponding to the markers on the vectors and the auxotrophy of the yeast mutants. In general, unless stated in the specific Examples, the resulting strains after transformation were given the following strain nomenclature FSX-Y-Z-V-W, where X is the strain background and Y, Z, V, W indicate vectors, integrative and 2 micron multicopy self-replicative, that have been transformed into that strain background X. For instance, taking strains Examples for FS01529-9-28 and FS09258-53-32-44-51 that appear in the following Examples, for strain FS01529-9-28, the strain background yeast strain X is 01529 and contains vectors Y and Z, which are vector RHO009 and RHO028. For strain FS09258-53-32-44-51, the strain background X is 09258 and the strain contains the vectors, Y, Z, V, W, which are RHO053, RHO032, RHO044 and RHO051, respectively.

Lipid Extraction from Yeast

Prior to lipid extraction, an estimation of dry-weight (DW) concentration of the culture was done and the culture either diluted or concentrated in $dH_2O$, such that a suspension with a dry-weight concentration of approximately 8 mg/ml was obtained.

The cells for extraction were prepared by transferring 1 ml cell suspension (ca 8 mg dry weight) to a trans-methylation tubes (100×16 mm) with “red” PTFE-lined “black” screw-on caps micro tube with screw cap (SciLabware Limited, Staffordshire, United Kingdom), centrifuged at 8000 rpm for 4 min and removing the supernatant. 50 μl internal standard was added (C23:0 FFA, >99% p.a., Larodan) with 1 ml methanol, 1 ml methanolic HCL and 600 μl heptane (with 0.02% BHT), the samples were vortexed and incubated for 60 min at 100° C. with thoroughly hand-shaking for 5 sec every 20 min. After incubation, the samples were allowed to cool down below room temperature in an ice bath. Subsequently, 2 ml of milli-Q $H_2O$ was added and vortexed briefly and the sample spun at 1730 rpm for 2 min. About 150 μl of the upper heptane phase was transferred to a GC vial with an insert (200 μl) and stored at −20° C. until GC analysis.

Gas Chromatography with FID Detection

FAME were analysed on a gas chromatograph (GC) (Agilent 7890A, Agilent) coupled to a flame-ionisation-detector (FID). The GC-FID was operated with an auto-injector (GC-Pal, CTC Analytics) and GC software, EZChrom Elite (version 3.3.1).

Sample injection volumes was 1 μl (2-6 mg/mL) and the split ratio 200:1 operated at an injector temperature of 250° C. Number of rinses with sample prior to injection was 1 and after injection the number of rinses with solvent was 5. Samples were separated on a DB-Wax column (10m×0.1 mmID, 0.1 μm film thickness) (J&W Scientifics). The column was fitted to a flame-ionization-detector (FID) for identification and quantification. Hydrogen was used as carrier gas and operated at a linear velocity of 30 ml/min Based on the polar nature of the column coating (100% DB-Wax) and an optimized temperature programme (see below), FAME were separated according to differences in polarity and boiling point. Oven temperature was initially set at 190° C. Immediately after injection it was increased to 230° C. at 40° C./min, then increased to 240° C. at 12° C./min and finally increased to 260° C. at 60° C./min and kept there for 0.5 min. Total run time was 3.0667 min.

On the FID side, nitrogen was used as makeup gas (25 mL/min) and the air/hydrogen ratio set at 13.33:1 (400:30 ml/min). The FID-detector was set at 275° C.

The FAME were identified based on relative retention time (RRT). Using the GC software (EzChrom Elite), RRTs were produced and updated using an array of commercially available FAME standards (GLC reference standard 68D, 409 and 85, Nu-Chek-Prep) and C22:4 (n-6), C23:0, C22:5 (n-3) and C18:4 (n-3) (Sigma, Larodan and Avanti). A quantitative FAME standard (GLC 68D, Nu-Chek-Prep) was run routinely to monitor the condition of the column and overall GC performance.

Fatty Acid Quantification and Yield

Quantification was based on FID data auto-integrated by the GC software and manually corrected for potential artefacts. Amounts of individual fatty acids (FA) and total FA (mg) were calculated based on the ISTD (C23:0 FFA), added during lipid extraction. The ISTD was made up in a solution of chloroform:methanol (2:1, v/v) and a suitable amount was added to represent 5-10% of total FA. FA yield (mg FA/g DW) was determined by calculation based on the ISTD and divided by the dry weight (DW) of the biomass in 1 ml of the initial cell suspension.

EXAMPLE 1

Isolation of Resveratrol Pathway Genes Encoding PAL2, C4H, ATR2, 4CL2, 4CL1 and VST1

Phenylalanine ammonia lyase (PAL2 gene) codon optimised for *S. cerevisiae* from *Arabidopsis thaliana* (Cochrane et al., 2004) (SEQ ID NO 14), cinnamate 4-hydroxylase (C4H gene) codon optimised for *S. cerevisiae* from *Arabidopsis thaliana* (Mizutani et al, 1997) (SEQ ID NO 15), cytochrome P450 reductase (ATR2 gene) codon optimised for *S. cerevisiae* from *Arabidopsis thaliana* (Mizutani and Ohta, 1998) (SEQ ID NO 16), 4-coumarate:coenzymeA ligase (4CL1) codon optimised for *S. cerevisiae* from *Arabidopsis thaliana* (Hamberger and Hahlbrock 2004; Ehlting et al., 1999) (SEQ ID NO 17), and resveratrol synthase (VST1 gene) from *Vitis vinifera* (grapevine) (Hain et al., 1993) (SEQ ID NO 18) codon optimized for expression in *S. cerevisiae* was synthesized by GenScript Corporation (Piscataway, N.J.). The synthetic codon optimized genes were delivered inserted in *E. coli* pUC57 vector. The synthetic genes were reamplified with PCR using the pUC57 vectors as templates. After DPN1 digestion the PCR products were purified from agarose gel using the QiaQuick Gel Extraction Kit (Qiagen).

4-coumarate:coenzymeA ligase (4CL2) (Hamberger and Hahlbrock 2004; Ehlting et al., 1999) (SEQ ID NO 19) was isolated via PCR from *A. thaliana* cDNA (BioCat, Heidelberg, Germany) using the forward primer 5'-GC GAATTC TT ATGACGACAC AAGATGTGAT AGTCAATGAT (SEQ ID NO 20) containing the underlined restriction site EcoRI and the reverse primer 5'-GC ACTAGT ATC CTA GTT CAT TAA TCC ATT TGC TAG TCT TGC T (SEQ ID NO 21) containing the underlined restriction site SpeI.

Resveratrol Producing Vector Construction

EXAMPLE 2

Construction of a Yeast Vector for Galactose Induced Expression of PAL2 and C4H:ATR2 Fusion Gene The gene encoding PAL2 from *A. thaliana* was reamplified via PCR from Genscript vector pUC-57-PAL2 using forward primer 5-CTC ACT AAA GGG CGG CCG CAT GGA CCA AAT TGA AGC AAT-3 (SEQ ID NO 22) containing the restriction site ECoRI and reverse primer containing the restriction site BGLII 5-TAA GAG CTC AGA TCT TTA GCA GAT TGG AAT AGG TG-3 (SEQ ID NO 23).

The gene encoding C4H from *A. thaliana* was reamplified via PCR from Genscript vector pUC-57-C4H using forward primer 5-GAA GAA GAC CTC GAG ATG GAT TTG TTA TTG CTG GA-3 (SEQ ID NO 24) and reverse primer 5-AGT AGA TGG AGT AGA TGG AGT AGA TGG AGT AGA TGG ACA ATT TCT GGG TTT CAT GA-3 (SEQ ID NO 25). ATR2 from *A. thaliana* was reamplified via PCR from Genscript vector pUC-57-ATR2 using forward 5-CCA TCT ACT CCA TCT ACT CCA TCT ACT CCA TCT ACT AGG AGG AGC GGT TCG GGC-3 (SEQ ID 26) and reverse primer 5-GCT AGC CGC GGT ACC TTA CCA TAC ATC TCT CAG ATA T-3 (SEQ ID NO 27).

The amplified PCR products C4H and ATR2 were used as templates for the creation of the fusion gene C4H:ATR2 using the forward primer 5-GAA GAA GAC CTC GAG ATG GAT TTG TTA TTG CTG GA-3 (SEQ ID NO 28) and the reverse primer 5-GCT AGC CGC GGT ACC TTA CCA TAC ATC TCT CAG ATA T-3 (SEQ ID NO 29).

The fusion gene C4H:ATR2 gene was digested with XhoI/KpnI and ligated into XhoI/KpnI digested pESC-URA-PAL2. The resulting plasmid, pESC-URA-PAL2-C4H:ATR2 (RHO003), contained the genes encoding PAL2 and C4H:ATR2 under the control of the divergent galactose induced <=GAL1/GAL10=> promoters. The sequence of the gene encoding C4H:ATR2 was verified by sequencing of two different clones of RHO003.

EXAMPLE 3

Construction of a Yeast Vector for Galactose Induced Expression of PAL2 and C4H:CYB5:ATR2 Fusion Gene The gene encoding PAL2 from *A. thaliana* was reamplified via PCR from Genscript vector pUC-57-PAL2 using forward primer 5-CTC ACT AAA GGG CGG CCG CAT GGA CCA AAT TGA AGC AAT-3 (SEQ ID NO 30) containing the restriction site ECoRI and reverse primer containing the restriction site BGLII 5-TAA GAG CTC AGA TCT TTA GCA GAT TGG AAT AGG TG-3 (SEQ ID NO 31).

The amplified PAL2 PCR-product was digested with EcoR1/BGLII and ligated into EcoR1/BGLII digested pESC-URA vector (Stratagene), resulting in vector pESC-URA-PAL2. Two different clones of pESC-URA-Pal2 were sequenced to verify the sequence of the cloned gene.

PAL2 from *A. thaliana* was reamplified via PCR from Genscript vector pUC-57-PAL2 using forward primer 5-GAA GAA GAC CTC GAG ATG GAT TTG TTA TTG CTG GA-3 (SEQ ID NO 32) and reverse primer 5-ACC TAG AGC ACC ACC ACA ATT TCT GGG TTT CAT GAC T-3 (SEQ ID NO 33). ATR2 from *A. thaliana* was reamplified via PCR from Genscript vector pUC-57-ATR2 using forward 5-GGT GCT ATT CTA GTT GGT AGG AGG AGC GGT TCG GGC-3 (SEQ ID NO 34) and reverse primer 5-GCT AGC CGC GGT ACC TTA CCA TAC ATC TCT CAG ATA T-3 (SEQ ID NO 35). CYB5 (encoded by *S. cerevisiae* gene YNL111c) was amplified using purified genomic DNA from *S. cerevisiae* as template using forward primer 5-CCA GCT CAA TCA GTT CCA GCT CTT TCA GTT CCT AAA GTT TAC AGT TAC C-3 (SEQ ID NO 36) and reverse primer 5-AAC TAG AAC TGA TTG AGC AGT TGG TGA TGG TTT ACT TTG GTT TTC AGA GG-3 (SEQ ID NO 37).

The amplified PCR products C4H, CYB5 and ATR2 were used as templates for the creation of the fusion gene C4H:CYB5:ATR2 using the forward primer 5-GAA GAA GAC CTC GAG ATG GAT TTG TTA TTG CTG GA-3 (SEQ ID NO 38) and the reverse primer 5-GCT AGC CGC GGT ACC TTA CCA TAC ATC TCT CAG ATA T-3 (SEQ ID NO 39).

The fusion gene C4H:CYB5:ATR2 gene was digested with XhoI/KpnI and ligated into XhoI/KpnI digested pESC-URA-PAL2. The resulting plasmid, pESC-URA-PAL2-C4H:CYB5:ATR2 (RHO004), contained the genes encoding PAL2 and C4H:CYB5:ATR2 under the control of the divergent galactose induced <=GAL1/GAL10=> promoters. The sequence of the gene encoding C4H:ATR2 was verified by sequencing of two different clones of (RHO004).

EXAMPLE 4

Construction of a Yeast Vector for Galactose Induced Expression of 4CL2 and VST1

The gene encoding 4CL2 was isolated as described in Example 5. The amplified 4CL2 PCR-product was digested with EcoR1/Spe1 and ligated into EcoR1/Spe1 digested pESC-HIS vector (Stratagene), resulting in vector pESC-HIS-4CL2. Two different clones of pESC-HIS-4CL2 were sequenced to verify the sequence of the cloned gene.

The gene encoding VST1 was reamplified from Genscript vector puc57-VST1 via PCR using the forward primer 5'-CC GGATCC ATG GCA TCC GTA GAG GAG TTC AGA A-3' (SEQ ID NO 40) containing the underlined BamHI restriction site and the reverse primer 5'-CG CTCGAG TCA TTA GTT AGT GAC AGT TGG AAC AGA GT-3' (SEQ ID NO 41) containing the underlined restriction site for XHOI. The amplified synthetic VST1 gene was digested with BamH1/Xho1 and ligated into BamH1/Xho1 digested pESC-HIS-4CL2. The resulting plasmid, pESC-HIS-4CL2-VST1 (Rh0043), contained the genes encoding 4CL2 and VST1 under the control of the divergent galactose induced <=GAL1/GAL10=> promoters. The sequence of the gene encoding VST1 was verified by sequencing of two different clones of pESC-HIS-4CL2-VST1.

EXAMPLE 5

Construction of a Yeast Vector for Galactose Induced Expression of 4CL1 and VST1

The gene encoding 4CL1 was isolated via PCR from the puc57-4CL1 vector using the forward primer 5'-TT-GAAAATTCGAATTC ATGGCCCCCCAAGAA-3' (SEQ ID NO 42) containing the underlined restriction site EcoRI and the reverse primer 5'-GCGAAGAATTGTTAATTAA TTAAAGACCGTTTGCTAGTTT-3' (SEQ ID NO 43) containing the underlined restriction site for PACI. The amplified 4CL1 PCR-product was digested with EcoR1/PAC1 and ligated into EcoR1/PAC1 digested pESC-HIS vector (Stratagene), resulting in vector pESC-HIS-4CL1. Two different clones of pESC-HIS-4CL1 were sequenced to verify the sequence of the cloned gene.

The gene encoding VST1 was reamplified from Genscript vector puc57-VST1 via PCR using the forward primer 5'-CC GGATCC ATG GCA TCC GTA GAG GAG TTC AGA A-3' (SEQ ID NO 40) containing the underlined BamH1 restriction site and the reverse primer 5'-CG CTCGAG TCA TTA GTT AGT GAC AGT TGG AAC AGA GT-3' (SEQ ID NO 45) containing the underlined restriction site for XHOI. The amplified synthetic VST1 gene was digested with BamH1/Xho1 and ligated into BamH1/Xho1 digested pESC-HIS-4CL1. The resulting plasmid, pESC-HIS-4CL1-VST1 (RhO001), contained the genes encoding 4CL1 and VST1 under the control of the divergent galactose induced <=GAL1/GAL10=> promoters. The sequence of the gene encoding VST1 was verified by sequencing of two different clones of pESC-HIS-4CL1-VST1 (RHO001).

EXAMPLE 6

Construction of Strong Constitutive Promoter Fragment TDH3

The 600 base pair TDH3 (GPD) promoter was amplified from *S. cerevisiae* genomic DNA using the forward primer 5'-GC GAGCTC AGT TTA TCA TTA TCA ATA CTC GCC ATT TCA AAG-3' (SEQ ID NO 46) containing a Sac1 restriction site and the reverse primer 5'-CG TCTAGA ATC CGT CGA AAC TAA GTT CTG GTG TTT TAA AAC TAA AA-3' (SEQ ID NO 47) containing a Xba1 restriction site. The amplified TDH3 fragment was digested with Sac1/Xba1 and ligated into Sac1/Xba1 digested plasmid pRS416 (Sikorski and Hieter, 1989) as described previously (Mumberg et al, 1995) resulting in plasmid pRS416-TDH3.

EXAMPLE 7

Construction of Constitutive Strong Promoter Fragment TEF2

The 400 base pair TEF2 promoter was amplified from *S. cerevisiae* genomic DNA using the forward primer 5'-GC GAGCTC ATA GCT TCA AAA TGT TTC TAC TCC TTT TTT ACT CTT-3' (SEQ ID NO 48) containing a Sac1 restriction site and the reverse primer 5'-CG TCTAGA AAA CTT AGA TTA GAT TGC TAT GCT TTC TTT CTA ATG A-3' (SEQ ID NO 49) containing a Xba1 restriction site. The amplified TEF2 fragment was digested with Sac1/Xba1 and ligated into Sac1/Xba1 digested plasmid pRS416 (Sikorski and Hieter, 1989) as described previously (Mumberg et al, 1995) resulting in plasmid pRS416-TEF2.

EXAMPLE 8

Construction of Fused Divergent Constitutive TEF and TDH3 Promoter Fragment

A divergent fusion fragment between TEF2 promoter and TDH3 promoter was constructed starting from PRS416-TEF and PRS416-TDH3.

The 600 base pair TDH3 fragment was reamplified from PRS416-TDH3 using the forward primer 5' TTGCGTATT GGGCGCTCTTCC GAG CTC AGT TTA TCA TTA TCA ATA CTC GC-3' (SEQ ID NO 50) containing the underlined overhang for fusion PCR to TEF2 fragment and the reverse primer 5' AT GGATCC TCT AGA ATC CGT CGA AAC TAA GTT CTG-3' (SEQ ID NO 51) containing the underlined BamH1 restriction site. This resulted in a fragment ready for fusion to the below TEF2 fragment.

The 400 base pair TEF2 fragment including a 277 base pair spacer upstream of the Sac1 restriction site was reamplified from PRS416-TEF2 using the forward primer 5' AT GAATTC TCT AGA AAA CTT AGA TTA GAT TGC TAT GCT TTC-3' (SEQ ID NO 52) containing the underlined EcoR1 restriction site and the reverse primer 5' TGATAATGATAAACTGAGCTCGGA AGA GCG CCC AAT ACG CAA AC-3' (SEQ ID NO 53) containing the underlined overhang for fusion to the TDH3 fragment. This resulted in a 680 base pair fragment ready for fusion to the TDH3 fragment.

The 680 base pair TEF2 fragment and the 600 base pair TDH3 fragments were joined together (fused) using fusion PCR with the forward primer 5' AT GAATTC TCT AGA AAA CTT AGA TTA GAT TGC TAT GCT TTC-3' (SEQ ID NO 54) and the reverse primer 5' AT GGATCC TCT AGA ATC CGT CGA AAC TAA GTT CTG-3' (SEQ ID NO 55), resulting in the divergent promoter fragment <=TEF2/TDH3=> (SEQ ID NO 56).

EXAMPLE 9

Construction of a Yeast Vector for Constitutive Expression of PAL2 and C4H:ATR2 Fusion Gene The vector pESC-URA-PAL2-C4H:ATR2 with divergent galactose inducible promoters GAL1/GAL10 was sequentially digested with NotI and BsiWI to remove the GAL1/GAL10 promoters.

The divergent constitutive <=TEF2/TDH3=> promoter fragment (Example 8) was re-amplified with forward primer 5-GC GCGGCCGC TCT AGA AAA CTT AGA TTA GAT TGC TAT GCT TTC-3 (SEQ ID NO 57) and reverse primer 5-ATT CGTACG TCT AGA ATC CGT CGA AAC TAA GTT CTG-3 (SEQ ID NO 58). The resulting PCR product was sequentially digested with NotI and BsiWI and ligated into the above vector without the GAL1/Ga110 fragment. This resulted in a vector pESC-URA-TDH3-PAL2-TEF1-C4H:ATR2 (RHO0019) with replaced promoters, from GAL1/Ga110 to TEF2/TDH3.

EXAMPLE 10

Construction of a Yeast Vector for Constitutive Expression of PAL2 and C4H:CYB5:ATR2 Fusion Gene The vector pESC-URA-PAL2-C4H:CYB5:ATR2 with divergent galactose inducible promoters GAL1/GAL10 was sequentially digested with NotI and BsiWI to remove the GAL1/GAL10 promoters.

The divergent constitutive <=TEF2/TDH3=> promoter fragment (Example 8) was re-amplified with forward primer 5-GC GCGGCCGC TCT AGA AAA CTT AGA TTA GAT TGC TAT GCT TTC-3 (SEQ ID NO 57) and reverse primer 5-ATT CGTACG TCT AGA ATC CGT CGA AAC TAA GTT CTG-3 (SEQ ID NO 58). The resulting PCR product was sequentially digested with NotI and BsiWI and ligated into the above vector without the GAL1/Gal10 fragment. This resulted in a vector pESC-URA-TDH3-PAL2-TEF1-

C4H:CYB5:ATR2 (RHO0025) with replaced promoters, from GAL1/GA110 to TEF2/TDH3.

EXAMPLE 11

Construction of a Yeast Vector for Constitutive Expression Induced of 4CL2 and VST1

The vector pESC-HIS-4CL2-VST1 with divergent galactose inducible promoters GAL1/GAL10 was sequentially digested with EcoR1 and BamH1 to remove the GAL1/GAL10 promoters.

The divergent constitutive <=TEF2/TDH3=> promoter fragment (Example 8) was sequentially digested with EcoR1 and BamH1 and ligated into the above linearized vector without the GAL1/GAL10 fragment. This resulted in a vector pesc-HIS3-TEF2-4CL2-TDH3-VST1 (RHO0011) with replaced promoters, from GAL1/GA110 to TEF2/TDH3.

EXAMPLE 12

Generation of Control Vectors RHO0020 and RHO0022

Vectors pESC-URA3 and pESC-HIS3 (Stratagene) were digested with BamH1 and EcOR1 to remove the divergent GAL1/Gal10 galactose promoters. The divergent TEF/TDH3 promoters were cut out from vector RHO009 and ligated into two opened Stratagene vector backbones to generate the empty control vectors pESC-URA3-TEF/TDH3 (RHO0020) and pESC-HIS3-TEF/TDH3 (RHO0022).

EXAMPLE 13

Generation of Vector RHO0028 from RHO0025 (Marker Exchange)

The URA3 marker in vector RHO0025 was exchanged for the HIS3 marker using the Infusion Technology. The RHO0025 vector backbone except for the URA3 marker cassette was linearized with PCR using the Herculase II polymerasae with the forward primer 5'-ATGCGTAAGGA-GAAAATACCGCATCAGG-3' (SEQ ID NO 59) and the reverse primer 5'-CTC TCA GTA CAA TCT GCT CTG ATG CCG-3' (SEQ ID NO 60). The HIS3 marker cassette was reamplified from pESC-HIS (Stratagene) using the forward primer 5' CAGAGCAGATTGTACTGAGAG GAG CTT GGT GAG CGC TAG GAG TCA and the reverse primer 5'-CGGTATTTTCTCCTTACGCAT GGA AAG CGC GCC TCG TTC AGA ATG-3' (SEQ ID NO 62) with the underlined homologous overhangs to the linearized RHO0025 vector. The two fragments were recombined using the Infusion Cloning Kit. The resulting vector pESC-HIS3-TDH3-PAL2-TEF1-C4H:CYB5:ATR2 (RHO0028).

EXAMPLE 14

Generation of Vector RHO009 from RHO0011 (Marker Exchange)

The HIS3 marker in vector RHO0011 was exchanged for the URA3 marker using the Infusion Technology. The RHO0011 vector backbone except for the HIS3 marker cassette was linearized with PCR using the Herculase II polymerasae with the forward primer 5'-TCG ACG GAT CTA TGC GGT GTG AAA TAC C-3' (SEQ ID NO 63) and the reverse primer 5'-ACT CTC AGT ACA ATC TGC TCT GAT GCC G-3' (SEQ ID NO 64). The URA3 marker cassette was reamplified from pESC-URA (Stratagene) using the forward primer 5'-AGAGCAGATTGTACTGAGAGT CAT CAG AGC AGA TTG TAC TGA GAG TGC-3' (SEQ ID NO 65) and the reverse primer 5'-CACACCGCATAGATCCGTCGA GGA TTT TGC CGA TTT CGG CCT ATT GG-3' (SEQ ID NO 66) with the underlined homologous overhangs to the linearized RHO0011 vector. The two fragments were recombined using the Infusion Cloning Kit. The resulting vector pESC-URA3-TEF2-4CL2-TDH3-VST1 was called RHO009.

EXAMPLE 15

Construction of a Yeast Vector for Constitutive Expression PAL2, C4H:ATR2, 4CL2 and VST1 Containing the ura3 Marker RHO0029

RHO0019 was used as template for PCR amplification (Herculase II) using forward primer 5-CAG AGC AGA TTG TAC TGA GAG TG-3 (SEQ ID NO 70) and reverse primer 5-ATG CCG CAT AGT TAA GCC A-3 (SEQ ID NO 67). RHO0011 was used as template for PCR amplification (Herculase II) using forward primer 5-TGG CTT AAC TAT GCG GCA TGA GCG ACC TCA TGC TAT ACC T-3 (SEQ ID NO 68) and reverse primer 5-TCT CAG TAC AAT CTGC TCT GCT GTG GAT AAC CGT ATT ACC G-3 (SEQ ID NO 69). The two fragments obtained by PCR was fused using InFusion Cloning technology resulting in the plasmid pESC-URA-TDH3-PAL2-TEF1-C4H:ATR2-TDH3-4CL2-TEF-VST1 (RHO0029).

EXAMPLE 16

Construction of a Yeast Vector for Constitutive Expression PAL2, C4H:ATR2, 4CL2 and VST1 Containing the His3 Marker RHO0030

RHO0011 was used as template for PCR amplification (Herculase II) using forward primer 5-CAG AGC AGA TTG TAC TGA GAG TG-3 (SEQ ID NO 70) and reverse primer 5-ATG CCG CAT AGT TAA GCC A-3 (SEQ ID NO 67). RHO0019 was used as template for PCR amplification (Herculase II) using forward primer 5-TGG CTT AAC TAT GCG GCA TGA GCG ACC TCA TGC TAT ACC T-3 (SEQ ID NO 68) and reverse primer 5-TCT CAG TAC AAT CTGC TCT GCT GTG GAT AAC CGT ATT ACC G-3 (SEQ ID NO 69).

The two fragments obtained by PCR was fused using InFusion Cloning technology resulting in the plasmid pESC-HIS-TDH3-PAL2-TEF1-C4H:ATR2-TDH3-4CL2-TEF-VST1 (RHO0030).

EXAMPLE 17

Construction of a Yeast Vector for Constitutive Expression PAL2, C4H:CYB5:ATR2, 4CL2 and VST1 Containing the His3 Marker RHO0032b RHO0025 was used as template for PCR amplification (Herculase II) using forward primer 5-CAG AGC AGA TTG TAC TGA GAG TG-3 (SEQ ID NO 70) and reverse primer 5-ATG CCG CAT AGT TAA GCC A-3 (SEQ ID NO 67). RHO0011 was used as template for PCR amplification (Herculase II) using forward primer 5-TGG CTT AAC TAT GCG GCA TGA GCG ACC TCA TGC TAT ACC T-3 (SEQ ID NO 68) and reverse primer 5-TCT CAG TAC AAT CTGC TCT GCT GTG GAT AAC CGT ATT ACC G-3 (SEQ ID NO 69).

The two fragments obtained by PCR was fused using InFusion Cloning technology resulting in the plasmid pESC-HIS-TDH3-PAL2-TEF1-C4H:CYB5:ATR2-TDH3-4CL2-TEF-VST1 (RHO0032b).

EXAMPLE 18

Construction of a Yeast Vector for Constitutive Expression PAL2, C4H:CYB5:ATR2, 4CL2 and VST1 Containing the Leu2 Marker RHO0044

Vector RHO0044 (The full resveratrol pathway on one 2 micron based self-replicative multicopy vector with leu2-marker) was constructed as follows. First the HIS3 marker was exchanged in plasmid pesc-HIS3-TDH3-4CL2-TEF-VST1 (RhO0011) using InFusion Cloning by fusing fragment i) linearized RHO0011 constructed by PCR with Herculase II and the forward primer 5'-TCG ACG GAT CTA TGC GGT GTG AAA TAC C (SEQ ID NO 63) and the reverse primer 5'-ACT CTC AGT ACA ATC TGC TCT GAT GCC G (SEQ ID NO 64) and fragment ii) constructed by amplifying the LEU2 expression cassette from pESC-LEU2 (Stratagene) with forward primer 5'-AGA GCAGATTGTA CTGAGAGT AAG ATG CAA GAG TTC GAA TCT CTT AGC AA (SEQ ID NO 71) and reverse primer 5'-CAC ACC GCA TAG ATC CGT CGA TCG ACT ACG TCG TAA GGC CGT TTC T-3' (SEQ ID NO 72). This resulted in vector pESC-LEU2-TDH3-4CL2-TEF-VST1 (RhO0072). The expression cassette containing TDH3-PAL2-TEF-C4H::CYb5::ATR2 was then inserted into RHO0072 by using Infusion Technology between fragment i) linearized RHO0072 constructed by PCR with Herculase II polymerase with forward primer 5'-AAGATGCAAGAGTTC-GAATCTCTTAGCAACC (SEQ ID NO 73) and reverse primer 5'-CTC TCA GTA CAA TCT GCT CTG ATG CC (SEQ ID NO 60) and fragment ii) constructed by PCR of plasmid RhO0025 with forward primer 5'-CAGAGCAGAT-TGTACTG AGAGGAGCGACCTCATGCTAT ACCT (SEQ ID NO 74) and the reverse primer 5'-AGATTC-GAACTCTTGCATCTT CTGTGGATAACCGTAT-TACCG-3'(SEQ ID NO 75). This resulted in vector pESC-LEU-TDH3-PAL2-TEF1-C4H:CYB5:ATR2-TDH3-4CL2-TEF-VST1 (RhO0044).

EXAMPLE 19

Construction of a Yeast Vector for Constitutive Expression PAL2, C4H:CYB5:ATR2, 4CL2 and VST1 Containing the Ura3-tag2 Marker RHO0053

RHO0025 was used as template for PCR amplification (Herculase II) removing the ura3 coding sequence using forward primer 5-CTC ATT TTG TTA TTC ATT TGT AAA AAA CTG TAT TAT AAG TAA ATG CAT GT-3 (SEQ ID NO 76) containing a ubiquitination tag and reverse primer 5-TCC TTA TAT GTA GCT TTC GAC AT-3 (SEQ ID NO 77).

RHO0020 was used as template for PCR amplification of the ura3 coding sequence using forward primer 5-ATG TCG AAA GCT ACA TAT AAG GAA CGT G-3 (SEQ ID NO 78) and reverse primer 5-CAA ATG AAT AAC AAA ATG AGA CAA AGA AGA AAA CCA ATT TTT ACA AGC GTT TTG CTG GCC-3 (SEQ ID NO 79) containing a ubiquitination tag. The two fragments obtained by PCR was fused using InFusion Cloning technology resulting in the plasmid pESC-URA3:TAG-TDH3-PAL2-TEF1-C4H:CYB5:ATR2. The plasmid was called RHO0058.

RHO0058 was linearized by PCR amplification (Herculase II) using forward primer 5-CAG AGC AGA TTG TAC TGA GAG TG-3 (SEQ ID NO 70) and reverse primer 5-ATG CCG CAT AGT TAA GCC A-3 (SEQ ID NO 67). RHO0011 was used as template for PCR amplification of the 4CL2 and VST1 expression cassettes (Herculase II) using forward primer 5-TGG CTT AAC TAT GCG GCA TGA GCG ACC TCA TGC TAT ACC T-3 (SEQ ID NO 68) and reverse primer 5-CT CAG TAC AAT CTGC TCT GCT GTG GAT AAC CGT ATT ACC G-3 (SEQ ID NO 69). The two fragments obtained by PCR was fused using InFusion Cloning technology resulting the plasmid pESC-URA3:TAG-TDH3-PAL2-TEF1-C4H:CYB5:ATR2-TDH3-4CL2-TEF-VST1. The tag sequence added to the C-terminal of the URA3 gene product was ACKNWFSSLSHFVIHL (SEQ ID NO 1). The plasmid was called RHO0053. A diagram of this expression system containing phenylalanine ammonia lyase and cinnamate-4-hydroxylase fusion gene, 4-coumarate-CoA ligase and resveratrol synthase appears in FIG. 4. The expression system has an added tag ACKNWFSSLSH-FVIHL (SEQ ID NO 1) positioned at the C-terminal end of the marker gene, in this case ura3. An alternative tag to use here would be FYYPIWFARVLLVHYQ (SEQ ID NO 3).

EXAMPLE 20

Transformation of Euroscarf Deletion Mutants Deleted for Putative Resveratrol to Screen for Putative Resveratrol Transporters We screened the deletion mutant strain collection from the European *S. cerevisiae* archive for functional analysis (Euroscarf). This collection consists of different mutants in which each mutant has a known gene deleted (Giaever, et al 2002). From this library we selected mutants with the deleted transporters, identified in Table 2, which were chosen as described above.

TABLE 2

Selected ABC transporters candidates for screening

| Euroscarf Strain Deleted ORF | Gene name for deleted ORF |
|---|---|
| YOOOO*1) | Control srain, No deletion |
| ΔYGR281w | YOR1 |
| ΔYDR406w | PDR15 |
| ΔYDR011w | SNQ2 |
| ΔYOR328w | PDR10 |
| ΔYOR153w | PDR5 |
| ΔYPL058c | PDR12 |
| ΔYNR070w | PDR18 |
| ΔYIL013c | PDR11 |

*1)The strain background (genotype) for the control yeast YOOOO is [BY4741 MATA his3Δ1; leu2Δ0; met15Δ0; ura3Δ0] and for strains with gene deletions it is [BY4741 MATA his3Δ1; leu2Δ0; met15Δ0; ura3Δ0 Gene:delta:KanMx] where Genne:delta:KanMX means that each gene has been deleted by the homologous incorporation of the kanamycin cassette (KANMM), resistance towards geneticin G418.

The Euroscarf deletion mutants and control in Table 2 were transformed with two vectors RHO009 and RHO0028, which together harboured the full heterologous resveratrol pathway divided on the two different multi copy 2 micron. Vector RHO009 contained the genes encoding the enzymes that convert phenylalanine to coumaric acid, that is phenylalanine ammonia lyase (PAL2) from *Arabidopsis thaliana* and Cinnamate-4-hydroxylase (C4H) from *Arabidopsis thaliana* fused in frame to its cytochromep-450-reductase (AR2) from *Arabidopsis thaliana*. RHO0028 contains the genes that convert coumaric acid into resveratrol, that is 4-coumarate:CoA-ligase (4CL2) from *A. thaliana* and resveratrol synthase (VST1) from *Vitis vinifera*. In detail Euroscarf yeast cells were taken out from the delivered agar slant from Euroscarf and inoculated in 5 ml YPD in sterile screening tubes over night at 30° C. Cells were transformed according to the standard lithium acetate method (Gitez and Schiestl, 1989) with vector RHO009 and RHO028.

Transformants as single colonies were selected on SC-URA-HIS agar plates.

EXAMPLE 21

Figure 8:
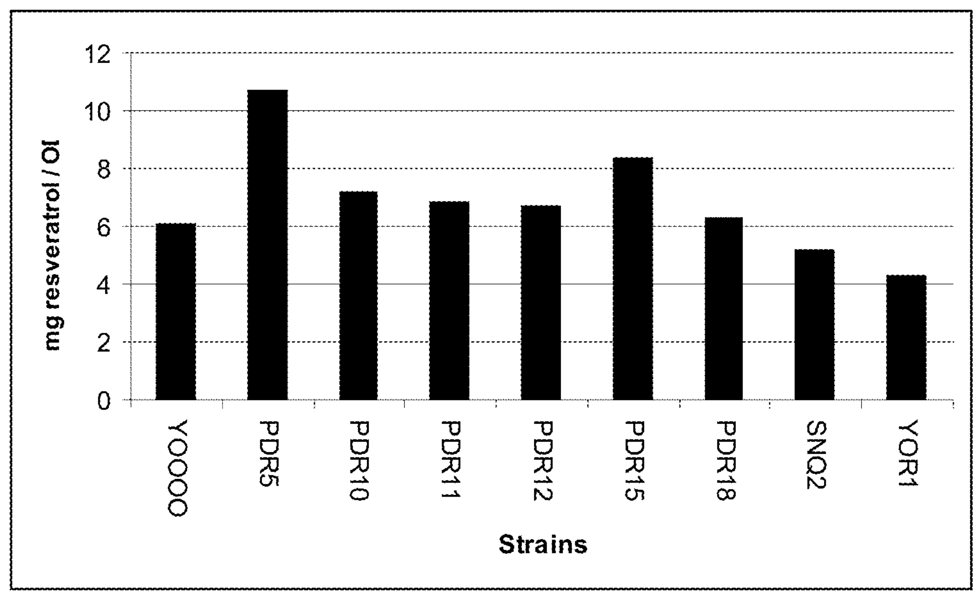
FIG. 8 shows amounts of resveratrol obtained in Example 21.

Test Tube Screening of Resveratrol Producing Euroscarf Transporter Deletion Mutants Transformants from the SC-ura-his plates were picked with sterile plastic inoculation loops and 5 colonies from each transformation plate were inoculated into 5 ml defined mineral medium containing 40 g/l glucose supplemented with 750 mg/l leucine and 300 mg/l methionine. Cells were grown for 72 hours until the glucose was depleted. We calculated the amount of produced resveratrol per produced biomass (OD600) at 72 hours when the glucose was depleted. The values are presented in FIG. 8 (mg resveratrol/OD). Results are presented as Total amount of resveratrol in mg per OD at 72 hours. Deletion mutants with low producers, such as SNQ2 and YOR1, were regarded as promising resveratrol transporter candidates.

EXAMPLE 22

Figure 9:
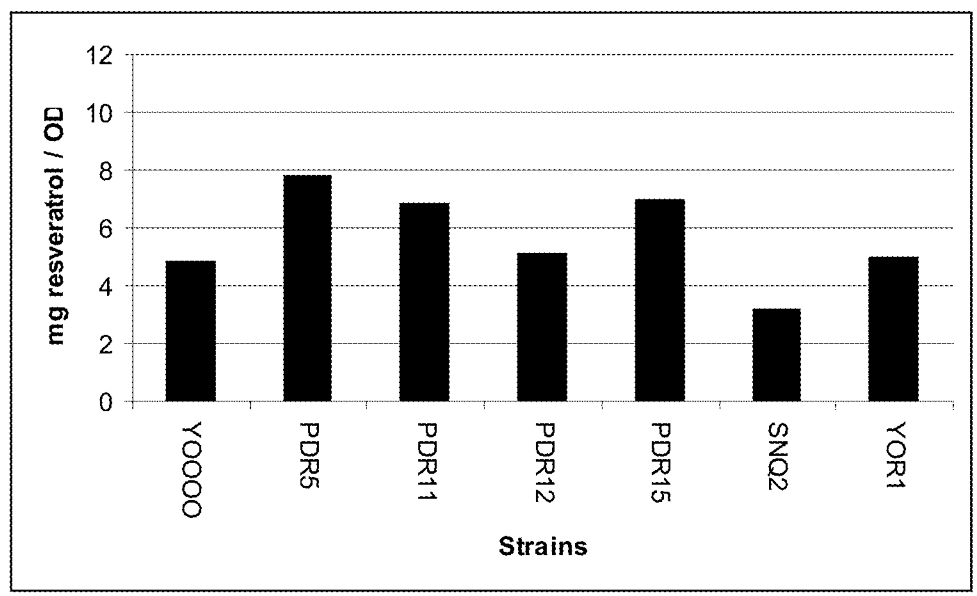
FIG. 9 shows amounts of resveratrol obtained in Example 22.

Shake Flask Screening of Resveratrol Producing Euroscarf Transporter Deletion Mutants The work in the screening tubes was repeated in shake flasks containing defined mineral medium with 40 g/l glucose, 750 mg/l leucine, and 300 mg/l methionine. The shake flasks were inoculated to an OD of 0.1 from the 72 hour cultured screening tubes (Example 21) and cultivated for 72 hours until glucose was depleted. We calculated the amount of produced resveratrol per produced biomass (OD600) at 72 hours when the glucose was depleted. The values are presented in FIG. 9 (mg resveratrol/OD). Results are presented as total amount of resveratrol in mg per OD at 72 hours. In the shake flask the only mutant that produced lower levels of resveratrol as compared to the control was the SNQ2 mutant, meaning that SNQ2 was a potential resveratrol transporter. In contrast to the screening tube results YOR1 was this time not regarded as a promising candidate.

EXAMPLE 23

Isolation of Resveratrol Transporter Genes

The ABC-transporter SNQ2 (encoded by gene YDR011w) (SEQ ID NO 80) was isolated via PCR using genomic DNA from *S. cerevisiae* CEN.PK113-5D K1, which had been prepared using the QIAamp DNA mini kit (Qiagen). The forward primer was 5'-TCGACGGATTCTAGAGGATCC ATG AGC AAT ATC AAA AGC ACG CAA GAT A (SEQ ID NO 81) and the reverse primer was 5'-ATC TTA GCT AGC CGC GGT ACC TTACTGCTTC TTTTTCCTTATGT TTTTAATTT TATTGA-3' (SEQ ID NO 82).

The ABC-transporter BcatrB from *Botrytis cinerea* (Schoonbeek et al, 2001) was synthesized by GenScript Corporation (Piscataway, N.J.) based on protein sequence for BcatrB gene (protein accession nr Q9UW03). The gene (SEQ ID NO 83) was codon optimized for expression in *S. cerevisiae*. The protein sequence in the data base for BcatrBp (protein Q9UW03) had an undefined amino acid sequence in position 99 called X. To reveal what amino acid X could be we blasted the BcatrB-Q9UW03-protein sequence towards other ABC-transporters at the Uniprot database (www.uniprot.org/) with the following results:

| | | |
|---|---|---|
| BcatrB/Q9UW03 | MPEL[1]---QAMQQQSDKD[2]-------------------QAKRRDLGVTWKNLTVKGIGADAX[3] | 99 |
| A6RVE0 | MPEL---QAMQQQSDKD-------------------QAKRRDLGVTWKNLTVKGIGADAA[4] | 99 |
| Q8TFM7 | MPEI[5]---QAMREQGEKD[6]-------------------QVKRRDLGVTWRNLTVKGIGADAA[7] | 106 |
| A7F7S9 | MPEI---QAIRNQEEKD[8]-------------------QVKRRDLGVTWKNLTVKGIGADAA[9] | 99 |
| Q96W59 | TEEL[10]---KQTQQQNEND[11]-------------------GAKDKKLGITWTDLDIKGIGADAA[12] | 93 |

[1]SEQ ID NO 186
[2]SEQ ID NO 189
[3]SEQ ID NO 84
[4]SEQ ID NO 85
[5]SEQ ID NO 187
[6]SEQ ID NO 190
[7]SEQ ID NO 86
[8]SEQ ID NO 191
[9]SEQ ID NO 87
[10]SEQ ID NO 188
[11]SEQ ID NO 192
[12]SEQ ID NO 88

Blast Search of BcatrB-protein and alignment using Clustal W, only partial sequences that are conserved are shown, neither the number nor the identity of intervening amino acids are indicated. The X at position 99 in BcatrB-protein aligns nicely with alanine in other ABC-transporter with high homology to BcatrBp.

Other sequences with a high level of identity to BcatrB-protein revealed that the X is most likely an alanine (A), which we included in the final order of the synthetic gene.

The gene was delivered in a standard *E. coli* puc-vector (Puc-57-BcatrB). The BcatrB gene was isolated by reamplifying the gene by PCR from the puc-BcatrB vector with primers For: TCGACGGATTCTAGAGGATCC ATG GCA GCA ATA GAG CCA GAA GGT TT (SEQ ID NO 89) and Rev: ATC TTA GCT AGC CGC GGT ACC TCA TTC AGC ACC TTT TGT TTT CTT TGT TCT C (SEQ ID NO 90).

EXAMPLE 24

Generation of Integration Vectors with Expression of Resveratrol Transporters

The integrative vector with constitutive TEF/TDH promoters and TRP1 marker, called pSF057, was constructed as follows. Vector RHO011 was digested with EcoRI and BamHI to get the fragment with the glucose promoters TDH3/TEF. Then vector pESC-TRP (Stratagene) was digested with the same restriction enzymes, EcoRI and BamHI, to remove the galactose promoters fragment (GAl1/GAl10) from this vector and the vector backbone was kept. The TEF/TDH3 glucose promoter fragment from RHO0011 was then ligated into the remaining backbone of pesc-TRP using T4-DNA ligase. The resulting vector was called pSF055. Plasmid pSF055 was digested with restriction enzyme AfeI and re-ligated with T4 DNA ligase. The AfeI digest removes most of the 2 micron origin and converts a multi copy self-replicative vector into an integrative vector. The resulting integrative vector was called pSF057.

The ABC-transporter BcatrB and SNQ2 genes, isolated with the primers described in Example 23, were cloned into vector pSF057 under the control of TDH3 promoter by infusion cloning between the PCR products of the transporters and linearized pSF057. The pSF057 was linearized with Herculase II polymerase and forward primer 5'-GGT ACC GCG GCT AGC TAA GAT CCG-3' (SEQ ID NO 91) and reverse primer 5'-GGA TCC TCT AGA ATC CGT CGA AAC TAA GTT-3' (SEQ ID NO 92). The resulting vectors pSF57-TRP1-TDH3-SNQ2 and PSF057-TRP1-TDH3-BCATRB were called RHO0051 and RHO0067, respectively.

EXAMPLE 25

Generation of a *S. Cerevisiae* Strain with Two Markers ura3-52 and his3.

A double marker yeast mutant strain FS01528 [MatA ura3-52, his3] and FS01529 [Matalpha ura3-52, his3] was constructed by cross breading FS01210 [Matalpha his3] and FS01202 [MatA ura3-52] dissecting spores and scoring the double deletion mutant on SC-Ura (synthetic complete medium lacking uracil) and SC-His (synthetic complete medium lacking histidine) and SC-Ura-His (synthetic complete medium lacking both uracil and histidine) agar plates.

EXAMPLE 26

Construction of a Strain Over Expressing Native *S. cerevisiae* ACC1 Gene Under the TPI-Promoter The yeast gene ACC1 (YNR016c), encoding acetyl-CoA carboxylase, was overexpressed with the strong constitutive yeast TPI1 promoter as described previously (WO2005/118814). This was done by replacing the native ACC1 promoter with the TPI1 promoter, using a slightly modified promoter-replacement method based on the bipartite gene-targeting method. One part of the bipartite substrate consisted of two thirds (towards the 3' end) of *K. lactis* URA3, fused to the TPI1 promoter sequence and a target sequence corresponding to the beginning of ACC1. The second part of the bipartite substrate consisted of a target sequence upstream of ACC1, fused to the TPI1 promoter sequence and two thirds (towards the 5' end) of *K. lactis* URA3. Following transformation with the bipartite substrate and selection on medium lacking uracil, transformants were obtained in which the native promoter had been knocked out and replaced with two copies of the TPI1 promoter sequence as a direct repeat on either side of the *K. lactis* URA3 marker gene. A second recombination event, resulting in looping out of the selection marker, was selected for by re-plating transformants on medium containing 5'-fluoroorotic acid (5-FOA), which is toxic to cells expressing the URA3 gene. This resulted in a strain, in which the native ACC1 promoter had been replaced with the TPI1 promoter.

In order to construct part 1 of the bipartite substrate, two thirds (towards the 3' end) of *K. lactis* ura3 was amplified from the plasmid pWJ716 using the primers 5' CTTGACGTTCGTTCGACTGATGAGC 3' (SEQ ID NO 93) and 5' CTGGAATTCGATGATGTAGTTTCTGG 3' (SEQ ID NO 94). Moreover, the TPI1 promoter sequence was amplified from genomic *S. cerevisiae* DNA using the primers 5' CTACATCATCGAATTCCAGCTACGTATGGTCATTTCTTCTTC 3' (SEQ ID NO 95) and 5' TTTTTGATTAAAATTAAAAAAACTTTTTAGTTTATGTATGTGTTTTTTG 3' (SEQ ID NO 96) and a downstream targeting sequence, consisting of the beginning of the ACC1 gene (i.e., the first 553 bp of the gene) was amplified from genomic *S. cerevisiae* DNA using the primers 5' AGTTTTTTTAATTTTAATCAAAAAATGAGCGAAGAAAGCTTATTCGAGTC 3' (SEQ ID NO 97) and 5' CACCTAAAGACCTCATGGCGTTACC 3' (SEQ ID NO 98). These three fragments were fused to each other in two rounds of PCR. First, the TPI1 promoter sequence was fused to the downstream targeting sequence, using the primers 5' CTACATCATCGAATTCCAGCTACGTATGGTCATTTCTTCTTC 3' (SEQ ID NO 95) and 5' CACCTAAAGACCTCATGGCGTTACC 3' (SEQ ID NO 98). The resulting product was then fused to the fragment containing two thirds (towards the 3' end) of *K. lactis* URA3. The resulting fragment, 3' 2/3 *K. lactis* URA3-pTPI1-DOWN(ACC1) was part 1 of the bipartite gene targeting substrate.

In order to construct part 2 of the bipartite substrate, two thirds (towards the 5" end) of *K. lactis* URA3 was amplified from the plasmid pWJ716 using the primers 5' CGGTCTGCATTGGATGGTGGTAAC 3' (SEQ ID NO 99) and 5' GAGCAATGAACCCAATAACGAAATC 3' (SEQ ID NO 100). The TPI1 promoter sequence was amplified from genomic *S. cerevisiae* DNA using the primers 5' CTACATCATCGAATTCCAGCTACGTATGGTCATTTCTTCTTC 3' (SEQ ID NO 95) and 5' CACCATCCAATGCAGACCGTTTTAGTTTATGTATGTGTTTTTTG 3' (SEQ ID NO 101), and a target sequence upstream of ACC1 was amplified from genomic *S. cerevisiae* using primers 5' TGTTCTGCTCTCTTCAATTTTCCTTTC 3' (SEQ ID NO 102) and 5' CTGGAATTCGATGATGTAGTTTCTAATTTTCTGCGCTGTTTCG 3' (SEQ ID NO 103). These three fragments were fused in two rounds of PCR. First, the upstream targeting sequence was fused to the TPI1 promoter sequence, using the primers 5' TGTTCTGCTCTCTTCAATTTTCCTTTC 3' (SEQ ID NO 102) and 5' CACCATCCAATGCAGACCGTTTTAGTTTATGTATGTGTTTTTTG 3' (SEQ ID NO 101). The resulting fragment was then fused to the fragment containing two thirds (towards the 5' end) of *K. lactis* URA3, resulting in the fragment UP(ACC1)-pTPI1-5' 2/3 *K. lactis* URA3, which constituted part 2 of the bipartite gene targeting substrate.

Yeast strain FS01529 [MATalpha ura3-52, his3] was transformed with the linear substrates UP(ACC1)-pTPI1-5' 2/3 *K. lactis* URA3 and 3' 2/3 *K. lactis* URA3-pTPI1-DOWN(ACC1). Transformants were selected and streak-purified on medium lacking uracil and were then transferred to plates containing 5-FOA. Pop-out recombinants were streak-purified on 5-FOA-containing medium. The resulting strain was named FS09216 and had the genotype [MATalpha ura3-52, his3, TPI-ACC1]. The correct integration of the TPI1 promoter was checked by colony PCR.

EXAMPLE 27

Construction of a Strain Deleted for the Gene ARO10 Encoded by YDR380w

The yeast gene ARO10, encoding phenylpyruvate decarboxylase (YDR380w), was deleted using the Cre/loxP method. One part of the bipartite substrate consisted of two thirds (towards the 3' end) of *K. lactis* URA3, a loxP site located between the marker gene and the target sequence corresponding to the sequence upstream of the coding sequence of ARO10. The second part of the bipartite substrate consisted of two thirds (towards the 5' end) of *K. lactis* URA3, a loxP site located between the marker gene and the target sequence corresponding to the sequence downstream of the coding sequence of ARO10. Furthermore a plasmid containing the HIS3 gene, a Cre-recombinase gene controlled by the GAL1 promoter was included in the transformation.

Following transformation with the bipartite substrate and selection on medium lacking uracil, and histidine transformants were obtained in which the coding sequence of ARO10 had been knocked out and replaced with two copies of the loxP sequence as a direct repeat on either side of the *K. lactis* URA3 marker gene. A second recombination event, resulting in looping out of the selection marker, was selected for by growing selected transformation in YP-galactose medium over night and re-plating transformants on YPD medium. This resulted in a strain, in which the native ARO10 coding sequence been replaced with one loxP site.

In order to construct part 1 of the bipartite substrate, two thirds (towards the 3' end) of *K. lactis* ura3 and a loxP site was amplified from the plasmid pUG72 using the primers 5' CCA ACA ATG ATG ATA TCT GAT C 3' (SEQ ID NO 104) and 5' CCG CTG CTA GGC GCG CCG TGG GCG CAA TTA TAA AAC ACT G 3' (SEQ ID NO 106). Moreover, the downstream homolog targeting sequence was amplified from genomic yeast DNA using the primers 5-CCG CTG CTA GGC GCG CCG TGG GCG CAA TTA TAA AAC ACT G-3 (SEQ ID NO 106) and 5-GTT TCA AAT AGA ACG AGG GAG-3 (SEQ ID NO 105). The two fragments were fused to each other by PCR using the PCR fragments as template and the primers 5-CCA ACA ATG ATG ATA TCT GAT C-3 (SEQ ID NO 104) and 5-GTT TCA AAT AGA ACG AGG GAG-3 (SEQ ID NO 105). The resulting fragment, 3' 2/3 *K. lactis* URA3-loxP-DOWN(ARO10) was part 1 of the bipartite gene targeting substrate.

In order to construct part 2 of the bipartite substrate, two thirds (towards the 5' end) of *K. lactis* URA3 and a loxP site was amplified from the plasmid pUG72 using the primers 5' GTC AGC GGC CGC ATC CCT GCT ACG CTG CAG GTC GAC AA 3' (SEQ ID NO 107) and 5' ATA CAT TTG CCT TTT GAA AAC 3' (SEQ ID NO 108). The target sequence upstream of ARO10 was amplified from genomic *S. cerevisiae* DNA using primers 5' GCC GTC ATA TAT TAC TTT GAG C 3' (SEQ ID NO 109) and 5' GCA GGG ATG CGG CCG CTG ACA CAG AAG TCG CGT CAA CTT G 3' (SEQ ID NO 110). The two fragments were fused by PCR using the generated PCR fragments as templates, using the primers 5' GCC GTC ATA TAT TAC TTT GAG C 3' (SEQ ID NO 109) and 5' ATA CAT TTG CCT TTT GAA AAC 3' (SEQ ID NO 108) resulting in the fragment UP(ARO10)-loxP-5' 2/3 *K. lactis* URA3, which constituted part 2 of the bipartite gene targeting substrate.

Yeast strain FS09216 [MATalpha ura3-52, his3, TPI-ACC1] was transformed with the linear substrates UP(ARO10)-loxP-5' 2/3 *K. lactis* URA3 and 3' 2/3 *K. lactis* URA3-loxP-DOWN(ARO10). Transformants were selected and streak-purified on medium lacking uracil and histidine. Selected strains were inoculated in liquid YP-galactose over night and plated onto YPD plates. Single colonies were streak purified on YPD plates and replica plated onto YPG, SC-URA and SC-HIS to confirm loss of marker and pettiness. The resulting strain was named FS09235 and had the genotype [matalpha ura3-52 his3-11 pTPI-Acc1 deltaaro10]. The correct integration of the TPI1 promoter was checked by colony PCR.

The LEU2 gene (encoded by YCL018W) was partially deleted to enable the use of LEU2 based vectors in the mutant yeast strains. The parental strain used for the deletion of LEU2 was FS09216 [Matalpha ura3-52 his3 pTPI-Acc1]. The LEU2 deletion was done using the bipartite gene-targeting method for gene deletions and *Klyuveromyces lactis* URA3 as selection marker followed by a URA3-marker rescue on 5-FOA (5-fluoro-orotic acid) plates (Erdeniz et al., 1997). One part of the bipartite substrate consisted of the target sequence corresponding to the beginning of LEU2 gene fused to two thirds (towards the 5' end) of *K. lactis* URA3. The second part of the bipartite substrate consisted of two thirds (towards the 3' end) of *K. lactis* URA3 fused to the target sequence downstream of LEU2 gene.

In detail, the LEU2-up target sequence fragment was constructed via PCR with genomic DNA from *S. cerevisiae* CEN.PK and forward primer (LEU2-up-F) 5'-CAGAGGTCGCCTGACGCATATACCT (SEQ ID NO 111) and reverse primer 5'-GCAGGGATGCGGCCGCTGACGCAAAGTTACATGGTCTTAAGTTGG. The LEU2-Down target sequence was constructed via PCR from genomic DNA of *S. cerevisiae* CEN.PK and forward primer 5'-CCGCTGCTAGGCGCGCCGT GCTCCAGATTTGCCAAAGAATAAGGTCAAC-3' (SEQ ID NO 112) and reverse primer (LEU2-Down-R) 5'-TGTTACACCTAACTTTTTGTGTGGTGCC.

The *K. lactis* up fragment (KLURA5-R of 865 bp) was generated by PCR with vector pWJ1042 as template (Sequence xx) and the forward primer 5'-GTCAGCGGCCGCATCCCTGC TTCGGCTTCATGGCAATTCCCG (SEQ ID NO 113) (dKL5') and the reverse primer 5' GAGCAATGAACCCAATAACGAAATC (SEQ ID NO 100) (Int3'). Vector pWJ1042 is an *E. coli* shuttle vector and contains the full *K. lactis* ura3 expression cassette flanked by two 144 bp homologous DNA repeat sequences on each side of the marker cassette for easy recombination and marker rescue on 5-FOA.

The *K. lactis* down fragment (KLURA3-R of 1246 bp) was generated by PCR with vector pWJ1042 as template and the forward primer (Int5') 5'-CTTGACGTTCGTTCGACTGATGAGC (SEQ ID NO 93) and the reverse primer 5'-CACGGCGCG CCTAGCAGCGG TAACGCCAGGG TTTTCCCAGTCAC (SEQ ID NO 114) (cKL3').

The leu2-up target sequence fragment was fused to the Klura5-R via PCR by using primers Leu2-up-F and Int 3'. The LEU2-Down target sequence fragment was fused to KLURA3-R using primers Int 5' and Leu2-Down-R.

These fused fragments were used to transform the yeast FS09216 using the standard lithium acetate transformation method. Transformants were grown in SC-URA plates for two days at 30° C. and subsequently streaked in 5-FOA plates to allow the pop-out and marker rescue of the gene segment to be deleted. After confirmation the LEU2 deletion and marker rescue was confirmed by replica plating onto SC-URA and SC-LEU. The new strain with LEU2 deletion was called FS09236 [MATalpha ura3-52 his3 leu2 pTPI1-Acc1].

EXAMPLE 29

Generation of Strain FS09240 Matalpha ura3-52, his 3, leu2, pTPI-ACC1, deltaAro10

The yeast gene ARO10, encoding phenylpyruvate decarboxylase, was deleted using the Cre/loxP method as described in Example 27.

Yeast strain FS09236 [MATalpha ura3-52 his3-11 leu2 pTPI1-Acc1] was transformed with the linear substrates UP(ARO10)-loxP-5' 2/3 *K. lactis* URA3 and 3' 2/3 *K. lactis* URA3-loxP-DOWN(ARO10). Transformants were selected and streak-purified on medium lacking uracil and histidine. Selected strains were inoculated in liquid YP-galactose over night and plated onto YPD plates. Single colonies were streak purified on YPD plates and replica plated onto YPG, SC-URA and SC-HIS to confirm loss of marker and pettiness. The resulting strain was named FS09240 and had the genotype [MATalpha ura3-52 his3-11 leu2 pTPI1-Acc1 deltaaro10]. The correct integration of the TPI1 promoter was checked by colony PCR.

EXAMPLE 30

Generation of Strain FS09258 Matalpha ura3-52, his3, Leu2, trp1, pTPI-ACC1 deltaAro10

The TRP1 gene (encoded by YDR007W) was partially deleted to create a non-revertant TRP1 marker in the yeast mutant and to enable the integration of the resveratrol transporters into the partially deleted TRP1 gene using the TRP1 based integrative vectors RHO0067 and RHO0051. The parental strain used for the deletion of TRP1 was FS09240 [Matalpha ura3-52 his3 delta-Leu2 pTPI-Acc1, delta-ARO10]. The deletion was done according to the bipartite CRE-lox method using the *Klyuveromyces lactis* Leu2 cassette flanked by LOXP targets (pUG73 vector Eursocarf) as reusable marker for the bi-partite fragments.

*Kluyveromyces lactis* LoxP-Leu2-up-fragment (1323 bp) was generated by PCR from vector pUG73 using forward primer (X1F) 5'-GTCAGC GGCCGCATCCC TGC-TACGCTGCAGGTCGACAA (SEQ ID NO 115) and reverse primer (KLEU-R) 5'-CAC ACT ACA CAG ATT ATA CCA TG (SEQ ID NO 116).

*Klyuveromyces lactis* Leu2-LoxP-down-fragment (1500 bp) was generated by PCR from vector pUG73 using forward primer (KLEU-F) 5'-TTCTCTAACG ACGAC-GAAATCG (SEQ ID NO 117) and reverse primer 5'CACG-GCGCGCCTAGCAGCGG AGGCCACTAGTGGATCT-GATAT (SEQ ID NO 118) (X2R).

The TRP1-up fragment was generated by PCR using *S. cerevisiae* genomic DNA as template and forward primer (TRP-up-F) 5'GAA GAG GAG TAG GGA ATA TTA CTG GCT (SEQ ID NO 119) and reverse primer 5' GCAGGGAT-GCG GCCGCTGAC ACT CCA AGC TGC CTT TGT GTG CTT AAT (SEQ ID NO 120).

The TRP1-down fragment was generated by PCR using *S. cerevisiae* genomic DNA as template and forward primer 5'CCGCTGCTAGGCGCGCCGTG CAA GAG TTC CTC GGT TTG CCA GTT ATT A (SEQ ID NO 121) and reverse primer (TRP-Down-R) 5'CCT GCG ATG TAT ATT TTC CTG TAC AAT CAA TC (SEQ ID NO 122).

TRP1-up fragment was fused to *Klyuveromyces lactis* LoxP-Leu2-up-fragment by fusion PCR using TRP-up-F and Kleu-R as primers. The *Klyuveromyces lactis* Leu2-LoxP-down-fragment was fused to The TRP1-down fragment by fusion PCR using KLEU-F and TRP-DOWN-R as primers.

FS09240 was transformed with 10 microliters each of the two fused PCR products (bi-partite substrate) and selected on SC-leu plates. Five to ten of the resulting transformants were pooled and used to transform with 3 microliter PSH47 (Cre-recombinase under GAL1 promoter on a URA3 vector) selected on SC-Leu plates). The resulting transformants were grown over night in YP-galactose (20 g/l galactose 10 g/l yeast extract and 20 g/l peptone) for induction of Cre-recombinase and marker rescue. One microliter of the over night culture was dissolved in 1 ml sterile water and 200 microliter was plated on YPD-agar plates. 40 colonies were scored for lack of growth on SC-TRP, SC-leu and SC-ura agar plates by replica plating, which indicated that the deletion of TRP1 and marker rescue had worked. The resulting strain with partial TRP1-deletion was confirmed by colony PCR using primer 5'-CTG GGA GCA GAT GAC GAG TTG GT (SEQ ID NO 123) and TRP-DOWN-R. The resulting delta-TRP1 strain has a partial deletion of TRP1 (where a region from the middle of the TRP1-ORF to the middle of the terminator has been deleted), and was called FS09258 [Matalpha ura3-52 his3 delta-leu2 delta-trp1 pTPI-Acc1, delta-ARO10].

EXAMPLE 31

Generation of Strain with Constitutive Expression of the Pathway to Resveratrol in the Yeast *S. Cerevisiae* FS01529-9-28

*S. cerevisiae* strain FS01529 (CEN.PK MATa ura3 His3) was co-transformed with RHO0028 (pESC-HIS3-TEF-PAL2-TDH3-C4H::CYB5:ATR2) and RHO009 (pESC-URA3-TEF2-4CL2-TDH3-VST1 and the transformed strain was named FS01529-9-28. Transformants were selected on medium lacking uracil and histidine and streak purified on the same medium.

EXAMPLE 32

Generation of Strain with Constitutive Expression of the Pathway to Resveratrol in the Yeast *S. Cerevisiae* FS09258-53-32-44-51

Strain FS09258 [Matalpha ura3-52 his3 delta-leu2 delta-trp1 pTPI-Acc1, delta-ARO10] was first transformed with plasmid RHO0051, linearized by HINDIII digestion, and selected on SC-trp solid agar plates. After re-streaking the transformants on new SC-trp solid agar plates the cells from this plate were inoculated into YPD and transformed with plasmids RHO0053 and RHO0032 and selected on SC-ura-his solid agar plates. The strains were then pre-grown in selective medium (liquid SC-ura-his medium) and transformed with plasmid RHO0044 and selected on SC-ura-his-leu solid agar plates. This resulted in strain FS09258-53-32-44-51.

A second strain was generated in the same way but instead of RHO0051 the RHO0067, linearized by HINDIII digestion, was used resulting in strain FS09258-53-32-44-67.

EXAMPLE 33

Shake Flask/Deep Well Cultivation and Media

The yeast strains were grown in 500 ml shake flasks with 50-100 ml working volume or in 10 ml deep well cultivation plates with 5 ml working volume ("Riplate BV" 850601 from HJ-Bioanalytik Gmbh, Germany) covered with Airpore Tape sheets (catalogue nr 19571) (Qiagen, Maryland, USA). Deep Well cultivation plates and shake flasks were inoculated at 250 rpm and 30 degrees.

Unless stated elsewhere the medium used for growth and stilbenoid production in the shake flask or deep well cultivations was a defined mineral medium (referred to as Delft medium) consisting of i) glucose or galactose as carbon source in general 40 g/l unless stated elsewhere ii) ammonium sulphate, $(NH4)_2SO_4$,30 g/l as nitrogen source iii) phosphate buffer consisting of 12 g/l $KH_2PO_4$ and 5 g/l $K_2HPO_4$ with the medium adjusted to pH 5.5 iV) 2 g/l $MgSO_4.7H_2O$ and V) 1 ml of a 1000× stock solution of vitamins and 1 ml of a 1000× stock solution of trace elements. The vitamin solution and trace element solution was prepared as described previously (Verduyn et al, 1992; Boer et al, 2003).

EXAMPLE 34

Creation of a Chimeric Protein Increasing the Hydroxylation of Cinnamic Acid Leading to Increased Resveratrol Production Cinnamate-4-hydroxylase (C4H) belongs to the cytochrome P450 monooxygenases (P450s) protein family. The enzyme is a heme-dependent membrane bound oxidase facilitating the addition of an oxygen atom by cleaving molecular di-oxygen (Werck-Reichhart and Feyereisen, 2000). C4H is supported by P450 reductase (CPR), an electron donor, and uses the electron to split atmospheric oxygen to reactive oxygen radicals. The enzyme complex is thought to co-operation with cytochrome $b_5$ which in theory facilitates the electron transfer. It has been shown that heterologous P450s in some cases do not possess the ability to accept electron donation from endogenous sources (Guengerich et al., 1993). Therefore to optimally exploit metabolic pathways containing monooxygenases in heterologous expression organisms, a chimeric enzyme is assembled containing hydroxylase, cytochrome $B_5$ and reductase activity.

Two strains were constructed containing pESC plasmids containing the resveratrol pathway with or without a chimeric protein (Table 3).

TABLE 3

| Strain name | Parent strain | Genotype |
|---|---|---|
| FS01529-1-2 | FS01529 | MATalpha ura3-52 his3 [pESC-ura-pGAL1-C4H-pGAL10-PAL2], [pESC-his-GAL1-4CL1-pGAL10-VST1] |

TABLE 3-continued

| Strain name | Parent strain | Genotype |
|---|---|---|
| FS01529-1-4 | FS01529 | MATalpha ura3-52 his3 [pESC-ura-pGAL1-C4H:CYB5:ATR2-pGAL10-PAL2], [pESC-his-GAL1-4CL1-pGAL10-VST1] |

The strains were grown in delft medium with 0.2% glucose and 1.8% galactose. The strains were cultivated for 71 hours reaching the stationary phase and samples were taken for extraction and subsequent HPLC analysis (Table 4).

TABLE 4

| Strain | OD600 | mg/l resveratrol | mg/l pinosylvin |
|---|---|---|---|
| FS01529-1-2 | 11.0 | 11.0 | 153.7 |
| FS01529-1-4 | 10.0 | 45.1 | 92.9 |

Expression of the chimeric protein increased the resveratrol titer by 310%.

EXAMPLE 35

Resveratrol Pathway on Different Vectors

We investigated whether there would be a difference between a strain having the full resveratrol pathway separated on two vectors, that is transformed with RHO009 and RHO0028 versus a strain having the full resveratrol pathway on one vector such as RHO0029 or RHO0030 and whether a strain harbouring two vectors, each with the full resveratrol pathway, would lead to higher titres than a strain having only one vector with the full resveratrol pathway from only one vector.

We therefore constructed the following strains:

i) FS0916-9-28 (having one copy of the resveratrol pathway divided on two different vectors.

ii) FS09216-29-22 having one URA3-based multicopy vector with the full resveratrol pathway and one empty HIS3 vector to remove the auxotrophy.

iii) FS09216-30-20 having one HIS3-based multicopy vector with the full resveratrol pathway and one empty URA3 vector to remove the auxotrophy.

iv) FS09216-29-30 having one URA3-based multicopy vector with the full resveratrol pathway and one HIS3-based multicopy vector with the full resveratrol pathway, that is in principle two copies of the full resveratrol pathway.

Figure 10:
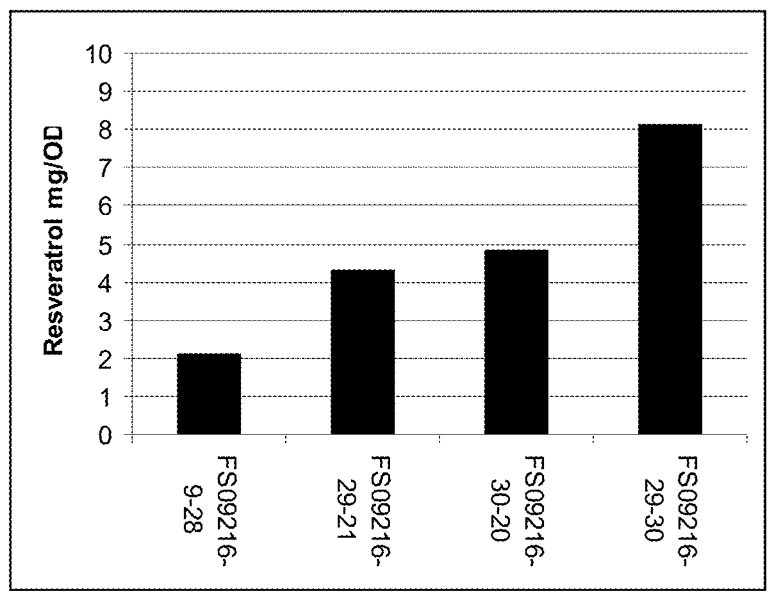
FIG. 10 shows amounts of resveratrol obtained in Example 35.

The strains were grown in shake flaks containing 100 ml of mineral medium with 40 g/l glucose as carbon source. After 72 hours the resveratrol per optical density (OD 600) was calculated. FIG. 10 shows the produced amount of resveratrol per optical density after 72 hour cultivations in strains with the resveratrol pathway on different vectors.

The amount of resveratrol produced per biomass was highest when two copies of the resveratrol pathway were present, that is in FS0916-29-30. Having one copy of the full resveratrol pathway on a HIS3 based vector (FS09216-30-20) or URA3 based vector (FS09216-29-21) gave similar results but lower than the strain with two copies. Having only one copy of the pathway separated on two different plasmids gave the lowest resveratrol yields (FS09216-9-28).

EXAMPLE 36

Strain Stability

Figure 11:
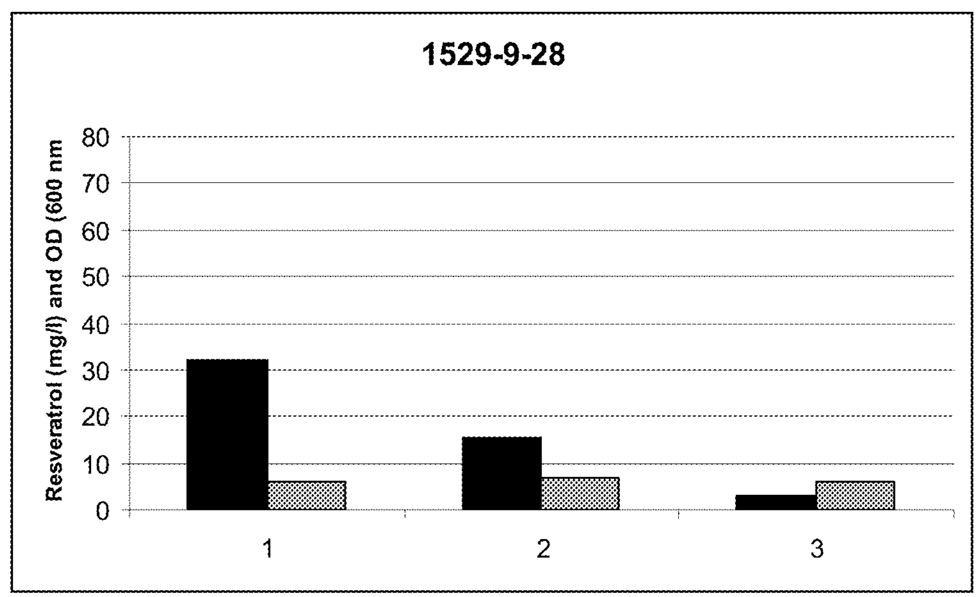
FIG. 11 shows amounts of resveratrol obtained in Example 36.
Figure 12:
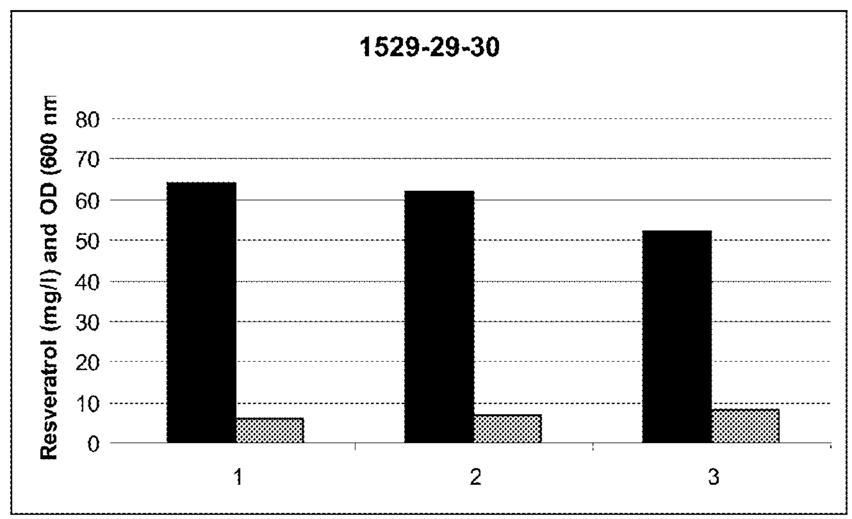
FIG. 12 shows amounts of resveratrol obtained in Example 36.

A strain with one copy of the resveratrol pathway divided on two vectors was constructed—FS01529-9-28. A second strain with two vectors each with the full resveratrol pathway was also constructed in the same background FS01529-29-30. The two strains were grown in 100 ml defined mineral medium with 40 g/l glucose in a series of three 500 ml shake flasks. Sampling and measurement of resveratrol was made at 72 hours. A serial transfer study was made where 50 microliters from shake flask 1 was inoculated to a new shake flask (shake flask 2) with the same medium as culture 1. After 72 hours the resveratrol and optical density were measured and a third shake flask was conducted in the same way with sampling at 72 hours. FIG. 11 shows resveratrol titres and ODF in three serial shake flaks for strain FS01529-9-28:

Black bars=resveratrol (mg/l), Grey bars=Optical density (OD600 nm) at 72 hours in each shake flask. FIG. 12 shows similarly resveratrol titres and OD in three serial shake flaks for strain FS01529-29-30.

From FIGS. 11 and 12 it is evident that the strain FS01529-29-30 with two plasmid each having the full resveratrol pathway leads to higher resveratrol titres than the strain with only one copy of the pathway separated on two vectors FS01529-9-28 as was also seen in Example 35 in another strain background. However, in this experiment we also demonstrate that the resveratrol production is more stable and maintained at high levels in serial shake flask transfers in strain FS01529-29-30 as compared to strain FS01529-9-28 where the resveratrol production is lowered after each transfer and almost no resveratrol is formed in shake flask 3. It is possible but not favourable to divide the resveratrol pathway onto different vectors since the plasmid distribution and copy number is most likely shifting throughout the population and time in each shake flask and this causes an uneven ratio between the resveratrol pathway enzymes leading to low resveratrol titres.

EXAMPLE 37

Comparison Resveratrol Transporters SNQ2, BcatrB and Control in Deep Well Cultivations Strain 9258-29-30-44-51 expressing the SNQ2 transporter, strain 9258-29-30-44-67 expressing the BcatrB transporter and the control strain 9240-29-30-44 were grown for 48 hours in deep well cultivation plates. The control strain produced 48 mg/l resveratrol at OD 5.6 after and the strain expressing SNQ2 produced 61 mg/l resveratrol at an OD of 5.7. The strains expressing the BcatrB (*Botrytis cinerea* resveratrol transporter) produced 56 mg/l resveratrol at an OD 8 after 48 hours.

Genotypes:

9240=Matalpha ura3-52 his3 Leu2 pTPI-Acc1, DARo10

9258=Matalpha ura3-52 his3 Leu2 pTPI-Acc1, DARo10, deltaTRP1

Inserted Vectors:

RHO0029

RHO0030

RHO0044

RHO0051

RHO0067

In fermentation the same strains as in Example 34 gave at 72 hours:

9240-29-30-44 gave 437 mg/l resveratrol.

9258-29-30-44-51 (including SNQ2 overexpression) gave 573 mg/l resveratrol.

Strain 9258-29-30-44-67 (including BcatrB overexpression) gave 951 mg/l resveratrol.

The conditions for fermentation and analysis are described below before Example 41.

Conclusion: The effect of overexpression of a transporter is most likely more apparent in a fed-batch fermentation where the total concentration of resveratrol exceeds 200 mg/l whereas in shake flask or deep well cultivations the resveratrol levels reached are lower, which may not be as inhibitory and thus the resveratrol transporter effect is obscured by this fact.

EXAMPLE 38

Development of a Stable High Copy Number Expression Vector System Using an Ubiquitination Tag Two strains were constructed one containing a p4-ura plasmid (Example 15) and the other containing a p4-ura-tag 2 plasmid (Example 19) (Table 5).

TABLE 5

| Strain name | Parent strain | Inserted expression system | Genes in expression system | Tag |
|---|---|---|---|---|
| FS01202-29 | FS01202 | Rho0029 | pTDH3-PAL2, pTEF1-C4H::CYB4::ATR2, pTDH3-4CL2, pTEF1-VST1 | None |
| FS01202-53 | FS01202 | Rho0053 | pTDH3-PAL2, pTEF1-C4H::CYB4::ATR2, pTDH3-4CL2, pTEF1-VST1 | Ubiquitination tag |

The strains were grown in delft medium with 2% glucose. The strains were cultivated for 72 hours reaching the stationary phase and samples were taken for extraction and subsequent HPLC analysis (Table 6).

TABLE 6

| Strain | Mg/l resveratrol | $OD_{600}$ | Yield on biomass | Yield on glucose |
|---|---|---|---|---|
| FS01227-29 | 28.0 | 9.8 | 2.9 | 0.70 |
| FS01227-53 | 54.8 | 8.3 | 6.6 | 1.37 |

From the results present in Table 6 the yield on biomass was increase by 127%, yield on glucose by 95% and titer by 96%.

EXAMPLE 39

Overexpression of Acetyl-CoA Carboxylase (ACC1) for Increased Resveratrol Production The two key yeast precursors for resveratrol production using the heterologous resveratrol pathway that starts with the phenylalanine ammonia lyase are phenylalanine and malonyl-CoA. To increase the production of malonyl-CoA the acetyl-CoA carboxylase (ACC1) converting acetyl-CoA to malonyl-CoA was overexpressed, leading to redirected acetyl-CoA flux from biomass accumulation and TCA cycle assimilation towards malonyl-CoA production, thereby increasing the availability of MAlonyl-CoA to increase the resveratrol titer.

Two strains were constructed containing pESC plasmids containing the resveratrol pathway. Furthermore one of the strains had the endogenous ACC1 promoter exchanged with the glycolytic triose phosphate isomerase promoter (TPI1). (Table 7).

TABLE 7

| Strain name | Parent strain | Genotype |
|---|---|---|
| FS01529-1-4 | FS01529 | MATalpha ura3-52 his3 [pESC-ura-pGAL1-C4H:CYB5:AR2-pGAL10-PAL2], [pESC-his-GAL1-4CL1-pGAL10-VST1] |
| FS09216-1-4 | FS01529 | MATalpha ura3-52 his3 pTPI-ACC1 [pESC-ura-pGAL1-C4H:CYB5:AR2-pGAL10-PAL2], [pESC-his-GAL1-4CL1-pGAL10-VST1] |

The strains were grown in delft medium with 0.2% glucose and 1.8% galactose. The strains were cultivated for 72 hours reaching the stationary phase and samples were taken for extraction and subsequent HPLC analysis (Table 8).

TABLE 8

| Strain | Mg/l resveratrol |
|---|---|
| FS01529-1-5 | 119 |
| FS09216-1-5 | 165 |

From the results present in Table 8 the genomic overexpression of acc1 increased the titer of resveratrol by 39%.

EXAMPLE 40

Deletion of Aro10 Phenylpyruvate Decarboxylase for Increased Phenylalanine Availability Resveratrol Production Two strains were constructed containing p4 containing the resveratrol pathway. Furthermore one of the strains had the endogenous ARO10 deleted (Table 9).

TABLE 9

| Strain name | Parent strain | Genotype |
|---|---|---|
| FS09216-29-30 | FS09216 | MATalpha ura3-52 his3 pTPI-ACC1 [p4-ura-pTDH3-PAL2, pTEF1-C4H::CYB4::ATR2, pTDH3-4CL2, pTEF1-VST1], [p4-his-pTDH3-PAL2, pTEF1-C4H::CYB4::ATR2, pTDH3-4CL2, pTEF1-VST1] |
| FS09235-29-30 | FS09216 | MATalpha ura3-52 his3 pTPI-ACC1 ΔARO10 [p4-ura-pTDH3-PAL2, pTEF1-C4H::CYB4::ATR2, pTDH3-4CL2, pTEF1-VST1], [p4-his-pTDH3-PAL2, pTEF1-C4H::CYB4::ATR2, pTDH3-4CL2, pTEF1-VST1] |

The strains were grown in delft medium with 2% glucose. The strains were cultivated for 72 hours reaching the stationary phase and samples were taken for extraction and subsequent HPLC analysis (Table 10).

TABLE 10

| Strain | mg/l coumaric acid | mg/l resveratrol | mg/OD600 coumaric acid | mg/OD600 resveratrol |
|---|---|---|---|---|
| FS09216-29-30 | 14 | 109 | 1.0 | 7.9 |
| FS09235-29-30 | 43 | 113 | 3.2 | 8.5 |

From the results presented in Table 10, the deletion of ARO10 lead to an increased yield on biomass of approximately 10% and 220% for resveratrol and coumaric acid respectively.

Fermentation Media and Conditions

The next group of examples describe fermentations performed in the following general manner.

Growth Medium for Fed-Batch Fermentation

The composition of the medium used in the initial batch phase of the fed-batch cultivations is shown in Table 11. The composition of the feeding medium is presented in Table 12, 13, 14. The nitrogen source used in the initial batch phase of the fed-batch cultivation was urea, whereas, in the feeding phase, ammonium hydroxide ($NH_4OH$, 25%) was used both as the nitrogen source and the base. In the major part of the cultivations, $NH_4OH$ (25%) was used as the base in both the batch and feeding phases. In some of the cultivations, the base used in the initial batch phase was KOH (2 N). For both the initial batch and feeding phases, HCl (2 N) was used as the acid.

TABLE 11

Composition of the minimal medium used in the initial batch of the fed-batch fermentation

| | Concentration |
|---|---|
| Glucose•$H_2O$ [g/l] | 110 |
| Urea [g/l] | 11.36 |
| $KH_2PO_4$ [g/l] | 15.00 |
| $MgSO_4$•$7H_2O$ [g/l] | 2.5 |
| Vitamin solution [ml/l] Table 13 | 5.00 |
| Trace element solution[ml/l] Table 14 | 5.00 |
| Antifoam 204 (Sigma A-8311) [μ/l] | 50.00 |

TABLE 12

Composition of the minimal medium used in the feed of the fed-batch cultivations

| | Concentration |
|---|---|
| Glucose•$H_2O$ [g/l] | 550 |
| $KH_2PO_4$ [g/l] | 9.00 |
| $MgSO_4$•$7H_2O$ [g/l] | 5.10 |
| $K_2SO_4$ [g/l] | 3.5 |
| $Na_2SO_4$ [g/l] | 0.28 |
| Vitamin solution [ml/l] Table 13 | 12.00 |
| Trace element solution [ml/l] Table 14 | 10.00 |
| Antifoam 204 (Sigma A-8311) [μ/l] | 50.00* |

*During fermentation additional Antifoam has to be added after demand when foaming occurs

TABLE 13

Composition of the vitamin solution used in fed-batch fermentation

| | Concentration [g/L] |
|---|---|
| Biotin | 0.05 |
| Calcium pantothenate | 1.0 |
| Nicotinic acid | 1.0 |

TABLE 13-continued

| Composition of the vitamin solution used in fed-batch fermentation | |
|---|---|
| | Concentration [g/L] |
| Myo-inositol | 25.0 |
| Thiamine HCL | 1.0 |
| Pyridoxal HCL | 0.2 |
| Para-aminobenzoic acid | 0.2 |

TABLE 14

| Composition of trace element solution used in fed-batch fermentation | |
|---|---|
| | Concentration [g/L] |
| EDTA (disodium) | 15 |
| $ZnSO_4 \cdot 7H_2O$ | 4.5 |
| $MnCl_2 \cdot 2H_2O$ | 1.0 |
| $CoCl_2 \cdot 6H_2O$ | 0.3 |
| $CuSO_4 \cdot 5H_2O$ | 0.3 |
| $Na_2MoO_4 \cdot 2H_2O$ | 0.4 |
| $CaCl_2 \cdot 2H_2O$ | 4.5 |
| $FeSO_4 \cdot 7H_2O$ | 3.0 |
| $H_3BO_3$ | 1.0 |
| KI | 0.1 |

Operating Conditions of Fed-Batch Fermentation

The operating conditions used in the initial batch phase and feeding phase of the fed-batch fermentations are shown in Table 15.

TABLE 15

| Operating conditions for the initial batch phase in fed-batch fermentation | |
|---|---|
| Parameter | Set-point |
| Volume of liquid (l) | 0.5 |
| Temperature (° C.) | 30.0 |
| pH | 5.5 |
| Agitation speed (rpm)[1] | 1200-1800 |
| Gas flow rate (vvm)[2, 3] | 1.5 |
| Gas flow rate (l/min) | 0.75 |

[1]automatically adjusted such that the dissolved oxygen is above 60% (100% set for 0.75 l/min and 1200 rpm, no cells)
[2]vvm = 1 gas/(l liquid × min)
[3]1 vvm for fermentation using strain FS09263-29-44-51

Preparation of Glycerol Stocks

Glycerol stocks were prepared using overnight 250 ml side baffled shake flask cultivations (conducted at 30° C. and stirred at 250 rpm). Such cultivations were inoculated with loop full of cells from an agar plate. Cells were harvested during late log-phase ($OD_{600}$~7-9) while there is residual glucose. Broth is transferred into sterile Falcon 50 ml centrifuge tubes and cells are spun down for 5 min. at approximately 4000 rpm at 4° C. Cells are re-suspended in ~15 ml of 15% (w/v) sterile glycerol solution. An aliquot of 1 ml of suspended cells is transferred into cryo-vials and stored at −80° C.

Seed Cultures and Inoculum

The seed cultures were prepared by conducting sequential shake-flask cultivations, such that the cells underwent a certain number of generations before being inoculated into the bioreactor. Shake flask culture were conducted in 500 ml shake flask using a working volume of 100 ml. The medium used in the cultivations is described above. The initial shake-flask was inoculated with a glycerol stock culture to a final OD600 of 0.01 or 0.001. The cells were incubated at 30° C. and 150 rpm and harvested when the OD600 reached approximately 1 (which corresponds to approximately 10 generations) and transferred into the following shake-flask. The process was repeated, such that a total of 4 shake-flask cultivations (or approximately 40 generations) were conducted before inoculation. The culture in the fourth flask was used to inoculate the reactor. The starting OD of all fermentation was approximately 0.001. When strain FS09258-53-32B-44-51 or FS09258-29-30-44-67 was used the start OD in the fermentation was approximately 0.05

Fed-Batch Cultivations in Bioreactors

The fed-batch cultivations were performed in bioreactors Biostat B plus (Sartorius BBI systems), with a working volume of 2 l. The initial volume of liquid used in all cultivations was 500 ml. The total volume of feed prepared was 1 l, such that the volume of liquid in the fermentor vessel did not exceed 1.5 l. The bioreactor was equipped with two Rushton four-blade disc turbines and baffles. Air was used for sparging the bioreactors. The concentrations of oxygen, carbon dioxide, and ethanol in the exhaust gas were monitored by a gas analyzer Innova 1313 with multiplexing. Temperature, pH, agitation, and aeration rate were controlled throughout the cultivations. The temperature was maintained at 30° C. The pH was kept at 5.5 by automatic addition of KOH (2N) or NH4OH (25%), in the course of the initial batch, and NH4OH (25%) and HCl (2 N), during the feeding phase. The stirrer speed was initially set to 1200 rpm and the aeration rate to 1.5 vvm (i.e., 0.75 l/h, for a volume of liquid of 500 ml). The aeration rate was set to 2.25 l/h, during the feeding process. When the levels of dissolved oxygen decreased below 60%, the stirrer speed was automatically increased to values up to 1800 rpm. The formation of foam was controlled using a foam sensor and through the automatic and/or manual addition of an anti-foam agent (Anti-foam 204) (diluted or pure). Samples were withdrawn at selected time points and analyzed for cell mass, extracellular metabolites, and stilbenoids.

After inoculation, the fed-batch fermentations went through a batch phase that lasted until no residual glucose was measured during the fermentation. Afterwards, an exponential feeding profile was used in order to secure a reduced constant specific growth rate.

Feeding Profiles

An exponential feeding profile leads to a constant specific growth rate and residual substrate concentration (Equation 1).

$$F(t) = \frac{Y_{XS}\mu_0}{S_{feed} - S_0} X_0 V_0 e^{\mu_0 t} \quad \text{(Equation 1)}$$

where $V_0$ [l] denotes the volume of liquid at the start of the fed-batch process; $X_0$ [g DW/l] and $S_0$ [g/l], the biomass and substrate concentrations at the start of the fed-batch process, respectively; $S_{feed}$ [g/l], the substrate concentration in the feed; $Y_{XS}$ [g/g DW], the inverse of biomass yield on substrate; and $\mu_0$ [1/h], the specific growth rate.

In all cultivations, pre-defined exponential feeding profiles were used (Table 16) after the batch phase, without any type of automatic control of the feed rate. The feed rate was manually adjusted in the course of the cultivations (to constant profiles), in order to avoid respiro-fermentative metabolism. The phase of exponential feeding was followed either one or two phases with reduced and constant feeding. In Table 17, parameters are listed upon which the fermentations were switched from batch phase to exponential feeding, to constant feeding phase 1, and to constant feeding phase 2.

TABLE 16

Parameters used for the calculation of pre-defined, exponential feeding profiles in the fed-batch phase.

| | $S_{feed}$ [g/l] | $V_0$ [l] | $X_0$ [g DW/l] | $Y_{XS}$ [g/g DW] | $\mu_0$ [1/h] |
|---|---|---|---|---|---|
| FS09258-51-53-32B-44 | 500 | 0.5 | 17.7 | 0.35 | 0.08 |
| FS09240-29-30-44 | 500 | 0.5 | 16.9 | 0.35 | 0.1 |
| FS09258-29-30-44-51 | 500 | 0.5 | 15.5 | 0.35 | 0.1 |
| FS09258-29-30-44-67 | 500 | 0.5 | 12.6 | 0.35 | 0.1 |
| FS09263-29-44-51 | 500 | 0.5 | 13.4 | 0.35 | 0.1 |
| FS09263-29-44-pSF057 | 500 | 0.5 | 15.1 | 0.35 | 0.1 |

TABLE 17

Approximate parameters at start of exponential feeding phase, constant feeding phase 1, constant feeding phase 2

| Strain | Start of | Time (h) | μ (1/h) or flow rate (ml/h) | $OD_{600}$ | Eth (g/L) |
|---|---|---|---|---|---|
| FS09258-51-53-32B-44 | exponential feeding phase | 25 | 0.08 1/h | 30 | 40 |
| | constant feeding phase 1 | 50 | 20 ml/h | 110 | 0.15 |
| | constant feeding phase 2 | 73 | 7.7 ml/h | 190 | 0 |
| FS09240-29-30-44 | exponential feeding phase | 43 | 0.1 1/h | 15 | 12 |
| | constant feeding phase 1 | 61 | 18 ml/h | 40 | 0 |
| | constant feeding phase 2 | 74 | 8.8 ml/h | 110 | 0 |
| FS09258-29-30-44-51 | exponential feeding phase | 43 | 0.1 1/h | 22 | 4 |
| | constant feeding phase 1 | 63 | 20 ml/h | 186 | 0 |
| | constant feeding phase 2 | None | None | None | None |
| FS09263-29-44-51 | exponential feeding phase | 42 | 0.1 1/h | 20 | 20 |
| | constant feeding phase 1 | 64 | 21 ml/h | 160 | 0 |
| | constant feeding phase 2 | 73 | 10.4 ml/h | 184 | 0 |
| FS09263-29-44-67 | exponential feeding phase | 24 | 0.1 l/h | 18 | 22.7 |
| | constant feeding phase 1 | 75 | 20 ml/h | 108 | 0 |
| | constant feeding phase 2 | None | None | None | None |
| FS09263-29-44-pSF057 | exponential feeding phase | 42 | 0.1 1/h | 21.5 | 18 |
| | constant feeding phase 1 | 63 | 21.3 ml/h | 174 | 0 |
| | constant feeding phase 2 | None | None | None | None |

Analysis of Stilbenoids

For quantitative analysis of coumaric acid, cinnamic acid, phloretic acid, trans-resveratrol, cis-resveratrol, dihydroresveratrol and pinosylvin, samples are subjected to separation by high-performance liquid chromatography (HPLC), using a HPLC-system from Dionex, prior to UVdiode-array detection at l=306 nm. A Phenomenex (Torrance, Calif., USA) Luna 2.5 micrometer C18 (100×2.00 mm) column is used at 60° C. The method comprises, as the mobile phase, a non-linear S-shaped gradient of acetonitrile and milliQ water (both containing 50 ppm trifluoroacetic acid), at a flow of 0.8 ml/min. The gradient profile varies from 10% to 100% acetonitrile over 5 minutes. The elution time is approximately 3.2 min for coumaric acid, 4.6 min for trans-resveratrol, 6.0 min for cinnamic acid, and 7.1 min for trans-pinosylvin. The following sample preparation procedure is used for analysis of stilbenoids:

Addition of ethanol (99.9%) to a final concentration of 50% (v/v);

Vortex (30 s);

Centrifugation (5 min, speed 13000);

Analysis of supernatant by HPLC.

The samples are appropriately diluted in distilled water prior to HPLC analysis, whenever required, such that the concentrations of stilbenoids fall within the linear ranges defined by the standards.

EXAMPLE 41

Fed-Batch Fermentation of FS09258-51-53-32B-44, FS09258-29-30-44-51, FS09240-29-30-44

Figure 13:
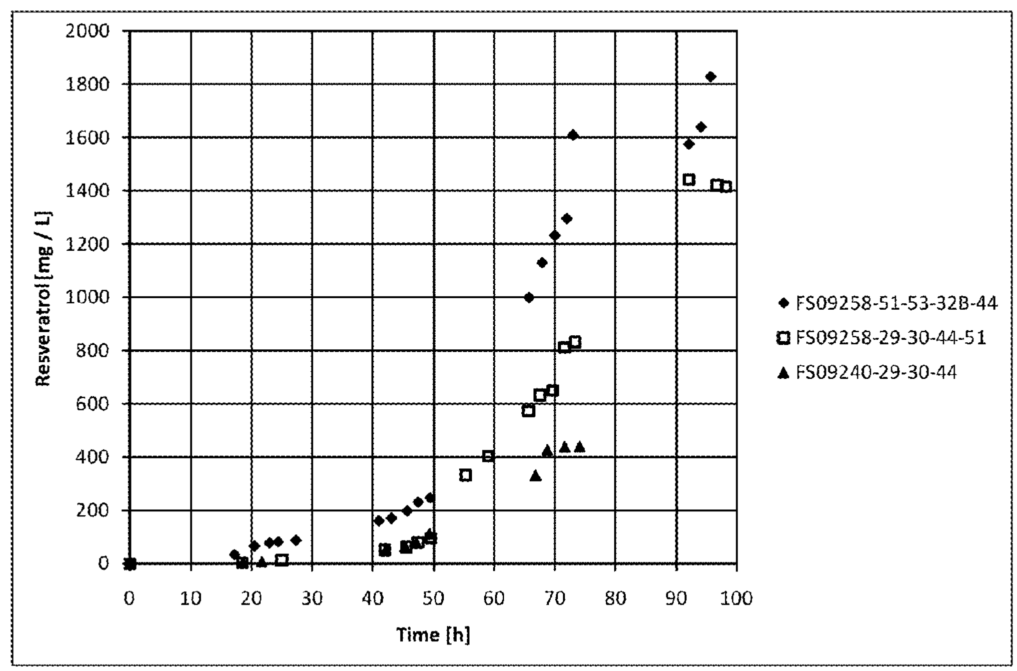
FIG. 13 shows production of resveratrol measured in Example 41.

The effect of overexpression of SNQ2 on resveratrol production was investigated in controlled fed-batch fermentation. FS09240-29-30-44 was used as reference strain and compared to a strain that additionally harbours an overexpression of SNQ2, that is FS09240-29-30-44-51. In a subsequent experiment the effect of using an ubiquitination tag on one of the plasmids (Rho 053) was further tested, and FS09258-51-53-32B-44 was compared to FS09240-29-30-44-51. The results of the conducted three fed-batch fermentations of strains FS09240-29-30-44, FS09258-29-30-51 and FS09258-51-53-32B-44 can be seen in FIG. 13.

It was found that the overexpression allowed an increase in final fermentation titres to approximately 1400 mg/L from 400 mg/L. The use of a ubiquitination tag on one of the plasmids allowed a further increase and titres beyond 1800 mg/L.

EXAMPLE 42

PUFA Example Tag System

The Delta 12 desaturase (MrD12D gene) from *Mucor Rouxii* (Passorn et al., unpublished) (SEQ ID NO 124), delta 6 desaturase (OtD6D gene) from Ostreococcus tauri (Domergue et al., 2005) (SEQ ID NO 125), delta 6 elongase (MaD6E gene) from *Mortiella alpine* (Tavares et al., 2008) (SEQ ID NO 126), and delta 5 desaturase (PtD5D gene) from *Paramecium tetraurelia* (Aury et al., 2006) (SEQ ID NO 127) codon optimized for expression in *S. cerevisiae* was synthesized by GenScript Corporation (Piscataway, N.J.). The synthetic codon optimized genes were delivered inserted in *E. coli* pUC57 vector. The synthetic genes were reamplified with via PCR using the pUC57 vectors as templates. After DPN1 digestion the PCR products were purified from agarose gel using the QiaQuick Gel Extraction Kit (Qiagen).

Delta 12 desaturase (MrD12D gene) from *Mucor Rouxii* was reamplified via PCR from genscript vector pUC57-MrD12D using forward primer 5-TAG AAC TAA AGG GCG GCC GCA TGG CAA CCA AGA GAA AC-3 (SEQ ID NO 128) and reverse primer 5-TTA ATT AAG AGC TCA GAT CTT TAG TTC TTA AAG AAG ACA ACA-3 (SEQ ID NO 129).

Delta 6 desaturase (OtD6D gene) from Ostreococcus tauri was reamplified via PCR from genscript vector pUC57-OtD6D using forward primer 5-TAT AGG GCC CGG GCG TCG ACA TGT GTG TTG AAA CAG AAA AT-3 (SEQ ID NO 130) and reverse primer 5-CGG TAC CAA GCT TAC TCG AGT TAT GCT GTT TTA CCA GAA TG-3 (SEQ ID NO 131).

Delta 6 elongase (MaD6E gene) from *Mortiella alpine* was reamplified via PCR from genscript vector pUC57-MaD6E using forward primer 5-TAG AAC TAA AGG GCG GCC GCA TGG AAT CTA TTG CTC AAT TC-3 (SEQ ID NO 132) and reverse primer 5-TTA ATT AAG AGC TCA GAT CTT TAT TGT AAC TTT CTA GCC TTT-3 (SEQ ID NO 133).

Delta 5 desaturase (PtDSD gene) from *Paramecium tetraurelia* was reamplified via PCR from genscript vector pUG57-PtD5D using forward primer 5-TAT AGG GCC CGG GCG TCG ACA TGG AAG GTA TCA TCA CTC A-3 (SEQ ID NO 134) and reverse primer 5-CGG TAC CAA GCT TAC TCG AGT TAT TCC ATT TTA GCA AAA CCA-3 (SEQ ID NO 135)

Plasmid Constructions

EXAMPLE 43

Construction of a Yeast Vector for Constitutive Expression of MrD12D and OtD6D Gene The amplified MrD12D PCR-product (Example 42) was ligated into NotI/BglII digested Rho0020 vector (Example 12) using InFusion technology, resulting in vector Rho20-MrD12D. The amplified OtD6D PCR product (Example 42) was ligated into SalI/XhoI digested Rho20-MrD12D vector using InFusion technology, resulting in vector Rho20-MrD12D-OtD6D. Two different clones of Rho20-MrD12D-OtD6D were sequenced to verify the sequence of the cloned gene.

EXAMPLE 44

Construction of a Yeast Vector for Constitutive Expression of MaD6E and PtD5D Gene The amplified MaD6E PCR-product (Example 42) was ligated into NotI/BglII digested Rho20 vector (Example 12) using InFusion technology, resulting in vector Rho20-MaD6E. The amplified PtD5D PCR-product (Example 42) was ligated into SalI/XhoI digested Rho20-MaD6E vector using InFusion technology, resulting in vector Rho20-MaD6E-PtD5D. Two different clones of Rho20-MaD6E-PtD5D were sequenced to verify the sequence of the cloned gene.

EXAMPLE 45

Construction of a Yeast Vector for Constitutive Expression of MrD12D, OtD6D, MaD6E and PtD5D Gene The vector Rho20-MrD12D-OtD6D (Example 43) was linearized by PCR amplification using forward primer 5-CAG AGC AGA TTG TAC TGA GAG TG-3 and reverse primer 5-ATG CCG CAT AGT TAA GCC A-3. The PCR fragment was cut with DpnI and purified from agarose gel using the QiaQuick Gel Extraction Kit (Qiagen).

The vector Rho20-MaD6E-PtD5D (Example 44) was used as template for PCR amplification of the MaD6E-PtD5D expression cassettes using forward primer 5-TGG CTT AAC TAT GCG GCA TGA GCG ACC TCA TGC TAT ACC T-3 (SEQ ID NO 68) and reverse primer 5-TCT CAG TAC AAT CTG CTC TGC TGT GGA TAA CCG TAT TAC CG-3. The amplified PCR fragment containing the MaD6E-PtD5D expression cassette was purified from agarose gel using the QiaQuick Gel Extraction Kit (Qiagen).

The PCR linearized Rho20-MrD12D-OtD6D vector and the MaD6E-PtD5D expression cassette was ligated using InFusion technology resulting in Rho20-MrD12D-OtD6D-MaD6E-PtD5D called p13. Two different clones of p16 were sequenced to verify the sequence of the cloned gene.

EXAMPLE 46

Construction of a Yeast Vector for Constitutive Expression of MrD12D, OtD6D, MaD6E and PtD5D Gene with the Marker Gene ura3 Fused to a Ubiquitination Tag Rho20-MrD12D-OtD6D (Example 43) was used as template for PCR amplification (Herculase II) removing the ura3 coding sequence using forward primer 5-CTC ATT TTG TTA TTC ATT TGT AAA AAA CTG TAT TAT AAG TAA ATG CAT GT-3 (SEQ ID NO 76) containing the ubiquitination tag and reverse primer 5-TCC TTA TAT GTA GCT TTC GAC AT-3 (SEQ ID NO 77).

Rho0020 (Example 12) was used as template for PCR amplification of ura3 using forward primer 5-ATG TCG AAA GCT ACA TAT AAG GAA CGT G-3 (SEQ ID NO 78) and reverse primer 5-CAA ATG AAT AAC AAA ATG AGA CAA AGA AGA AAA CCA ATT TTT ACA AGC GTT TTG CTG GCC-3 (SEQ ID NO 79) containing the ubiquitination tag.

The two fragments obtained by PCR was fused using InFusion Cloning technology resulting in the plasmid Rho20-ura3-tag2-MrD12D-OtD6D.

Rho20-ura3-tag2-MrD12D-OtD6D was linearized by PCR amplification (Herculase II) using forward primer 5-CAG AGC AGA TTG TAC TGA GAG TG-3 (SEQ ID NO 70) and reverse primer 5-ATG CCG CAT AGT TAA GCC A-3 (SEQ ID NO 67). The PCR fragment was cut with DpnI and purified from agarose gel using the QiaQuick Gel Extraction Kit (Qiagen).

Rho20-MaD6E-PtD5D (Example 44) was used as template for PCR amplification (Herculase II) of the expression cassettes containing MaD6E and PtD5D using forward primer 5-TGG CTT AAC TAT GCG GCA TGA GCG ACC TCA TGC TAT ACC T-3 (SEQ ID NO 68) and reverse primer 5-TCT CAG TAC AAT CTG CTC TGC TGT GGA TAA CCG TAT TAC CG-3 (SEQ ID NO 137). The two fragments obtained by PCR was ligated using InFusion technology resulting in the plasmid Rho20-ura3-tag2-MrD12D-OtD6D-MaD6E-PtD5D called p16. Two different clones of p16 were sequenced to verify the sequence of the cloned gene.

Results

Strain FS01529 was used as expression host for either plasmid p13 or p16 (See Table 18).

TABLE 18

| Strain name | Parent strain | Inserted expression system | Genes in expression system | Tag |
|---|---|---|---|---|
| FS01529-p13 | FS01529 | P13 | pTDH3-OtD6D, pTEF1-MrD12D, pTDH3-PtD5D, pTEF1-MaD6E | None |
| FS01529-p16 | FS01529 | P16 | pTDH3-OtD6D, pTEF1-MrD12D, pTDH3-PtD5D, pTEF1-MaD6E | Ubiquitination tag |

The strains were grown in a 24 well deep well plate containing delft medium with 2% glucose. The strains were cultivated for 72 hours reaching the stationary phase and samples were taken for lipid extraction and subsequent GC-FID analysis (see Table 19).

TABLE 19

| Strain | Arachidonic acid as % of total fatty acid composition |
|---|---|
| FS01529-p13 | 0.3 |
| FS01529-p16 | 1.2 |

From the results present in Table 19 the percentage of the total fatty acid in the cell was 4 fold higher using tag plasmid (p16) compared to a non tag plasmid (p13).

EXAMPLE 47

Isolation of the Metabolic Engineering Target Genes Encoding Aro4 and Aro7

3-deoxy-D-arabino-heptulosonate-7-phosphate synthase (Aro4 gene) (Luttik et al., 2008) (SEQ ID NO 138) and Chorismate mutase (Aro7 gene) (Luttik et al., 2008) (SEQ ID NO 139) from *Saccharomyces cerevisiae* codon optimized for expression in *S. cerevisiae* was synthesized by GenScript Corporation (Piscataway, N.J.). ARO4 catalyzes the conversion of phosphoenolpyruvate, D-erythrose 4-phosphate and water to 3-deoxy-D-arabino-kept-2-ulosonate 7-phosphate and phosphate; ARO7 catalyzes the conversion of chorismate to prephanate. The synthetic codon optimized genes were delivered inserted in *E. coli* pUC57 vector. The synthetic genes were reamplified with PCR using the pUC57 vectors as templates. After DPN1 digestion the PCR products were purified from agarose gel using the QiaQuick Gel Extraction Kit (Qiagen).

EXAMPLE 48

Isolation of STS a Resveratrol Synthase Originating from *Vitis Pseudoreticulata*

Resveratrol synthase (STS gene) (www.ncbi.nlm.nih.gov/protein/ABF06883.1) (SEQ ID NO 140) from *Vitis pseudoreticulata* codon optimized for expression in *S. cerevisiae* was synthesized by GenScript Corporation (Piscataway, N.J.). The synthetic codon optimized genes were delivered inserted in *E. coli* pUC57 vector. The synthetic genes were reamplified with PCR using the pUC57 vectors as templates. After DPN1 digestion the PCR products were purified from agarose gel using the QiaQuick Gel Extraction Kit (Qiagen).

EXAMPLE 49

Construction of the Yeast Vector Rho0098 for Constitutive Expression of VST1 and STS Containing the His3 Marker pUC57-STS was used as template for PCR amplification (Herculase II) using forward primer 5-GGC CCG GGC GTC GAC ATG GCT TCT GTT GAA GAA ATT A-3 (SEQ ID NO 141) and reverse primer 5-CCA AGC TTA CTC GAG TCA TTA ATT AGA ATC AGT ACC A-3 (SEQ ID NO 142). Rho0011 was used as template for PCR amplification (Herculase II) using forward primer 5-CTA AAG GGC GGC CGC ATG GCA TCC GTA GAG GAG-3 (SEQ ID NO 143) and reverse primer 5-TCC ATC GAT ACT AGT TCA TTA GTT AGT GAC AGT TG-3 (SEQ ID NO 144). Rho0022 was digested with spel, SalI, and XhoI.

The three fragments obtained by PCR were fused using InFusion Cloning System (Clonetech). The resulting plasmid was cut with PvuII for verification. The plasmid was used as template for PCR amplification (Herculase II) using forward primer 5-ATG GCA TCC GTA GAG GAG TTC-3 (SEQ ID NO 44) and reverse primer 5-ATG GCT TCT GTT GAA GAA ATT A-3 (SEQ ID NO 141). Rho0011 was used as template for PCR amplification (Herculase II) using forward primer 5-CTC TAC GGA TGC CAT GAA TTC TCT AGA ATC CGT CGA AAC TAA GTT CTG-3 (SEQ ID NO 145) and reverse primer 5-TTC AAC AGA AGC CAT GGA TCC TCT AGA AAA CTT AGA TTA GAT TGC TAT G-3 (SEQ ID NO 146). The two fragments obtained by PCR was fused using InFusion Cloning System (Clonetech) resulting in the plasmid Rho0098 (SEQ ID NO 178).

Two different clones of Rho0098 were sequenced and the sequence of the cloned gene was verified.

EXAMPLE 50

Construction of the Yeast Vector p0161 for Constitutive Expression of VST1 and STS Containing the His3 Marker Rho0098 was used as template for PCR amplification (Herculase II) using forward primer 5-GCA ATG GAT CAG TTA CGT TAT ATC TTC GAG CGT CCC AAA A-3 (SEQ ID NO 147) and reverse primer 5-ATA ACG TAA CTG ATC CAT TGC TTC CTC GCT CAC TGA CTC-3 (SEQ ID NO 148).

The fragment obtained by PCR was fused using InFusion Cloning System (Clonetech) resulting in the plasmid p0161 (SEQ ID NO 180). Two different clones of p0161 were sequenced and the sequence of the cloned gene was verified.

EXAMPLE 51

Construction of a Yeast Vector for Constitutive Expression PAL2 and C4H:CYB5:ATR2 Containing the Ura3-Tag2 Marker p0160

Rho0058 was used as template for PCR amplification (Herculase II) using forward primer 5-GCA ATG GAT CAG TTA CGT TAT ATC TTC GAG CGT CCC AAA A-3 (SEQ ID NO 147) and reverse primer 5-ATA ACG TAA CTG ATC CAT TGC TTC CTC GCT CAC TGA CTC-3 (SEQ ID NO 148).

The fragment obtained by PCR was fused using InFusion Cloning System (Clonetech) resulting in the plasmid p0160

(SEQ ID NO 179). Two different clones of p0160 were sequenced and the sequence of the cloned gene was verified.

EXAMPLE 52

Construction of a Yeast Replicative Vector, p0202, Bearing pTEF1-C4H::CYB5::ATR2 and pCUP1-PAL2, URA3-tag2 as Selective Marker p0160 was used as template for a PCR amplification using primer 5-ACG TAT TCT TTG AAA TGG CG-3 and 5-ATG GAC CAA ATT GAA GCA ATG CTA-3. The promoter of CUP1 gene, pCUP1, was PCR amplified from *S. cerevisiae* CEN.PK genomic DNA using primers 5-TTT CAA AGA ATA CGT TTA CCG ACA TTT GGG CGC-3 (SEQ ID NO 149) and 5-TTC AAT TTG GTC CAT ACA GTT TGT TTT TCT TAA TAT C-3 (SEQ ID NO 150). The two above-mentioned fragments were fused using InFusion Cloning technology resulting in the plasmid p0202.

EXAMPLE 53

Construction of the Yeast Vector Rho0021 with Constitutive Expression Cassettes and the Leu2 Marker (SEQ ID NO 176)

pESC-leu (Stratagene) was used as template for PCR amplification (Herculase II) using forward primer 5-CAG AGC AGA TTG TAC TGA GAG TG-3 (SEQ ID NO 70) and reverse primer 5-ATG CCG CAT AGT TAA GCC A-3 (SEQ ID NO 67). RHO0011 was used as template for PCR amplification (Herculase II) using forward primer 5-TGG CTT AAC TAT GCG GCA TGA GCG ACC TCA TGC TAT ACC T-3 (SEQ ID NO 68) and reverse primer 5-TCT CAG TAC AAT CTGC TCT GCT GTG GAT AAC CGT ATT ACC G-3 (SEQ ID NO 69).

The two fragments obtained by PCR were fused using InFusion Cloning System (Clonetech) resulting in the plasmid Rho0021 (SEQ ID NO 176). Two different clones of Rho0021 were sequenced and the sequence of the cloned gene was verified

EXAMPLE 54

Construction of the Yeast Rho0039 Vector for Constitutive Expression of Aro7 and Aro4 Containing the Leu2 Marker Vector Rho0021 was digested with restriction enzyme NotI and BglII. The gene encoding Aro4 from *S. cerevisiae* was reamplified via PCR from Genscript vector pUC-57-Aro4 using forward primer 5-ACT AAA GGG CGG CCG ATG TCA GAG TCT CCA ATG T-3 (SEQ ID NO 151) and reverse primer 5-TAA GAG CTC AGA TCT CTA CTT CTT ATT TAC CTC TCT T-3 (SEQ ID NO 152) with homologous overhangs to the linearized RHO0021 vector.

The two fragments were recombined using the Infusion Cloning System (Clonetech). The resulting vector was called Rho0021-Aro4. Two different clones of pESC-URA-Pal2 were sequenced and the sequence of the cloned gene was verified.

Vector Rho0021-Aro4 was digested with restriction enzyme SalI and XhoI. The gene encoding Aro7 from *S. cerevisiae* was reamplified via PCR from Genscript vector pUC-57-Aro7 using forward primer 5-GGC CCG GGC GTC GAC ATG GAT TTT ACA AAG CCA GAA-3 (SEQ ID NO 153) and reverse primer 5-CCA AGC TTA CTC GAG TCA TTC TTC CAA TCT TCT CAA-3 (SEQ ID NO 154) with homologous overhangs to the linearized Rho0021-Aro4 vector.

The two fragments were recombined using the Infusion Cloning System (Clonetech). The resulting vector was called Rho0039 (SEQ ID NO 177). Two different clones of pESC-URA-Pal2 were sequenced to verify the sequence of the cloned gene.

EXAMPLE 55

Achieving High Expression Levels of Genes of Interest Through Multiple Integrations in *S. Cerevisiae* Genomic DNA Using TY-Delta Regions Achieving high production yields of a product of interest often requires molecular biology tools for high level gene expression. The use of replicative, multicopy vectors and strong promoters are often chosen to trigger the expression of genes of interest. Unfortunately strains constructed upon these plasmid borne expression systems are frequently prone to instability through DNA rearrangements, variations in plasmid copy number or even loss of plasmids.

In order to achieve high production levels of resveratrol, whilst providing a stable strain, we designed an expression system based on multiple integration of genes of interest at TY-delta regions. TY-delta regions are "long terminal repeats" (LTR) which are left out after the sequential insertion and excision of a Ty1 or Ty2 retrotransposon. A total of 331 retrotransposon insertions were identified on *S. cerevisiae*'s genome, 85% of which correspond to solo LTRs or to LTR fragments (Kim et al, Transposable Elements and Genome Organization: A Comprehensive Survey of Retrotransposons Revealed by the Complete *Saccharomyces cerevisiae* Genome Sequence(Genome Research, 2009). *S. cerevisiae*'s retrotransposons are divided into 5 different families designated Ty1-Ty5 (Kim et al, 2009).

In order to specifically integrate a chosen DNA sequence of interest into TY-delta regions by homologous recombination, a TY-delta consensus sequence was identified by aligning a number of TY-delta DNA sequences retrieved from *Saccharomyces* Genome Database (www.yeastgenome.org). By modifying 2 nucleotides, a BglII restriction site was added to the consensus sequence. The final sequence is presented in FIG. 14.

EXAMPLE 56

Construction of a Yeast Vector p0179 for Multiple Integration Using a Ty-Delta Consensus Sequence and *Schizosaccharomyces Pombe* HIS5 Marker Tagged by Tag2

HIS5 coding DNA sequence was PCR amplified from *Schizosaccharomyces pombe* genomic DNA (Phusion® High-fidelity DNA polymerase, Finnzymes) using forward primer 5-CAA GAT AAA CGA AGG CAA AGA TGG GTA GGA GGG CTT TT-3 (SEQ ID NO 155) and reverse primer 5-ATG AGA CAA AGA AGA AAA CCA ATT TTT ACA AGC CAA CAC TCC CTT CGT GCT T-3. pSF127 was used as template for PCR amplification (Herculase II) using forward primer 5-TCT TCT TTG TCT CAT TTT GTT ATT CAT TTG TAG TGA CAC CGA TTA TTT AAA GCT G-3 (SEQ ID NO 157) and reverse primer 5-CTT TGC CTT CGT TTA TCT TG-3 (SEQ ID NO 158). The two fragments obtained by PCR was fused using InFusion Cloning System (Clontech) resulting in the plasmid p0179. p0179 was verified by sequencing.

EXAMPLE 57

Construction of the Yeast Vector p0246 for Multiple Integration Using a Ty-Delta Consensus Sequence and the His3 Marker p0246 p0179 was used as template in a PCR reaction using primer 5-GCA ATG GCG GCC GCT TAC GTT ATC TTC CTC GCT CAC TGA CT-3 (SEQ ID NO 159) and 5-ATA ACG TAA GCG GCC GCC ATT GCA TTG GAG ACT TGA CCA AAC CT-3 (SEQ ID NO 160) removing the ADH1 terminator. The fragment obtained by PCR was fused to itself using InFusion Cloning technology resulting in the plasmid p0246 (SEQ ID NO 181). Two different clones of p0246 were sequenced and the sequence of the cloned gene was verified.

EXAMPLE 58

Construction of the Yeast Vector p0249 for Multiple Integration Using a Ty-Delta Consensus Sequence and the KanMX Marker p0249 p0246 was used as template in a PCR reaction using primer 5-CTT TGC CTT CGT TTA TCT TG-3 (SEQ ID NO 158) and 5-TGA CAC CGA TTA TTT AAA GCT GC-3 (SEQ ID NO 161) removing the entire His S-tag2 coding sequence. p0191 was used as template in a PCR reaction using primer 5-CAA GAT AAA CGA AGG ATG GGT AAG GAA AAG ACT CAC-3 (SEQ ID NO 162) and 5-GCA GCT TTA AAT AAT CGG TTA GAA AAA CTC ATC GAG CAT CAA ATG-3 (SEQ ID NO 163) removing the entire His S-tag2 coding sequence. The two fragments obtained by PCR were fused using InFusion Cloning System (Clonetech) resulting in the plasmid p0249 (SEQ ID NO 182). Two different clones of p0249 were sequenced and the sequence of the cloned gene was verified.

EXAMPLE 59

Construction of the Yeast Vector p0280 for Constitutive Expression and Integration of Aro7 and Aro4 Containing the KanMX Marker RHO0039 was used as template for PCR amplification (Herculase II) using forward primer 5-AAT TGG AGC TCC ACC GCG GCT TCG AGC GTC CCA AAA CCT TC-3 (SEQ ID NO 164) and reverse primer 5-GCT TGA TAT CGA ATT CGA GCG ACC TCA TGC TAT ACC TG-3 (SEQ ID NO 165). p0249 was digested using the restriction enzymes SacII and EcorRI. The two fragments obtained by PCR and restriction enzyme digestion were fused using InFusion Cloning technology resulting in the plasmid p0245-pTDH3-Aro7-pTEF1-Aro4 (p0280 (SEQ ID NO 184)). Two different clones of p0280 were sequenced and the sequence of the cloned gene was verified.

EXAMPLE 60

Construction of the Yeast Vector p0262 for Constitutive Expression and Integration of VST1 and STS Containing the KanMX Marker p0161 was used as template for PCR amplification (Herculase II) using forward primer 5-AAT TGG AGC TCC ACC GCG GCT TCG AGC GTC CCA AAA CCT TC-3 (SEQ ID NO 164) and reverse primer 5-GCT TGA TAT CGA ATT CGA GCG ACC TCA TGC TAT ACC TG-3 (SEQ ID NO 165). p0245 was digested using the restriction enzymes SacII and EcorRI. The two fragments obtained by PCR and restriction enzyme digestion were fused using InFusion Cloning technology resulting in the plasmid p0245-pTDH3-Aro7-pTEF1-Aro4 (p0280). Two different clones of p0262 (SEQ ID NO 183) were sequenced and the sequence of the cloned gene was verified.

EXAMPLE 61

Construction of Integrative Plasmids pSF126 and pSF127, for Multiple Integrations at TY-Delta Regions pSF126 is a URA3 based vector, pSF127 is based on HIS3. These two plasmids were synthetically assembled by Genscript.

These vectors are non-replicative in *S. cerevisiae* and can be specifically targeted for insertion at TY-delta regions by digestion using either BglII or Xho1 (both restriction sites are present in the previously identified LTR consensus sequence).

EXAMPLE 62

Construction of a Yeast Vector p0140 for Multiple Integration Using a Ty-Delta Consensus Sequence, Bearing *Saccharomyces Cerevisiae* HIS3 Marker, pTDH3-4CL2 and pTEF1-VST1

Rho0011 (Example 11) was used as template for PCR amplification (Phusion® High-fidelity DNA polymerase, Finnzymes) using forward primer 5-CTA GTG GAT CCC CCG GGT TGG AGC GAC CTC ATG CTA TAC C-3 (SEQ ID NO 166) and reverse primer 5-GAA TTC CTG CAG CCC GGG CGA GCG TCC CAA AAC CTT CTC AAG-3 (SEQ ID NO 167). pSF127 was linearized by digestion using SmaI endonuclease. The two obtained fragments were fused using InFusion Cloning System (Clontech) resulting in a yeast vector suitable for multiple integration at TY-delta regions (Example 55), bearing *Saccharomyces cerevisiae* HIS3 marker, pTDH3-4CL2 and pTEF1-VST1. In order to allow the linearization of the vector by BglII, thus allowing multiple integrations at TY-delta elements, the plasmid abovementioned was on the one hand PCR amplified (Phusion® High-fidelity DNA polymerase, Finnzymes) using forward primer 5-GGC GAA GAA TTG TTA ATT AAG AGC TCT GAT CTT ATC G-3 (SEQ ID NO 168) and reverse primer 5-GGC GCA GCA AGT CGA CGG CGA G-3 (SEQ ID NO 169); on the other hand the same plasmid was digested by Pad and SalI endonucleases. The two fragments, after agarose gel purification, were fused using InFusion Cloning technology resulting in the plasmid p0140. p0140 was verified by sequencing.

EXAMPLE 63

Construction of a Yeast Vector p0180 for Multiple Integration Using a Ty-Delta Consensus Sequence, Bearing *Schizosaccharomyces Pombe* HIS5 Marker Tagged by Tag2, pTDH3-4CL2 and pTEF1-VST1 p0140 was used as template for PCR amplification (Herculase II) using forward primer 5-CTA GTG GAT CCC CCG GGT TGG AGC GAC CTC ATG CTA TAC C-3 (SEQ ID NO 166) and reverse primer 5-GAA TTC CTG CAG CCC GGG CGA GCG TCC CAA AAC CTT CTC AAG-3 (SEQ ID NO 167). p0179 was linearized by digestion using SmaI endonuclease. The two fragments obtained were fused using InFusion Cloning technology resulting in the plasmid p0180. p0180 was verified by sequencing.

EXAMPLE 64

Construction of a Yeast Vector, p0204, for Multiple Integration Using a Ty-Delta Consensus Sequence, Bearing *Saccharomyces cerevisiae* URA3 Auxotrophic Marker, pTEF1-C4H::CYB5::ATR2 and pCUP1-PAL2 pSF126 was digested by KpnI and SacII endonucleases. p0202 was used as template to PCR amplify (Herculase II) the expression cassette pTEF1-C4H::CYB5::ATR2/pCUP1-PAL2 using forward primer 5-GGG AAC AAA AGC TGG GTA CCC TGT GGA TAA CCG TAT TAC C-3 (SEQ ID NO 170) and reverse primer 5-AAT TGG AGC TCC ACC GCG GGA GCG ACC TCA TGC TAT ACC-3 (SEQ ID NO 171). The two fragments, after agarose gel purification, were fused using InFusion Cloning technology resulting in the plasmid p0204.

EXAMPLE 65

Generation of Strain FS09308 Matalpha Ura3-52 his3 leu2 pTPI-ACC1, Delta-aro10, Delta-trp1, p0204 (pTEF1-C4H::CYB5::ATR2 and pCUP1-PAL2, TY-delta Consensus Element, URA3), p0180 (pTDH3-4CL2 and pTEF1-VST1, TY-Delta Consensus Element, *S. pombe* HIS5-Tag2)

*S. cerevisiae* strain FS09258 (Example 30) was transformed concomitantly with on the one hand plasmid p0204 digested by XhoI and on the other hand plasmid p0180 digested by BglII. Transformants were selected on SC-ura-his. 43 clones were inoculated in 48 deep-well plates containing Delft minimal medium, $20gL^{-1}$ glucose, supplemented with leucine and tryptophan. Additionally, the latter medium was supplemented by CuSO4 (0.15 mM) or not. The best performing transformant, referred to as "C3" in FIG. 15, was later named strain FS09308 [Matalpha ura3-52 his3 leu2 pTPI-ACC1, Delta-aro10, Delta-trp1, p0204 (pTEF1-C4H::CYB5::ATR2 and pCUP1-PAL2, TY-delta consensus element, URA3), p0180 (pTDH3-4CL2 and pTEF1-VST1, TY-delta consensus element, *S. pombe* HIS5-Tag2)].

The production of biomass (OD600), coumaric acid, cinnamic acid, pinosylvin, phloretic acid and resveratrol from 7 different clones arising from the transformation of *S. cerevisiae* FS09258 with linearized plasmids p0204 and p0180 is presented in FIG. 15. The different clones were cultivated in Delft medium (Example 33), 20 g.L-1 glucose, supplemented with leucine (60 mg.L-1), tryptophan (20 mg.L-1) and copper sulfate (0.15 mM). Sample was taken after 72 h of cultivation.

EXAMPLE 66

Generation of Strain FS09322 Matalpha ura3-52 his3 leu2, trp1 pTPI-Acc1, ΔaRo10, p204 (pTEF-C4H::CYB5::ATR2 pCUP1-PAL2, TY Element, URA3), p180 (pTDH3-4CL2 pTEF1-VST1, TY Element, *S. pombe* HIS5-Tag2), Rho51 (TEF1-Snq2, TRP1), p0262 (pTDH3-VST1 pTEF1-STS, TY Element, LEU2)

Yeast strain FS09313 [Matalpha ura3-52 his3 leu2 trp1 pTPI-Acc1, ΔaRo10, p204 (pTEF-C4H::CYB5::ATR2 pCUP1-PAL2, TY element, URA3), p180 (pTDH3-4CL2 pTEF1-VST1, TY element, *S. pombe* HIS5-Tag2), Rho51 (TEF1-Snq2, TRP11)] was transformed with the linear substrates originating from two PCR reactions using p0262 as template and primer 5-GAG GAG AAC TTC TAG TAT ATT CTG TAT ACC-3 (SEQ ID NO 172) and primer 5-GAG GAT ATA GGA ATC CAC AAA AGG G-3 (SEQ ID NO 173) for the first PCR reaction and primer 5-ATC TAT GAA TAA CAT ATA AAA CGA AAA GAG GAA TAA TC-3 (SEQ ID NO 174) and primer 5-CTT ATT ACA TTA TCA ATC CTT GCA TTT CAG C-3 (SEQ ID NO 175) for the second PCR reaction. Transformants were selected inoculated into delft medium containing 20 g/l glucose. 24 colonies were screened for increased resveratrol production and the highest producer was isolated.

The resulting strain was named FS09322 and had the genotype [Matalpha ura3-52 his3 leu2 trp1 pTPI-Acc1, ΔARo10, p204 (pTEF-C4H::CYB5::ATR2 pCUP1-PAL2, TY element, URA3), p180 (pTDH3-4CL2 pTEF1-VST1, TY element, *S. pombe* HISS-Tag2), Rho51 (TEF1-Snq2, TRP1), p0262 (pTDH3-VST1 pTEF1-STS, TY element, LEU2)]. The integration of VST1 and STS was checked by PCR and verified.

A comparison between strain FS09332 and strain FS09258-53-32-44-51 is shown below:

| FS09258-53-32-44-51 (previous strain) | FS09322 (new strain) |
|---|---|
| Deletion of URA3 | Deletion of URA3 |
| Deletion of HIS3 | Deletion of HIS3 |
| Deletion of LEU2 | Deletion of LEU2 |
| Deletion of TRP1 | Deletion of TRP1 |
| Deletion ARO 10 | Deletion ARO 10 |
| Overexpression of ACC1 | Overexpression of ACC1 |
| — | |
| — | |
| Plasmid pESC-URA3(tag2)-TDH3-PAL2-TEF1-C4H::CYB5::ATR2-TDH3-4CL2-TEF1-VST1 (Rho53) | Integrative plasmid p0204 pSF126 (URA3) (pCUP1-PAL2, pTEF1-C4H::CYB5::ATR2, URA3-without a tag sequence) |
| Plasmid pESC-HIS3-TDH3-PAL2-TEF1-C4H::CYB5::ATR2-TDH3-4CL2-TEF1-VST1 (Rho32) | Integrative plasmid p0180 (pTEF1-VST, pTDH3-4CL2; Marker: HIS5 from *S. pombe* attached to ubiquitin degradation Tag 2) |
| Plasmid pESC-LEU2-TDH3-PAL2-TEF1-C4H::CYB5::AR2-TDH3-4CL2-TEF1-VST1 (Rho44) | Integrative plasmid p0262 (pTEF1-STS, pTDH3-VST1) |
| Plasmid Snq2 Transporter | Plasmid rho0051 Snq2 Transporter |
| Antibiotic marker (Ampicillin) | Antibiotic marker (Ampicillin) |

FS09322 contains four integrative plasmids that contain the plant heterologous resveratrol pathway genes and resveratrol transporter genes and carries a deletion in the genes Aro10, Ura3, His3, Leu2, Trp1 and an overexpression of the genes ACC1 and SNQ2.

EXAMPLE 67

Generation of Strain FS09324 Matalpha ura3-52 his3 Leu2 trp1 pTPI-Acc1, ΔARo10, p204 (pTEF-C4H::CYB5::ATR2 pCUP1-PAL2, TY element, URA3), p180 (pTDH3-4CL2 pTEF1-VST1, TY Element, *S. pombe* HIS5-Tag2), Rho51 (TEF1-Snq2, TRP1), p0262 (pTDH3-VST1 pTEF1-STS, TY Element, Leu2), p0280 (pTDH3-Aro7, pTEF1-Aro4, TY Element, KanMX)

Yeast strain FS09322 was transformed with the linear substrates originating from two PCR reactions using p0280 as template and primer 5-GAG GAG AAC TTC TAG TAT ATT CTG TAT ACC-3 (SEQ ID NO 172) and primer 5-GAG GAT ATA GGA ATC CAC AAA AGG G-3 (SEQ ID NO 173) for the first PCR reaction and primer 5-ATC TAT GAA TAA CAT ATA AAA CGA AAA GAG GAA TAA TC-3 (SEQ ID NO 174) and primer 5-CTT ATT ACA TTA TCA ATC CTT GCA TTT CAG C-3 (SEQ ID NO 175) for the second PCR reaction. Transformants were selected inoculated into delft medium containing 20 g/l glucose. 24 colonies were screened for increased resveratrol production and the highest producer was isolated.

The resulting strain was named FS09324 and had the genotype [Matalpha ura3-52 his3 Leu2 pTPI-Acc1, DARo10, deltaTRP1, p204 (pTEF-C4H::CYB5::ATR2 pCUP1-PAL2, TY element, URA3), p180 (pTDH3-4CL2 pTEF1-VST1, TY element, *S. pombe* HIS5-Tag2), Rho51 (TEF1-Snq2, TRP1), p0262 (pTDH3-VST1 pTEF1-STS, TY element, Leu2), p0280 (pTDH3-Aro7, pTEF1-Aro4, TY element, KanMX)]. The integration of Aro7 and pTEF1-Aro4 was checked by PCR and verified.

EXAMPLE 68

Generation of Strain FS09313 Matalpha ura3-52 his3 leu2 pTPI-ACC1, Delta-aro10, Delta-trp1, p0204 (pTEF1-C4H::CYB5::ATR2 and pCUP1-PAL2, TY-delta Consensus Element, URA3), p0180 (pTDH3-4CL2 and pTEF1-VST1, TY-Delta Consensus Element, *S. pombe* HIS5-Tag2), Rho0051 (pTEF1-SNQ2, TRP1)

*S. cerevisiae* strain FS09308 was transformed with plasmid Rho0051 digested by HindIII for integration by single cross-over into trp1 coding DNA sequence. The resulting strain was named FS09313 [Matalpha ura3-52 his3 leu2 pTPI-ACC1, Delta-aro10, Delta-trp1, p0204 (pTEF1-C4H::CYB5::ATR2 and pCUP1-PAL2, TY-delta consensus element, URA3), p0180 (pTDH3-4CL2 and pTEF1-VST1, TY-delta consensus element, *S. pombe* HIS5-Tag2), Rho0051 (pTEF1-SNQ2, TRP1)].

EXAMPLE 69

Generation of Strain FS09326 Matalpha ura3-52 his3 leu2 pTPI-ACC1, Delta-aro10, Delta-trp1, p0204 (pTEF1-C4H::CYB5::ATR2 and pCUP1-PAL2, TY-Delta Consensus Element, URA3), p0180 (pTDH3-4CL2 and pTEF1-VST1, TY-Delta Consensus Element, *S. pombe* HIS5-Tag2), Rho0051 (pTEF1-SNQ2, TRP1), Rho0039 (pTDH3-ARO7, pTEF1-ARO4, LEU2)

*S. cerevisiae* strain FS09313 was transformed with plasmid Rho0039 (pTDH3-ARO7, pTEF1-ARO4, LEU2). The resulting strain was named FS09326 [Matalpha ura3-52 his3 leu2 pTPI-ACC1, Delta-aro10, Delta-trp1, p0204 (pTEF1-C4H::CYB5::ATR2 and pCUP1-PAL2, TY-delta consensus element, URA3), p0180 (pTDH3-4CL2 and pTEF1-VST1, TY-delta consensus element, *S. pombe* HIS5-Tag2), Rho0051 (pTEF1-SNQ2, TRP1), Rho0039 (pTDH3-ARO7, pTEF1-ARO4, LEU2)].

EXAMPLE 70

Production of Resveratrol with Strain FS09324 Compared to FS09322 in Deep Well Plate Cultivation The two strains FS09322 and FS09324 were constructed (Example 66 and 67) where FS09324 in comparison to FS09322 had also Aro7 and Aro4 overexpressed. The strains were grown in a 24 deep well plate with delft medium containing 2% glucose and 0.15 mM $CuSO_4*H_2O$. The strains were cultivated for 72 hours reaching the stationary phase and samples were taken for extraction and subsequent HPLC analysis (Table 20).

TABLE 20

| Strain | Mg/l resveratrol | $OD_{600}$ | Yield on biomass | Yield on glucose |
|---|---|---|---|---|
| FS09322 | 182 | 10.0 | 18.2 | 9.1 |
| FS09324 | 291 | 9.0 | 32.2 | 14.6 |

From the results present in Table 20 the resveratrol yield on biomass was increased by 77%, the resveratrol yield on glucose by 60% and the resveratrol titre by 60%.

EXAMPLE 71

Fermentation Media and Conditions for the Characterization of Strain FS09322 and FS09326 in Fed-Batch Fermentation Fed-batch fermentation of FS09322 and FS09326 have been conducted as described in under "Fermentation media and conditions" above with the changes described below.

In the cultivation of FS09322 and FS09326, pre-defined exponential feeding profiles were used (Table 21) after the batch phase, the feed rate were adjusted in the course of the cultivations in order to avoid respiro-fermentative metabolism. In case of ethanol production, the phases of exponential feeding can be followed by phase with reduced and constant feeding. In Table 22, parameters are listed upon which the fermentations were switched from batch phase to exponential feeding, using various feeding media as described in Table 22.

During the course of fermentation of FS09322 0.9 ml of 150 mM CuSO4 were added after 8 h, 37 h and 48.5 h, respectively. During the course of fermentation of FS09326 1.67 150 mM $CuSO_4$ were added after 43.25 h into the fermentation.

Fermentation using strain FS09326 was conducted using a 5 liter vessel with 1 L starting working volume.

TABLE 21

Parameters used for the calculation of pre-defined, exponential feeding profiles in the fed-batch phase using FS09322 and FS09326. Three different feeding media were used.

| | F40 | F160 | F620 |
|---|---|---|---|
| FS09322 | | | |
| Sf (g/L) | 41.15 | 172.22 | 594.17 |
| V0 (L) | 0.30 | 0.57 | 0.71 |
| Vmax (L) | 5.00 | 5.00 | 5.00 |
| X0 (g DW/L) | 1.50 | 7.67 | 17.88 |
| S0 (g/L) | 0.00 | 0.00 | 0.00 |
| Ysx (g DW/g) | 0.35 | 0.35 | 0.35 |
| Yxs (g/g DW) | 2.86 | 2.86 | 2.86 |
| μ0 (1/h) | 0.10 | 0.10 | 0.10 |
| FS09326 | | | |
| Sf (g/L) | 40.00 | 153.91 | 620.00 |
| V0 (L) | 1.00 | 1.00 | 1.16 |
| Vmax (L) | 5.00 | 5.00 | 5.00 |
| X0 (g DW/L) | 2.00 | 1.50 | 9.30 |
| S0 (g/L) | 0.00 | 0.00 | 0.00 |
| Ysx (g DW/g) | 0.35 | 0.35 | 0.35 |
| Yxs (g/g DW) | 2.86 | 2.86 | 2.86 |
| μ0 (1/h) | 0.10 | 0.10 | 0.10 |

TABLE 22

Approximate parameters at start of exponential feeding phase, constant feeding phase 1, constant feeding phase 2

| Strain | Start of | Time (h) |
|---|---|---|
| FS09322 | exponential feeding phase using F40 | 8 |
| | exponential feeding phase using F160 | 29.5 |
| | exponential feeding phase using F620, μ = 0.095 1/h | 42.5 |
| | exponential feeding phase using F620, μ = 0.025 1/h | 55 |
| FS09326 | exponential feeding phase using F40 | Not used |
| | exponential feeding phase using F160 | 9.5 |
| | exponential feeding phase using F620, μ = 0.095 1/h | 27 |
| | exponential feeding phase using F620, μ = 0.025 1/h | 49 |

EXAMPLE 72

Fed-Batch Fermentation of FS09258-51-53-32B-44, FS09326 and FS09322

Figure 16:
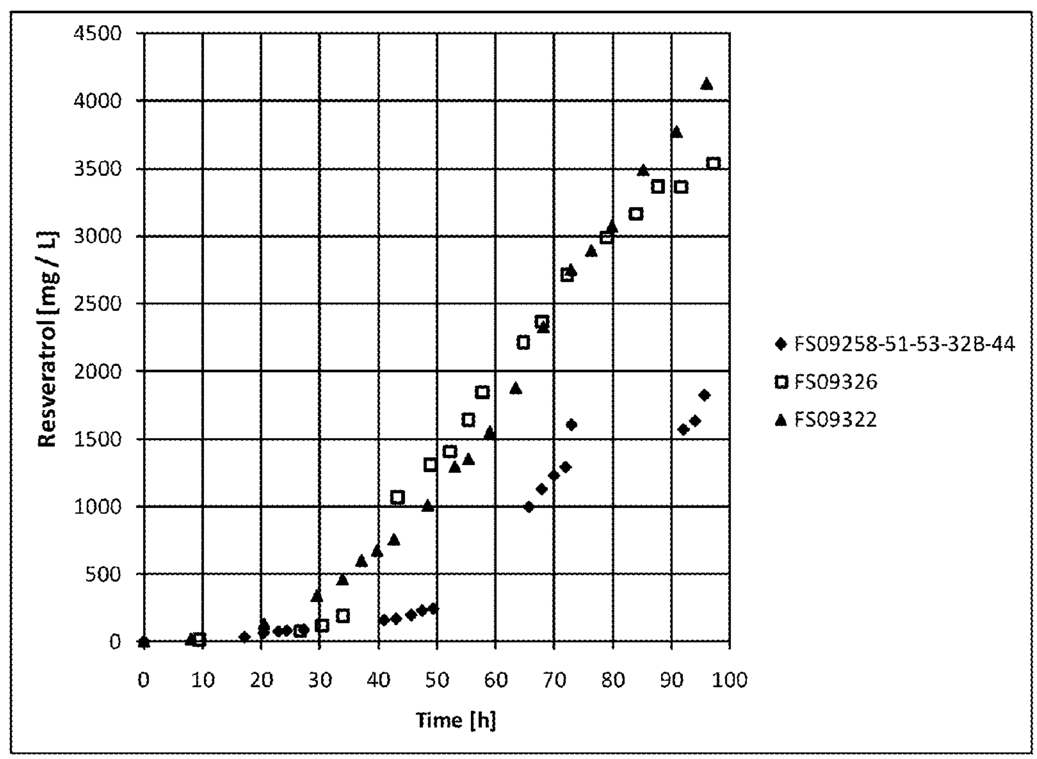
FIG. 16 shows results of the conducted fed-batch fermentations described in Example 72 using strains FS09258-51-53-32B-44, FS09326 and FS09322.

The effect of integration of resveratrol pathway and transporter genes was investigated in controlled fed-batch fermentation. FS09258-51-53-32B-44 was used as reference strain and compared to FS09326 which has part of the resveratrol pathway integrated into the genome, and to FS09322 which has all resveratrol pathway genes and transporters integrated into the pathway. The results of the conducted fed-batch fermentations of FS09258-51-53-32B-44, FS09326 and FS09322 can be seen in FIG. 16.

Plasmid maps for plasmids referred to above are as follows:

Plasmid Rho0021.
Features Rho0021

| Name | Type | Region |
|---|---|---|
| ADH1 | Terminator | complement (2999 . . . 3163) |
| CYC1 | Terminator | 4809 . . . 4998 |
| pUC | Replication origin | 5185 . . . 5852 |
| 2 mu | Replication origin | 6994 . . . 8149 |
| TEF1 | Promoter | complement (3371 . . . 3771) |
| TDH3 | Promoter | 4061 . . . 4715 |
| LEU2 | ORF | complement(663 . . . 1757) |
| F1 origin | ORF | complement (2597 . . . 2903) |
| bla | ORF | complement (6003 . . . 6860) |
| Flag tag | ORF | complement (3315 . . . 3338) |
| c-myc tag | ORF | 4747 . . . 4782 |

Plasmid Rho0039.
Features Rho0039

| Name | Type | Region |
|---|---|---|
| CYC1 | Terminator | 6853 . . . 6973 |
| ADH1 | Terminator | complement (2999 . . . 3163) |
| 2 um | Replication origin | 8812 . . . 9967 |
| pUC | Replication origin | 7003 . . . 7670 |
| F1 | Replication origin | complement (2597 . . . 2903) |
| TDH3 | Promoter | 5138 . . . 5792 |
| TEF | Promoter | complement (4448 . . . 4848) |
| ARO7 | ORF | 5824 . . . 6594 |
| ARO4 | ORF | complement (3314 . . . 4426) |
| Leu2 | ORF | complement (668 . . . 1757) |
| Bla | ORF | complement (7818 . . . 8678) |

Plasmid Rho0098.
Features Rho0098

| Name | Type | Region |
|---|---|---|
| CYC1 | Terminator | 6076 . . . 6265 |
| ADH1 | Terminator | complement (1961 . . . 2125) |
| pUC | Replication origin | 6452 . . . 7119 |
| 2 mu | Replication origin | 8261 . . . 9416 |
| STS | Replication origin | 4862 . . . 6040 |
| F1 origin | Replication origin | 1555 . . . 1861 |
| TEF1 | Promoter | 4449 . . . 4849 |
| TDH3 | Promoter | complement (3505 . . . 4159) |
| HIS3 | ORF | 504 . . . 1163 |
| Bla | ORF | complement (7267 . . . 8127) |
| VST1 | ORF | complement (2311 . . . 3492) |

Plasmid p0160.

| Name | Type | Region |
|---|---|---|
| ADH1 | Terminator | complement (1933 . . . 2097) |
| CYC1 | Terminator | 9581 . . . 9770 |
| pUCori | Replication origin | 9913 . . . 10580 |
| 2 mu | Replication origin | 11722 . . . 12877 |
| TDH3 | Promoter | complement (4413 . . . 5067) |
| TEF1 | Promoter | 5357 . . . 5758 |

-continued

| Plasmid p0160. | | |
|---|---|---|
| Name | Type | Region |
| F1 | ORF | complement (1531 . . . 1837) |
| URA3-tag2 | ORF | 417 . . . 1268 |
| BLA | ORF | complement (10728 . . . 11600) |
| PAL2 | ORF | complement (2247 . . . 4400) |
| C4H | ORF | 5770 . . . 7320 |
| ATR2 | ORF | 7636 . . . 9561 |
| CYB5 | ORF | 7336 . . . 7626 |

| Plasmid p0161. | | |
|---|---|---|
| Name | Type | Region |
| CYC1 | Terminator | 5761 . . . 5950 |
| ADH1 | Terminator | complement(1661 . . . 1813) |
| pUCori | Replication origin | 6092 . . . 6759 |
| 2 mu | Replication origin | 7901 . . . 9056 |
| TEF1 | Promoter | 4137 . . . 4537 |
| TDH3 | Promoter | complement (3193 . . . 3847) |
| HIS3 | ORF | 504 . . . 1163 |
| Bla | ORF | complement (6907 . . . 7767) |
| VST1 | ORF | complement (1999 . . . 3180) |
| STS | ORF | 4550 . . . 5725 |

| Plasmid p0246. Features p0246 | | |
|---|---|---|
| Name | Type | Region |
| HIS3 | Terminator | 19 . . . 225 |
| pUC | Replication origin | 1235 . . . 1902 |
| f1ori | Replication origin | 457 . . . 763 |
| HIS3 | Promoter | join (3677 . . . >3678, <3679 . . . 3993) |
| bla | Promoter | complement (2911 . . . 3041) |
| Tag2 | ORF | 4645 . . . 4677 |
| bla | ORF | complement (2050 . . . 2910) |
| pombe HIS5 | ORF | 3994 . . . 4644 |
| loxP | Misc. structure | 226 . . . 274 |
| MCS | Misc. structure | 971 . . . 1048 |
| loxP | Misc. structure | 3628 . . . 3676 |
| Ty | Misc. structure | 3295 . . . 3627 |

| Plasmid p0249. Features p0249 | | |
|---|---|---|
| Name | Type | Region |
| HIS3 | Terminator | 1623 . . . 1824 |
| pUCori | Replication origin | 2834 . . . 3501 |
| f1ori | Replication origin | 2056 . . . 2362 |
| pbla | Promoter | complement(4510 . . . 4640) |
| HIS3 | Promoter | 501 . . . 812 |
| bla | ORF | complement (3649 . . . 4509) |
| KanMX | ORF | 813 . . . 1622 |
| loxP | Misc. structure | 1825 . . . 1873 |
| MCS | Misc. structure | 2570 . . . 2647 |
| loxP | Misc. structure | 452 . . . 500 |
| Ty | Misc. structure | 119 . . . 451 |

| Plasmid p0262. | | |
|---|---|---|
| Name | Type | Region |
| CYC1 | Terminator | complement (3544 . . . 3733) |
| LEU2 | Terminator | 2309 . . . 2784 |
| ADH1 | Terminator | 7681 . . . 7845 |
| f1 | Replication origin | 3016 . . . 3322 |
| pUC | Replication origin | 8056 . . . 8723 |
| TEF1 | Promoter | complement (4957 . . . 5357) |
| TDH3 | Promoter | 5647 . . . 6301 |
| LEU2 | Promoter | 567 . . . 1213 |
| bla | Promoter | complement (9732 . . . 9862) |
| LEU2 | ORF | 1214 . . . 2308 |
| PvVST | ORF | complement (3766 . . . 4944) |
| VvVST | ORF | 6314 . . . 7492 |
| bla | ORF | complement (8871 . . . 9731) |
| loxP | Misc. structure | 2785 . . . 2833 |
| Ty | Misc. structure | 185 . . . 517 |
| loxP | Misc. structure | 518 . . . 566 |

| Plasmid p0280. Features p0280 | | |
|---|---|---|
| Name | Type | Region |
| HIS3 | Terminator | 1 . . . 202 |
| ADH1 | Terminator | 4615 . . . 4779 |
| CYC1 | Terminator | complement (962 . . . 1151) |
| f1 origin | Replication origin | 434 . . . 740 |
| pUCori | Replication origin | 4990 . . . 5657 |
| TDH3 | Promoter | complement (1986 . . . 2640) |
| TEF1 | Promoter | 2930 . . . 3330 |
| bla | Promoter | complement (6666 . . . 6796) |
| HIS3 | Promoter | 7432 . . . 7743 |
| Bla | ORF | complement (5805 . . . 6665) |
| KanMX | ORF | 7744 . . . 8553 |
| Aro4 | ORF | 3352 . . . 4464 |
| Aro7 | ORF | complement (1184 . . . 1954) |
| loxP | Misc. structure | 203 . . . 251 |
| MCS | Misc. structure | 948 . . . 4803 |
| loxP | Misc. structure | 7383 . . . 7431 |
| Ty | Misc. structure | 7050 . . . 7382 |

Figure 17:
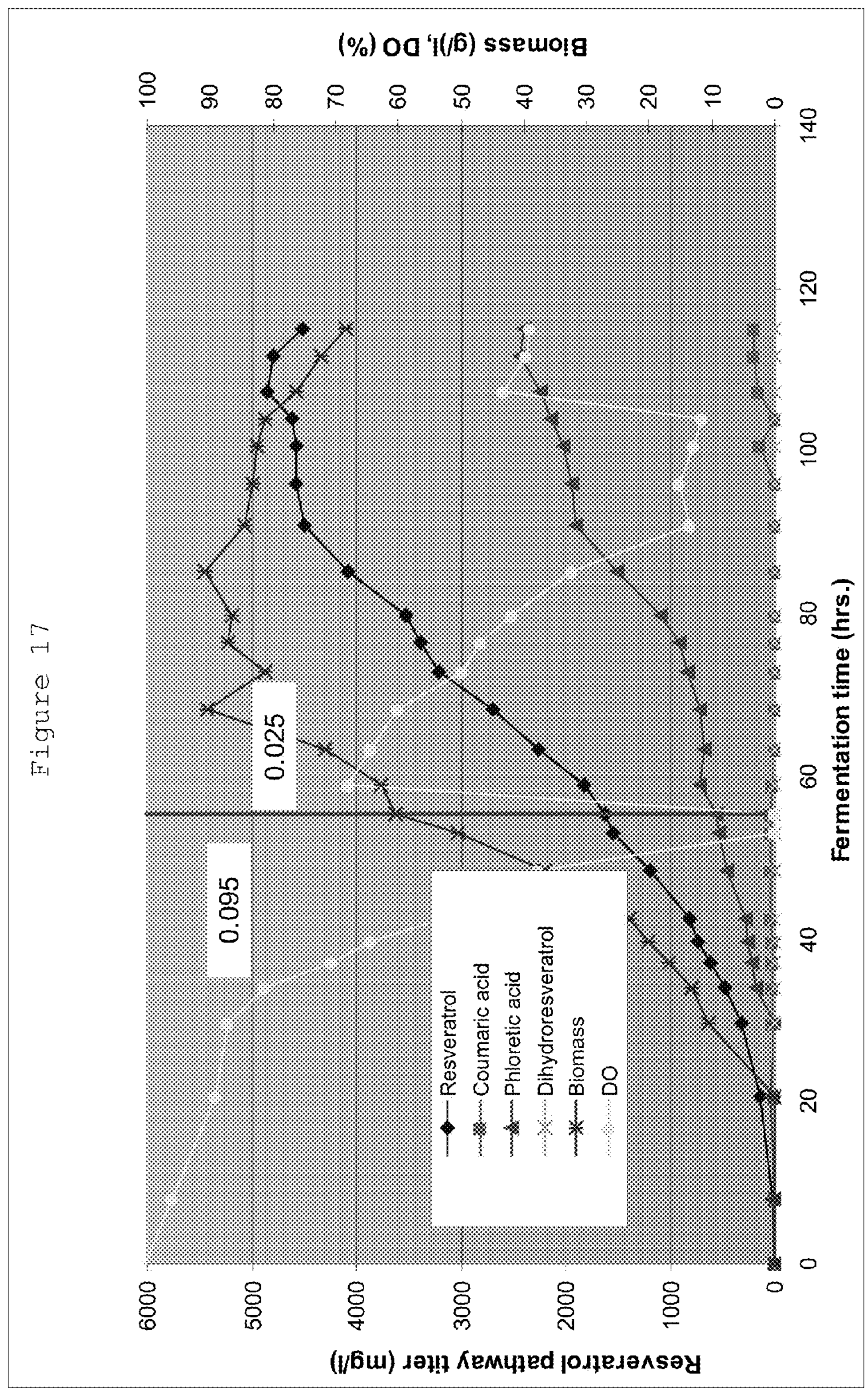
FIG. 17 shows a typical time profile of the production of resveratrol and other products in the cultivation of strain FS09322 of *Saccharomyces cerevisiae* according to the invention. The vertical bar at about 55 minutes indicates the time of switching to a production phase.

As seen in FIG. 17, strains of *S. cerevisiae* according to the invention are capable of producing above 4,000 mg/l of resveratrol. Levels of over 5,000 mg/l are achievable.

In this specification, unless expressly otherwise indicated, the word 'or' is used in the sense of an operator that returns a true value when either or both of the stated conditions is met, as opposed to the operator 'exclusive or' which requires that only one of the conditions is met. The word 'comprising' is used in the sense of 'including' rather than in to mean 'consisting of'. All prior teachings acknowledged above are hereby incorporated by reference. No acknowledgement of any prior published document herein should be taken to be an admission or representation that the teaching thereof was common general knowledge in Australia or elsewhere at the date hereof.

REFERENCES

Aury J M, Jaillon O, Duret L, Noel B, Jubin C, Porcel B M, Ségurens B, Daubin V,Anthouard V, Aiach N, Arnaiz O, Billaut A, Beisson J, Blanc I, Bouhouche K, Camara F, Duharcourt S, Guigo R, Gogendeau D, Katinka M, Keller A M, Kissmehl R, Klotz C, Koll F, Le Mouël A, Lepère G, Malinsky S, Nowacki M, Nowak J K, Plattner H, Poulain J, Ruiz F, Serrano V, Zagulski M, Dessen P, Bétermier M, Weissenbach J, Scarpelli C, Schächter V, Sperling L, Meyer E, Cohen J, Wincker P. *Global trends* of whole-genome duplications revealed by the ciliate Paramecium tetraurelia. Nature. 2006 Nov. 9; 444(7116): 171-8.

Andrade A C, Del Sorbo G, Van Nistelrooy J G, Waard M A.

The ABC transporter AtrB from *Aspergillus nidulans* mediates resistance to all major classes of fungicides and some natural toxic compounds. Microbiology. 2000:146:1987-97.

Banerjee D, Lelandais G, Shukla S, Mukhopadhyay G, Jacq C, Devaux F, Prasad R.

Responses of pathogenic and nonpathogenic yeast species to steroids reveal the functioning and evolution of multidrug resistance transcriptional networks.

Eukaryot Cell. 2008:7:68-77.

Boer V M, de Winde J H, Pronk J T, Piper M D.

The genome-wide transcriptional responses of *Saccharomyces cerevisiae* grown on glucose in aerobic chemostat cultures limited for carbon, nitrogen, phosphorus, or sulfur.

J Biol. Chem. 2003:278:3265-74.

Chloupková M, Pickert A, Lee J Y, Souza S, Trinh Y T, Connelly S M, Dumont M E, Dean M, Urbatsch I L.

Expression of 25 human ABC transporters in the yeast *Pichia pastoris* and characterization of the purified ABCC3 ATPase activity.

Biochemistry. 2007:46:7992$^{-8003}$.

Cochrane F C, Davin L B, Lewis N G.

The *Arabidopsis* phenylalanine ammonia lyase gene family: kinetic characterization of the four PAL isoforms.Phytochemistry. 2004:65:1557-64.

Connolly M S, Sakihama Y, Phuntumart V, Jiang Y, Warren F, Mourant L, Morris P F.

Heterologous expression of a pleiotropic drug resistance transporter from *Phytophthora sojae* in yeast transporter mutants.

Curr Genet. 2005:48:356-65.

Del Sorbo G, Andrade A C, Van Nistelrooy J G, Van Kan J A, Balzi E, De Waard M A.

Multidrug resistance in *Aspergillus nidulans* involves novel ATP-binding cassette transporters.

Mol Gen Genet. 1997:254:417-26.

Del Sorbo G, Ruocco M, Schoonbeek H J, Scala F, Pane C, Vinale F, De Waard M A.

Cloning and functional characterization of BcatrA, a gene encoding an ABC transporter of the plant pathogenic fungus *Botryotinia fuckeliana* (*Botrytis cinerea*).

Mycol Res. 2008:112:737-46.

Domergue F, Abbadi A, Zähringer U, Moreau H, Heinz E. In vivo characterization of the first acyl-CoA Delta6-desaturase from a member of the plant kingdom, the microalga Ostreococcus tauri. Biochem J. 2005 Jul. 15; 389 (Pt 2):483-90.

Ehlting J, Büttner D, Wang Q, Douglas C J, Somssich I E, Kombrink E.

Three 4-coumarate:coenzyme A ligases in *Arabidopsis thaliana* represent two evolutionarily divergent classes in angiosperms. Plant J. 1999:19:9-20.

Erdeniz N, Mortensen U H, Rothstein R

Cloning-Free PCR-Based Allele Replacement Methods

Genome Res. 1997 7: 1174-1183

Etschmann M Mw, Bluemke W, Sell D, Schrader J

Biotechnological production of 2-phenylethanol

Appl Microbiol Biotechnol 2002:59:1-8

Giaever G, Chu A M, Ni L, Connelly C, Riles L, Véronneau S, Dow S, Lucau-Danila A, Anderson K, André B, Arkin A P, Astromoff A, El-Bakkoury M, Bangham R, Benito R, Brachat S, Campanaro S, Curtiss M, Davis K, Deutschbauer A, Entian K D, Flaherty P, Foury F, Garfinkel D J, Gerstein M, Gotte D, Güldener U, Hegemann J H, Hempel S, Herman Z, Jaramillo D F, Kelly D E, Kelly S L, Kotter P, LaBonte D, Lamb D C, Lan N, Liang H, Liao H, Liu L, Luo C, Lussier M, Mao R, Menard P, Ooi S L, Revuelta J L, Roberts C J, Rose M, Ross-Macdonald P, Scherens B, Schimmack G, Shafer B, Shoemaker D D, Sookhai-Mahadeo S, Storms R K, Strathern J N, Valle G, Voet M, Volckaert G, Wang C Y, Ward T R, Wilhelmy J, Winzeler E A, Yang Y, Yen G, Youngman E, Yu K, Bussey H, Boeke J D, Snyder M, Philippsen P, Davis R W, Johnston M.

Functional profiling of the *Saccharomyces cerevisiae* genome.

Nature. 2002:418:387-91.

Gietz R D, Schiestl R H. Applications of high efficiency lithium acetate transformation of intact yeast cells using single-stranded nucleic acids as carrier.

Yeast. 1991:7:253-63.

Guengerich F P, Gillam E M, Ohmori S, Sandhu P, Brian W R, Sari M A, Iwasaki M. Expression of human cytochrome P450 enzymes in yeast and bacteria and relevance to studies on catalytic specificity.

Toxicology. 1993:82:21-37. Review.

Gilon T, Chomsky O, Kulka R G

Degradation signals for ubiquitin system proteolysis in *Saccharomyces cerevisiae*

The EMBO Journal 1998:17:2759-2766

Hain R, Reif H J, Krause E, Langebartels R, Kindl H, Vornam B, Wiese W, Schmelzer E, Schreier P H, Stöcker R H, et al. Disease resistance results from foreign phytoalexin expression in a novel plant.Nature. 1993:361:153-6.

Hamberger B, Hahlbrock K.

The 4-coumarate:CoA ligase gene family in *Arabidopsis thaliana* comprises one rare, sinapate-activating and three commonly occurring isoenzymes.Proc Natl Acad Sci USA. 2004:101:2209-14.

Johansson B and Hahn-Hagerdal B

Overproduction of pentose phosphate pathway enzymes using a new CRE-loxP expression vector for repeated genomic integration in *Saccharomyces cerevisiae*

Yeast 2002:19:225-231.

Jungwirth H, Kuchler K.

Yeast ABC transporters—a tale of sex, stress, drugs and aging.

FEBS Lett. 2006:580:1131-8.

Kunji E R, Slotboom D J, Poolman B.

*Lactococcus* lactis as host for overproduction of functional membrane proteins.

Biochim Biophys Acta. 2003:1610:97-108. Review.

Mizutani M, Ohta D, Sato R.

Isolation of a cDNA and a genomic clone encoding cinnamate 4-hydroxylase from *Arabidopsis* and its expression manner in planta.

Plant Physiol. 1997:113:755-63.

Mizutani M, Ohta D.

Two isoforms of NADPH:cytochrome P450 reductase in *Arabidopsis thaliana*. Gene structure, heterologous expression in insect cells, and differential regulation.Plant Physiol. 1998:116:357-67.

Moriya H, Shimizu-Yoshida Y, Kitano H.

In vivo robustness analysis of cell division cycle genes in *Saccharomyces cerevisiae.*

PLoS Genet. 2006 July; 2(7):e111. Epub 2006 Jun. 5.

Erratum in: PLoS Genet. 2006 December; 2(12):e218.

Muhitch M J, McCormick S P, Alexander N J, Hohn T M.

Transgenic expression of the TRI101 or PDR5 gene increases resistance of tobacco to the phytotoxic effects of the trichothecene 4,15-diacetoxyscirpenol.

Plant Sci. 2000:157:201-207.

Mumberg D, Müller R, Funk M.

Yeast vectors for the controlled expression of heterologous proteins in different genetic backgrounds. Gene.

1995:156:119-22.

Nimii M et al,

Functional analysis of fungal drug efflux transporters by heterologous expression in *S. cerevisiae*

Jpn. J. Infect Disease 2005:58:1-7

Pan Z, Agarwal A K, Xu T, Feng Q, Baerson S R, Duke S O, Rimando A M. Identification of molecular pathways affected by pterostilbene, a natural dimethylether analog of resveratrol.

BMC Med. Genomics. 2008:20:1-7.

Passorn, S., Laoteng, K., Rachadawong, S., Tanticharoen, M.

and Cheevadhanarak,S. Heterologous expression of *Mucor rouxii* delta(12)-desaturase gene in *Saccharomyces cerevisiae*; Biochem. Biophys. Res. Commun. 263 (1), 47-51 (1999)

Rogers B, Decottignies A, Kolaczkowski M, Carvajal E, Balzi E, Goffeau A. The pleitropic drug ABC transporters from *Saccharomyces cerevisiae*. J Mol Microbiol Biotechnol. 2001:3:207-14.

Schoonbeek H, Del Sorbo G, De Waard M A.

The ABC transporter BcatrB affects the sensitivity of *Botrytis cinerea* to the phytoalexin resveratrol and the fungicide fenpiclonil.

Mol Plant Microbe Interact. 2001:14:562-71.

Mol Gen Genet. 1993 January; 236(2-3):214-8.

Gene SNQ2 of *Saccharomyces cerevisiae*, which confers resistance to 4-nitroquinoline-N-oxide and other chemicals, encodes a 169 kDa protein homologous to ATP-dependent permeases.

Servos J, Haase E, Brendel M.

Sikorski R S, Hieter P.

A system of shuttle vectors and yeast host strains designed for efficient manipulation of DNA in

*Saccharomyces cerevisiae.*

Genetics. 1989:122:19-27.

Song W Y, Sohn E J, Martinoia E, Lee Y J, Yang Y Y, Jasinski M, Forestier C, Hwang I, Lee Y.

Engineering tolerance and accumulation of lead and cadmium in transgenic plants.

Nat. Biotechnol. 2003:21:914-9.

Tavares,S, and Gunnarsson,N, GenBank, www.ncbi.nim.nih.gov/nuccore/291481146?report=genbank, Trott A, West J D, Klaie L, Westerheide S D, Silverman R B, Morimoto R I, Morano K A.

Activation of heat shock and antioxidant responses by the natural product celastrol: transcriptional signatures of a thiol-targeted molecule.

Mol Biol Cell. 2008:19:1104-12.

Verduyn C, Postma E, Scheffers W A, Van Dijken J P.

Effect of benzoic acid on metabolic fluxes in yeasts: a continuous-culture study on the regulation of respiration and alcoholic fermentation. Yeast. 1992:8:501-17.

Vuralhan Z, Luttik M A H, Tai S L, Boer V M, Morais M A, Schipper D, Almering M J H, Kotter P, Dickinson J R, Daran J, Pronk J T Physiological Characterization of the ARO10-Dependent, Broad-Substrate-Specificity 2-Oxo Acid Decarboxylase Activity of *Saccharomyces cerevisiae*

Applied and Environmental Microbiology 2005:71:3276-3284

Werck-Reichhart D, Feyereisen R.

Cytochromes P450: a success story

Genome Biology 2000:1:3003.1-3003.9

Yoon Y G, Posfai G, Szybalski W, Kim S C

Cre/loxP-mediated in vivo excision of large segments from yeast genome and their amplification based on the 2 mm plasmid-derived system Gene 1998:223:67-76

Zwiers L H, Stergiopoulos I, Van Nistelrooy J G, De Waard M A.

ABC transporters and azole susceptibility in laboratory strains of the wheat pathogen *Mycosphaerella graminicola.*

Antimicrob Agents Chemother. 2002 December; 46(12):3900-6.

The invention claimed is:

1. A recombinant *Saccharomyces cerevisiae* micro-organism which produces and excretes into culture medium resveratrol, wherein the micro-organism comprises:

(a) a resveratrol producing metabolic pathway comprising a phenylalanine ammonia lyase (PAL) or a tyrosine ammonia lysase (TAL), a cinnamate 4-hydroxylase (C4H), a 4-coumarate-CoA ligase (4CL) and a stilbene synthase;

(b) a greater than native expression level of SNQ2, (c) a functionally disabled or deleted ARO10, and (d) a greater than native expression level of an acetyl coenzymeA carboxylase (ACC1) enzyme, and wherein the micro-organism is capable of producing above 4,000 mg/L of resveratrol when cultured for a time and under conditions wherein the recombinant micro-organism produces resveratrol.

2. The recombinant micro-organism of claim 1, wherein said SNQ2 is an expression product of the gene SNQ2 of *Saccharomyces cerevisiae*.

3. The recombinant micro-organism of claim 1, wherein a gene expressing said SNQ2 is endogenous and is present in a higher copy number than in the native micro-organism.

4. The recombinant micro-organism of claim 1, wherein the stilbene synthase is a resveratrol synthase.

5. The recombinant micro-organism of claim 4, wherein the resveratrol synthase is from *Vitis pseudoreticulata*.

6. The recombinant micro-organism of claim 4, wherein the resveratrol synthase is from *Vitis vinifera*.

7. The recombinant micro-organism of claim 1, in which the gene products of the *Saccharomyces cerevisiae* genes Aro4 and Aro7 are expressed at levels in excess of those produced in the wild type of the micro-organism by replacing a native promoter of the Aro4 and Aro7 genes with a strong promoter providing a higher level of expression.

8. The recombinant micro-organism of claim 7, wherein the strong promoter providing a higher level of expression is TDH3, TEF1, TPI1, ADH1 or TEF2.

9. The recombinant micro-organism of claim 7, wherein the Aro4 gene is encoded by SEQ ID NO.:138 and the Aro7 gene is encoded by SEQ ID NO.:139.

10. The recombinant micro-organism of claim 1, wherein the micro-organism is capable of producing over 5,000 mg/L of resveratrol when cultured for a time and under conditions wherein the recombinant micro-organism produces resveratrol.

11. The recombinant micro-organism of claim 1, wherein the micro-organism is capable of producing at least about 4,000 mg/L of resveratrol to about 5,000 mg/L of resveratrol when cultured for a time and under conditions wherein the recombinant micro-organism produces resveratrol.

12. The recombinant micro-organism of claim 1, wherein said SNQ2 gene is exogenous or is endogenous to said micro-organism and is expressed at a level higher than the native expression level in the micro-organism by replacing a native promoter of a gene expressing said SNQ2 gene with a strong promoter providing a higher level of expression in the micro-organism.

13. The recombinant micro-organism of claim 12, wherein the strong promoter providing a higher level of expression is TDH3, TEF1, TPI1, ADH1 or TEF2.

14. A dried biomass of the recombinant micro-organism of claim 1.

15. An animal feed comprising the recombinant micro-organism of claim 1 or the dried biomass of claim 14.

* * * * *